US009125864B2

(12) United States Patent
Grifantini et al.

(10) Patent No.: US 9,125,864 B2
(45) Date of Patent: Sep. 8, 2015

(54) OMV VACCINES

(75) Inventors: Renata Maria Grifantini, Siena (IT); Erika Bartolini, Castelnuovo Berardenga (IT); Oretta Finco, Rapolano Terme (IT); Guido Grandi, Segrate (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/702,949

(22) PCT Filed: Jun. 10, 2011

(86) PCT No.: PCT/IB2011/002341

§ 371 (c)(1), (2), (4) Date: Apr. 9, 2013

(87) PCT Pub. No.: WO2011/161551

PCT Pub. Date: Dec. 29, 2011

(65) Prior Publication Data

US 2013/0195907 A1 Aug. 1, 2013

(30) Foreign Application Priority Data

Jun. 11, 2010 (GB) .................................. 1009861.4

(51) Int. Cl.

| | |
|---|---|
| ***A61K 39/118*** | (2006.01) |
| ***A61K 45/00*** | (2006.01) |
| ***A61K 39/02*** | (2006.01) |
| ***A61K 39/385*** | (2006.01) |
| ***C12N 1/20*** | (2006.01) |
| ***C12N 1/00*** | (2006.01) |
| ***C12N 1/12*** | (2006.01) |
| ***C07K 14/245*** | (2006.01) |
| ***C07K 14/295*** | (2006.01) |
| ***C12P 21/02*** | (2006.01) |
| *A61K 39/00* | (2006.01) |

(52) U.S. Cl.

CPC ............. *A61K 39/118* (2013.01); *C07K 14/245* (2013.01); *C07K 14/295* (2013.01); *C12P 21/02* (2013.01); *A61K 2039/522* (2013.01); *A61K 2039/523* (2013.01); *A61K 2039/55505* (2013.01); *A61K 2039/6037* (2013.01); *A61K 2039/6068* (2013.01)

(58) Field of Classification Search

CPC . A61K 2300/00; A61K 33/24; A61K 31/337; A61K 31/4745; A61K 31/513; A61K 31/51; A61K 2039/6037; C07K 14/295

See application file for complete search history.

(56) References Cited

U.S. PATENT DOCUMENTS 6,153,406 A * 11/2000 Tai et al. ...................... 435/69.3

FOREIGN PATENT DOCUMENTS

| | | | |
|---|---|---|---|
| WO | WO 02/062378 A2 | | 8/2002 |
| WO | WO 02/062380 A2 | | 8/2002 |
| WO | WO 2006/046143 A2 | * | 5/2006 |

OTHER PUBLICATIONS

Haddad et al., FEMS Immunology and Medical Microbiology, 1995; 12: 175-186.*
Woodruff et al., Journal of Bacteriology, 1989; 171(6): 3304-3309 (copy provided by applicant was cut off at the top).*
Malhotra et al., Indian J. Med Res, 2013; 138(3): 303-316 (18 pages in total (print format).*
Cascales et al., Molecular Microbiology, 2004; 51(3): 873-885.*
Hoelzle et al., J. Vet. Med. B, 2003; 50: 383-389.*
Zhou et al., Acta Microbiologica Sinica, 2007; 47(3): 512-516; translated abstract only).*
Bernadac Alain et al., "*Escherichia coli* Tol-Pal Mutants Form Outer Membrane Vesicles," Journal of Bacteriology, American Society for Microbiology, 180(18):4872-4878 (1998).
Douglas M. Molina et al., "Identification of Immunodominant Antigens of *Chlamydia trachomatis* Using Proteome Microarrays," Vaccine, Elsevier Ltd, GB, 28(17):3014-3024 (2010).
Mikihito Kajiya et al., "Aggregatibacter Actinomycetemcomitans OMP29 is Associated With Bacterial Entry to Gingivalepithelial Cells BT F-Actin Rearrangement," plos one, 6(4):E18287 (2011).
O. Finco et al., "Approach to Discover T-And B-Cell Antigena of Intracellular Pathogens Applied to the Design of *Chlamydia trachomatis* Vaccines," Proceedings of the National Academy of Sciences, 108(24):9969-9974 (2011).
Scorza Francesco Berlanda et al., "Proteomics Characterization of Outer Membrane Vesicles From the Extraintestinal Pathogenic *Escherichia coli* Delta TO1R IHE3034 Mutanr," Molecular & Cellular Proteomics, American Society for Biochemistry and Molecular Biology, Inc., 7(3):473-485 (2008).
Woodruff et al., "*Pseudomonas aeruginosa* Outer Membrane Protein F: Structural Role and Relationship to the *Escherichia coli* Ompa Protein," Journal of Bacteriology, 171(6):3304-3309 (1989).

* cited by examiner

*Primary Examiner* — Gary Nickol
*Assistant Examiner* — Lakia Tongue
(74) *Attorney, Agent, or Firm* — Robins Law Group; Roberta L. Robins

(57) ABSTRACT

The invention is in the field of outer membrane vesicles (OMV) and their uses. More particularly the present invention provides OMV obtained from a bacterium being an ompA mutant and/or a mutant in one or more components of the TolPal complex and presenting a heterologous antigen on its surface. The heterologous antigen is selected from the group consisting of *Chlamydia trachomatis* CT823, CT681, CT372, CT443, CT043, CT733, CT279, CT601 and CT153 for the treatment, prevention or diagnosis of *Chlamydia* infection.

20 Claims, 31 Drawing Sheets

FIGURE 1
FIG 1A
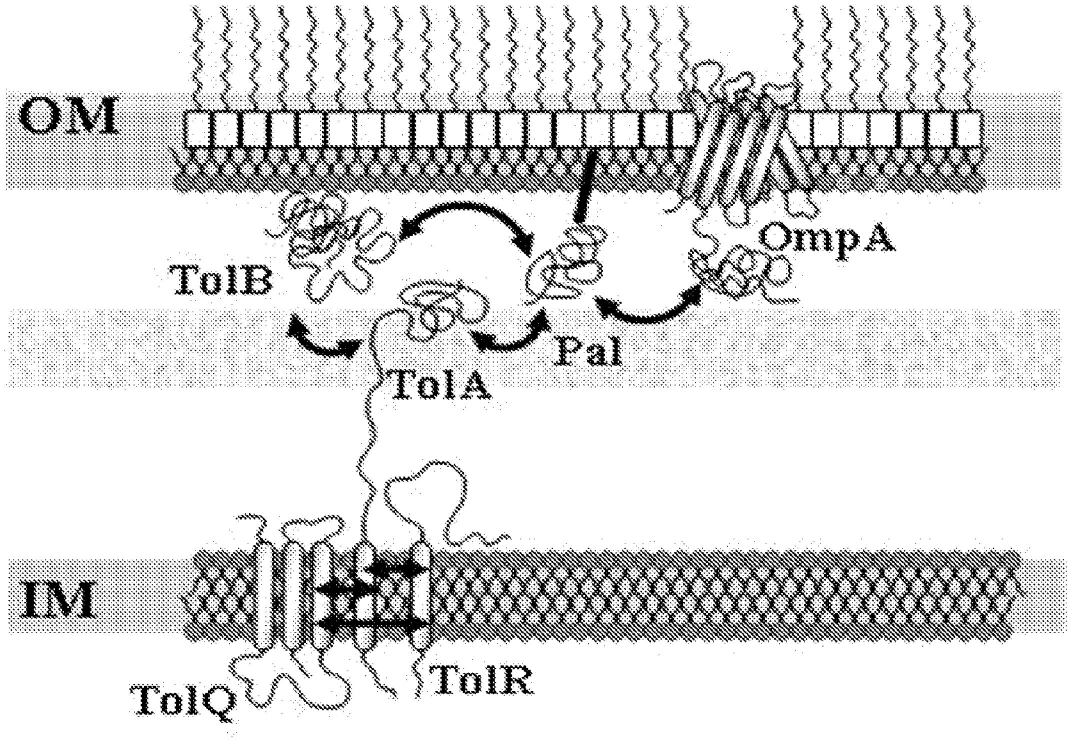
FIG. 1B
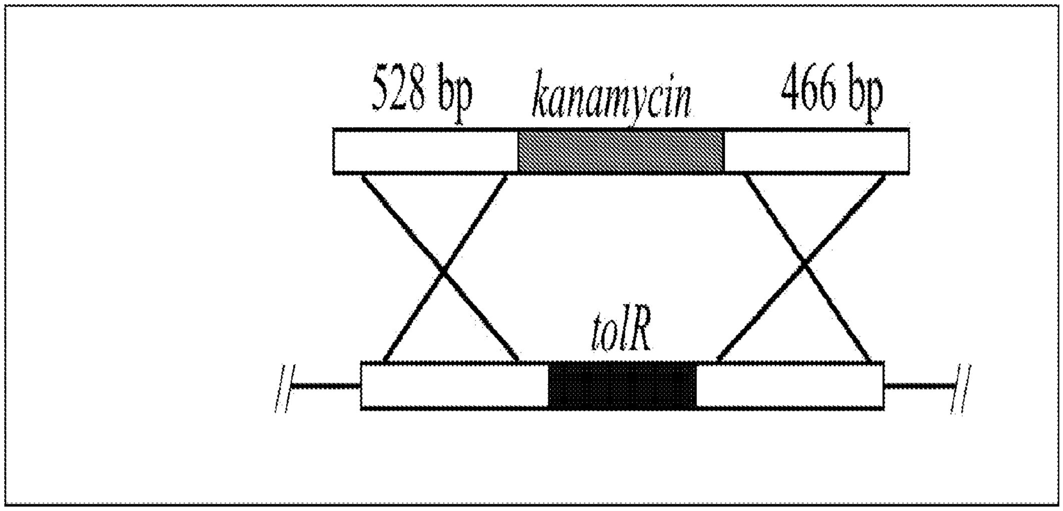

FIGURE 5
FIGURE 5A
(i)
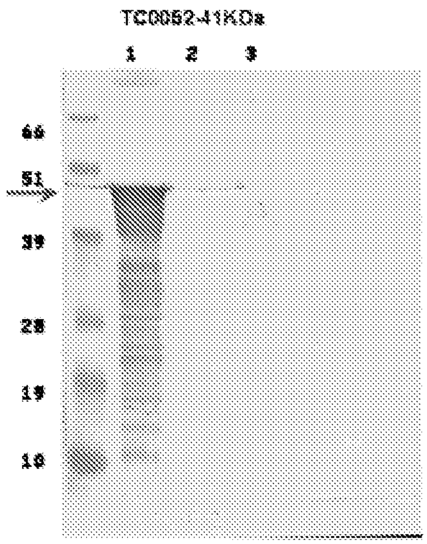
(ii)
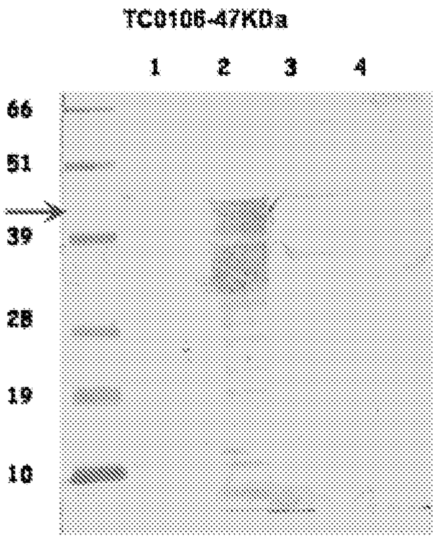
(iii)
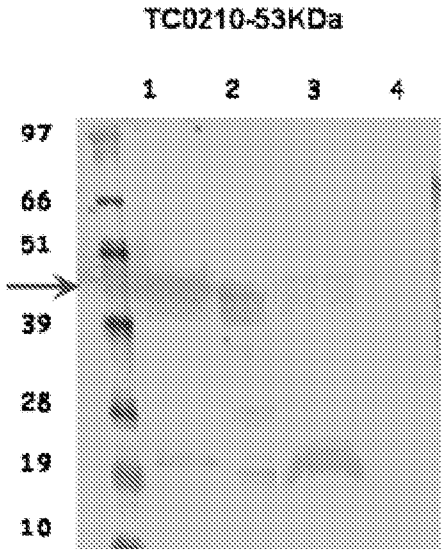
(iv)
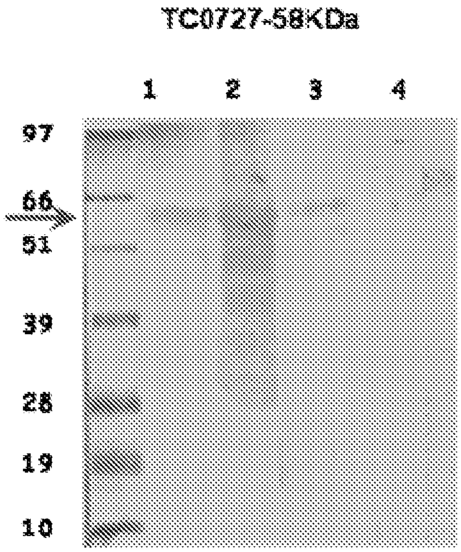

FIGURE 8

*MASCOT SEARCH RESULTS*
*PROTEIN VIEW*

Match to: TC_0210 Score: 43 serine protease, HtrA/DegQ/DegS family (htrA) [3.4.21.-] {Chlamydia muridarum strain Nigg}

Found in search of \\Chisie06646\MassLynx\PKL_files\Service_OMV_shaving_210_8may2009.pkl Nominal mass ($M_r$): 53261; Calculated pI value: 6.36

NCBI BLAST search of TC_0210 against nr

Unformatted sequence string for pasting into other applications

Semi-specific cleavage, (peptide can be non-specific at one terminus only)

Cleavage by semi Trypsin: cuts C-term side of KR unless next residue is P

Sequence Coverage: 2%

Matched peptides shown in Bold

```
  1 MMKRLLCVLL STSVFSSPML GYSAPKKDSS TGICLAASQS DRELSQEDLL
 51 KEVSRGFSKV AAQATPGVVY IENFPKTGSQ AIASPGNKRG FQENPFDYFN
101 DEFFNRFFGL PSHREQPRPQ QRDAVRGTGF IVSEDGYVVT NHHVVEDAGK
151 IHVTLHDGQK YTAKIIGLDP KTDLAVIKIQ AKNLPFLTFG NSDQLQIGDW
201 SIAIGNPFGL QATVTVGVIS AKGRNQLHIV DFEDFIQTDA AINPGNSGGP
251 LLNIDGQVIG VNTAIVSGSG GYIGIGFAIP SLMAKRVIDQ LISDGQVTRG
301 FLGVTLQPID SELAACYKLE KVYGALITDV VKGSPAEKAG LRQEDVIVAY
351 NGKEVESLSA LRNAISLMMP GTRVVLKVVR EGKFIEIPVT VTQIPAEDGV
401 SALQKMGVRV QNLTPEICKK LGLASDTRGI FVVSVEAGSP AASAGVVPGQ
451 LILAVNRQRV SSVEELNQVL KNAKGENVLL MVSQGEVIRF VVLKSDE
```

FIGURE 9

```
>CMU:TC0210 HTRA; SERINE PROTEASE ; K01362
TOP
          LENGTH = 497

>CTR:CT823 HTRA; DO SERINE PROTEASE ; K01362
TOP
          LENGTH = 497

 SCORE =  931 BITS (2406), EXPECT = 0.0,   METHOD: COMPOSITIONAL MATRIX ADJUST.
 IDENTITIES = 464/497 (93%), POSITIVES = 483/497 (97%)

QUERY: 1   MMKRLLCVLLSTSVFSSPMLGYSAPKKDSSTGICLAASQSDRELSQEDLLKEVSRGFSKV 60
           MMKRLLCVLLSTSVFSSPMLGYSA KKDS   ICLA S  D+E+SQEDLLKEVSRGFS+V
SBJCT: 1   MMKRLLCVLLSTSVFSSPMLGYSASKKDSKADICLAVSSGDQEVSQEDLLKEVSRGFSRV 60

QUERY: 61  AAQATPGVVYIENFPKTGSQAIASPGNKRGFQENPFDYFNDEFFNRFFGLPSHREQPRPQ 120
           AA+ATPGVVYIENFPKTG+QAIASPGNKRGFQENPFDYFNDEFFNRFFGLPSHREQ RPQ
SBJCT: 61  AAKATPGVVYIENFPKTGNQAIASPGNKRGFQENPFDYFNDEFFNRFFGLPSHREQQRPQ 120

QUERY: 121 QRDAVRGTGFIVSEDGYVVTNHHVVEDAGKIHVTLHDGQKYTAKIIGLDPKTDLAVIKIQ 180
           QRDAVRGTGFIVSEDGYVVTNHHVVEDAGKIHVTLHDGQKYTAKI+GLDPKTDLAVIKIQ
SBJCT: 121 QRDAVRGTGFIVSEDGYVVTNHHVVEDAGKIHVTLHDGQKYTAKIVGLDPKTDLAVIKIQ 180

QUERY: 181 AKNLPFLTFGNSDQLQIGDWSIAIGNPFGLQATVTVGVISAKGRNQLHIVDFEDFIQTDA 240
           A+ LPFLTFGNSDQLQIGDW+IAIGNPFGLQATVTVGVISAKGRNQLHIVDFEDFIQTDA
SBJCT: 181 AEKLPFLTFGNSDQLQIGDWAIAIGNPFGLQATVTVGVISAKGRNQLHIVDFEDFIQTDA 240

QUERY: 241 AINPGNSGGPLLNIDGQVIGVNTAIVSGSGGYIGIGFAIPSLMAKRVIDQLISDGQVTRG 300
           AINPGNSGGPLLNI+GQVIGVNTAIVSGSGGYIGIGFAIPSLMAKRVIDQLISDGQVTRG
SBJCT: 241 AINPGNSGGPLLNINGQVIGVNTAIVSGSGGYIGIGFAIPSLMAKRVIDQLISDGQVTRG 300

QUERY: 301 FLGVTLQPIDSELAACYKLEKVYGALITDVVKGSPAEKAGLRQEDVIVAYNGKEVESLSA 360
           FLGVTLQPIDSELA CYKLEKVYGAL+TDVVKGSPAEKAGLRQEDVIVAYNGKEVESLSA
SBJCT: 301 FLGVTLQPIDSELATCYKLEKVYGALVTDVVKGSPAEKAGLRQEDVIVAYNGKEVESLSA 360

QUERY: 361 LRNAISLMMPGTRVVLKVVREGKFIEIPVTVTQIPAEDGVSALQKMGVRVQNLTPEICKK 420
           LRNAISLMMPGTRVVLK+VREGK IEIPVTVTQIP EDGVSALQKMGVRVQN+TPEICKK
SBJCT: 361 LRNAISLMMPGTRVVLKIVREGKTIEIPVTVTQIPTEDGVSALQKMGVRVQNITPEICKK 420

QUERY: 421 LGLASDTRGIFVVSVEAGSPAASAGVVPGQLILAVNRQRVSSVEELNQVLKNAKGENVLL 480
           LGLA-DTRGI VV+VEAGSPAASAGV PGQLILAVNRQRV+SVEELNQVLKN+KGENVLL
SBJCT: 421 LGLAADTRGILVVAVEAGSPAASAGVAPGQLILAVNRQRVASVEELNQVLKNSKGENVLL 480

QUERY: 481 MVSQGEVIRFVVLKSDE 497
           MVSQG+V+RF+VLKSDE
SBJCT: 481 MVSQGDVVRFIVLKSDE 497
```

FIGURE 17C
(i)
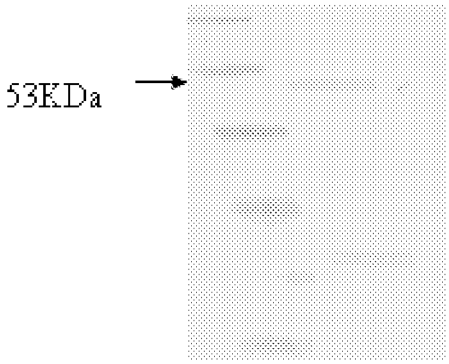
(ii)
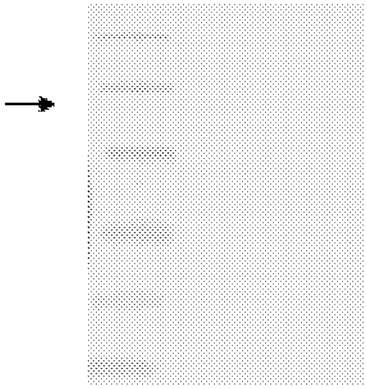

FIGURE 21
(i)
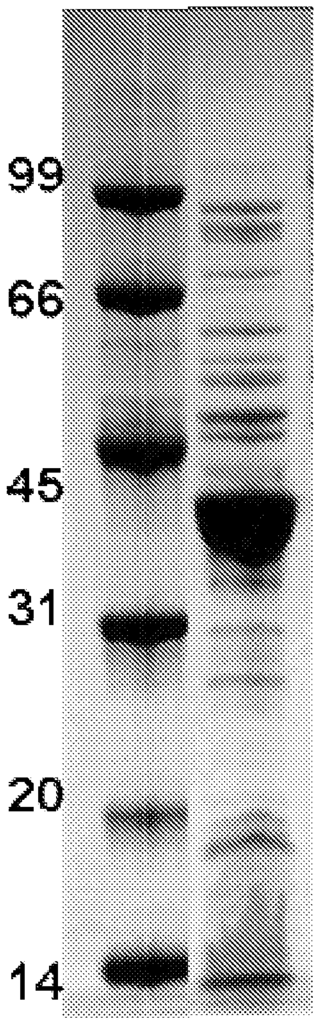
(ii)
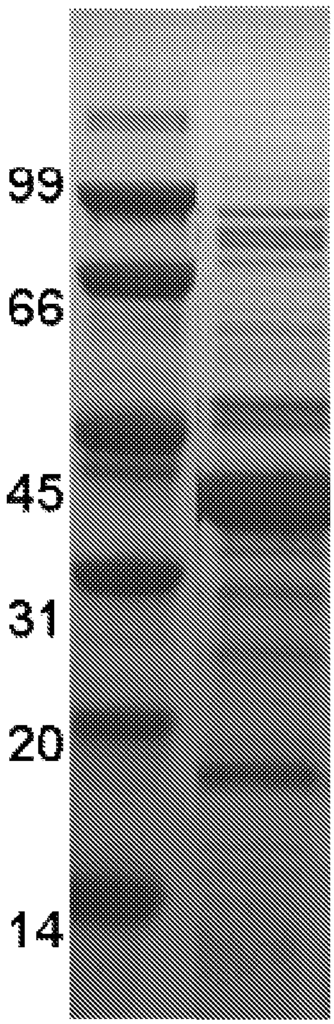

FIGURE 23

Match to: TC_0210 Score: 102 Expect: 2.3e-006 serine protease, HtrA/DegQ/DegS family (htrA) [3.4.21.-] {Chlamydia muridarum strain Nigg}

Nominal mass ($M_r$): 53261; Calculated pI value: 6.36
NCBI BLAST search of TC_0210 against nr Variable modifications: Oxidation (M)
Cleavage by Trypsin: cuts C-term side of KR unless next residue is P
Number of mass values searched: 57
Number of mass values matched: 13
Sequence Coverage: 34%

Matched peptides shown in Bold

1 MMKRLLCVLL STSVFSSPML GYSAPKKDSS TGICLAASQS DRELSQEDLL
51 KEVSRGFSKV AAQATPGVVY IENFPKTGSQ AIASPGNKRG FQENPFDYFN
101 DEFFNRFFGL PSHREQPRPQ QRDAVRGTGF IVSEDGYVVT NHHVVEDAGK
151 IHVTLHDGQK YTAKIIGLDP KTDLAVIKIQ AKNLPFLTFG NSDQLQIGDW
201 SIAIGNPFGL QATVTVGVIS AKGRNQLHIV DFEDFIQTDA AINPGNSGGP
251 LLNIDGQVIG VNTAIVSGSG GYIGIGFAIP SLMAKRVIDQ LISDGQVTRG
301 FLGVTLQPID SELAACYKLE KVYGALITDV VKGSPAEKAG LRQEDVIVAY
351 NGKEVESLSA LRNAISLMMP GTRVVLKVVR EGKFIEIPVT VTQIPAEDGV
401 SALQKMGVRV QNLTPEICKK LGLASDTRGI FVVSVEAGSP AASAGVVPGQ
451 LILAVNRQRV SSVEELNQVL KNAKGENVLL MVSQGEVIRF VVLKSDE

| Start - End | Observed | Mr(expt) | Mr(calc) | ppm | Miss | Sequence |
|---|---|---|---|---|---|---|
| 60 - 76 | 1803.89 | 1802.88 | 1802.96 | -41 | 0 | K.VAAQATPGVVYIENFPK.T |
| 90 - 106 | 2185.96 | 2184.96 | 2184.92 | 17 | 0 | R.GFQENPFDYFNDEFFNR.F |
| 107 - 114 | 960.43 | 959.42 | 959.50 | -76 | 0 | R.FFGLPSHR.E |
| 115 - 122 | 1038.46 | 1037.45 | 1037.54 | -81 | 0 | R.EQPRPQQR.D |
| 127 - 150 | 2530.42 | 2529.42 | 2529.21 | 80 | 0 | R.GTGFIVSEDGYVVTNHHVVEDAGK.I |
| 172 - 182 | 1199.55 | 1198.55 | 1198.73 | -152 | 1 | K.TDLAVIKIQAK.N |
| 287 - 299 | 1443.67 | 1442.66 | 1442.77 | -78 | 0 | R.VIDQLISDGQVTR.G |
| 339 - 353 | 1632.76 | 1631.75 | 1631.86 | -67 | 1 | K.AGLRQEDVIVAYNGK.E |
| 339 - 362 | 2617.63 | 2616.63 | 2616.39 | 91 | 2 | K.AGLRQEDVIVAYNGKEVESLSALR.N |
| 384 - 405 | 2355.39 | 2354.38 | 2354.27 | 45 | 0 | K.FIEIPVTVTQIPAEDGVSALQK.M |
| 410 - 419 | 1144.52 | 1143.51 | 1143.60 | -73 | 0 | R.VQNLTPEICK.K |
| 472 - 489 | 1973.00 | 1971.99 | 1972.04 | -26 | 1 | K.NAKGENVLLMVSQGEVIR.F Oxidation(M) |
| 475 - 489 | 1659.77 | 1658.77 | 1658.87 | -61 | 0 | K.GENVLLMVSQGEVIR.F Oxidation (M) |

NO MATCH TO: 650.21, 656.18, 672.07, 697.35, 741.33, 777.37, 785.37, 861.00, 964.39, 986.43, 1002.43, 1111.49, 1155.52, 1170.52, 1243.57, 1249.46, 1287.59, 1295.51, 1331.61, 1333.59, 1367.62, 1375.63, 1388.63, 1580.64, 1717.72, 1745.71, 1763.84, 1825.89, 1847.82, 1904.86, 1932.88, 1954.02, 1974.94, 2034.92, 2149.07, 2240.07, 2275.26, 2378.32, 2553.36, 2619.60, 2645.60, 2916.71, 2970.85, 3217.98

OMV VACCINES

CROSS-REFERENCE TO RELATED APPLICATIONS

This application is a §371 filing of PCT/IB2011/002341, filed Jun. 10, 2011, and claims the benefit of GB application no. 1009861.4, filed Jun. 11, 2010, from which applications priority is claimed pursuant to the provisions of 35 U.S.C. §§119/120, which applications are incorporated herein by reference in their entireties.

TECHNICAL FIELD

The invention is in the field of outer membrane vesicles that present a heterologous antigen on their surface and their uses.

BACKGROUND

*C. trachomatis* is a Gram-negative bacterium which is an obligate intracellular pathogen. It is a common cause of urogenital tract infections, which leads to pelvic inflammatory disease (10-20% of cases), infertility and ectopic pregnancy. Such conditions are common in industrialised countries and are caused by serovars D-K.

*C. trachomatis* is also a leading cause of ocular infections, resulting in trachoma (150 million cases annually) and blindness (6 million cases annually), mainly in developing countries. These conditions are caused by serovars A-C. Infection with serovars L1-L3 of *C. trachomatis* causes lymphogranuloma venereum.

Vaccine development has been identified as essential to controlling infection with *C. trachomatis*. Vaccines against *C. trachomatis* appear to depend on a Th1-polarized cell-mediated immune response, in particular on CD4+ lymphocytes that produce IFN-γ. For example, depletion of CD4+ T cells in mice results in loss of protective immunity [1], and adoptive transfer of *Chlamydia*-specific CD4+ T cells confers protection against challenge with *C. trachomatis* ([2],[3]). Furthermore, recent studies report that *C. trachomatis* infection in mice induces a CD4-Th1 protective immune response, indicating that critical *Chlamydia* antigens are processed and presented via the MHC class II pathway ([4]; [5]).

Immune protection against infection with *C. trachomatis* is likely to be mediated by immunization with *C. trachomatis* proteins that are targets of CD4+ T cells and that are capable of inducing B-cell responses. B-cells and antibodies have been shown to be important for enhancing the protective effector T-cell response against primary infection [6]. B-cells and antibodies also play an important role in resolution of secondary infection ([7],[8]).

Neutralizing antibodies have been shown to play an important role in protection against *Chlamydia* infection.

Numerous studies on the most promising vaccine candidate (Major Outer Membrane Protein, MOMP) have shown that an effective vaccine is likely to be based on several *C. trachomatis* antigens. The homologue proteins CT823 of *Chlamydia trachomatis* (Ct) and TC0210 of *Chlamydia muridarum* (Cm) are annotated as serine proteases and share a 93.36 percent sequence identity. Previous studies, with mass spectrometric and cytofluorimetric analysis on CT823 have confirmed its localization on the surface of the bacterium [9]. The CT823 antigen is able to induce a specific CD4-Th1 response in splenocytes isolated from mice infected with *C. trachomatis* and has been predicted to contain MHC class II epitopes ([10]; [11]).

It is an object of the invention to provide a vehicle for delivering antigens such as *Chlamydia* CT823 in vaccine formulations.

DISCLOSURE OF THE INVENTION

The present invention provides an outer membrane vesicle (OMV) presenting a heterologous antigen on its surface, wherein the OMV is obtained from a bacterium which is an ompA mutant and/or which is a mutant in one or more components of the Tol-Pal complex. The Tol-Pal complex is shown in FIG. 1*a*.

Gram-negative bacteria naturally shed OMVs which are released into the growth medium. Heterologous antigens are expressed in the Gram-negative bacteria such that they assemble in the membrane that is then released in the culture supernatant. OMVs from Gram-negative bacteria are representative of the outer membrane and periplasmic bacterial compartments and allow the presentation of membrane proteins in their natural composition and conformation. As the OMVs carry the recombinant proteins in the proper conformation, they represent an excellent choice as delivery vehicles for heterologous membrane proteins.

The use of OMVs to express outer membrane proteins is described in WO 2002/062380 (GlaxoSmithKline Biologicals S.A.). WO 2002/062380 discloses a Gram-negative bacterial OMV presenting on its surface one or more outer membrane proteins from *Chlamydia*. Presentation of the PorB outer membrane protein from *C. trachomatis* is said to be preferred. The presentation of PmpG and MOMP outer membrane proteins from *C. trachomatis* is also described.

WO 2002/062380 describes methods to optimize the outer membrane protein (OMP) and LPS composition of OMV ("bleb") vaccines by deleting immunodominant variable OMPs, as well as non-protective OMPs, by creating conserved OMPs by deletion of variable regions, by upregulating expression of protective OMPs and by eliminating control mechanisms for expression of protective OMPs.

WO 2006/046143 (Novartis Vaccines & Diagnostics, SRL) discloses that disruption of the pathways involved in degradation of peptidoglycan (the murein layer) gives bacteria that release vesicles into their culture medium, and that these vesicles are rich in immunogenic outer membrane proteins and can elicit broad-ranging bactericidal immune responses. In particular, the inventors of WO 2006/046143 found that knocking out the meningococcal mltA homolog gives bacteria that spontaneously release vesicles that are rich in immunogenic outer membrane proteins and that can elicit cross-reactive antibody responses with higher bactericidal titres than OMVs prepared by normal production processes. *E. coli* having a knock out of one or more of the components of the Tol-Pal complex, such as tolA, tolQ, tolB, pal and/or tolR are also described.

The inventors have surprisingly found that the use of the OMVs of the present invention as delivery vehicles enables the antigenicity of promising antigens to be increased compared to when the antigens are delivered in their purified form. For example, it has been found that antigens which are not protective when tested in a chlamydial animal model when administered in their purified form, may become protective when presented in an OMV of the invention.

Bacteria

One aspect of the invention relates to a mutant bacterium, which expresses a heterologous antigen.

The invention allows the production of OMVs from a bacterium of choice. The bacterium from which the OMV of the invention is prepared may be Gram-positive, but it is preferably Gram-negative. The bacterium may be any suitable bacterium, for example, *Bordetella pertussis, Borrelia burgdorferi, Brocella melitensis, Brucella ovis, Chlamydia psittaci, Chlamydia trachomatis, Escherischia coli, Haemophilus influenzae, Legionella pneumophila, Neisseria meningitidis* or *N. gonorrhoeae, Moraxella catarrhalis, Pseudomonas aeruginosa, Yersinia enterocolitica, Shigella flexneri, Treponema, Porphyromonas, Helicobacter* or *Salmonella enterica serovar typhimurium.*

For example, the bacterium may be from the *Escherichia* genus. In preferred embodiments, the bacterium is *E. coli*. Any suitable *E. coli* strain may be used. For example, in some embodiments, the *E. coli* is from the BL21 strain, for example, *E. coli* BL21(DE3). The present inventors have surprisingly found that the use of an *E. coli* BL21(DE3) strain is an excellent delivery vehicle for presenting heterologous antigens. In some embodiments, the bacterium is from the K1 or K12 strain.

The bacterium will typically have been generated by mutation of at least one component of the Tol-Pal complex and/or of the OmpA gene in a chosen starting strain.

Where the bacterium is not *E. coli*, the bacterium may have a mutation of the homologue of the ompA gene and/or of one or more components of the homologue of the *E. coli* Tol-Pal complex.

In some embodiments, one or more (e.g. 2, 3, 4, 5) components of the *E. coli* Tol-Pal complex is mutated. A schematic diagram of the Tol-Pal complex is shown in FIG. 1*a* (see also [12], [13], [14]). For example, in some embodiments, any combination of tolA, tolQ, tolB, pal and/or tolR is mutated. For example, one, two, three, four or all of tolA, tolQ, tolB, pal and/or tolR may be mutated. For example, one or more (e.g. 2 or more, 3 or more, 4 or more or all) of tolA, tolQ, tolB, pal and/or tolR may be mutated. Mutation of tolR is preferred.

In one embodiment, the OMV is obtained from a bacterium which is an ompA mutant. In another embodiment, the OMV is obtained from a bacterium which is an ompA mutant and a mutant in at least one component of its Tol-Pal complex, for example, a tolR mutant. In preferred embodiments, the OMV is obtained from a bacterium which is an ompA mutant but which is wild type in the genes encoding the Tol-Pal complex, or which expresses a functional Tol-Pal complex. Preferably, in embodiments in which the bacterium is an ompA mutant, the bacterium is wild type in its tolR gene or expresses a functional TolR protein. In most preferred embodiments, the bacterium is an ompA mutant and all other genes are wild type genes.

Preferably, the bacterium is an *E. coli* ompA mutant or an *E. coli* ompA and tolR mutant. In some embodiments, the bacterium is selected from *E. coli* BL21(DE3)ΔompA, *E. coli* BL21(DE3)ΔompAΔtolR, or *E. coli* BL21(DE3)ΔtolR. The Δ symbol is used herein to refer to a bacterial strain from which the coding sequence of the gene recited after the Δ symbol has been deleted. Thus, a bacterial strain which is "ΔompA" does not comprise the coding sequence for the ompA gene. Likewise, a bacterial strain which is "ΔtolR" does not comprise the coding sequence for the tolR gene. Preferably, the entire coding sequence is deleted. However, the coding sequence may alternatively be deleted in part. For example, the N-terminal half or the C-terminal half may be deleted.

The present inventors have surprisingly found that *E. coli* ΔtolR mutant strains and *E. coli* ΔompA mutant strains over-produce OMVs relative to wild type *E. coli*. Thus, the mutation of the ompA gene and/or one or more components of the Tol-Pal complex preferably results in the mutant bacterium producing an increased number of OMVs compared to its respective wild type strain which carries a wild type ompA gene and/or Tol-Pal complex. OmpA is an integral membrane protein and is the most abundant of the outer membrane proteins in *E. coli*. It is, therefore, particularly surprising that an *E. coli* lacking the OmpA protein is viable. Indeed, according to Murakami et al. [15], an *E. coli* ompA single mutant cannot promote vesicle release.

Hyperblebbing Gram-negative bacteria from which blebs may more easily be made in higher yield and may be more homogeneous in nature are described in WO 02/062378 (Smithkline Beecham Biologicals S.A.). The blebs are derived from bacteria selected from the group consisting of *Neisseria meningitidis, Neisseria lactamica, Neisseria gonorrhoeae, Helicobacter pylori, Salmonella typhi, Salmonella typhimurium, Vibrio cholerae, Shigella* spp., *Haemophilus influenzae, Bordetella pertussis, Pseudomonas aeruginosa* and *Moraxella catarrhalis*. Such bacteria have been genetically modified by down-regulation of expression of one or more tol genes and mutations of one or more gene(s) encoding a protein comprising a peptidoglycan-associated site to attenuate the peptidoglycan-binding activity of the protein(s) whilst ensuring that the truncated protein folds correctly in the outer membrane.

The present inventors have surprisingly found that OMVs from *E. coli* ΔompA mutant strains express a higher percentage of outer membrane proteins compared to *E. coli* ΔtolR mutant strains (see Example 9). Thus, in some embodiments, the mutant bacterium expresses a higher percentage of outer membrane proteins compared to its respective wild type strain, more preferably, compared to a tolR mutant strain. In some embodiments, the OMV produced from the bacterium expresses a higher percentage of outer membrane proteins compared to an OMV from the respective wild type strain of the bacterium, more preferably, compared to a tolR mutant from the same strain. For example, the protein composition of the OMV of the invention may comprise 60% or more outer membrane proteins. In some embodiments, the protein composition of the OMV comprises at least 70%, at least 75%, at least 80%, at least 85%, at least 90% or at least 95% outer membrane proteins. Preferably, the protein composition of the OMV comprises at least 98% or at least 99% outer membrane proteins. Most preferably, the OMV comprises 100% outer membrane proteins. In some embodiments, the protein composition of the OMV comprises 25% or less cytoplasmic proteins (e.g. 20% or less, 15% or less, 10% or less, 5% or less, 3% or less, 2% or less, 1% or less). Preferably, the OMV comprises no cytoplasmic proteins. The percentage of outer membrane proteins and cytoplasmic proteins is preferably assessed according to the method described in Example 9.

The present inventors have also surprisingly found that an OMV of the present invention from an *E. coli* ΔompA mutant strain expresses an increased amount of the heterologous antigen compared to an OMV from an *E. coli* ΔtolR mutant strain (see Example 10). Thus, in some embodiments, the mutant bacterium expresses an increased amount of the heterologous antigen compared to its respective wild type strain, more preferably compared to a tolR mutant strain. In some embodiments, the OMV produced from the bacterium expresses a larger amount of the heterologous antigen compared to an OMV from the respective wild type strain of the bacterium, more preferably, compared to an OMV produced by a tolR mutant from the same strain. For example, in some embodiments, the OMV of the invention expresses 105% or more (for example, 110% or more, 125% or more, 150% or more, 175% or more, 200% or more or 250% or more) heterologous antigen compared to an OMV from the respective wild type strain of the bacterium, or more preferably, compared to an OMV from a tolR mutant from the same strain.

The mutation of the ompA gene and/or one or more components of the Tol-Pal complex is preferably a knock out mutation. For example, part or all of the gene sequence may be deleted such that only a fragment of the protein is expressed or such that no protein is expressed. For example, a fragment of the coding sequence may be deleted, for example, at least 20%, at least 40%, at least 60%, at least 80%, at least 90%, at least 95% of the coding sequence. In some embodiments, the expressed protein lacks one or more than one domain. In preferred embodiments, the mutation is a deletion of the entire coding sequence of the OmpA protein and/or the at least one component of the Tol-Pal complex. In such embodiments, this results in the bacterium not expressing the OmpA protein and/or at least one component of the Tol-Pal complex (preferably TolR).

Consequently, the OMV does not express the OmpA protein and/or the at least one component of the Tol-Pal complex.

The at least one component of the Tol-Pal complex or the OmpA protein may be knocked out by any suitable method. In one embodiment, the at least one component of the Tol-Pal complex and/or the ompA gene is deleted using recombinant DNA techniques, such as homologous recombination techniques. Such techniques are well known in the art (e.g. using Red/ET recombineering technology such as the *E. coli* gene deletion kit from Gene Bridges, GmbH) [16]. For example, the at least one component of the Tol-Pal complex and/or the ompA gene may be replaced with an antibiotic resistance cassette as a selection marker. In some embodiments, the tolR gene is replaced with a kanamycin resistance gene by homologous recombination, as shown in FIG. 1*b*.

In other embodiments, the one or more mutations in at least one component of the Tol-Pal complex and/or the ompA gene, may each independently be a substitution, an insertion or a deletion. For example, each mutation may involve a single amino acid, such as a point mutation. A truncation is an example of a deletion. Truncations may involve deletion of up to 10, up to 20, up to 30 or up to 40 (or more) amino acids at the N-terminus and/or C-terminus. Preferably, such mutations result in the production of a non-functional protein.

Mutant Bacteria—Expression of Other Genes

OMVs from a double mutant of *E. coli* that lacks both the Braun lipoprotein (lpp) and OmpA are described in U.S. Pat. No. 6,558,677. In preferred embodiments, the bacterium has a wild type Braun lipoprotein gene. In some embodiments, the bacterium expresses a mutated but functional version of the Braun lipoprotein.

Murakami et al. [15] discloses that an *E. coli* ompA mutant itself could not promote vesicle release; however, ompA, pal and major lipoprotein lpp mutants formed large numbers of vesicles. Thus, the present invention provides that, in some embodiments, the OMV is from a bacterium which is wild type in its pal and major lipoprotein lpp genes. In some embodiments, the bacterium expresses a mutated but functional version of the pal and major lipoprotein genes.

Mutant Bacteria—Mutations of Other Genes

In some embodiments, in addition to having a mutation of the ompA gene and/or one or more components of the Tol-Pal complex, the bacterium may have one or more mutations of other gene(s). To reduce pyrogenic activity, for instance, the bacterium should have low endotoxin (lipo-oligosaccharide (LOS)/lipopolysaccharide (LPS)) levels, and this can be achieved by knock out of enzymes involved in LPS biosynthesis. OMVs of the invention preferably contain no more than 20% by weight of LOS/LPS, measured relative to the total protein (i.e. there should be at least 4 times more protein than LOS/LPS, by weight). The maximum LOS/LPS level is preferably even lower than 20% e.g. 15%, 10%, 5% or lower. Processes for preparing LPS depleted outer membranes from Gram-negative bacteria are disclosed in European Patent No. 0624376.

As well as having mutations or knock outs of particular endogenous genes, the bacterium may express one or more genes that are not endogenous. For example, the invention may use a recombinant strain that expresses new genes relative to the corresponding wild-type strain. Expression of non-endogenous genes in this way can be achieved by various techniques, e.g., chromosomal insertion, knock in mutations, expression from extra-chromosomal vectors e.g. from plasmids, etc.

Further, as well as down-regulating expression of specific proteins, the bacterium may in some embodiments over-express (relative to the corresponding wild-type strain) other immunogens.

Vesicle Compositions

The invention provides the OMVs that are spontaneously released into culture medium by bacteria of the invention. These OMVs are distinct from the vesicles that can be prepared artificially from the same bacteria, such as the sarkosyl-extracted OMVs prepared in Adu-Bobie et al [17] from 'ΔGNA33' meningococci. They are also distinct from microvesicles (MVs [18]) and 'native OMVs' ('NOMVs' [19]), although vesicles of the invention seem to be more similar to MVs and NOMVs than to sarkosyl-extracted OMVs. The vesicles are also distinct from blebs, which are outer-membrane protrusions that remain attached to bacteria prior to release as MVs ([20]; [21]).

The vesicles of the invention have a diameter of 50-100 nm by electron microscopy, which is smaller than that of artificial meningococcal OMVs (diameter ~270 nm, [22]). The diameter is roughly the same as that of artificial OMVs that have been heat-denatured (~105 nm, [22]), but the vesicles of the invention retain antigenicity whereas heat-denatured artificial OMVs lose their antigenicity. Moreover, the OMVs of the invention are substantially free from cytoplasmic contamination.

Unlike the starting culture, the OMV-containing compositions of the invention will generally be substantially free from whole bacteria, whether living or dead. The size of the OMVs of the invention means that they can readily be separated from whole bacteria by filtration through a 0.22 μm filter e.g. as typically used for filter sterilisation. Thus the invention provides a process for preparing OMVs of the invention, comprising filtering the culture medium from bacteria of the invention through a filter that retards whole bacteria but that lets the OMVs pass through e.g. a 0.22 μm filter. Although OMVs will pass through standard 0.22 μm filters, these can rapidly become clogged by other material, and so it is preferred to perform sequential steps of filter sterilisation through a series of filters of decreasing pore size, finishing with a standard sterilisation filter (e.g. a 0.22 μm filter). Examples of preceding filters would be those with pore size of 0.8 μm, 0.45 μm, etc. The filtrate can be further treated e.g. by ultracentrifugation.

Vesicle Combinations

The invention also provides methods for preparing OMVs from more than one bacterial strain, and the OMVs from the different bacteria can be combined. Thus the invention provides a composition comprising a mixture of n sets of OMVs of the invention, prepared from n different strains of a bacterium. The value of n can be 1, 2, 3, 4, 5, etc. The different strains can be in the same or different serogroups.

The invention also provides a kit comprising OMVs of the invention prepared from n different strains of a bacterium. The OMVs can be kept and stored separately in the kit until they are required to be used together e.g. as an admixture, or for simultaneous, separate or sequential use.

The invention also provides a process comprising: preparing n sets of OMVs of the invention, one from each of n different strains of a bacterium; and combining the n sets of OMVs. The different sets can be combined into a kit or into an admixture.

As well as being selected from different strains of a bacterium, such as different *Escherichia* strains, OMVs can be selected from different bacterial genera, or from different pathogens. Thus the invention provides a composition comprising a mixture of n sets of OMVs of the invention, prepared from n different species of bacteria.

Similarly, the invention provides a kit comprising OMVs of the invention prepared from n different species of bacteria, and provides a process comprising the step of preparing n sets of OMVs of the invention, one from each of n different species of bacteria.

In some embodiments, different heterologous antigens are expressed on the different OMVs.

Heterologous Antigens

A "heterologous" antigen is an antigen derived from a pathogenic species that is different from the species of bacterium from which the OMV is obtained, and is preferably an antigen from a pathogen genus different from the genus of bacterium from which the OMV is obtained.

The heterologous antigen is preferably from a bacterium or virus. For example, in some embodiments, the heterologous antigen is a bacterial antigen, such as an antigen from *Chlamydia, Mycobacterium tuberculosis, Mycobacterium leprae, Streptococcus, Pseudomonas, Shigella, Campylobacter, Salmonella, Yersinia pestis, Rickettsia prowazekii, Neisseria* or *Helicobacter*. In some embodiments, the heterologous antigen is a viral antigen, such as an antigen from a virus of the Adenoviridae, Picornaviridae, Herpesviridae, Hepadnaviridae, Flaviviridae, Retroviridae, Orthomyxoviridae, Paramyxoviridae, Papovaviridae, Rhabdoviridae or Togaviridae family, for example, an antigen from HIV or influenza.

In preferred embodiments, the heterologous antigen is a Chlamydial antigen, for example, an antigen from *C. trachomatis, C. pneumoniae, C. psittaci, C. pecorum, C. muridarum* or *C. suis*. In embodiments in which the heterologous antigen is from *Chlamydia*, the bacterium from which the outer membrane vesicle is obtained is not from the same species of *Chlamydia* and is preferably not from the *Chlamydia* genus.

The human serovariants ("serovars") of *C. trachomatis* are divided into two biovariants ("biovars"). Serovars A-K elicit epithelial infections primarily in the ocular tissue (A-C) or urogental tract (D-K). Serovars L1, L2 and L3 are the agents of invasive lymphogranuloma venereum (LGV). The heterologous antigen may be selected from any one of serovars A, B, C, D, E, F, G, H, I, J, K, L1, L2 or L3. Preferably, the heterologous antigen is from *C. trachomatis* serovar D, or from another epidemiologically prevalent serotype.

Preferably, the heterologous antigen is a membrane protein, more preferably an outer membrane protein.

Examples of antigens from *C. trachomatis* which are suitable for use in the present invention are CT823, CT601, CT372, CT443, CT043, CT733, CT279, CT153 and MOMP (CT681). Examples of antigens from *C. muridarum* which are suitable for use in the present invention are TC0210, TC0052, TC0106, TC0313, TC0431, TC0551, TC0651, TC0727 and TC0890. Examples of other antigens suitable for use in the invention are TC0660 and TC0741.

In preferred embodiments, the heterologous antigen is CT823 or TC0210. The sequences of CT823 and TC0210 are presented in FIG. 9. CT823 from *Chlamydia trachomatis* (Ct) and TC0210 from *Chlamydia muridarum* (Cm) are protein homologues which are annotated as serine proteases and share a 93.36 percent sequence identity. Together with the high temperature requirement A (HtrA) protein of *E. coli* and the homologues in other bacteria and eukaryotes, these proteins constitute the HtrA protease family. The chief role of these proteases is to degrade misfolded proteins in the periplasm ([23]; [24]; [25]). HtrA from *Chlamydia trachomatis* (also referred to herein as "CtHtrA" or "CT823") has been characterised as a serine endoprotease, specific for unfolded proteins, which is temperature activated above 34° C. ([26]). Chaperone activity has been observed, although this appears to be target-dependent.

CT823 is an outer membrane protein. In order for a protective immune response to be raised against this heterologous antigen, the heterologous antigen should preferably be presented in its correctly folded state.

The inventors have surprisingly found that expression of TC0210 in a mutant OMV according to the invention results in a neutralising immune response being raised against both *C. muridarum* and *C. trachomatis*. The immune response is improved compared to the response generated by the purified TC0210 antigen (i.e. when it is not expressed in an OMV).

The heterologous antigen is preferably the wild type antigen. However, in some embodiments, the heterologous antigen is a variant of a wild type antigen. For example, the variant may have at least 75%, at least 80%, at least 85%, at least 90%, at least 95%, at least 98% or at least 99% sequence identity to the wild type antigen. Methods of determining sequence identity are well known in the art. Identity between heterologous antigens is preferably determined by the Smith-Waterman homology search algorithm as implemented in the MPSRCH program (Oxford Molecular), using an affine gap search with parameters gap open penalty=12 and gap extension penalty=2. Such variants include homologs, orthologs, allelic variants and functional mutants. In embodiments in which the heterologous antigen is a variant of a wild type antigen, the immunogenicity of the variant is preferably the same as or very similar to the immunogenicity of the wild type antigen when tested under the same conditions, such as when used in an ELISA assay or in a neutralization assay.

Where the heterologous antigen is a variant of a wild type antigen, the amino acid sequence of the variant preferably contains fewer than twenty mutations (e.g. 19, 18, 17, 16, 15, 14, 13, 12, 11, 10, 9, 8, 7, 6, 5, 4, 3, 2 or 1) relative to the wild type sequence. Each mutation preferably involves a single amino acid and is preferably a point mutation. The mutations may each independently be a substitution, an insertion or a deletion. Preferred mutations are single amino acid substitutions. The variant may also include one or more (e.g. 1, 2, 3, 4, 5, 6, 7, 8, 9, etc.) single amino acid deletions relative to the wild type sequences. The variant may also include one or more (e.g. 1, 2, 3, 4, 5, 6, 7, 8, 9, etc.) insertions (e.g. each of 1, 2, 3, 4 or 5 amino acids) relative to the wild type sequences. Deletions, substitutions or insertions may be at the N-terminus and/or C-terminus, or may be between the two termini. Thus a truncation is an example of a deletion. Truncations may involve deletion of up to 10, up to 20, up to 30, up to 40 (or more) amino acids at the N-terminus and/or C-terminus.

Amino acid substitutions may be to any one of the other nineteen naturally occurring amino acids. In preferred embodiments, one or more mutations is a conservative substitution. In another embodiment, one or more mutations is a non-conservative substitution. A conservative substitution is commonly defined as a substitution introducing an amino acid having sufficiently similar chemical properties, e.g. having a related side chain (e.g. a basic, positively charged amino acid should be replaced by another basic, positively charged amino acid), in order to preserve the structure and the biological function of the molecule. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Further examples of conservative substitutions that may be used in the invention are presented in Table I.

TABLE 1

| Amino Acid | Synonymous Groups | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

Examples of non-conservative substitutions that may be used in the invention include the substitution of an uncharged polar amino acid with a nonpolar amino acid, the substitution of a nonpolar amino acid with an uncharged polar amino acid, the substitution of an acidic amino acid with a basic amino acid and the substitution of a basic amino acid with an acidic amino acid.

In some embodiments in which the heterologous antigen is a variant of a wild type antigen, the variant may comprise one or more amino acid derivatives. By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG, Switzerland; Bachem, USA).

In some embodiments, the heterologous antigen comprises or consists of a fragment of a wild type antigen or of a variant thereof. The fragment should comprise at least n consecutive amino acids from the wild type antigen or from the variant thereof and, depending on the particular sequence, n is 5 or more, 6 or more, 7 or more, 8 or more, 9 or more, 10 or more, 11 or more, 12 or more, 15 or more, 20 or more, 30 or more, 40 or more, 50 or more (e.g. 60, 90, 120, 150, 180, 210, 240, 270, 300, 330, 360, 390, 420, 450, 480 or more). Such fragments do not comprise the full length sequence of the wild type antigen. In some embodiments, the fragment is 481 amino acids or less in length (for example, 400 or less, 300 or less, 200 or less, 100 or less, 50 or less, 40 or less, 30 or less, 25 or less, 22 or less or 20 or less amino acids in length).

Preferably the fragment comprises one or more epitopes from the wild type antigen. Such epitopes may be defined using epitope mapping techniques such as those described in Example 8. In some embodiments, the heterologous antigen is a fragment of the *C. muridarum* TC0210 antigen. For example, the fragment may comprise or consist of a sequence selected from the group consisting of DYFNDEFFNRFF-GLP (SEQ ID NO: 36), SHREQ (SEQ ID NO: 37), ALQK-MGVRVQNLTPE (SEQ ID NO: 38), NQVLKNAKGENV-LLM (SEQ ID NO: 39), SPMLGYSAPKKDSSTGICLA (SEQ ID NO: 40), EDLLKEVSRGFSKVAAQATP (SEQ ID NO: 41), TGSQAIASPGNKRGFQENPF (SEQ ID NO: 42), PRPQQRDAVR (SEQ ID 43), IAIGNPF-GLQATVTVGVISAKGRNQLHIVD (SEQ ID NO: 44) and NTAIVSGSGGYIGIGFAIPSLMAKRVIDQL (SEQ ID NO: 45). For example, it may comprise or consist of a sequence selected from the group consisting of DYFNDEFFNRFF-GLP (SEQ ID NO: 36), SHREQ (SEQ ID NO: 37), ALQK-MGVRVQNLTPE (SEQ ID NO: 38) and NQVLKNAK-GENVLLM (SEQ ID 39). DYFNDEFFNRFFGLP (SEQ ID NO: 36) is particularly preferred.

In some embodiments, the heterologous antigen is a fragment of the *C. muridarum* TC0210 antigen which comprises or consists of a sequence selected from the group consisting of VAAQATPGVVYIENFPK (SEQ ID NO: 46), GFQEN-PFDYFNDEFFNRFFGLPSHREQPRPQQR (SEQ ID NO: 47), GTGFIVSEDGYVVTNHHVVEDAGK (SEQ ID 48), TDLAVIKIQAK (SEQ ID NO: 49), VIDQLISDGQVTR (SEQ ID NO: 50), AGLRQEDVIVAYNGKEVESLSALR (SEQ ID NO: 51), FIEIPVTVTQIPAEDGVSALQK (SEQ ID NO: 52), VQNLTPEICK (SEQ ID NO: 53), NAKGENV-LLMVSQGEVIR (SEQ ID NO: 54) and GENVLLMVSQ-GEVIR (SEQ ID NO: 55).

In some embodiments, the heterologous antigen is selected from the group consisting of the corresponding fragments from the *C. trachomatis* CT823 antigen. For example, the fragment may comprise or consist of a sequence selected from the group consisting of DYFNDEFFNRFFGLP (SEQ ID NO: 56), SHREQ (SEQ ID NO: 57), ALQK-MGVRVQNITPE (SEQ ID NO: 58), NQVLKNSKGENV-LLM (SEQ ID NO: 59), SPMLGYSASKKDSKADICLA (SEQ ID NO: 60), EDLLKEVSRGFSRVAAKATP (SEQ ID NO: 61), TGNQAIASPGNKRGFQENPF (SEQ ID NO: 62), IAIGNPFGLQATVTVGVISAKGRNQLHIVD (SEQ ID NO: 63) and NTAIVSGSGGYIGIGFAIPSLMAKRVIDQL (SEQ ID NO: 64). For example, it may comprise or consist of a sequence selected from the group consisting of DYFND-EFFNRFFGLP (SEQ ID NO: 56), SHREQ (SEQ ID NO: 57), ALQKMGVRVQNITPE (SEQ ID NO: 58) and NQVLKN-SKGENVLLM (SEQ ID NO: 59). DYFNDEFFNRFFGLP (SEQ ID NO: 56) is particularly preferred.

Preferably, the heterologous antigen is immunogenic when it is presented in the OMV. In embodiments in which the heterologous antigen comprises or consists of a fragment of a wild type antigen or of a variant thereof, the fragment is preferably immunogenic. The term "immunogenic", in the context of an immunogenic heterologous antigen, means that the heterologous antigen is capable of eliciting an immune response, such as a cell-mediated and/or an antibody response, against the pathogen (such as a bacterium or a virus) from which the antigen is derived, for example, against the antigen in the context of the pathogen. Preferably, the immune response is elicited against the wild type pathogen from which the antigen is derived. For example, such an immune response may be elicited when the OMV of the invention is used to immunise a subject (preferably a mammal, more preferably a human or a mouse). In one embodiment, the OMV of the invention is capable of stimulating in vitro CD4+ IFN+-γ cells in splenocytes purified from mice infected with the live pathogen (such as *C. trachomatis*) and/or elicits antibodies that recognise the pathogen (such as *C. trachomatis*). The heterologous antigen preferably elicits antibodies that recognise the pathogen from which the heterologous antigen is derived. For example, the heterologous antigen preferably elicits antibodies that can bind to, and preferably neutralise the infection and/or virulence of the pathogen from which the heterologous antigen is derived. Preferred heterologous antigens are those which are recognised by anti-sera upon infection with a pathogen of interest. More preferred are those heterologous antigens which elicit a protective immune response against a pathogen of interest.

In some embodiments, the heterologous antigen is immunogenic when it is presented in the OMV but is not immunogenic when administered in purified form.

In some embodiments, the heterologous antigen presented in the OMV of the invention elicits an immune response which is cross-reactive with an antigen from a different species of the pathogen and thus the heterologous antigen may be used to raise an immune response against that different pathogen species. For example, where the heterologous antigen is from *C. muridarum*, the immune response may cross-react with an antigen from *C. trachomatis* or *C. pneumoniae*. Similarly, where the heterologous antigen is from *C. trachomatis*, the immune response may cross-react with an antigen from *C. pneumoniae* or *C. muridarum*. Further, where the heterologous antigen is from *C. pneumoniae*, the immune response may cross-react with an antigen from *C. trachomatis* or *C. muridarum*.

The heterologous antigen presented on the surface of the OMV is in the form of a polypeptide which comprises or consists of the heterologous antigen. Thus, in some embodiments, the polypeptide contains amino acid sequence N-terminal and/or C-terminal to the heterologous antigen.

Combinations with Other Antigens

In some embodiments, an OMV of the invention presents only one heterologous antigen on its surface. In other embodiments, an OMV of the invention presents more than one heterologous antigen on its surface, for example two, three, four, five, six or more, ten or more, fifteen or more, etc. For example, the OMV may present TC0210 and an additional heterologous antigen; or CT823 and an additional heterologous antigen. The additional heterologous antigen may be any heterologous antigen as described herein but is preferably a *Chlamydia* antigen.

In embodiments in which the OMV comprises more than one heterologous antigen, the two or more heterologous antigens may be in the form of separate polypeptides or may be present in the same polypeptide as a fusion protein. For example, the polypeptide may comprise two or more full length antigens. Alternatively, the polypeptide may comprise an epitope string of heterologous antigens which are epitopes from one or more antigens. For example, the epitope string may comprise two or more of the fragments from *C. muridarum* and/or *C. trachomatis* that are described above. The epitopes may be directly linked without any intervening sequence or may be linked by a length of amino acid sequence (for example, 1, 2, 3, 4, 5, 6, 7, 8, 9, 10, or 11 or more amino acids). In some embodiments, an OMV of the invention comprises a combination of heterologous antigens comprising full length wild type antigens or variants thereof and heterologous antigens comprising fragments of wild type antigens or variants thereof.

In some embodiments, a composition is provided which comprises a first OMV of the invention together with one or more additional antigens. The one or more additional antigens may be in the context of an OMV as described herein, or may be administered in an alternative form, for example, as a purified antigen or as its encoding nucleic acid. Preferably the additional antigen is a heterologous antigen in accordance with the present invention which is different from the heterologous antigen presented on the first OMV.

The invention also includes an immunogenic composition comprising a combination of antigens, e.g., *Chlamydia* antigens, said combination comprising an OMV of the invention in combination with one or more additional antigens, such as *Chlamydia* antigens. Also provided is an OMV of the invention for a use as described herein, wherein the OMV is for use in combination with one or more additional *Chlamydia* antigens (or their encoding nucleic acids). The one or more additional antigens (e.g. 2, 3, 4, 5, 6, 7 or more additional antigens) may be administered simultaneously, separately or sequentially with the OMV of the invention, for example as a combined preparation.

Examples of combinations of heterologous antigens for use in the invention include TC0106+TC0431; TC0660+TC0741; TC0551+TC0890; TC0106+TC0210+TC0741+TC0313; and TC0551+TC0890+TC106+TC431.

PCT/IB2010/050988 (Novartis Vaccines and Diagnostics, SRL) discloses that immunization with three combinations of these antigens (TC0106-TC0431; TC0660-TC0741; TC0551-TC0890) provided a significant IFU reduction in the lungs of *C. muridarum* infected mice. The contribution of individual antigens to protection was also assessed in the mouse model, leading to the identification of 4 antigens (TC0106, TC0210, TC0741 and TC0313) which were able to partially reduce the IFU load per lung (approximately 0.5-1 Log). It was then evaluated whether higher protection could be achieved by administering 4-antigen combinations. Compared to the 2-antigen combination, the 4-antigen combination (TC0551+TC0890+TC0106+TC0431) appeared to have an additive protective effect in the reduction of bacteria shed in the lung, (2.2 $\log_{10}$ reduction with P=0.0003). A slightly greater efficacy in accelerating the bacterial clearance was also observed, with 29% of animals resolving the infection completely.

In one embodiment, the one or more additional antigens are *Chlamydia* antigens selected from the antigens presented in Table 2. For example, one or more (for example, all) of the additional antigens are selected from the *Chlamydia trachomatis* antigens listed in Table 2, but may alternatively or additionally be selected from the *Chlamydia pneumoniae* antigens listed in Table 2. In one embodiment, one or more of the one or more additional antigens are selected from CT823, CT372, CT443, CT043, CT153, CT279, CT601, CT711, CT114, CT480, CT456, CT381, CT089, CT734 and CT016. These additional antigens are listed in Table 2 and their sequences are set out in the "Sequences" section that follows Table 2.

In one embodiment, an OMV of the invention is combined with CT089. In another embodiment, an OMV of the invention is combined with CT089 and CT381. Preferred combinations are an OMV of the invention with one or more antigens selected from CT372, CT443, CT601, CT153 and CT279. Another preferred combination includes an OMV of the invention in combination with 1, 2 or 3 of CT456, CT733 and/or CT043 (in particular a combination of all four antigens).

Preferably, CT823 is the heterologous antigen presented by the OMV of the invention. Preferred combinations include CT823+CT089; CT823+CT089+CT381; CT823 with one or more antigens selected from CT372, CT443, CT601, CT153 and CT279 (for example CT823+CT372; CT823+CT443, CT823+CT601, CT823+CT153 and CT823+CT279); CT823 with 1, 2 or 3 of CT456, CT733 and/or CT043 (for example, CT823+CT456; CT823+CT733; CT823+CT043 or more preferably, CT823+CT456+CT733+CT043).

Advantageous combinations of the invention are those in which two or more antigens act synergistically. Thus, the protection against *Chlamydia* achieved by their combined administration exceeds that expected by mere addition of their individual protective efficacy.

The one or more additional *Chlamydia* antigens may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to a sequence presented in Table 2; and/or (b) comprising a fragment of at least 'n' consecutive amino acids of a sequence presented in Table 2, wherein 'n' is 7 or more (e.g. 8, 10, 12, 14, 16, 18, 20, 25, 30, 35, 40, 50, 60, 70, 80, 90, 100, 150, 200, 250 or more). These one or more additional *Chlamydia* antigens include variants of a sequence presented in Table 2. Preferred fragments of (b) comprise an epitope from a sequence presented in Table 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of a sequence presented in Table 2, while retaining at least one epitope of a sequence presented in Table 2. Other fragments omit one or more protein domains. When an additional *Chlamydia* antigen comprises a sequence that is not identical to a complete sequence from Table 2 (e.g. when it comprises a sequence with less than 100% sequence identity thereto, or when it comprises a fragment thereof), it is preferred in each individual instance that the additional *Chlamydia* antigen can elicit an antibody that recognises a protein having the complete sequence from the Table 2 antigen from which it is derived.

TABLE 2

| *C. pneumoniae* accession number & annotation | *C. trachomatis* accession number & annotation | CT No. |
|---|---|---|
| | Hypothetical protein (AAC67968) | CT372 |
| | omcB (AAC68042) | CT443 |
| | Hypothetical protein (AAC67634) | CT043 |
| | Hypothetical protein (AAC67744) | CT153 |
| | Nqr3 (AAC67872) | CT279 |
| | papQ (AAC68203) | CT601 |
| | hypothetical protein (AAC68306) | CT711 |
| | hypothetical protein (AAC67705) | CT114 |
| | oppA_4 (AAC68080) | CT480 |
| | hypothetical protein (AAC68056) | CT456 |
| | ArtJ (AAC67977) | CT381 |
| | IcrE (AAC67680) | CT089 |
| | hypothetical protein (AAC68329) | CT734 |
| | hypothetical protein (AAC67606) | CT016 |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376733\|gb\|AAD18593.1\| Polymorphic Outer Membrane Protein G Family | gi\|3328840\|gb\|AAC68009.1\| Putative outer membrane protein A | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376754\|gb\|AAD18611.1\| Polymorphic Outer Membrane Protein (Frame-shift with C | gi\|3329344\|gb\|AAC68467.1\| Putative Outer Membrane Protein E | |
| gi\|4376260\|gb\|AAD18163.1\| Polymorphic Outer Membrane Protein G Family | gi\|3329346\|gb\|AAC68469.1\| Putative Outer Membrane Protein G | |
| gi\|4376262\|gb\|AAD18165.1\| hypothetical protein | gi\|3328765\|gb\|AAC67940.1\| hypothetical protein | |
| gi\|4376269\|gb\|AAD18171.1\| hypothetical protein | gi\|3328825\|gb\|AAC67995.1\| hypothetical protein | |
| gi\|4376270\|gb\|AAD18172.1\| Polymorphic Outer Membrane Protein G Family | gi\|3329350\|gb\|AAC68472.1\| Putative Outer Membrane Protein I | |
| gi\|4376272\|gb\|AAD18173.1\| Predicted OMP {leader peptide: outer membrane) | gi\|3328772\|gb\|AAC67946.1\| hypothetical protein | CT351 |
| gi\|4376273\|gb\|AAD18174.1\| Predicted OMP {leader peptide} | gi\|3328771\|gb\|AAC67945.1\| hypothetical protein | CT350 |
| gi\|4376296\|gb\|AAD18195.1\| hypothetical protein | gi\|3328520\|gb\|AAC67712.1\| Ribulose-P Epimerase | |
| gi\|4376362\|gb\|AAD18254.1\| YbbP family hypothetical protein | gi\|3328401\|gb\|AAC67602.1\| hypothetical protein | |
| gi\|4376372\|gb\|AAD18263.1\| Signal Peptidase I | gi\|3328410\|gb\|AAC67610.1\| Signal Peptidase I | |
| gi\|4376397\|gb\|AAD18286.1\| CHLPS hypothetical protein | gi\|3328506\|gb\|AAC67700.1\| CHLPS hypothetical protein | |
| gi\|4376402\|gb\|AAD18290.1\| ACR family | gi\|3328505\|gb\|AAC67699.1\| ACR family | |
| gi\|4376419\|gb\|AAD18305.1\| CT149 hypothetical protein | gi\|3328551\|gb\|AAC67740.1\| possible hydrolase | |
| gi\|4376446\|gb\|AAD18330.1\| hypothetical protein | gi\|3329261\|gb\|AAC68390.1\| hypothetical protein | |

TABLE 2-continued

| *C. pneumoniae* accession number & annotation | *C. trachomatis* accession number & annotation | CT No. |
|---|---|---|
| gi\|4376466\|gb\|AAD18348.1\| Oligopeptide Binding Protein | gi\|3328604\|gb\|AAC67790.1\| Oligopeptide Binding Protein | CT198 |
| gi\|4376467\|gb\|AAD18349.1\| Oligopeptide Binding Protein | gi\|3328604\|gb\|AAC67790.1\| Oligopeptide Binding Protein | |
| gi\|4376468\|gb\|AAD18350.1\| Oligopeptide Binding Protein | gi\|3328539\|gb\|AAC67730.1\| Oligopeptide Binding Protein | |
| gi\|4376469\|gb\|AAD18351.1\| Oligopeptide Binding Protein | gi\|3328579\|gb\|AAC67766.1\| Oligopeptide binding protein permease | |
| gi\|4376520\|gb\|AAD18398.1\| Polysaccharide Hydrolase-Invasin Repeat Family | gi\|3328526\|gb\|AAC67718.1\| predicted polysaccharide hydrolase-invasin repeat family | |
| gi\|4376567\|gb\|AAD18441.1\| Inclusion Membrane Protein C | gi\|3328642\|gb\|AAC67825.1\| Inclusion Membrane Protein C | |
| gi\|4376576\|gb\|AAD18449.1\| Omp85 Analog | gi\|3328651\|gb\|AAC67834.1\| Omp85 Analog | CT241 |
| gi\|4376577\|gb\|AAD18450.1\| (OmpH-Like Outer Membrane Protein) | gi\|3328652\|gb\|AAC67835.1\| (OmpH-Like Outer Membrane Protein) | CT242 |
| gi\|4376601\|gb\|AAD18472.1\| Low Calcium Response D | gi\|3328486\|gb\|AAC67681.1\| Low Calcium Response D | |
| gi\|4376602\|gb\|AAD18473.1\| Low Calcium Response E | gi\|3328485\|gb\|AAC67680.1\| Low Calcium Response E | CT089 |
| gi\|4376607\|gb\|AAD18478.1\| Phopholipase D Superfamily | gi\|3328479\|gb\|AAC67675.1\| Phopholipase D Superfamily {leader (33) peptide} | |
| gi\|4376615\|gb\|AAD18485.1\| YojL hypothetical protein | gi\|3328472\|gb\|AAC67668.1\| hypothetical protein | CT077 |
| gi\|4376624\|gb\|AAD18493.1\| Solute Protein Binding Family | gi\|3328461\|gb\|AAC67658.1\| Solute Protein Binding Family | |
| gi\|4376639\|gb\|AAD18507.1\| Flagellar Secretion Protein | gi\|3328453\|gb\|AAC67651.1\| Flagellar Secretion Protein | |
| gi\|4376664\|gb\|AAD18529.1\| Leucyl Aminopeptidase A | gi\|3328437\|gb\|AAC67636.1\| Leucyl Aminopeptidase A | CT045 |
| gi\|4376672\|gb\|AAD18537.1\| CBS Domain protein (Hemolysin Homolog) | gi\|3328667\|gb\|AAC67849.1\| Hypothetical protein containing CBS domains | |
| gi\|4376679\|gb\|AAD18543.1\| CT253 hypothetical protein | gi\|3328664\|gb\|AAC67846.1\| hypothetical protein | |
| gi\|4376696\|gb\|AAD18559.1\| CT266 hypothetical protein | gi\|3328678\|gb\|AAC67859.1\| hypothetical protein | CT266 |
| gi\|4376717\|gb\|AAD18579.1\| Phospholipase D superfamily | gi\|3328698\|gb\|AAC67877.1\| Phospholipase D superfamily | |
| gi\|4376727\|gb\|AAD18588.1\| Polymorphic Outer Membrane Protein G/I Family | gi\|3329346\|gb\|AAC68469.1\| Putative Outer Membrane Protein G | |
| gi\|4376728\|gb\|AAD18589.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376733\|gb\|AAD18593.1\| Polymorphic Outer Membrane Protein G Family | gi\|3328840\|gb\|AAC68009.1\| Putative outer membrane protein A | |
| gi\|4376735\|gb\|AAD18594.1\| Polymorphic Outer Membrane Protein (truncated) A/I Fam | gi\|3328840\|gb\|AAC68009.1\| Putative outer membrane protein A | |
| gi\|4376736\|gb\|AAD18595.1\| Polymorphic Outer Membrane Protein G Family | gi\|3329346\|gb\|AAC68469.1\| Putative Outer Membrane Protein G | |
| gi\|4376737\|gb\|AAD18596.1\| Polymorphic Outer Membrane Protein H Family | gi\|3329347\|gb\|AAC68470.1\| Putative Outer Membrane Protein H | |
| gi\|4376751\|gb\|AAD18608.1\| Polymorphic Outer Membrane Protein E Family | gi\|3329344\|gb\|AAC68467.1\| Putative Outer Membrane Protein E | |
| gi\|4376752\|gb\|AAD18609.1\| Polymorphic Outer Membrane Protein E Family | gi\|3329344\|gb\|AAC68467.1\| Putative Outer Membrane Protein E | |
| gi\|4376753\|gb\|AAD18610.1\| Polymorphic Outer Membrane Protein E/F Family | gi\|3329344\|gb\|AAC68467.1\| Putative Outer Membrane Protein E | |
| gi\|4376757\|gb\|AAD18613.1\| hypothetical protein | gi\|3328701\|gb\|AAC67880.1\| PP-loop superfamily ATPase | |
| gi\|4376767\|gb\|AAD18622.1\| Arginine Periplasmic Binding Protein | gi\|3328806\|gb\|AAC67977.1\| Arginine Binding Protein | CT381 |
| gi\|4376790\|gb\|AAD18643.1\| Heat Shock Protein-70 | gi\|3328822\|gb\|AAC67993.1\| HSP-70 | CT396 |
| gi\|4376802\|gb\|AAD18654.1\| CT427 hypothetical protein | gi\|3328857\|gb\|AAC68024.1\| hypothetical protein | |
| gi\|4376814\|gb\|AAD18665.1\| CT398 hypothetical protein | gi\|3328825\|gb\|AAC67995.1\| hypothetical protein | CT398 |
| gi\|4376829\|gb\|AAD18679.1\| polymorphic membrane protein A Family | gi\|3328840\|gb\|AAC68009.1\| Putative outer membrane protein A | |
| gi\|4376830\|gb\|AAD18680.1\| polymorphic membrane protein B Family | gi\|3328841\|gb\|AAC68010.1\| Putative outer membrane protein B | |
| gi\|4376832\|gb\|AAD18681.1\| Solute binding protein | gi\|3328844\|gb\|AAC68012.1\| Solute-binding protein | CT415 |
| gi\|4376834\|gb\|AAD18683.1\| (Metal Transport Protein) | gi\|3328846\|gb\|AAC68014.1\| (Metal Transport Protein) | |
| gi\|4376847\|gb\|AAD18695.1\| Tail-Specific Protease | gi\|3328872\|gb\|AAC68040.1\| Tail-Specific Protease | |
| gi\|4376848\|gb\|AAD18696.1\| 15 kDa Cysteine-Rich Protein | gi\|3328873\|gb\|AAC68041.1\| 15 kDa Cysteine-Rich Protein | |
| gi\|4376849\|gb\|AAD18697.1\| 60 kDa Cysteine-Rich OMP | gi\|3328874\|gb\|AAC68042.1\| 60 kDa Cysteine-Rich OMP | CT443 |
| gi\|4376850\|gb\|AAD18698.1\| 9 kDa-Cysteine-Rich Lipoprotein | gi\|3328876\|gb\|AAC68043.1\| 9 kDa-Cysteine-Rich Lipoprotein | CT444 |
| gi\|4376878\|gb\|AAD18723.1\| 2-Component Sensor | gi\|3328901\|gb\|AAC68067.1\| 2-component regulatory system-sensor histidine kinase | CT467 |
| gi\|4376879\|gb\|AAD18724.1\| similarity to CHLPS IncA | gi\|3328451\|gb\|AAC67649.1\| hypothetical protein | |
| gi\|4376884\|gb\|AAD18729.1\| CT471 hypothetical protein | gi\|3328905\|gb\|AAC68071.1\| hypothetical protein | |
| gi\|4376886\|gb\|AAD18731.1\| YidD family | gi\|3328908\|gb\|AAC68073.1\| hypothetical protein | |
| gi\|4376890\|gb\|AAD18734.1\| CT476 hypothetical protein | gi\|3328911\|gb\|AAC68076.1\| hypothetical protein | |
| gi\|4376892\|gb\|AAD18736.1\| Oligopeptide Permease | gi\|3328913\|gb\|AAC68078.1\| Oligopeptide Permease | |
| gi\|4376894\|gb\|AAD18738.1\| Oligopeptide Binding Lipoprotein | gi\|3328915\|gb\|AAC68080.1\| Oligopeptide Binding Lipoprotein | |
| gi\|4376900\|gb\|AAD18743.1\| Glutamine Binding Protein | gi\|3328922\|gb\|AAC68086.1\| Glutamine Binding Protein | |
| gi\|4376909\|gb\|AAD18752.1\| Protease | gi\|6578107\|gb\|AAC68094.2\| Protease | |
| gi\|4376952\|gb\|AAD18792.1\| Apolipoprotein N-Acetyltransferase | gi\|3328972\|gb\|AAC68136.1\| Apolipoprotein N-Acetyltransferase | |
| gi\|4376960\|gb\|AAD18800.1\| FKBP-type peptidyl-prolyl cis-trans isomerase | gi\|3328979\|gb\|AAC68143.1\| FKBP-type peptidyl-prolyl cis-trans isomerase | CT541 |
| gi\|4376968\|gb\|AAD18807.1\| CT547 hypothetical protein | gi\|3328986\|gb\|AAC68149.1\| hypothetical protein | CT547 |
| gi\|4376969\|gb\|AAD18808.1\| CT548 hypothetical protein | gi\|3328987\|gb\|AAC68150.1\| hypothetical protein | |

TABLE 2-continued

| *C. pneumoniae* accession number & annotation | *C. trachomatis* accession number & annotation | CT No. |
|---|---|---|
| gi\|4376998\|gb\|AAD18834.1\| Major Outer Membrane Protein | gi\|3329133\|gb\|AAC68276.1\| Major Outer Membrane Protein | CT681 |
| gi\|4377005\|gb\|AAD18841.1\| YopC/Gen Secretion Protein D | gi\|3329125\|gb\|AAC68269.1\| probable Yop proteins translocation protein | |
| gi\|4377015\|gb\|AAD18851.1\| FHA domain; (homology to adenylate cyclase) | gi\|3329115\|gb\|AAC68259.1\| (FHA domain; homology to adenylate cyclase) | |
| gi\|4377033\|gb\|AAD18867.1\| CHLPN 76 kDa Homolog__1 (CT622) | gi\|3329069\|gb\|AAC68226.1\| CHLPN 76 kDa Homolog | CT622 |
| gi\|4377034\|gb\|AAD18868.1\| CHLPN 76 kDa Homolog__2 (CT623) | gi\|6578109\|gb\|AAC68227.2\| CHLPN 76 kDa Homolog | CT623 |
| gi\|4377035\|gb\|AAD18869.1\| Integral Membrane Protein | gi\|3329071\|gb\|AAC68228.1\| Integral Membrane Protein | |
| gi\|4377072\|gb\|AAD18902.1\| CT648 hypothetical protein | gi\|3329097\|gb\|AAC68825.1\| hypothetical protein | |
| gi\|4377073\|gb\|AAD18903.1\| CT647 hypothetical protein | gi\|3329096\|gb\|AAC68824.1\| hypothetical protein | CT647 |
| gi\|4377085\|gb\|AAD18914.1\| CT605 hypothetical protein | gi\|3329050\|gb\|AAC68208.1\| hypothetical protein | |
| gi\|4377090\|gb\|AAD18919.1\| Peptidoglycan-Associated lipoprotein | gi\|3329044\|gb\|AAC68202.1\| Peptidoglycan-Associated Lipoprotein | CT600 |
| gi\|4377091\|gb\|AAD18920.1\| macromolecule transporter | gi\|3329043\|gb\|AAC68201.1\| component of a macromolecule transport system | |
| gi\|4377092\|gb\|AAD18921.1\| CT598 hypothetical protein | gi\|3329042\|gb\|AAC68200.1\| hypothetical protein | |
| gi\|4377093\|gb\|AAD18922.1\| Biopolymer Transport Protein | gi\|3329041\|gb\|AAC68199.1\| Biopolymer Transport Protein | CT597 |
| gi\|4377094\|gb\|AAD18923.1\| Macromolecule transporter | gi\|3329040\|gb\|AAC68198.1\| polysaccharide transporter | |
| gi\|4377101\|gb\|AAD18929.1\| CT590 hypothetical protein | gi\|3329033\|gb\|AAC68192.1\| hypothetical protein | |
| gi\|4377102\|gb\|AAD18930.1\| CT589 hypothetical protein | gi\|3329032\|gb\|AAC68191.1\| hypothetical protein | CT589 |
| gi\|4377106\|gb\|AAD18933.1\| hypothetical protein | gi\|3328796\|gb\|AAC67968.1\| hypothetical protein | |
| gi\|4377111\|gb\|AAD18938.1\| Enolase | gi\|3329030\|gb\|AAC68189.1\| Enolase | CT587 |
| gi\|4377127\|gb\|AAD18953.1\| General Secretion Protein D | gi\|3329013\|gb\|AAC68174.1\| Gen. Secretion Protein D | |
| gi\|4377130\|gb\|AAD18956.1\| predicted OMP {leader peptide} | gi\|3329010\|gb\|AAC68171.1\| predicted OMP | CT569 |
| gi\|4377132\|gb\|AAD18958.1\| CT567 hypothetical protein | gi\|3329008\|gb\|AAC68169.1\| hypothetical protein | CT567 |
| gi\|4377133\|gb\|AAD18959.1\| CT566 hypothetical protein | gi\|3329007\|gb\|AAC68168.1\| hypothetical protein | |
| gi\|4377140\|gb\|AAD18965.1\| Yop Translocation J | gi\|3329000\|gb\|AAC68161.1\| Yop proteins translocation lipoprotein J | CT559 |
| gi\|4377170\|gb\|AAD18992.1\| Outer Membrane Protein B | gi\|3329169\|gb\|AAC68308.1\| Outer Membrane Protein Analog | CT713 |
| gi\|4377177\|gb\|AAD18998.1\| Flagellar M-Ring Protein | gi\|3329175\|gb\|AAC68314.1\| Flagellar M-Ring Protein | |
| gi\|4377182\|gb\|AAD19003.1\| CT724 hypothetical protein | gi\|3329181\|gb\|AAC68319.1\| hypothetical protein | |
| gi\|4377184\|gb\|AAD19005.1\| Rod Shape Protein | gi\|3329183\|gb\|AAC68321.1\| Rod Shape Protein | |
| gi\|4377193\|gb\|AAD19013.1\| CT734 hypothetical protein | gi\|3329192\|gb\|AAC68329.1\| hypothetical protein | |
| gi\|4377206\|gb\|AAD19025.1\| CHLTR possible phosphoprotein | gi\|3329204\|gb\|AAC68339.1\| CHLTR possible phosphoprotein | |
| gi\|4377222\|gb\|AAD19040.1\| Muramidase (invasin repeat family) | gi\|3329221\|gb\|AAC68354.1\| Muramidase (invasin repeat family) | CT759 |
| gi\|4377223\|gb\|AAD19041.1\| Cell Division Protein FtsW | gi\|3329222\|gb\|AAC68355.1\| Cell Division Protein FtsW | |
| gi\|4377224\|gb\|AAD19042.1\| Peptidoglycan Transferase | gi\|3329223\|gb\|AAC68356.1\| Peptidoglycan Transferase | CT761 |
| gi\|4377225\|gb\|AAD19043.1\| Muramate-Ala Ligase & D-Ala-D-Ala Ligase | gi\|3329224\|gb\|AAC68357.1\| UDP-N-acetylmuramate-alanine ligase | |
| gi\|4377248\|gb\|AAD19064.1\| Thioredoxin Disulfide Isomerase | gi\|3329244\|gb\|AAC68375.1\| Thioredoxin Disulfide Isomerase | |
| gi\|4377261\|gb\|AAD19076.1\| CT788 hypothetical protein - {leader peptide-periplasmi | gi\|3329253\|gb\|AAC68383.1\| {leader (60) peptide-periplasmic} | |
| gi\|4377280\|gb\|AAD19093.1\| Insulinase family/Protease III | gi\|3329273\|gb\|AAC68402.1\| Insulinase family/Protease III | |
| gi\|4377287\|gb\|AAD19099.1\| Putative Outer Membrane Protein D Family | gi\|3329279\|gb\|AAC68408.1\| Putative Outer Membrane Protein D | |
| gi\|4377306\|gb\|AAD19116.1\| DO Serine Protease | gi\|3329293\|gb\|AAC68420.1\| DO Serine Protease | CT823 |
| gi\|4377342\|gb\|AAD19149.1\| ABC transporter permease | gi\|3329327\|gb\|AAC68451.1\| ABC transporter permease - pyrimidine biosynthesis protein | |
| gi\|4377347\|gb\|AAD19153.1\| CT858 hypothetical protein | gi\|6578118\|gb\|AAC68456.2\| predicted Protease containing IRBP and DHR domains | |
| gi\|4377353\|gb\|AAD19159.1\| CT863 hypothetical protein | gi\|3329337\|gb\|AAC68461.1\| hypothetical protein | |
| gi\|4377367\|gb\|AAD19171.1\| Predicted OMP | gi\|3328795\|gb\|AAC67967.1\| hypothetical protein | |
| gi\|4377408\|gb\|AAD19209.1\| hypothetical protein | gi\|3328795\|gb\|AAC67967.1\| hypothetical protein | |
| gi\|4377409\|gb\|AAD19210.1\| Predicted Outer Membrane Protein (CT371) | gi\|3328795\|gb\|AAC67967.1\| hypothetical protein | |
| gi\|4376411\|gb\| | gi\|3328512\|gb\|AAC67705.1\| hypothetical protein | CT114 |
| gi\|4376508\|gb\| | gi\|3328585\|gb\|AAC67772.1\| hypothetical protein | CT181 |
| gi\|4376710\|gb\| | gi\|3328692\|gb\|AAC67872.1\| NADH (Ubiquinone) Oxidoreductase, Gamma | CT279 |
| gi\|4376777\|gb\| | gi\|3328815\|gb\|AAC67986.1\| hypothetical protein | CT389 |
| gi\|4376782\|gb\| | gi\|3328817\|gb\|AAC67988.1\| hypothetical protein | CT391 |
| gi\|4376863\|gb\| | gi\|3328887\|gb\|AAC68054.1\| Arginyl tRNA transferase | CT454 |
| gi\|4376866\|gb\| | gi\|3328889\|gb\|AAC68056.1\| hypothetical protein | CT456 |
| gi\|4376972\|gb\| | gi\|3328991\|gb\|AAC68153.1\| D-Ala-D-Ala Carboxypeptidase | CT551 |
| gi\|4377139\|gb\| | gi\|3329001\|gb\|AAC68162.1\| hypothetical protein | CT560 |
| gi\|4377154\|gb\| | gi\|3329154\|gb\|AAC68295.1\| hypothetical protein | CT700 |
| gi\|4377191\|gb\|AAD19012.1\| hypothetical protein | gi\|3329191\|gb\|AAC68328.1\| hypothetical protein | CT733 |

The additional *Chlamydia* antigens used in the invention may be present in the composition as individual separate polypeptides. Alternatively, the combination may be present as a hybrid polypeptide in which two or more (i.e. 2, 3, 4, 5, 6, 7, 8, 9, 10, 11, 12, 13, 14, 15, 16, 17, 18, 19 or 20 or more) of the antigens are expressed as a single polypeptide chain. Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful. Different hybrid polypeptides may be mixed together in a single formulation. Within such combinations, a *Chlamydia trachomatis* antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-{-X-L-}$_n$-B—COOH, wherein: at least one X is an amino acid sequence of a heterologous antigen as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-L1-$X_2$-L2-COOH, $NH_2$—$X_1$—$X_2$—COOH, $NH_2$—$X_1$-L1-$X_2$—COOH, $NH_2$—$X_1$—$X_2$-L2-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO: 65), with the Gly-Ser dipeptide being formed from a BamHI restriction site, thus aiding cloning and manipulation, and the $(Gly)_4$ tetrapeptide being a typical poly-glycine linker.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1$=$X_2$=$X_3$ (ii) $X_1$=$X_2$≠$X_3$ (iii) $X_1$≠$X_2$=$X_3$ (iv) $X_1$≠$X_2$≠$X_3$ or (v) $X_1$=$X_3$≠$X_2$, etc.

The invention also provides a kit comprising an OMV of the invention and one or more additional antigens for simultaneous, separate or sequential administration.

The heterologous antigen may be presented by any suitable method. In some embodiments, the coding sequence of the heterologous antigen is fused to a leader peptide sequence, for example, the leader peptide sequence of OmpA, and the fusion is placed under the control of a promoter in a plasmid. The lac promoter is an example of a suitable promoter. Any suitable plasmid may be used, for example, the multicopy plasmid pET. As mentioned above, the heterologous antigen may be presented in the context of a longer polypeptide sequence, for example, with additional, sequence N-terminal and/or C-terminal to the heterologous antigen. In such cases, the leader peptides will be fused to the longer polypeptide sequence.

In preferred embodiments, the derived plasmid is used to transform the bacterium and the recombinant clones are grown in liquid cultures. The OMVs released may be purified by any suitable method, for example, centrifugation.

Antibodies

The heterologous antigen preferably induces antibodies able to neutralize infection or virulence of the pathogen from which the antigen is derived. These neutralizing antibodies may be used as a vaccine capable of neutralising the infection or virulence of the pathogen, for example of *Chlamydia*, more particularly, of *C. trachomatis* or *C. pneumoniae.*

According to a further aspect, the invention provides one or more antibodies which bind to a heterologous antigen presented by an OMV of the invention. Preferably, the antibody does not bind to the heterologous antigen when it is not presented in an OMV of the present invention. For example, the antibody preferably does not bind to the heterologous antigen in its purified form. Preferably, the antibody binds to an epitope that is immunoaccessible and in its native conformation when the heterologous antigen is presented in an OMV of the invention but which is not immunoaccessible and/or not in its native conformation when presented by the antigen in its purified form. For example, the present inventors have found that different epitopes are recognised in TC0210 when it is presented by an OMV of the invention than when it is presented in its purified form (see results of Example 8). Thus, in some embodiments, there is provided an OMV, composition or vaccine of the invention for use in raising antibodies that bind to one or more epitopes in the heterologous antigen that are not immunoaccessible when the heterologous antigen is administered in a purified form.

The term "antibody" includes intact immunoglobulin molecules, as well as fragments thereof which are capable of binding an antigen. These include hybrid (chimeric) antibody molecules ([27], [28]); $F(ab')_2$ and F(ab) fragments and Fv molecules; non-covalent heterodimers ([29]; [30]); single-chain Fv molecules (sFv) [31]; dimeric and trimeric antibody fragment constructs; minibodies [32],[33]; humanized antibody molecules [34],[35],[36]; and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred.

The antibodies may be polyclonal or monoclonal and may be produced by any suitable means. The antibody may include a detectable label.

Also provided is a method for preparing antibodies comprising immunising a mammal (such as a mouse or a rabbit) with an OMV of the invention and obtaining polyclonal antibodies or monoclonal antibodies by conventional techniques.

For example, polyclonal antisera may be obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). Monoclonal antibodies may be prepared using the standard method of Kohler & Milstein [37], or a modification thereof, or by any other suitable method. A polyclonal antibody preparation prepared by this method is also provided.

Antibody titres and specificities can be measured using standard methods available in the art. Other methods of testing the immunogenicity of proteins are also well known in the art.

The antibodies of the invention may be used in combination with one or more antibodies specific for one or more additional antigens (e.g. *Chlamydia* antigens) for use in diagnosis of infections (e.g. *Chlamydia* infections).

Immunogenic Compositions and Medicaments

The OMV, medicament or bacterium may be in the form of a composition. These compositions may be suitable as immunogenic compositions (e.g. vaccines), or as diagnostic reagents. Generally, the composition will comprise multiple copies of the same OMV or bacterium.

It is particularly advantageous to use an OMV of the invention in an immunogenic composition such as a vaccine. Preferably, the final formulation of the vaccine is more stable compared with immunogenic compositions that comprise the heterologous antigen in purified form.

In embodiments in which the immunogenic composition comprises one or more bacteria of the invention, it is preferred that the bacterium is a non-pathogenic bacterium. In such embodiments, the OMVs are generated in vivo.

An immunogenic composition of the invention comprises an OMV according to the invention. Immunogenic compositions according to the invention may either be prophylactic (i.e. to prevent infection) or therapeutic (i.e. to treat infection), but will typically be prophylactic. Where the immunogenic composition is for prophylactic use, the human is preferably a child (e.g. a toddler or infant) or a teenager; where the immunogenic composition is for therapeutic use, the human is preferably a teenager or an adult. An immunogenic composition intended for children may also be administered to adults e.g. to assess safety, dosage, immunogenicity, etc.

In some embodiments, the immunogenic composition is for treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, patients infected with cervical squamous cell carcinoma, and/or HIV infection, etc.), preferably, *C. trachomatis* infection. In some embodiments, the immunogenic composition is effective against *C. pneumoniae.*

Immunogenic compositions used as vaccines comprise an immunologically effective amount of the OMV of the invention, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of the individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition, then two antigens may be present at the same dose as each other or at different doses.

In general, a composition of the invention will comprise a heterologous antigen at a concentration that will be sufficient to elicit an immune response against that antigen. Heterologous antigens in the composition will typically be present at a concentration of at least 1 μg/ml each. For example, in some embodiments, one dose of a composition of the invention comprises 1 to 600 μg of the heterologous antigen, for example, 1 to 500 μg, 100-500 μg, 100-200 μg, 1 to 300 μg, 1 to 100 μg, 1 to 50 μg, 1 to 35 μg, 1 to 25 μg, 10 to 30 μg, 20 to 30 μg, 23 to 27 μg or 24 to 26 μg of heterologous antigen. Preferably, one dose of a composition of the present invention comprises 25 μg of the heterologous antigen. These dose preferences may be applied to the methods of the invention mutatis mutandis.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

The pH of a composition will generally be between 5.0 and 8.1, and more typically between 6.0 and 8.0, e.g. 6.5 and 7.5, or between 7.0 and 7.8, preferably about 7. pH may be maintained by the use of a buffer.

The composition is preferably sterile. The composition is preferably non-pyrogenic e.g. containing <1 EU (endotoxin unit, a standard measure) per dose, and preferably <0.1 EU per dose. The composition is preferably gluten free. The composition may be isotonic with respect to humans.

Immunogenic compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. [38]) or transcutaneous (See e.g. [39] and [40]), intranasal (See e.g. [41]), ocular, aural, pulmonary or other mucosal administration.

Pathogen infections (such as *Chlamydia* infections) affect various areas of the body and so the immunogenic compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The invention also provides a delivery device pre-filled with an immunogenic composition of the invention.

The invention also provides a kit comprising a first component and a second component wherein neither the first component nor the second component is a composition of the invention as described herein, but wherein the first component and the second component can be combined to provide a composition of the invention as described herein. The kit may further include a third component comprising one or more of the following: instructions, syringe or other delivery device, adjuvant, or pharmaceutically acceptable formulating solution.

The composition may be in kit form, designed such that a combined composition is reconstituted just prior to administration to a patient. Such kits may comprise one or more OMVs in liquid form and one or more lyophilised agents.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Compositions may thus be pharmaceutically acceptable. They will usually include components in addition to the OMV (s) e.g. they typically include one or more pharmaceutical carrier(s) and/or excipient(s). A thorough discussion of such components is available in reference 166.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Thus the invention provides an immunogenic composition comprising a combination of: (1) an OMV of the invention; and (2) an adjuvant, such as an aluminium hydroxide adjuvant (for example, one or more antigens may be adsorbed to aluminium hydroxide).

Adjuvants which may be used in compositions of the invention include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref. 42). Aluminum salts include hydroxides, phosphates, sulfates, etc., with the salts taking any suitable form (e.g. gel, crystalline, amorphous, etc.). Adsorption to these salts is preferred (e.g. all antigens may be adsorbed). The mineral containing compositions may also be formulated as a particle of metal salt [43].

The adjuvants known as aluminum hydroxide and aluminum phosphate may be used. These names are conventional, but are used for convenience only, as neither is a precise description of the actual chemical compound which is present (e.g. see chapter 9 of reference 48). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4/Al$ molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Adsorption of *S. aureus* protein antigens (except IsdA, Sta019 and Sta073) to an aluminium hydroxide adjuvant is advantageous, particularly in a multi-protein combination (in which all antigens may be adsorbed). A histidine buffer can usefully be included in such adjuvanted compositions.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

B. Oil Emulsions

Oil emulsion compositions suitable for use as adjuvants in the invention include squalene-water emulsions, such as MF59 [Chapter 10 of ref. 48; see also ref. 44] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidizer to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [45-47], as described in more detail in Chapter 10 of ref. 48 and chapter 12 of ref. 49. The MF59 emulsion advantageously includes citrate ions e.g. 10 mM sodium citrate buffer.
- An emulsion of squalene, a tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2 or at a weight ratio of about 11:5.

One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [50].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [51] (0.05-1% Thr-MDP, 5% squalane, 2.5% Pluronic L121 and 0.2% polysorbate 80). It can also be used without the Thr-MDP, as in the "AF" adjuvant [52] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [53]. The emulsion may also include one or more of: alditol; a cryoprotective agent (e.g. a sugar, such as dodecylmaltoside and/or sucrose); and/or an alkylpolyglycoside. The emulsion may include a TLR4 agonist [54]. Such emulsions may be lyophilized.

An emulsion of squalene, poloxamer 105 and Abil-Care [55]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 56, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 57, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [58].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [59].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [59].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Where a composition includes a tocopherol, any of the α, β, γ, δ, ϵ or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [60]. They also have antioxidant properties that may help to stabilize the emulsions [61]. A preferred α-tocopherol is DL-α-tocopherol, and the preferred salt of this tocopherol is the succinate. The succinate salt has been found to cooperate with TNF-related ligands in vivo.

C. Saponin Formulations [Chapter 22 of Ref. 48]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 62. Saponin formulations may also comprise a sterol, such as cholesterol [63].

Combinations of saponins and cholesterols can be used to form unique particles called immunostimulating complexes (ISCOMs) [chapter 23 of ref. 48]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 63-65. Optionally, the ISCOMS may be devoid of additional detergent [66].

A review of the development of saponin based adjuvants can be found in refs. 67 & 68.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 69-74. Virosomes are discussed further in, for example, ref. 75

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 76. Such "small particles" of 3dMPL are small enough to be sterile filtered through a 0.22 mm membrane [76]. Other non-toxic LPS derivatives include monophosphoryl lipid A mimics, such as aminoalkyl glucosaminide phosphate derivatives e.g. RC-529 [77,78].

Lipid A derivatives include derivatives of lipid A from *Escherichia coli* such as OM-174. OM-174 is described for example in refs. 79 & 80.

Immunostimulatory oligonucleotides suitable for use as adjuvants in the invention include nucleotide sequences containing a CpG motif (a dinucleotide sequence containing an unmethylated cytosine-linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 81, 82 and 83 disclose possible analog substitutions e.g. replacement of guanosine with 2'-deoxy-7-deazaguanosine. The adjuvant effect of CpG oligonucleotides is further discussed in refs. 84-89.

The CpG sequence may be directed to TLR9, such as the motif GTCGTT or TTCGTT [90]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 91-93. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 90 & 94-, 96.

A useful CpG adjuvant is CpG7909, also known as ProMune™ (Coley Pharmaceutical Group, Inc.). Another is CpG1826. As an alternative, or in addition, to using CpG sequences, TpG sequences can be used [97], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 97), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 97), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC-31™ [98]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-$(IC)_{13}$-3' (SEQ ID NO: 66). The polycationic polymer may be a peptide comprising 11-mer amino acid sequence KLKLLLLLKLK (SEQ ID NO: 67). The oligonucleotide and polymer can form complexes e.g. as disclosed in references 99 & 100.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 101 and as parenteral adjuvants in ref. 102. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 103-110. A useful CT mutant is or CT-E29H [111]. Numerical reference for amino acid substitutions is preferably based on the alignments of the A and B subunits of ADP-ribosylating toxins set forth in ref. 112, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [113], etc.) [114], interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [115] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [116].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 48)

Examples of liposome formulations suitable for use as adjuvants are described in refs. 117-119.

J. Polyoxyethylene Ether and Polyoxyethylene Ester Formulations

Adjuvants suitable for use in the invention include polyoxyethylene ethers and polyoxyethylene esters [120]. Such formulations further include polyoxyethylene sorbitan ester surfactants in combination with an octoxynol [121] as well as polyoxyethylene alkyl ethers or ester surfactants in combination with at least one additional non-ionic surfactant such as an octoxynol [122]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes

A phosphazene, such as poly[di(carboxylatophenoxy) phosphazene] ("PCPP") as described, for example, in references 123 and 124, may be used.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquimod ("R-837") [125,126], Resiquimod ("R-848") [127], and their analogs; and salts thereof (e.g. the hydrochloride salts). Further details about immunostimulatory imidazoquinolines can be found in references 128 to 132.

N. Substituted Ureas

Substituted ureas useful as adjuvants include compounds of formula I, II or III, or salts thereof:

I

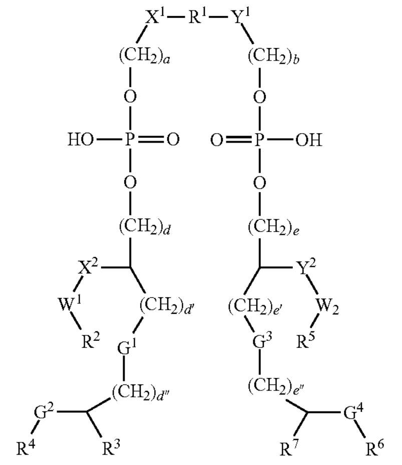

II

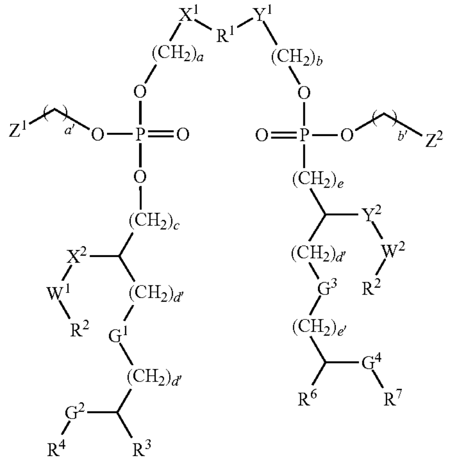

III

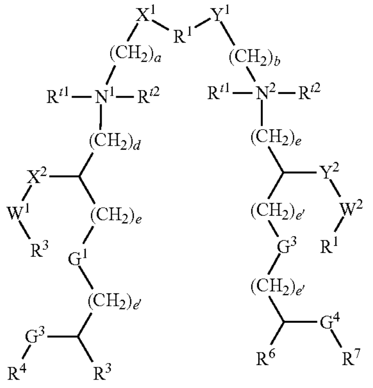

as defined in reference 133, such as 'ER 803058', 'ER 803732', 'ER 804053', ER 804058', 'ER 804059', 'ER 804442', 'ER 804680', 'ER 804764', ER 803022 or 'ER 804057' e.g.:

ER804057

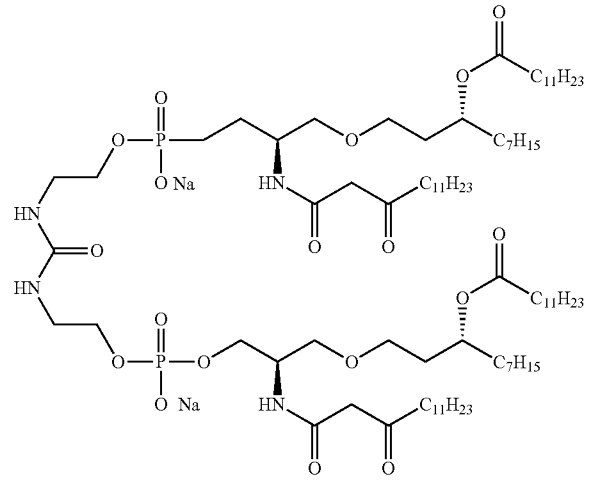

ER-803022

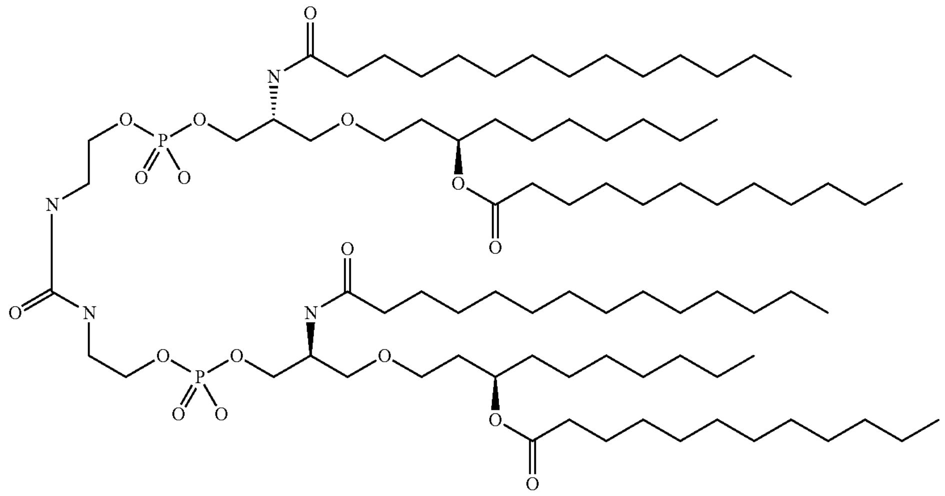

O. Further Adjuvants

Further adjuvants that may be used with the invention include:

Cyclic diguanylate ('c-di-GMP'), which has been reported as a useful adjuvant for *S. aureus* vaccines [134].

A thiosemicarbazone compound, such as those disclosed in reference 135. Methods of formulating, manufacturing, and screening for active compounds are also described in reference 135. The thiosemicarbazones are particularly effective in the stimulation of human peripheral blood mononuclear cells for the production of cytokines, such as TNF-α.

A tryptanthrin compound, such as those disclosed in reference 136. Methods of formulating, manufacturing, and screening for active compounds are also described in reference 136. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

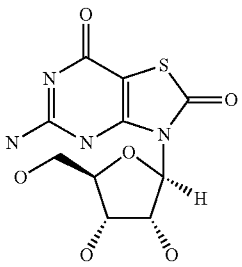 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 137 to 139 Loxoribine (7-allyl-8-oxoguanosine) [140].

Compounds disclosed in reference 141, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [142,143], Hydrapthalamide compounds, Benzophenone compounds, Isoxazole compounds, Sterol compounds, Quinazilinone compounds, Pyrrole compounds [144], Anthraquinone compounds, Quinoxaline compounds, Triazine compounds, Pyrazalopyrimidine compounds, and Benzazole compounds [145].

Compounds containing lipids linked to a phosphate-containing acyclic backbone, such as the TLR4 antagonist E5564 [146,147]:

A polyoxidonium polymer [148,149] or other N-oxidized polyethylene-piperazine derivative.

Methyl inosine 5'-monophosphate ("MIMP") [150].

A polyhydroxlated pyrrolizidine compound [151], such as one having formula:

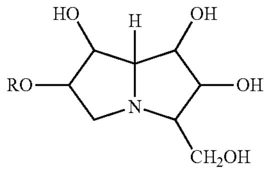

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [152-159] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [160] or derivative thereof, such as algammulin.

derivative (e.g. 3dMPL)+a cholesterol; (4) a saponin (e.g. QS21)+3dMPL+IL-12 (optionally+a sterol) [163]; (5) combinations of 3dMPL with, for example, QS21 and/or oil-in-water emulsions [164]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 48.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used.

To improve thermal stability, a composition may include a temperature protective agent. This component may be particularly useful in adjuvanted compositions (particularly those containing a mineral adjuvant, such as an aluminium salt). As described in reference 165, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human admin-

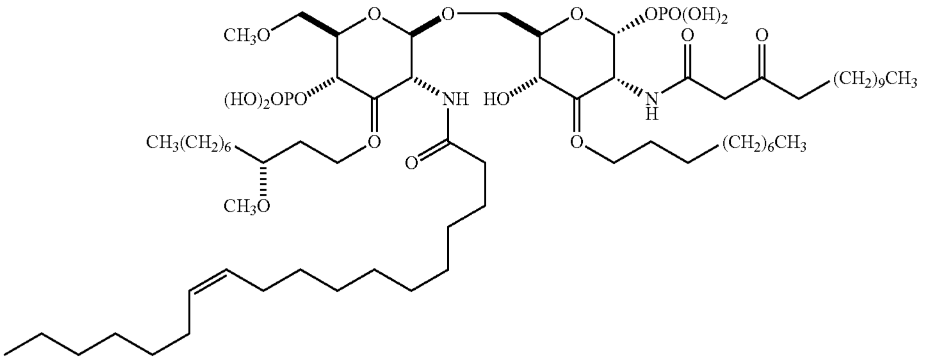

Adjuvant Combinations

The invention may also comprise combinations of one or more of the adjuvants identified above. For example, the following adjuvant compositions may be used in the invention: (1) a saponin and an oil-in-water emulsion [161]; (2) a saponin (e.g. QS21)+a non-toxic LPS derivative (e.g. 3dMPL) [162]; (3) a saponin (e.g. QS21)+a non-toxic LPS istration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

The invention provides an immunogenic composition comprising: (i) one or more OMV(s) of the invention and (ii) a temperature protective agent. This composition may be formed by mixing (i) an aqueous composition comprising one or more OMV(s) of the invention, with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising one or more OMV(s) of the invention, with (ii) a liquid composition comprising the temperature protective agent. Thus component (ii) can be used to reconstitute component (i).

The compositions of the invention may elicit both a cell mediated immune response as well as a humoral immune response. This immune response will preferably induce long lasting (e.g. neutralising) antibodies and a cell mediated immunity that can quickly respond upon exposure to the pathogen (e.g. to *Chlamydia*).

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment, and Administration of the Vaccine

The invention also provides a method for raising an immune response in a mammal comprising the step of administering an effective amount of an OMV or immunogenic composition of the invention. The immune response is preferably protective and preferably involves antibodies and/or cell-mediated immunity. The method may raise a booster response.

The invention also provides a method for immunising a mammal against *Chlamydia* infection, preferably against *C. trachomatis* infection, comprising the step of administering an effective amount of an OMV or immunogenic composition of the invention.

The invention also provides an OMV of the invention in combination with an additional antigen for combined use as a medicament for simultaneous, separate or sequential administration, e.g. for use in raising an immune response in a mammal.

The invention also provides an OMV, antibody or immunogenic composition of the invention for use in therapy.

The invention also provides the use of an OMV of the invention in the manufacture of a medicament for raising an immune response in a mammal. By raising an immune response in the mammal by these uses and methods, the mammal can be protected against infection by the pathogen, for example, against *Chlamydia* infection. More particularly, the mammal may be protected against infection by *Chlamydia trachomatis*. The invention is effective against *Chlamydia* of various different serotypes, but can be particularly useful in protecting against disease resulting from *Chlamydia* infection by strains in serovar D.

Thus, according to a further aspect, the invention also provides an OMV, antibody or immunogenic composition according to the invention for use as a medicament (e.g. a vaccine) or a diagnostic reagent. In one embodiment, the OMV, antibody or immunogenic composition is used for treatment, prevention or diagnosis of *Chlamydia* infection (preferably *C. trachomatis*) in a mammal. The invention also provides a method of treating, preventing of diagnosing *Chlamydia* infection (preferably, *C. trachomatis* infection) in a patient (preferably a mammal), comprising administering a therapeutically effective amount of an OMV or antibody of the invention.

Preferably, the OMV or antibody according to the invention is for use in the treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, cervical squamous cell carcinoma, HIV infection, etc.), preferably, *C. trachomatis* infection (such as an ocular condition, urogenital tract condition or invasive lymphogranumoa venereum that is caused by *C. trachomatis*). The immunogenic composition may additionally or alternatively be effective against *C. pneumoniae*.

In some embodiments, the OMV of the present invention is for use in raising neutralising antibodies against infection by a particular pathogen. The pathogen is preferably a bacteria or a virus. Examples of suitable bacteria are *chlamydia, Streptococcus, Salmonella, E. coli* and *Helicobacter*. Examples of suitable viruses are HIV, influenza and Epstein Barr virus. Preferably, the OMV is for use in raising neutralising antibodies against *Chlamydia*, for example, against *C. trachomatis, C. pneumoniae* or *C. muridarum.*

The mammal is preferably a human. Vaccines prepared according to the invention may be used to treat both children and adults. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Thus a human patient may be less than 1 year old, 1-5 years old, 5-15 years old, 15-55 years old, or at least 55 years old. Preferred patients for receiving the vaccines are people going through puberty, teenagers, sexually active people, the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a human papillomavirus vaccine such as Cervarix® or Gardasil®; a tetanus, diphtheria and acellular pertussis vaccine such as TDaP, DTaP or Boostrix®; a rubella vaccine such as MMR; or a tuberculosis vaccine such as the BCG. Examples of other vaccines that the vaccine produced by the invention may be administered at substantially the same time as are a measles vaccine, a mumps vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

In a preferred embodiment, the OMV of the invention is used to elicit antibodies that are capable of neutralising the infectivity or virulence of *Chlamydia*, for example, of *Chlamydia trachomatis*. Neutralizing antibodies may be used as a vaccine capable of neutralising infectious EB. In one embodiment, the OMV of the invention is used to elicit antibodies that are capable of neutralising *Chlamydia* infectivity and/or virulence. Thus, the invention also provides the antibodies of the invention for neutralising *Chlamydia* infectivity and/or virulence.

The invention also provides the use of an OMV or antibody of the invention in the manufacture of: (i) a medicament for treating or preventing bacterial infection; (ii) a diagnostic reagent for detecting the presence of bacteria or of antibodies raised against bacteria; and/or (iii) a reagent which can raise antibodies against bacteria. Said bacteria is preferably a *Chlamydia*, e.g. *Chlamydia trachomatis* or *Chlamydia pneumoniae*, but is preferably *Chlamydia trachomatis.*

Detection and Diagnostic Methods

The invention provides a method for detecting a pathogen, such as a *Chlamydia* bacterium (e.g. *C. trachomatis*) in a sample. The method can involve detecting the presence or absence of an antigen from the pathogen or of nucleic acid encoding an antigen from the pathogen. The method can be used for microbiological testing, clinical or non-clinical diagnosis, etc. Detection of the antigen may involve e.g. contacting the sample with an antibody of the invention, such as a labelled antibody of the invention. Detection of the nucleic acid antigen may involve any convenient method e.g. based on nucleic acid hybridisation, such as by using northern or southern blots, nucleic acid microarrays or 'gene chips', amplification reactions (e.g. PCR, SDA, SSSR, LCR, TMA, NASBA, etc.).

The invention also provides a method for detecting if a patient has been infected with a pathogen (e.g. a *Chlamydia* bacterium such as *C. trachomatis*), comprising a step of detecting in a sample taken from the patient the presence or absence of an antibody according to the invention. Detection of the antigen may involve, for example, contacting the sample with an antibody of the invention.

Presence of the antigen (e.g. the CT823), or of nucleic acid encoding the antigen (e.g. the CT823 antigen), or of an antibody (e.g. an anti-CT823 antibody), indicates the presence of the pathogen (e.g. *C. trachomatis*) in the sample. In a clinical diagnostic setting, therefore, the results of the method may be used to educate or dictate a therapeutic strategy for a patient e.g. a choice of antibiotics, etc.

The invention also provides a process for detecting an antigen (e.g. CT823), comprising the steps of: (a) contacting an antibody (e.g. an anti-CT823 antibody) with a biological sample under conditions suitable for the formation of an antibody-antigen complex; and (b) detecting the complex.

The invention also provides a process for detecting antibodies (e.g. anti-CT823 antibodies), comprising the steps of: (a) contacting an antigen with a biological sample (e.g. a blood or serum sample) under conditions suitable for the formation of an antibody-antigen complexes; and (b) detecting the complexes.

Also provided is a method for diagnosing an infection by a pathogen (e.g. *Chlamydia* infection), comprising:

(a) raising an antibody against a heterologous antigen presented in the context of an OMV according to the invention;

(b) contacting the antibody of step (a) with a biological sample suspected of being infected with the pathogen (e.g. *Chlamydia*) under conditions suitable for the formation of antibody-antigen complexes; and (c) detecting said complexes, wherein detection of said complex is indicative of pathogen infection (e.g. *Chlamydia* infection).

OMVs of the invention can be used in immunoassays to detect antibody levels (or, conversely, antibodies of the invention can be used to detect protein levels). Immunoassays based on well defined, recombinant antigens can be developed to replace invasive diagnostics methods. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Testing Efficacy of Compositions

The efficacy of the immunogenic compositions of the present invention can be evaluated in in vitro and in vivo animal models prior to host, e.g., human, administration. For example, in vitro neutralization by Peterson et al (1988) is suitable for testing vaccine compositions directed toward *Chlamydia trachomatis.*

One way of checking efficacy of therapeutic treatment involves monitoring infection (e.g. *C. trachomatis* infection) after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens (e.g. against the *Chlamydia trachomatis* antigens) in the compositions of the invention after administration of the composition. Typically, serum pathogen (e.g. *Chlamydia*) specific antibody responses are determined post-immunisation but pre-challenge whereas mucosal pathogen (e.g. *Chlamydia*) specific antibody responses are determined post-immunisation and post-challenge.

One example of such an in vitro test is described as follows. Hyper-immune antisera is diluted in PBS containing 5% guinea pig serum, as a complement source. *Chlamydia trachomatis* ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with *Chlamydia* specific antibody, such as anti-MOMP. Inclusion-bearing cells are counted in ten fields at a magnification of 200×. Neutralization titer is assigned on the dilution that gives 50% inhibition as compared to control monolayers/IFU.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the heterologous antigen in question. This method may also be used to identify immunodominant antigens and/or epitopes within antigens.

The efficacy of vaccine compositions can also be determined in vivo by challenging animal models of infection (e.g. *Chlamydia trachomatis* infection), e.g., guinea pigs or mice, with the vaccine compositions. For example, in vivo vaccine composition challenge studies in the guinea pig model of *Chlamydia trachomatis* infection can be performed. A description of one example of this type of approach follows. Female guinea pigs weighing 450-500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells (Rank et al. (1988)). Each animal receives approximately $1.4\times10^7$ inclusion forming units (IFU) contained in 0.05 ml of sucrose-phosphate-glutamate buffer, pH 7.4 (Schacter, 1980). The course of infection monitored by determining the percentage of inclusion-bearing cells by indirect immunofluorescence with GPIC specific antisera, or by Giemsa-stained smear from a scraping from the genital tract (Rank et al 1988). Antibody titers in the serum is determined by an enzyme-linked immunosorbent assay.

Alternatively, in vivo vaccine compositions challenge studies can be performed in the murine model of *Chlamydia trachomatis* (Morrison et al 1995). A description of one example of this type of approach is as follows. Female mice 7 to 12 weeks of age receive 2.5 mg of depo-provera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 166-173, etc.

Where the invention concerns an "epitope", this epitope may be a B-cell epitope and/or a T-cell epitope. Such epitopes can be identified empirically (e.g. using PEPSCAN [174,175] or similar methods), or they can be predicted (e.g. using the Jameson-Wolf antigenic index [176], matrix-based approaches [177], MAPITOPE [178], TEPITOPE [179,180], neural networks [181], OptiMer & EpiMer [182, 183], ADEPT [184], Tsites [185], hydrophilicity [186], antigenic index [187] or the methods disclosed in references 188-192, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 193. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 194.

BRIEF DESCRIPTION OF DRAWINGS

FIG. 1A shows the components of the Tol-Pal complex;

FIG. 1B is a schematic representation of knocking out the tolR gene in the chromosomal DNA of *E. coli* IHE 3034 using homologous recombination and replacing it with the kanamycin resistance cassette;

FIG. 5A shows Western blot results for (i) TC0052 (41 kDa), (ii) TC0106 (47 kDa), (iii) TC0210 (53 kDa) and (iv) TC0727 (58 kDa). For Western blot (i), the following protein samples were analyzed: *E. coli* BL21(DE3)ΔTolR expressing the heterologous antigen (lane 1); total proteins contained in OMV expressing the heterologous antigen (lane 2); and proteins contained in OMV prepared from *E. coli* BL21(DE3) ΔTolR not expressing chlamydial antigen (lane 3). For each of Western blots (ii), (iii) and (iv), the following protein samples were analyzed: recombinant protein purified from expressing *E. coli* clones (lane 1); *E. coli* BL21(DE3)ΔTolR expressing the heterologous antigen (lane 2); total proteins contained in OMV expressing the heterologous antigen (lane 3); and proteins contained in OMV prepared from *E. coli* BL21(DE3) ΔTolR not expressing chlamydial antigen (lane 4). Each Western blot was incubated with sera obtained by immunizing mice with the respective purified chlamydial recombinant antigen. The arrows indicate the bands corresponding to the respective heterologous antigens.

FIG. 5D (i) shows total TC0431 protein contained in OMV expressing the heterologous antigen (see lane 1).

FIG. 8 shows the sequence of the TC0210 antigen from *C. muridarum* (SEQ ID NO:19). The peptide recognised in the shaving and mass spectrometry analysis is highlighted in bold and underlined.

FIG. 9 is a sequence alignment of *C. muridarum* TC0210 (query sequence, SEQ ID NO:19) and *C. trachomatis* CT823 (subject sequence, SEQ ID NO:1);

FIG. 17*c* shows the Western Blots for (i) Group 2 and (ii) Group 4 in more detail. The arrow indicates the 53 kDa TC0210 protein. A serum dilution of 1:200 was used;

FIG. 21 shows two SDS PAGE gels in which were loaded: (i) 20 μg of an E. coli BL21(DE3)ΔtolR OMV preparation (left hand gel); and (ii) 20 μg of an E. coli BL21(DE3)ΔompA OMV preparation (right hand gel);

FIG. 23 shows the results of a mass spectrometry experiment carried out to confirm the presence of the TC0210 antigen in the OMV preparation. The top sequence is the TC0210 antigen (SEQ ID NO:19) with epitopes highlighted in bold; The lower 13 sequences (SEQ ID NOS:87-99, respectively) show the bolded epitopes flanked by amino acids at the N- and C-termini.

MODES FOR CARRYING OUT THE INVENTION

Example 1

Materials and Methods

Figure 2:
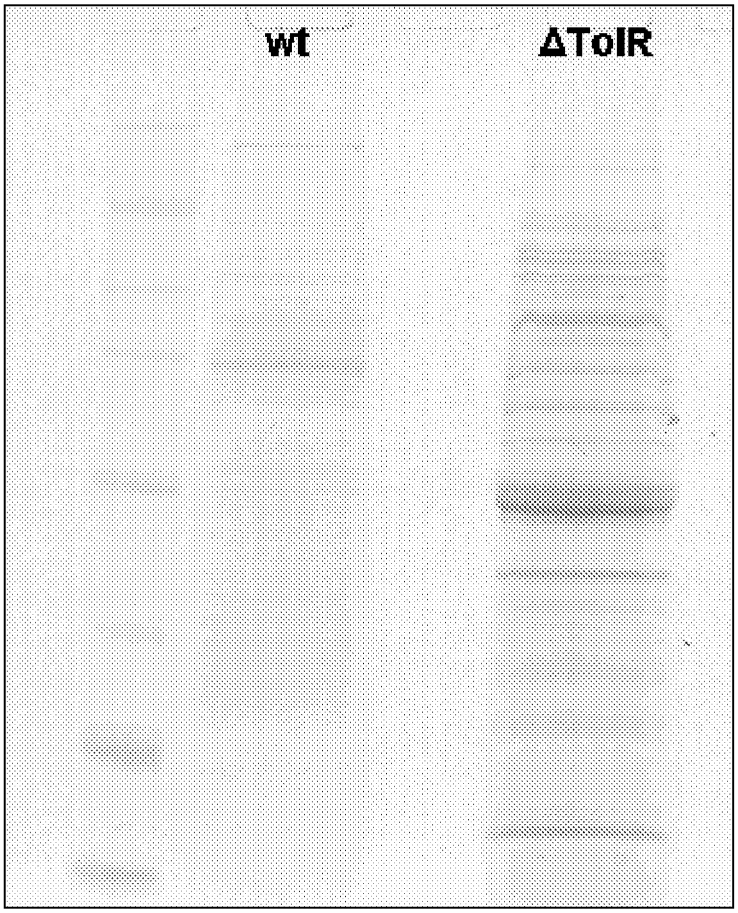
FIG. 2 shows the protein content released into the culture supernatant from wild type *E. coli* (left hand lane) and from the *E. coli* ΔTolR strain (right hand lane)

The following materials and methods are used in the examples unless stated otherwise:
1) Bacterial Strains, Cultures, and Reagents:

*Chlamydia muridarum* strain Nigg and *C. trachomatis* serovar D strain D/UW-3/CX were grown on confluent monolayers of LLC-MK2 (ATCC CCL7) in Earle's minimal essential medium (EMEM) as described previously [195]; [196]. Purification of *C. trachomatis* and *C. muridarum* EBs was carried out by Renografin density gradient centrifugation as described previously [195]. *Escherichia coli* BL21(DE3) was grown aerobically in Luria broth (LB) medium (Difco) at 37° C. When appropriate, ampicillin (100 μg/ml) and isopropyl-β-D-galactopyranoside (IPTG; 1 mM) were added to the medium. Unless specified, all chemicals used in this study were purchased from Sigma. Restriction enzymes and DNA modification enzymes were from New England Biolabs.
2) Gene Cloning and Protein Purification:

To produce recombinant proteins such as CT823, TC0210, TC0727, TC0651, TC0313, TC0106, TC0551, TC0431, TC0890, CT681 (*C. trachomatis* MOMP [MOMP$_{Ct}$]) and TC0052 (*C. muridarum* MOMP [MOMP$_{Cm}$]), genes were PCR amplified from *C. trachomatis* and *C. muridarum* chromosomal DNA using specific primers annealing at the 5' and 3' ends of either gene and cloned into plasmid pET21b⁺ (Invitrogen) so as to fuse a six-histidine tag sequence at the 3' end. Cloning and purification of His fusions were performed as already described [196]. TC0727, TC0651, TC0106, TC0551, TC0431, TC0890, MOMP$_{Ct}$ and MOMP$_{Cm}$ expressed as His fusion proteins were purified from the insoluble protein fraction, while TC0313, CT823 and TC0210 expressed as His fusion proteins were purified from the soluble protein fraction according to the manufacturer's procedure.

3) Construction of BL21(DE3) ΔtolR Deletion Mutant:

The ΔtolR mutant was produced by replacing tolR coding sequence with a kanamycin resistance ("kmr") cassette. To this aim, a three-step PCR protocol was used to fuse the tolR upstream and downstream regions to the kmr gene. Briefly, the 528-bp upstream and 466-bp downstream regions of the tolR gene were amplified from *E. coli* BL21(DE3) genomic DNA with the specific primer pairs UpF (TCTGGAATC-GAACTCTCTCG) (SEQ ID NO: 68)/UpR-kan (ATTTTGAGACACAACGTGGCTTTCATG-GCTTACCCCTTGTTG) (SEQ ID NO: 69); DownF-kan (TTCACGAGGCAGACCTCATAAACATCT-GCGTTTCCCTTG) (SEQ ID NO: 70)/DownR (TTGCT-TCTGCTTTAACTCGG) (SEQ ID 71), respectively. In parallel, the kmr cassette was amplified from plasmid pUC4K using the primers kan-F (ATGAGCCATATTCAACGG-GAAAC) (SEQ ID NO: 72) and kan-R (TTAGAAAAACT-CATCGAGCATCAAA) (SEQ ID NO: 73). Finally, the three amplified fragments were fused together by mixing 100 ng of each in a PCR containing the UpF/DownR primers. The linear fragment obtained, in which the kmr gene was flanked by the tolR upstream and downstream regions, was used to transform the BL21(DE3) *E. coli* strain (made electrocompetent by three washing steps in cold water), and tolR mutants were selected by plating transformed bacteria on Luria-Bertani (LB) plates containing 30 ug/ml of kanamycin.

Recombination BL21(DE3) cells were produced by using the highly proficient homologous recombination system (red operon) [197]. Briefly, electrocompetent bacterial cells were transformed with 5 ug of plasmid pAJD434 by electroporation (5.9 ms at 2.5 kV). Bacteria were then grown for 1 h at 37° C. in 1 ml of SOC broth and then plated on LB plates containing trimethoprim (100 ug/ml). Expression of the red genes carried by pAJD434 was induced by adding 0.2% L-arabinose to the medium. The gene deletion of the tolR gene was confirmed by PCR genomic DNA amplification using primers pairs UpF/Kan-R; Kan-F/Kan-R; Kan-F/DownR. The deletion was confirmed also using the primers tolR-F (CGGACCCGTATTCTTAAC) (SEQ ID NO: 74) and tolR-R (GCCTTCGCTTTAGCATCT) (SEQ ID NO: 75) annealing further upstream and downstream from the 5'- and 3'-flanking regions, respectively.

4) Construction of BL21(DE3) ΔompA Deletion Mutant:

The ΔompA mutant was produced by replacing ompA coding sequence with a Chloramphenicol resistance ("Cmr") cassette using specific primers. The procedure is the same as that utilized to produce BL21(DE3)ΔtolR (see section 3) above). In particular, primers used to amplify the about 530 bp upstream and about 470 bp downstream regions of the ompA gene were amplified from BL21(DE3) genomic DNA with the specific primer pairs ompA_Up for: (GATCGGT-TGGTTGGCAGAT) (SEQ ID NO: 76)/ompA cm_Up-rev: (CACCAGGATTTATTTATTCT-GCGTTTTTGCGCCTCGTTATCAT) (SEQ ID NO: 77); ompA cm_Down for: (TACTGCGATGAGTGGCAGGCG-CAGGCTTAAGTTCTCGTC) (SEQ ID NO: 78)/ompA Down rev: (AAAATCTTGAAAGCGGTTGG) (SEQ ID NO: 79); CMr FOR: (CGCAGAATAAATAAATCCTGGTG) (SEQ ID NO: 80)/CMr REV: (CCTGCCACTCATCG-CAGTA) (SEQ ID NO: 81). Finally the three amplified fragments were fused together by mixing 100 ng of each in a PCR containing the ompA_Up for/ompA Down rev primers.

The linear fragment obtained, in which the Cmr gene was flanked by the ompA upstream and downstream regions, was used to transform the BL21(DE3) *E. coli* strain (made electrocompetent by three washing steps in cold water). ompA mutants were selected by plating transformed bacteria on Luria-Bertani (LB) plates containing 20 ug/ml of Chloramphenicol.

The gene deletion of the ompA gene was confirmed by PCR genomic DNA amplification using primers specifically annealing to Cmr cassette (CMr FOR/CMr REV), or ompA_Up for/CMr REV, or using primers specific for ompA in order to further verify the deletion of this gene (ompA FOR: (ATGAAAAAGACAGCTATCGC) (SEQ ID NO: 82)/ompA REV: (TTAAGCCTGCGGCTGAGTT) (SEQ ID NO: 83).

5) Expression of Chlamydial Antigens on BL21(DE3) ΔtolR or on BL21(DE3) ΔompA:

To express the 9 *Chlamydia muridarum* antigens (TC0052, TC0106, TC0210, TC0313, TC0431, TC0551, TC0651, TC0727, TC0890) on the outer membrane of *E. coli* mutant strains, genes coding for chlamydial antigens were fused in frame to the *E. coli* OmpA leader peptide. These fusions were then inserted in pET 21b (Invitrogen), a plasmid previously modified for cloning with the pipe method [198], by using specific primers annealing to the six-histidine tag sequence at the 3' end and to the gene coding for the *E. coli* OmpA leader peptide at the 5' end. The fusions were placed under the control of a lac promoter in the multicopy plasmid (pET). The obtained plasmid is called pET-TC0xyz. Plasmids were transformed in *E. coli* HK100 cells, made $CaCl_2$ competent after several successive washes in cold, $MgCl_2$ and $CaCl_2$ solutions [198].

Cells were plated on LB containing 100 ug/ml of Amp. at 37° C. O.N. Positives clones were grown in LB in order to produce mini preparations of plasmids (by using Qiagen mini prep kit).

BL21(DE3) ΔtolR and BL21(DE3) ΔompA *E. coli* strain (made electrocompetent by three washing steps in cold water) were transformed with 10 ng of each pET-TC0xyz plasmid mini preparation. Bacteria were grown for 1 h at 37° C. in 1 ml of SOC broth and then plated on LB plates containing Amp. (100 ug/ml) and incubated O.N. at 37° C.

6) OMV Preparation:

BL21(DE3)ΔtolR and BL21(DE3)ΔompA *E. coli* cells expressing or not expressing chlamydial antigens were inoculated from fresh plate into 500 ml of LB (Luria Bertani broth)+Amp (100 ug/ml) and were incubated at 37° C. with shaking (200 r.p.m.) and growth. The induction of recombinant protein expression is made by addition of IPTG 0.1 mM at O.D.=0.4. Bacteria culture were grown until at 37° C. the O.D.=1. At that point, culture media were filtered through a 0.22 μm pore-size filter (Millipore, Bedford, Mass.). The filtrates were subjected to high speed centrifugation (200,000×g for 90 min), and the pellets containing the OMVs were washed with PBS and finally resuspended with PBS [199].

7) Western Blot Analysis:

20 ug of OMV preparations and 200 ng of TC0210 His were respectively size-separated by SDS-PAGE (4-12% gel) under reducing conditions and electroblotted onto nitrocellulose membranes. Membranes were saturated overnight with Milk Marwell 10% in PBS (phosphate Buffer) 0.1% Triton, shaking at 4° C. Then, membranes were incubated with specific mouse sera at RT for 2 hours (sera dilution 1:200). Anti mouse horseradish peroxidase conjugated IgG (Amersham Biosciences) was used as secondary antibody. Colorimetric staining was performed with the Opti 4CN substrate kit (Bio-Rad).

8) ELISA Assay:

IgG directed to recombinant purified TC0210 were assayed by enzyme-linked immunosorbent assay (ELISA). Individual wells of micro-ELISA plates (Nunc Maxisorp) were coated with 1 μg of recombinant protein in PBS (pH 7.4) at 4° C. overnight. The plates were washed, treated for 1 h at 37° C. with PBS-1% BSA, and 100 μl aliquots of antisera at different serial dilutions in PBS-0.1% Tween were added to the wells. After incubation for 2 h at 37° C., plates were again washed and incubated for 1 h at 37° C. with alkaline-phosphatase conjugated goat anti-mouse IgG (Sigma) diluted 1:2500 in PBS-Tween. Thereafter 100 μl of PNPP (Sigma) were added to the samples and incubated for 30 min. at room temperature. Optical densities were read at 405 nm and the sera-antibody titers were defined as the serum dilution yielding an OD value of 0.5.

9) Neutralization Assay:

Sera obtained by immunizing mice (BALB/c or CD1) with OMV-TC0210 were tested in vitro for the neutralization activity. In vitro neutralization assays were performed on LLC-MK2 (Rhesus monkey kidney) epithelial cell cultures. Three serial dilutions of each sera pool were tested by diluting them 1:30, 1:90, 1:270 in Sucrose phosphate Buffer (SP). Also, purified infectious *C. muridarum* EB were diluted in the same Buffer to contain $3\times10^{(5)}$ IFU/ml, and 15 ul of EB suspension were added to each serum dilution in a final volume of 150 ul. Antibody-EB interaction was allowed by incubating for 30 min. at 37° C. Also, EB were incubated without sera as an infection control. 100 ul of each reaction mix, including EB diluted in SP without sera, were used to inoculate LLC-MK2 confluent monolayers (in duplicate for each serum dilution) in a 96-well tissue culture plate, and centrifuged at 2000 g for 1 hour at 37° C. After centrifugation, Earle's minimal essential medium containing Earle's salts, 10% fetal bovine serum and 1 ug/ml cycloheximide were added. Infected cultures were incubated at 37° C. for 24 hours, while in neutralization assays, in which EB of *C. trachomatis* were used for infection, infected cultures were incubated for 48 hours. Then, cell cultures were fixed by adding 100 ul of methanol for 5 minutes and the chlamydial inclusions were detected by staining with a mouse anti-*Chlamydia* fluorescein-conjugated monoclonal antibody (Merifluor *Chlamydia*, Meridian Diagnostics, Inc.). Finally, all inclusions for each well were counted at of 10× magnification.

Calculations of the infectivity reduction by each sera pool were carried out using pre immune sera neutralization titers as basal levels.

10) Epitope Mapping:

On a nitrocellulose membrane 95 synthetic peptides of TC0210 were spotted. Each peptide is constituted by 15 amino acids and overlaps 10 mers with the following peptide. Three membranes, made with the same design, were washed with TBS (Tris-HCl 50 mM, NaCl 137 mM, KCl 2.7 mM) containing 0.05% of tween 20 (T-TBS), and then were incubated overnight at 4° C. with 2% milk Marwell in TBS (MBS). Then, on the three membranes, different sera pools (sera dilution 1:100) were tested respectively: sera of mice immunized with a) OMV expressing TC0210, b) TC0210His, and c) OMV alone.

Finally, an anti-mouse horseradish peroxidase conjugated IgG (Amersham Biosciences) was used as a secondary antibody (sera dilution 1:5000). Colorimetric staining was performed with the Opti 4CN substrate kit (Bio-Rad).

Example 2

Construction of an *E. Coli* BL21(DE3)ΔtolR Deletion Mutant

BL21 (DE3)ΔtolR is a mutant *E. coli* strain in which the ΔtolR mutation was introduced by replacing the tolR coding sequence with a Kanamycin resistance cassette. This strain is able to release a large quantity of outer membrane vesicles in the culture supernatant. It was found that the protein content released in the culture supernatant from the ΔtolR mutant strain is higher compared to that released from the wild type strain (see FIG. 2).

Example 3

Expression of Chlamydial Antigens in BL21(DE3)ΔtolR or in BL21(DE3)ΔompA

To allow presentation of each of the 9 *Chlamydia muridarum* antigens (TC0052, TC0106, TC0210, TC0313, TC0431, TC0551, TC0651, TC0727 and TC0890-see Table 3 below) on the outer membrane of *E. coli* mutant strains, genes coding for chlamydial antigens were fused in frame to the *E. coli* OmpA leader peptide.

TABLE 3

*Chlamydia* promising antigens

| *C. muridarum* | ANNOTATION | *C. trachomatis* homolog |
|---|---|---|
| TC0052 | MOMP | CT681 |
| TC0651 | hypothetical protein | CT372 |
| TC0727 | 60 Kda Cystein Rich OMP | CT443 |
| TC0210 | DO serine protease | CT823 |
| TC0313 | hypothetical protein | CT043 |
| TC0106 | hypothetical protein | CT733 |
| TC0551 | Na(+)-translocating NADH-quinone reductase | CT279 |
| TC0431 | MAC-Perforine protein | CT153 |
| TC0890 | Invasine repeat family phosphatase | CT601 |

The fusions were placed under the control of a lac promotor in the multicopy plasmid pET21b+ (Novagen). The obtained plasmid is called pET-TC0xyz.

Figure 3:
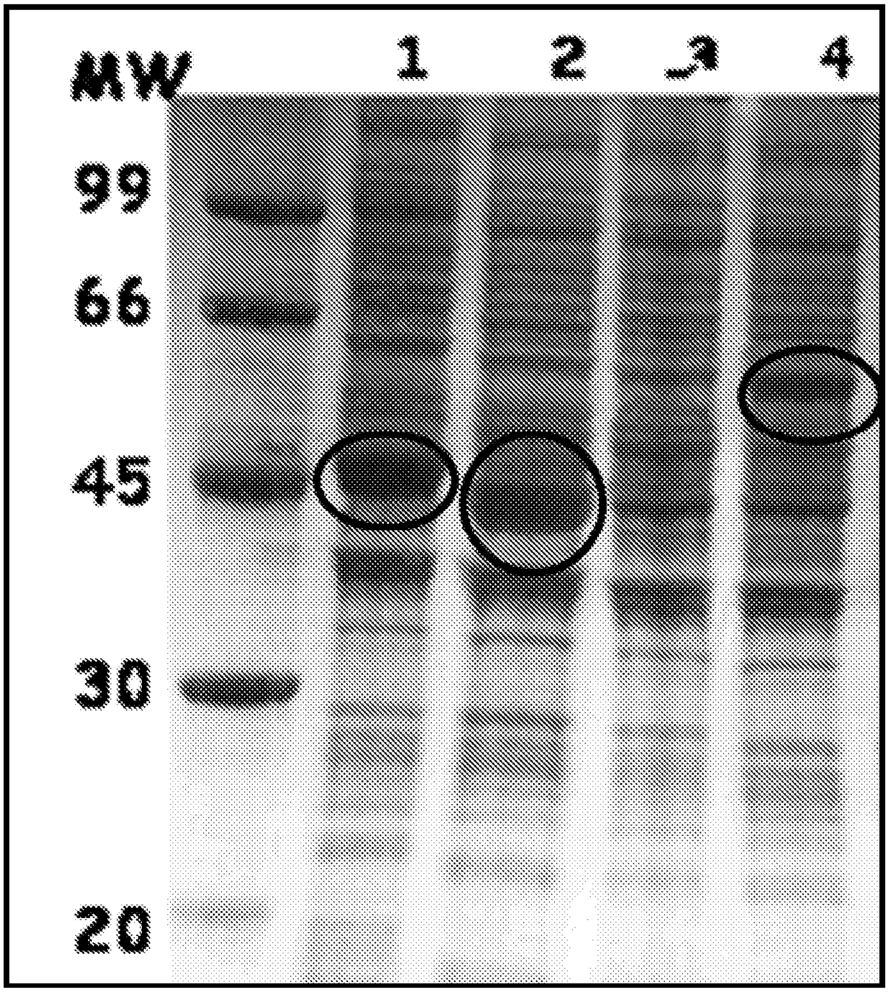
FIG. 3 is an SDS-PAGE gel that shows total proteins from *E. coli* ΔTolR expressing TC0106 (lane 1), TC0052 (lane 2), TC0727 (lane 3) and TC0210 (lane 4). Low molecular weight markers are provided on the left hand side of the gel. The circles in lanes 1, 2 and 4 indicate expression of the TC0106, TC0052 and TC0210 proteins, respectively.

The 9 different pET-TC0xyz plasmids were transformed in *E. coli* BL21(DE3)ΔtolR and *E. coli* BL21(DE3)ΔompA strains. The SDS PAGE gel analysis in FIG. 3 shows that the expression of chlamydial antigen was clearly visible in the culture total extracts of *E. coli* BL21(DE3)ΔtolR expressing TC0106, TC0052 and TC0210 (see lanes 1, 2 and 4 of FIG. 3). On the contrary, expression of TC0727 in *E. coli* was not clearly visible (see lane 3 of FIG. 3).

Example 4

OMV Preparation

Figure 4:
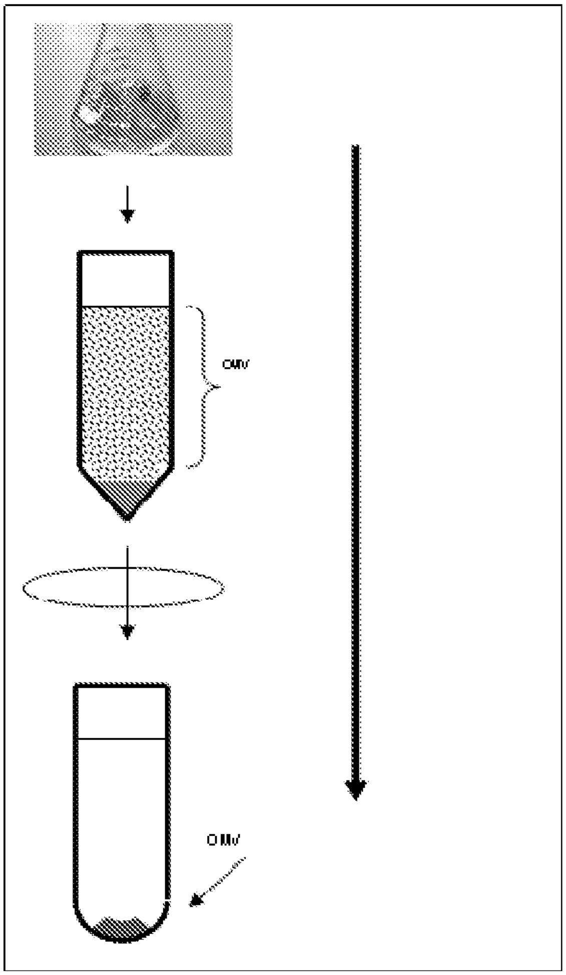
FIG. 4 is a schematic representation of an OMV preparation protocol.

A schematic diagram of OMV preparation is shown in FIG. 4. Bacteria were induced when they reached an OD600 of 0.4. The bacteria were grown to OD600=1 and were then centrifuged at 6,000 g. Culture media of BL21(DE3)ΔtolR and pET-TC0xyz BL21(DE3)ΔtolR strains were filtered through a 0.22 μm filter, centrifuged at high-speed (200,000×g, 120 min.) and the OMVs were recovered in the pellet were washed with phosphate and were then resuspended in phosphate to obtain the OMVs [199].

Example 5

Analysis of OMV Preparations

Figure 5B:
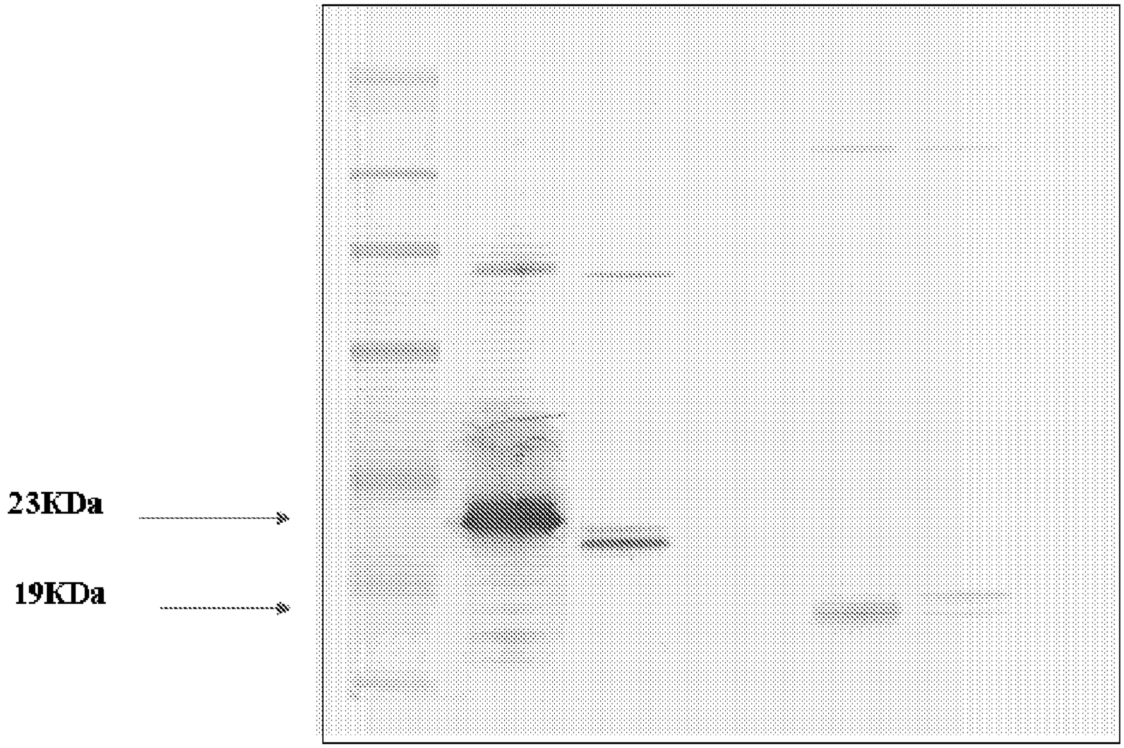
FIG. 5B shows Western blot results for TC0313 and TC0890. The samples that were analyzed are as follows: molecular weight standard markers (left hand lane); recombinant TC0313His (23 kDa) purified from expressing *E. coli* clones (lane 1); total TC0313 protein contained in OMV expressing the heterologous antigen (lane 2); proteins contained in OMV prepared from *E. coli* BL21(DE3)ΔTolR not expressing chlamydial antigen (lane 3); recombinant TC0890His (19 kDa) purified from expressing *E. coli* clones (lane 4); total TC0890 protein contained in OMV expressing the heterologous antigen (lane 5); proteins contained in OMV prepared from *E. coli BL*21(DE3)ΔTolR not expressing chlamydial antigen (lane 6). Lanes 1, 2 and 3 were incubated with sera obtained by immunizing mice with purified TC0313 recombinant antigen (23 kDa), whilst lanes 4, 5 and 6 were incubated with sera obtained by immunizing mice with purified TC0890 recombinant antigen (19 kDa). The lanes are numbered from left to right. The arrows indicate the bands corresponding to the heterologous antigens of 23 kDa and 19 kDa respectively.
Figure 5C:
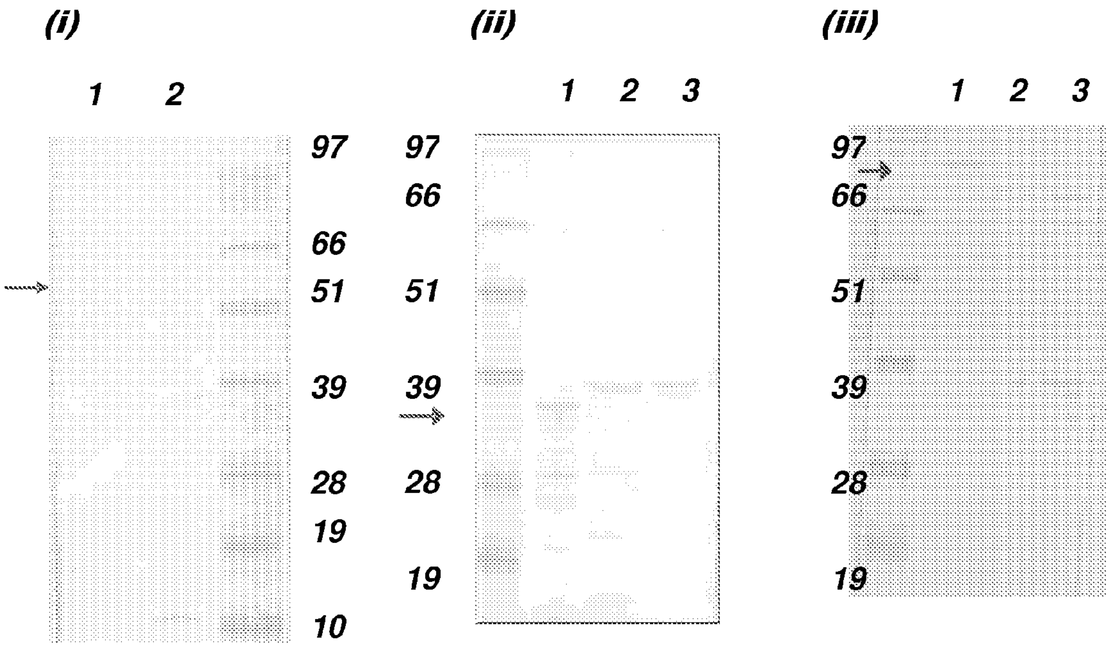
FIG. 5C shows Western blot results from left to right for (i) TC0651 (53 kDa), (ii) TC0551 (32 kDa) and (iii) TC0431 (9010a), respectively. For TC0651, lane 1 shows proteins contained in OMV prepared from *E. coli* BL21(DE3)ΔTolR not expressing chlamydial antigen whilst lane 2 shows total TC0651 protein contained in OMV expressing the heterologous antigen. For TC0551, lane 1 shows recombinant TC0551His (32 kDa) purified from expressing *E. coli* clones, lane 2 shows TC0551 contained in OMV prepared from *E. coli* BL21(DE3)ΔTolR expressing TC0551 and lane 3 shows proteins contained in OMV prepared from *E. coli* BL21(DE3) ΔTolR not expressing chlamydial antigen. For TC0431, lane 1 shows recombinant TC0431His (90 kDa) purified from expressing *E. coli* clones, lane 2 shows proteins contained in OMV prepared from *E. coli* BL21(DE3)ΔTolR not expressing chlamydial antigen and lane 3 shows TC0431 contained in OMV prepared from *E. coli* BL21(DE3)ΔTolR expressing TC0431.

Western blot analysis was used to determine whether the OMV preparations expressed the heterologous antigens. Six out of the nine recombinant OMVs were shown to carry the heterologous proteins. FIGS. 5A and 5B indicate that each of TC0052, TC0106, TC0210, TC0727, TC0313 and TC0890 were expressed in the recombinant OMVs. On the contrary, FIG. 5C shows that TC0651, TC0551 and TC0431 were not expressed in the recombinant OMVs.

Figure 5D:
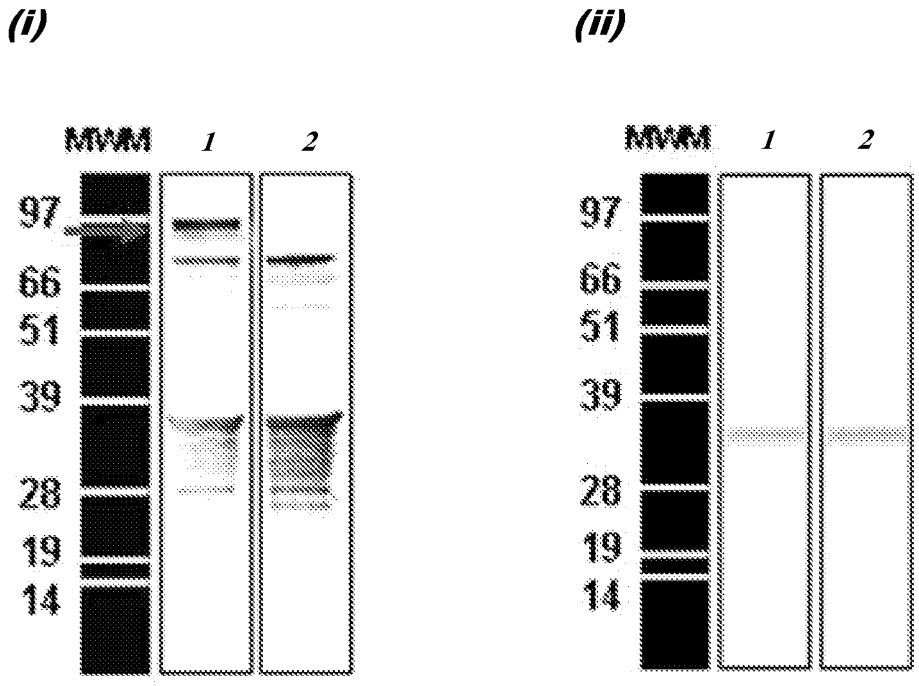
FIG. 5D shows Western blot results from left to right for (i) TC0431 (90 kDa), and (ii) TC0052 (41 kDa). For each Western blot, lane 1 was loaded with an OMV preparation prepared from *E. coli* BL21(DE3)ΔTolR expressing chlamydial antigen, while lane 2 was loaded with an OMV preparation prepared from *E. coli* BL21(DE3)ΔTolR not expressing chlamydial antigens (used as a negative control).

However, in follow up experiments TC0431 was in fact shown to be expressed in the recombinant OMVs but at a low level as can be seen from FIG. 5D (i) wherein the amount of OMV preparations loaded onto the gel was doubled in order to obtain detectable levels of the antigen. On the other hand, the expression of TC0052 was not detected in the follow up experiments (see FIG. 5D (ii)). The reason for this apparent variability is believed to be the result of instability of engineered strains encoding TC0052, such instability leading to lysis of the bacteria during growth in culture.

Figure 6:
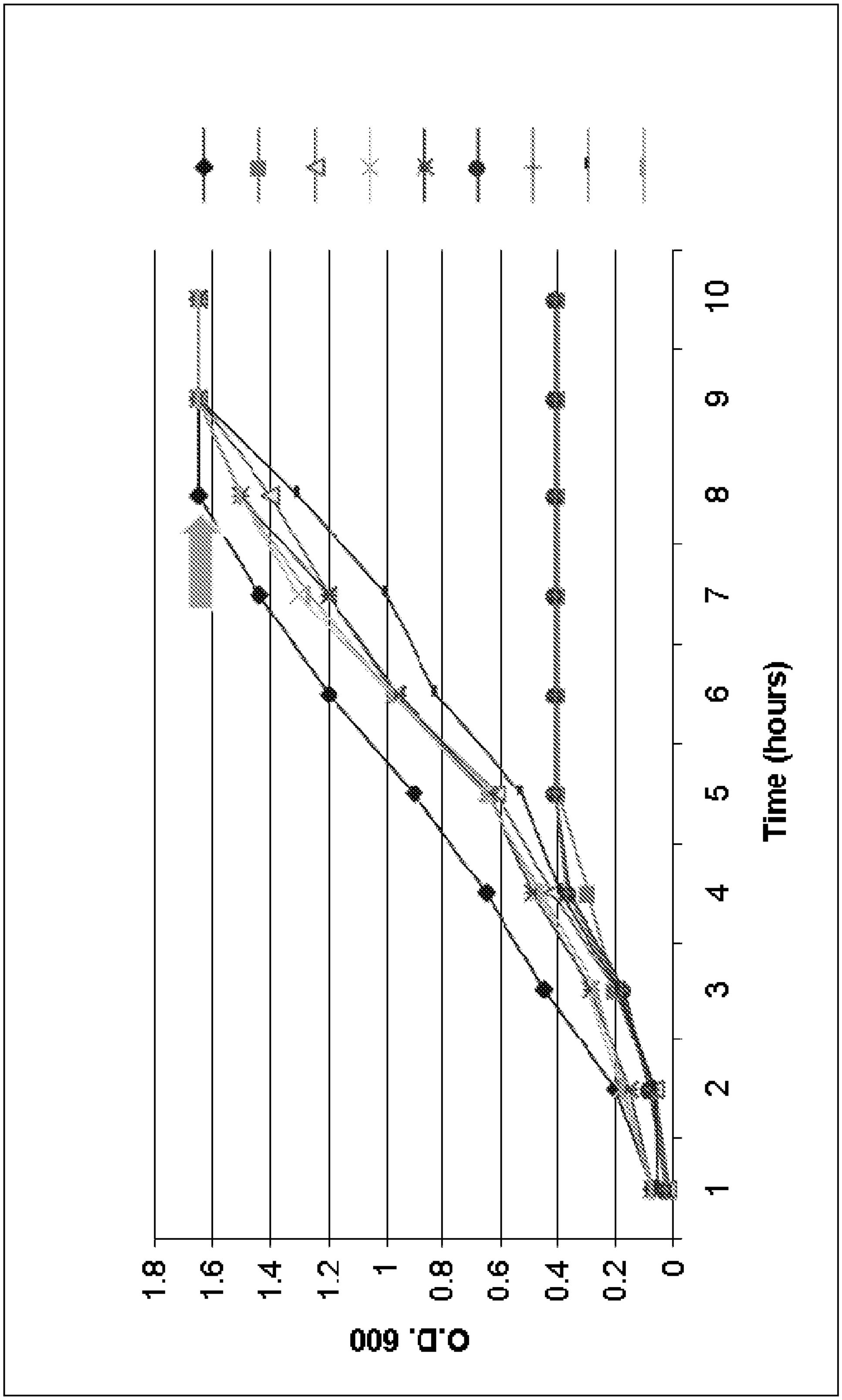
FIG. 6 shows the *E. coli* growth curve for the various mutant *E. coli* ΔTolR prepared in Example 3. Time in hours is indicated along the X axis; OD600 is indicated along the Y axis. The growth curve of *E. coli* expressing the TC0210 is indicated with an arrow. (-◆-) is TC0210pET BL21(DE3) ΔTolR; (-■-) is TC0052pET BL21(DE3)ΔTolR; (-▲-) is TC0106pET BL21(DE3)ΔTolR; (-✕-) is TC0313pET BL21 (DE3)ΔTolR; (✱) is TC0431pET BL21(DE3)ΔTolR; (-●-) is TC0551pET BL21(DE3)ΔTolR; (—+—) is TC0651pET BL21(DE3)ΔTolR; (▬▬) is TC0727pET BL21(DE3) ΔTolR and (▬▬) is TC0890pET BL21(DE3)ΔTolR.

The growth curve of *E. coli* BL21(DE3)ΔtolR prepared in Example 3 expressing each of the 9 chlamydial antigens is shown in FIG. 6. *E. coli* expressing TC0210 had the greatest rate of growth. The rate of growth of *E. coli* expressing TC0313, TC0890, TC0431 or TC0106 was similar but was slower than the rate of growth of *E. coli* expressing TC0210. The rate of growth of *E. coli* expressing TC0727 was slower than *E. coli* expressing any of TC0313, TC0890, TC0431 or TC0106. *E. coli* expressing TC0052, TC0551 or TC0651 had the slowest rate of growth.

Figure 7:
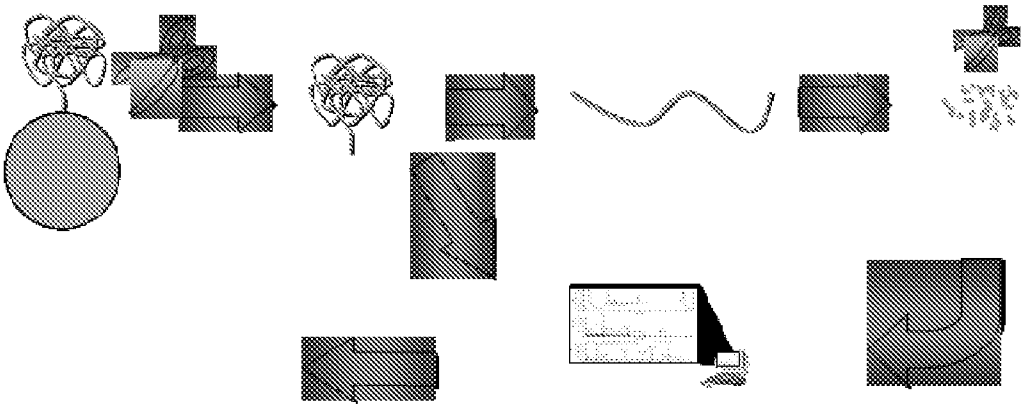
FIG. 7 is a schematic diagram of shaving and mass spectrometry experiments carried out to confirm the presence of the heterologous antigen in the OMV preparation. The diagram shows (starting from top left and progressing in a clockwise direction): i) shaving the OMV, ii) Recovery of supernatants, iii) DTT+detergent 100° C. for 10 mins, iv) Recovery of peptides; v) Separation of the peptides by RP chromatography and peptide fragmentation by MS/MS ESI-Q-TOF, and vi) Protein identification.

TC0210-OMV was found to be the best preparation in terms of yield and quantity of *Chlamydia* antigen that was expressed. Mass spectrometry confirmed the presence of the TC0210 peptide on the surface of TC0210-OMV preparations after the shaving of the same OMV preparation (the technique of *Chlamydia* shaving is described in WO 2007/110700 and a schematic diagram is shown in FIG. 7). The peptide identified in the shaving experiment corresponds to amino acids 65-75 of the full length TC0210 protein. The matched peptide is shown in bold and underlined (see also FIG. 8):

```
  1 MMKRLLCVLL STSVFSSPML GYSAPKKDSS TGICLAASQS DRELSQEDLL
 51 KEVSRGFSKV AAQATPGVVY IENFPKTGSQ AIASPGNKRG FQENPFDYFN
101 DEFFNRFFGL PSHREQPRPQ QRDAVRGTGF IVSEDGYVVT NHHVVEDAGK
151 IHVTLHDGQK YTAKIIGLDP KTDLAVIKIQ AKNLPFLTFG NSDQLQIGDW
201 SIAIGNPFGL QATVTVGVIS AKGRNQLHIV DFEDFIQTDA AINPGNSGGP
251 LLNIDGQVIG VNTAIVSGSG GYIGIGFAIP SLMAKRVIDQ LISDGQVTRG
301 FLGVTLQPID SELAACYKLE KVYGALITDV VKGSPAEKAG LRQEDVIVAY
351 NGKEVESLSA LRNAISLMMP GTRVVLKVVR EGKFIEIPVT VTQIPAEDGV
```

-continued

```
401 SALQKMGVRV QNLTPEICKK LGLASDTRGI FVVSVEAGSP AASAGVVPGQ

451 LILAVNRQRV SSVEELNQVL KNAKGENVLL MVSQGEVIRF VVLKSDE
```

TC0210 has the properties that are shown in Table 4.

TABLE 4

| TC0210 | | | | |
|---|---|---|---|---|
| *C. muridarum*/ *C. trachomatis* antigen | *C. muridarum*/ *C. trachomatis* % Similarity | Protein name/ annotation | Novartis scientific data | Other data from literature |
| TC0210/CT823 | 91.8 | HtrA/DO serine protease | Surface exposed Antibody and CD4-th1 inducer in mouse and humans Highly homologous among the 8 major serovars | Serine endoprotease, temperature-activated shows both chaperon and protease activities (Huston et al., FEBS Lett., 2007); Immunogenic in humans (Sanchez-Campillo et al., Electrophoresis, 1999) |

A sequence alignment of *C. muridarum* TC0210 with *C. trachomatis* CT823 is provided in FIG. 9. TC0210 is 93% identical to CT823.

Figures 10, 10A:
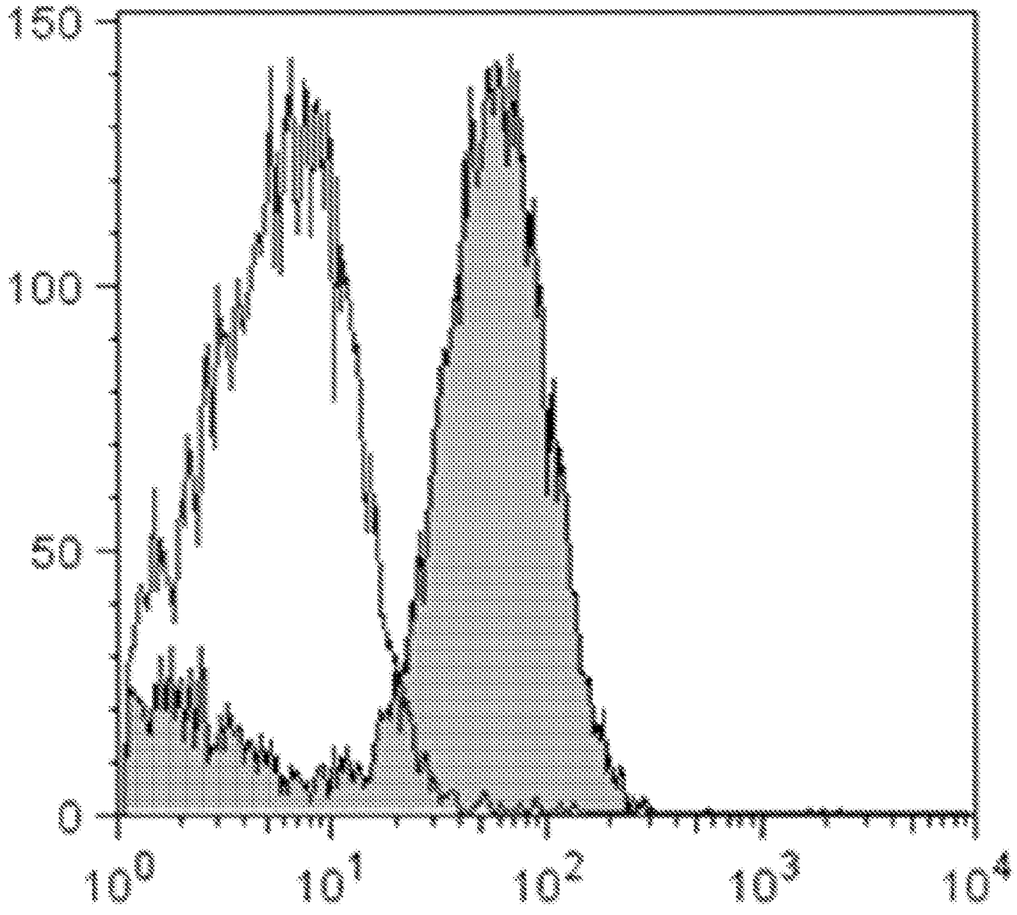
FIG. 10A shows a FACS analysis of antibody binding the surface of chlamydial whole cells.
FIG. 10 D shows Western blot results with sera obtained from mice immunised with from left to right (i) TC0210His (ii) OMV preparation from BL21(DE3)ΔTolR TC0210 and (iii) OMV preparation from BL21(DE3)ΔTolR, respectively. 200 ng of recombinant HtrA (lane 1) and *C. muridarum* EBs (approximately $10^4$ EBs) (lane 2) were dissolved in loading buffer and size-separated by SDS-PAGE (4-12% gel) under reducing conditions and electroblotted onto nitrocellulose membranes. Membranes were saturated overnight with Milk Marwell 10% in PBS (phosphate Buffer) 0.1% Triton, and then were incubated with sera obtained from mice immunised with, from left to right, (i) TC0210His, (ii) OMV preparation from BL21(DE3)ΔTolR TC0210, and (iii) OMV preparation from BL21(DE3)ΔTolR, respectively. An anti-mouse horseradish peroxidase conjugated IgG (Amersham Bioscience™) was used as the secondary antibody.
Figure 10B:
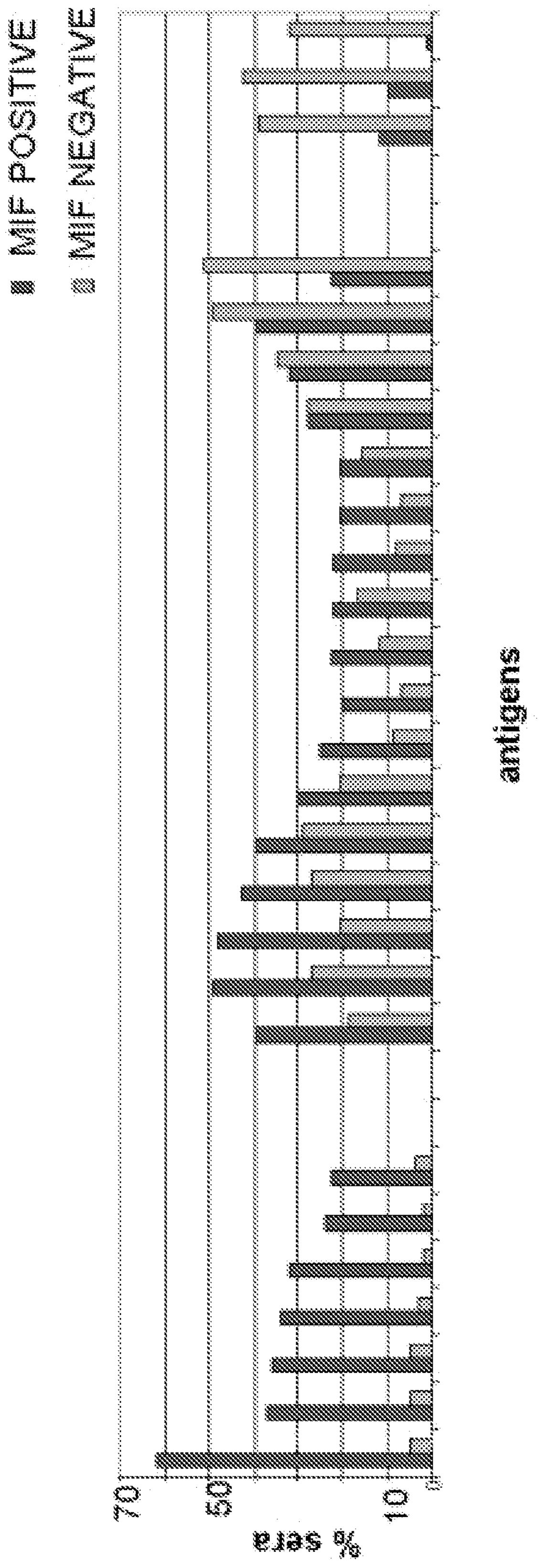
FIG. 10B shows the results of a protein microarray experiment in which chlamydial antigens were expressed in *E. coli*, affinity purified and spotted on glass slides in a microarray format. Two groups of human sera were used for each antigen: MIF positive sera (left hand bar) and MIF negative sera (right hand bar). Antigens are listed on the X axis. From left to right, the antigens listed on the X axis are CT681His, CT823His, CT443His, CT456GST, CT110GST, CT622His, CT089His, CT415GST, CT119GST, CT049GST, CT589GST, CT372GST, CT077His, CT559His, CT322His, CT316His, CT350GST, CT381His, CT355GST, CT389GST, CT127GST, CT157GST, CT567His, CT266His, CT470His, CT398His and CT114His. The % sera is on the Y axis. Each vertical bar represents the mean intensity obtained with the sera (MIF positive vs MIF negative sera) on single antigens. The data second from the left relates to CT823.

FIG. 10B shows the results of a protein microarray experiment in which the chlamydial antigens were expressed in *E. coli*, affinity purified and spotted on glass slides in a microarray format. The instruments and the protocols were as described in Bombaci, M. et al [200]. The slides were immuno-stained with hundreds of different human sera and the staining intensity of every spot was measured. The proteins recognised with a fluorescence intensity of more than 1000 are shown. Two groups of human sera were used for each antigen: MIF positive sera (left hand bar) and MIF negative sera (right hand bar) (where "MIF" stands for the Micro Immuno Fluorescence assay [201], which is used to check if the patient sera contains antibodies against the pathogen (MIF positive) or not (MIF negative)).

The analysis of the protein chip shown in FIG. 10B using MIF positive and MIF negative sera shows that there are three groups of chlamydial antigens: one group of antigens is recognized mainly by MIF positive sera (CT681His, CT823His, CT443His, CT456GST, CT110GST, CT622His, CT089His), another group is recognized both by MIF positive and MIF negative sera (CT415GST, CT119GST, CT049GST, CT589GST, CT372GST, CT077His, CT559His, CT322His, CT316His, CT350GST, CT381His, CT355GST, CT389GST, CT127GST, CT157GST, CT567His and CT266His), and a third group of antigens is mainly recognized by MIF negative sera (CT470His, CT398His and CT114His). The CT823 antigen is clearly recognized by MIF positive sera but not by MIF negative sera, suggesting that CT823 is a chlamydial antigen capable of eliciting a humoral immune response during natural infections in man. Thus, CT823 is immunogenic in humans.

This is supported by FIG. 10A, which shows that CT823 is exposed on the EB surface (KS=19.1, see FIG. 10A). The assay was performed as previously described [196]. A mouse polyclonal antibody serum was used which had been prepared by immunizing mice with TC0210His. Background control sera were from mice immunized with *E. coli* contaminant proteins. The shift between the background control histogram and the immune serum testing histogram was taken as a measure of antibody binding to the EB cell surface. The Kolmogorov-Smirnov (K-S) two-sample test I.T. was performed on the two overlapped histograms. The D/s(n) value (an index of dissimilarity between the two curves) is reported as the "K-S score". A K-S of 19.1 was obtained (T(X)=1146; Max T value=1719; Max. difference=78.5% at value 19.1; Confidence in difference is greater than 99.9%; SED percentage positive: 82.6; Population comparison data 0.06)

Figure 10C:
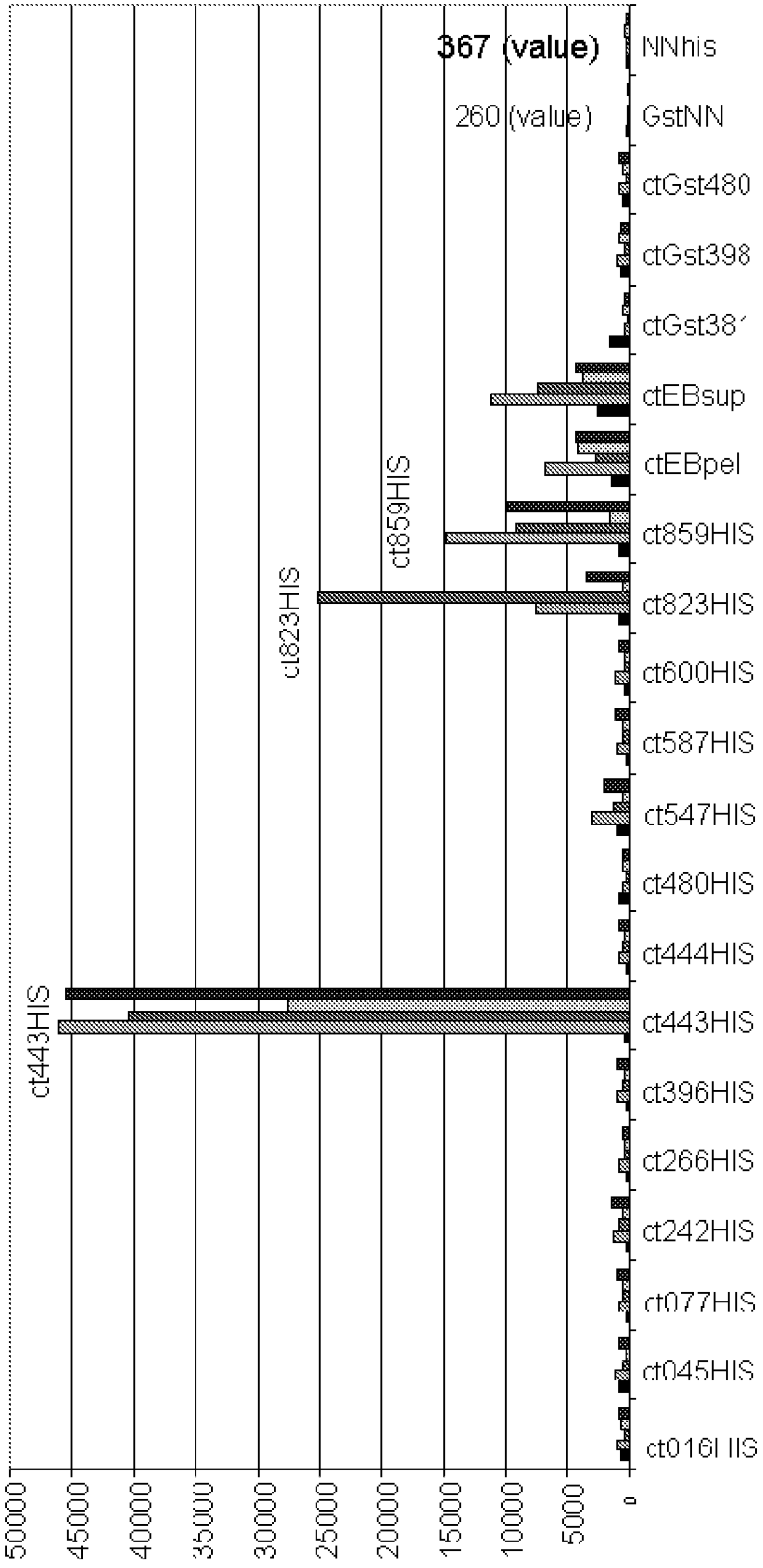
FIG. 10C shows antigens that give a high signal in a sign-bkg assay. The antigens are listed on the X axis and the signal is given on the Y axis. Chlamydial protein microchips were analysed by immunostaining with sera from mice that were (from left to right) i) never immunized (preimmune sera), ii) immunized with heat inactivated EBs (anti-heat inactivated EBs pre-challenge), iii) immunized with heat inactivated EBs and then challenged with live EBs (anti-heat inactivated EBs post-challenge), iv) immunised with live EBs (anti-live EBs pre-challenge); and v) immunised with live EBs and then re-challenged again with live EBs (anti-live EBs post-challenge). The antibodies are at a dilution of 1:100. Antigens giving a low signal of less than 800 are not shown. From left to right, the antigens are: CT016His, CT045His, CT077His, CT242His, CT266His, CT396His, CT443His, CT444His, CT480His, CT547His, CT587His, CT600His, CT823His, CT859His, ctEBpel ctEBsup, ctGst381, ctGst398, ctGst480, GstNN and NNhis.

FIG. 10C shows that the CT823 antigen is one of three antigens strongly recognized by sera from mice immunized with whole *C. trachomatis* EBs. This suggests that native CT823 is contained in EBs and in an amount that is sufficient to elicit an antibody response in mice.

Figure 10D:
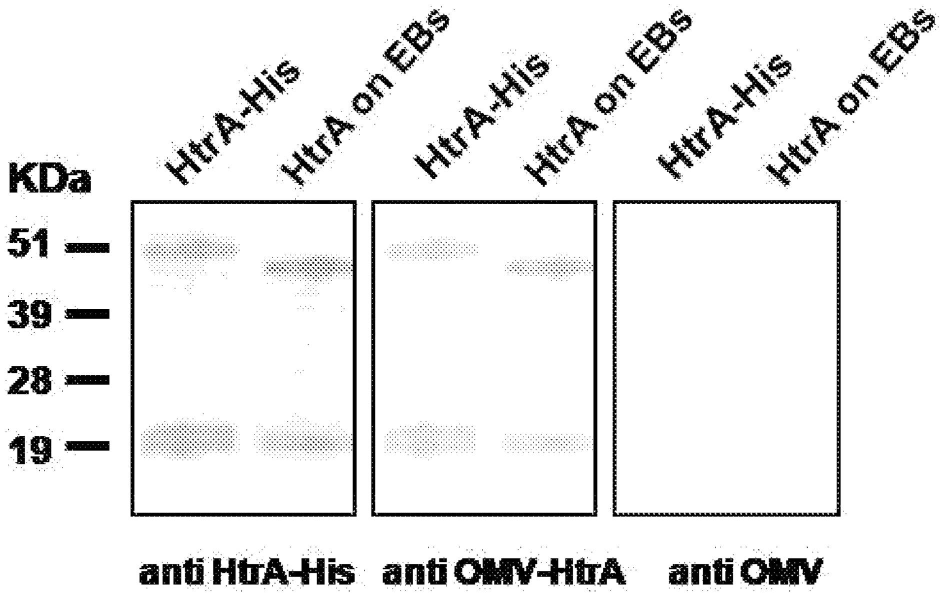
FIG. 10E shows a FACS analysis of antibody binding the surface of chlamydial whole cells. The peaks, from left to right correspond to purified *C. muridarum* EBs incubated with (i) anti-His sera (filled peak, far left), (ii) serum obtained from mice immunized with OMV preparation from BL21 (DE3)ΔTolR (peak second from left), (iii) serum obtained from mice immunized with TC210 (peak second from right), or (iv) BL21(DE3)ΔTolR TC0210 (far right peak).

Recombinant HtrA and the native HtrA contained in the *C. muridarum* EBs was also recognized by a mouse polyclonal antibody serum which has been prepared by immunizing mice with OMV preparation from BL21(DE3)ΔTolR TC0210 as shown by Western Blot in FIG. 10D.

Figure 10E:
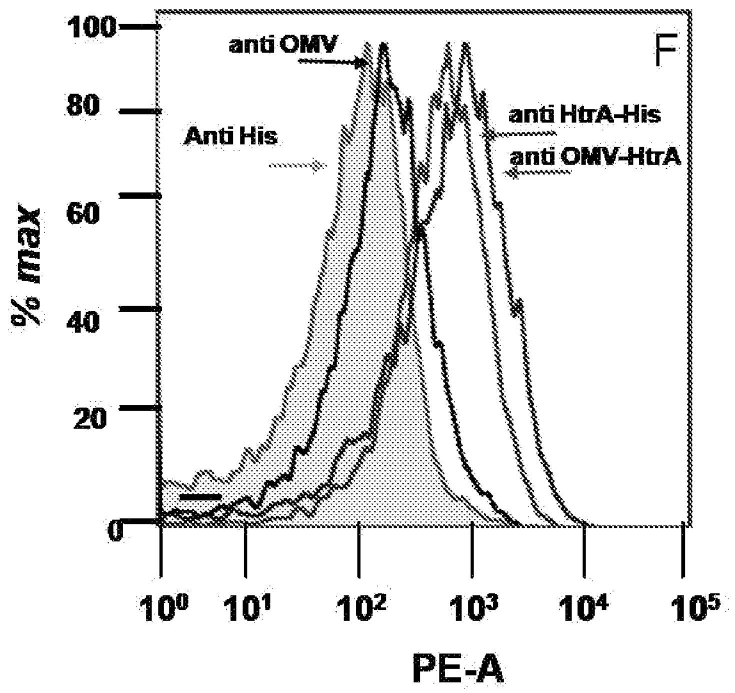

The FACS analysis described above for FIG. 10A, was repeated using mouse polyclonal antibody serum obtained from mice immunized with OMV preparation from BL21 (DE3)ΔTolR TC0210. Having previously demonstrated in FIG. 10A that flow cytometry can be used to follow antibody binding the surface of EBs, the data presented in FIG. 10E showed that the polyclonal antibodies raised against TC0210 in the context of the OMV were able to recognize the HtrA exposed on the *C. muridarum* EBs' surface (FIG. 10E).

Example 6

Immunization of BALB Mice with OMV-TC0210

Figure 11:
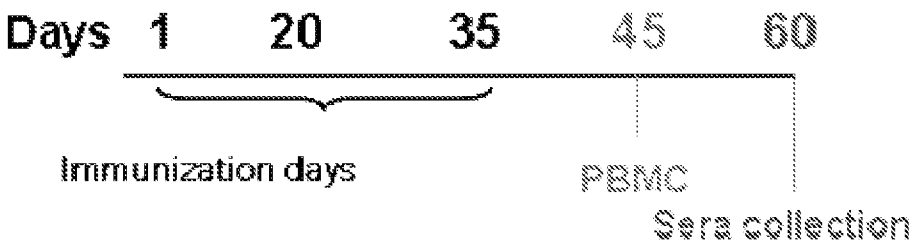
FIG. 11 is a schematic diagram of an immunisation protocol for BALB/c mice.

Mice were immunised according to the schedule shown in FIG. 11. Specifically, BALB mice (5/6 weeks old) were immunised intramuscularly at days 1, 20 and 35 before PBMC were taken at day 45 and sera collected at day 60. The mice were divided into 5 groups, with 12 mice for each group, and immunisation was carried out according to the following scheme: GROUP 1: PBS+Alum; GROUP 2: PBS+Alum+5 μg OMV preparation from *E. coli* BL21(DE3)ΔTolR; GROUP 3: PBS+Alum+5 μg OMV preparation from BL21 (DE3)ΔTolR TC0210; GROUP 4: PBS+Alum+50 mg OMV preparation from BL21(DE3)ΔTolR; and GROUP 5: PBS+ Alum+50 μg OMV preparation from BL21(DE3)ΔTolR TC0210.

Western Blot and ELISA Assay

Figure 13:
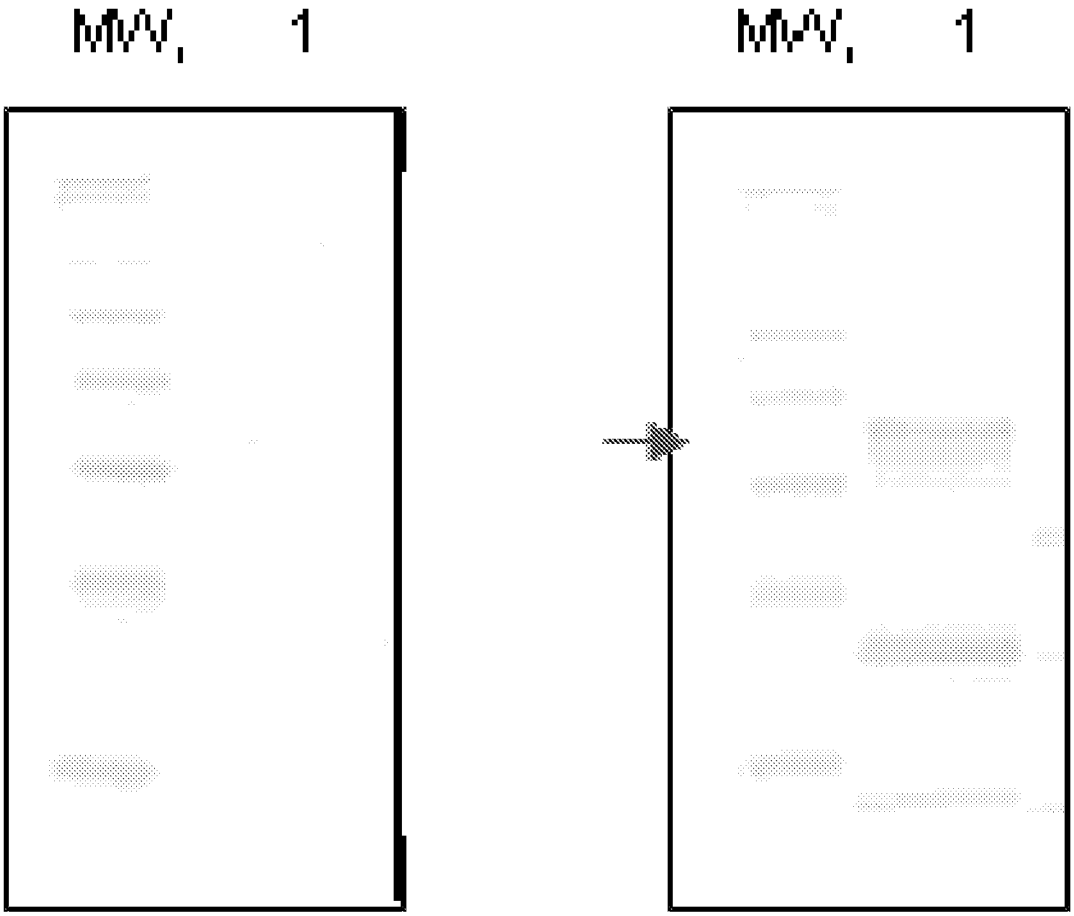
FIG. 13 is the results of two Western blots. The membranes were incubated with sera obtained by immunizing mice with PBS+alum+50 μg OMV preparation from *E. coli* BL21(DE3) ΔTolR (left Western blot) or PBS+alum+50 μg OMV preparation from *E. coli* BL21(DE3)ΔTolR-TC0210. In each Western blot, molecular weight markers are presented on the left hand side and lane 1 is loaded with 200 ng of TC0210His (53 kDa) purified protein. The arrow shows the band corresponding to the 53 kDa protein TC0210His.

Following immunisation of the mice, the mice sera were tested by Western blot analysis and ELISA in order to evaluate the production of anti-TC0210 antibodies. For each Western blot, the purified *C. muridarum* recombinant protein TC0210 was loaded. FIG. 13 shows that the sera of mice immunized with OMV preparations expressing TC0210 were able to recognize the recombinant protein, while the sera of mice immunized with OMV preparations without TC0210 were not.

Figure 14:
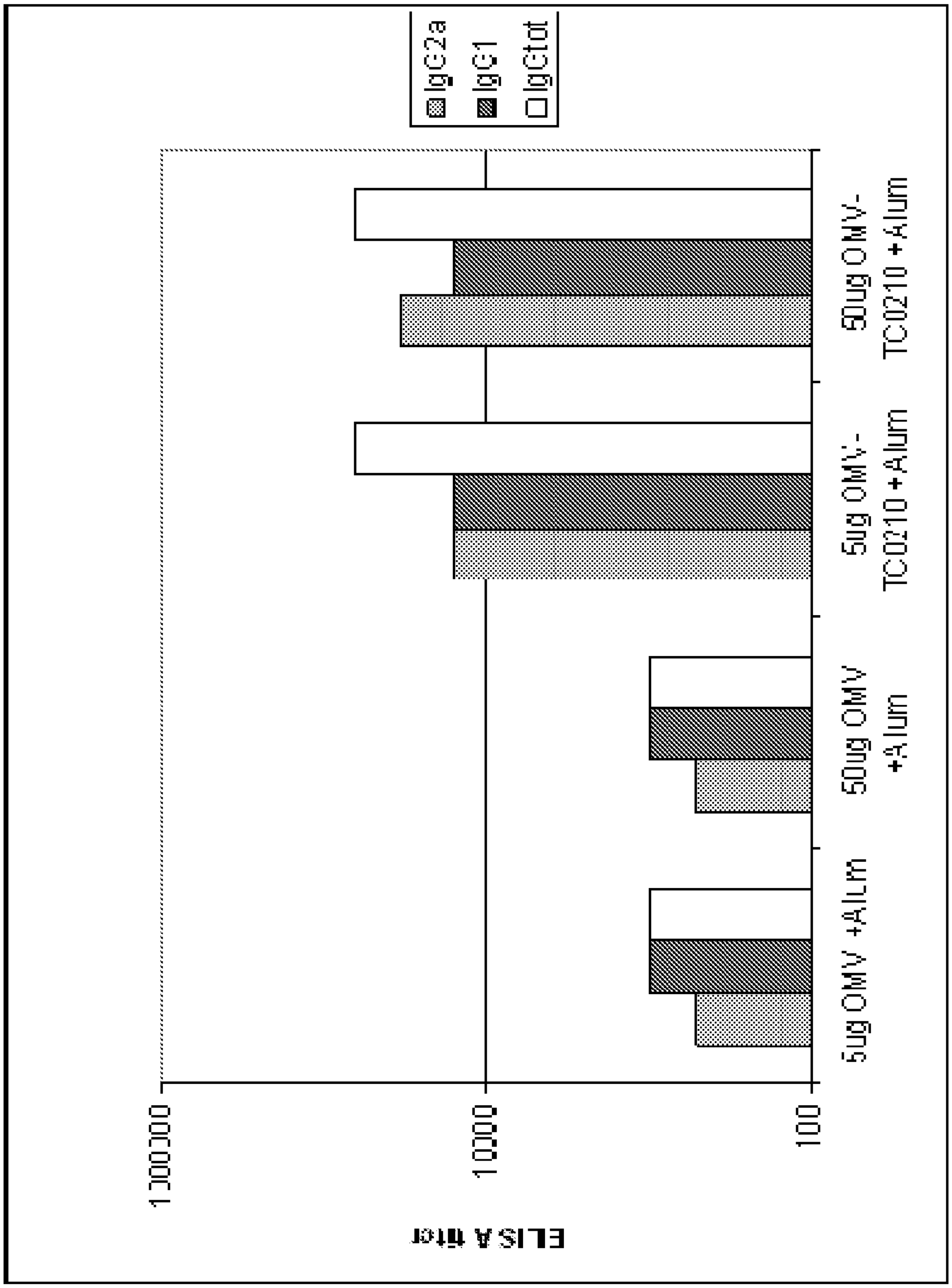
FIG. 14 is a bar chart showing the results of an ELISA assay. The four serum samples that were used are from mice immunised with (from left to right) 5 μg OMV+alum; 50 μg OMV+alum; 5 μg OMV-TC0210+alum; 50 μg OMV-TC0210+alum. Three results are provided for each serum sample as follows (from left to right): IgG2a, IgG1 and IgG-tot. ELISA titer is shown on the Y axis.

The ELISA results of FIG. 14 show that for mice immunised with 5 μg OMV-TC0210 (Group 3 mice), an equal amount of IgG1 and IgG2a antibodies were raised. However, for mice immunised with 50 μg OMV-TC0210 (Group 5 mice), more IgG2a than IgG1 antibodies were raised. The total amount of IgG antibodies raised was about the same in both cases. Thus, the 50 μg dose works better in terms of quality of elicited antibodies (as shown by the neutralization titer). More IgG antibodies were raised in mice immunised with OMVs expressing TC0210 than were raised in mice immunised with OMVs alone+Alum.

Neutralization of Infection with E.B. Of *C. muridarum.*

Figure 15:
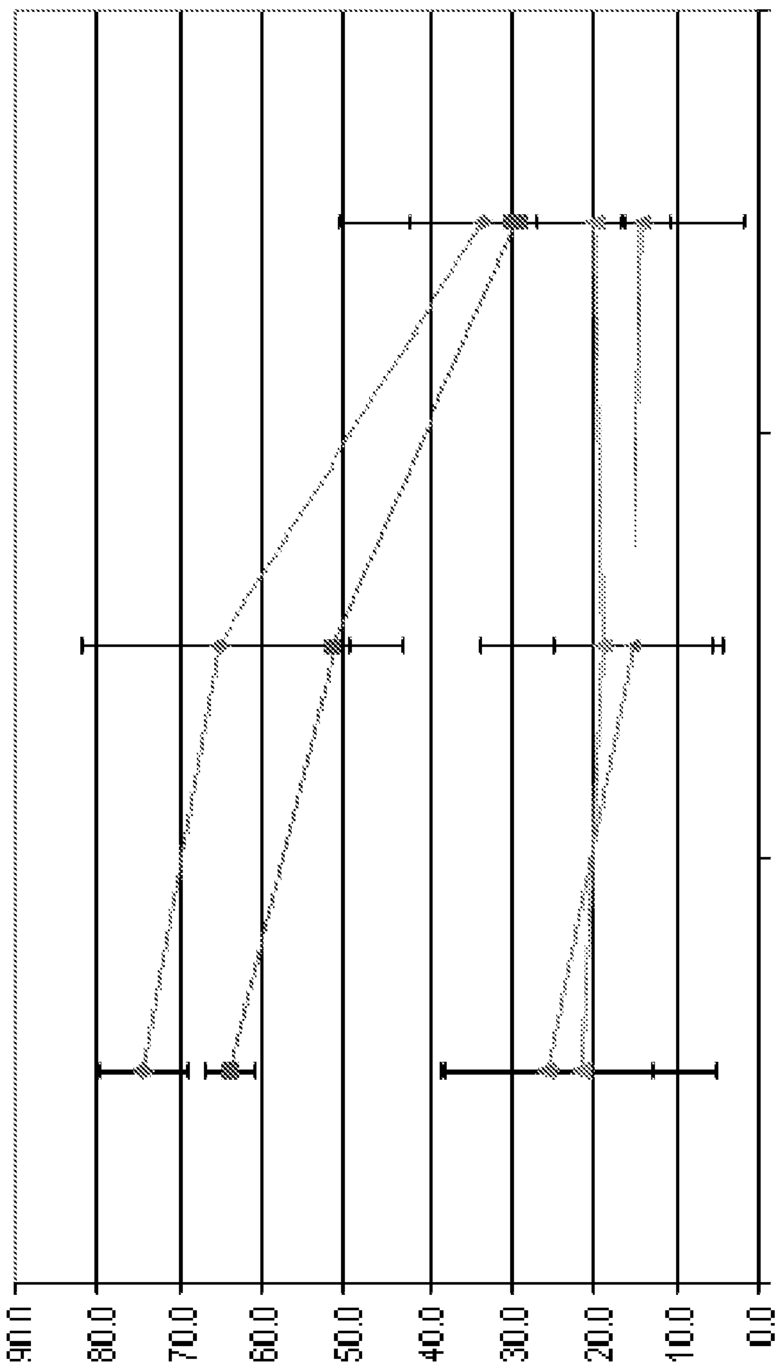
FIG. 15 is a graph showing the results of a *C. muridarum* neutralisation assay using sera of BALB/c mice that had been immunised with OMVs from *E. coli* BL21(DE3)ΔtolR presenting TC0210 (50 μg) (-■-); with purified recombinant TC0210His (20 μg) (-▲-), with MOMP (20 μg) (-◆-) and with the OMVs alone (50 μg) (-▲-). Results are the mean of 6 independent experiments. Serum dilution is presented along the X axis and % of neutralisation is presented on the Y axis.

There is much evidence to support an important role for neutralizing antibodies in the protection against *Chlamydia* infection. In order to evaluate this, a neutralization assay was performed using sera of immunized mice with the OMV preparation expressing the chlamydial antigen TC0210. The results are shown in FIG. 15, which shows the percentage of neutralization against infection with *C. muridarum* with respect to three different sera dilutions (mean of six independent experiments).

Sera of mice immunized with 50 μg OMVs expressing TC0210 (Group 5 mice) are able to neutralize in vitro *C. muridarum* infection with a titer of 1:90 (the neutralization titer is defined as the serum dilution able to reduce EB infection by 50%) (see (-■-) line). This sera is almost as potent at neutralising *C. muridarum* in vitro as the sera obtained by immunizing mice with purified recombinant MOMP (positive control—see the (-◆-) line). In contrast, sera of mice immunized with purified recombinant TC0210 are not able to neutralize the *C. muridarum* infection; in fact neutralization percentages are very low also at minimal serum dilution (1:30) (see the (-△-) line). The (-▲-) line shows the percentage of neutralization relative to OMV without chlamydial antigens. Thus, the neutralisation percentage for purified recombinant TC0210 is very similar for the neutralisation percentage obtained for OMV alone. These calculations have been done versus pre-immune sera. This is one of the first examples in which antibodies directed against a chlamydial antigen, other than MOMP, have been able to neutralize chlamydial infectivity in vitro. Surprisingly, these data show that the TC0210 antigen, which is not protective when tested in a chlamydial animal model when administered in its purified form, becomes protective when presented in an OMV of the invention.

Figure 12:
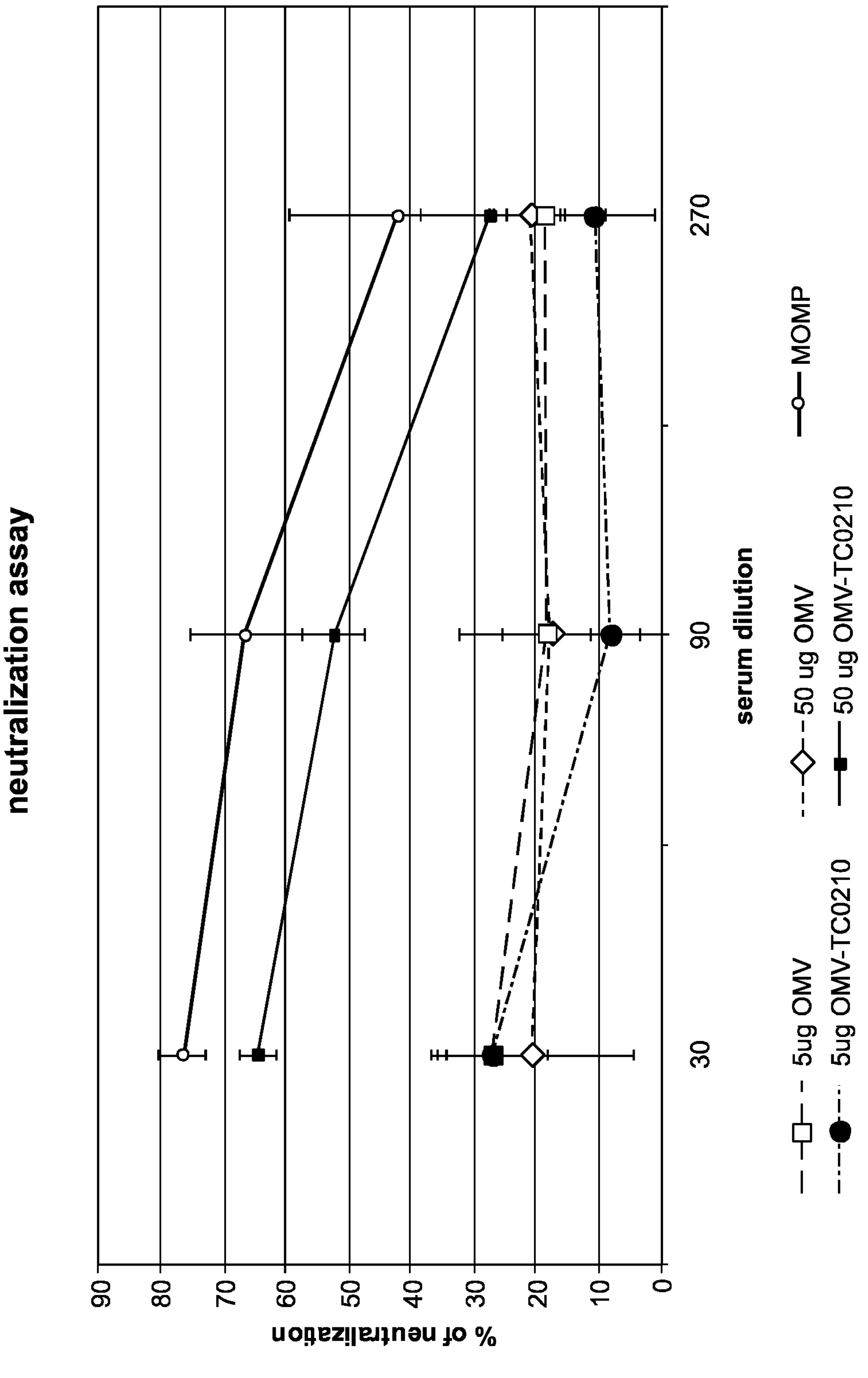
FIG. 12 is a graph showing the results of a *C. muridarum* neutralisation assay using sera of BALB/c mice that had been immunised with OMVs from *E. coli* BL21(DE3)ΔtolR presenting OMV (5 μg) (--□--), OMV-TC0210 (5 μg) (--●--), OMV (50 μg) (--◇--), OMV-TC0210 (50 μg) (-■-), and MOMP (-○-). Serum dilution is presented along the X axis and % of neutralisation is presented on the Y axis.

The neutralisation assay was repeated again and the results are shown in FIG. 12. The results in FIG. 12 support the findings discussed above.

Neutralization of Infection with E.B. Of *C. trachomatis.*

CT823 is the *C. trachomatis* homologous protein to TC0210. The ability of the anti OMV-TC0210 sera to neutralize in vitro infection by *Chlamydia trachomatis* was tested.

Figure 16:
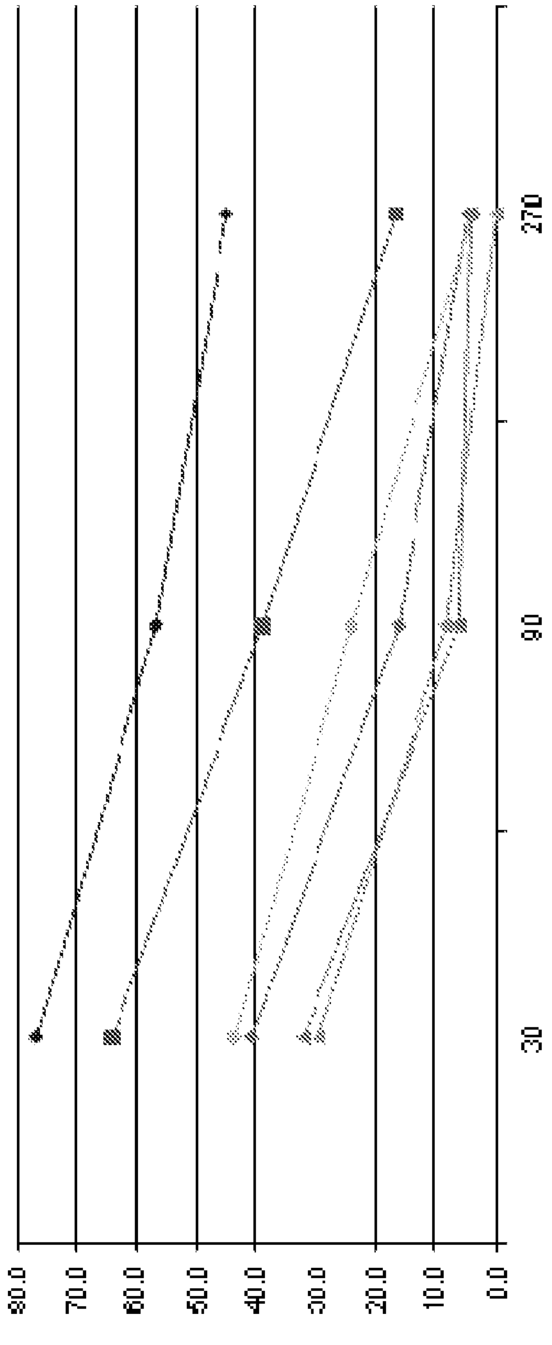
FIG. 16 is a graph showing the results of a *C. trachomatis* neutralisation assay using sera of BALB/c mice that had been immunised with: MOMP from *C. trachomatis* (20 μg) (-◆-); OMV-TC0210 (50 μg) (-■-); MOMP *C. muridarum* (20 μg) (-◆-); CT823-His (20 μg) (-●-); TC0210-His (20 μg) (-▲-) and OMV (50 μg) (-▲-). Serum dilution is presented on the X axis and % of neutralisation is presented on the Y axis. The results are the mean of two experiments.

Purified *C. trachomatis* EBs were incubated with mouse sera at three different dilutions at 37° C. for 30 min. Residual infectivity was determined on LLC-MK2 cells by counting IFU/cs. Neutralization percentages were measured in two independently performed neutralization assays and calculated versus preimmune sera FIG. 16 shows the results. Anti OMV-TC0210 mouse polyclonal serum (see (-■-) line) is able to neutralize *C. trachomatis* efficiently in vitro (with a similar titer observed by infecting with E.B. of *C. muridarum*). Indeed, anti-OMV-TC0210 mouse polyclonal serum was found to be almost as potent at neutralising *C. trachomatis* infectivity as the sera of mice immunised with MOMP from *C. trachomatis* (see the (-◆-) line, which is the positive control). The neutralizing percentage of this serum is also higher than that obtained after immunization with the homologue recombinant purified protein of *C. trachomatis*, CT823 (see (-●-) line). The (-◆-) line represents the neutralizing percentage of sera immunized with MOMP of *C. muridarum*; this serum does not neutralize the chlamydial infection. Likewise, sera of mice immunized with OMV (see (-▲-) line) or with TC0210His (see (-△-) line) did not neutralize the chlamydial infection. It was found that OMV-TC0210 specific-antibody neutralises *C. trachomatis* infection in vitro at the same level observed for *C. muridarum*. Thus, an immune response raised against the *C. muridarum* antigen may also neutralise infection against *C. trachomatis.*

Example 7

Immunization of CD1 Mice with OMV-TC0210

Figure 17A:
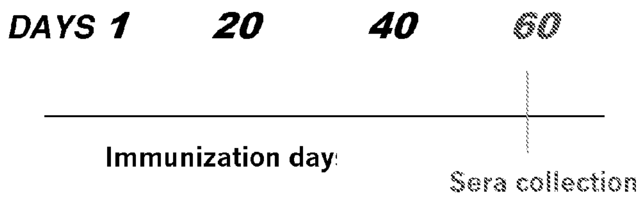
FIG. 17*a* is a schematic diagram of a CD1 mice immunization protocol.

In order to confirm the neutralization results of Example 6, immunization was repeated in CD1 mice (5-6 weeks old). Groups of CD1 mice (5 mice in each group) were immunised according to the following immunisation scheme: Group 1: 50 μg OMV+Alum; Group 2: 50 μg OMV-TC0210+Alum; Group 3: 20 μg TC0210His+50 μg OMV+Alum; Group 4: 1 μg TC0210His+50 μg OMV+Alum; Group 5: 1 μg TC0210His+Alum; Group 6: 20 μg TC0210His+Alum. The scheme was devised also to test whether there is an adjuvant effect of OMV (see Groups 3 and 4). Mice were immunized on days 1, 20 and 40. Sera were collected for the neutralization assay on day 60 (see FIG. 17A).

Immunogenicity Comparison Between TC0210 Expressed on the OMV and the Recombinant Form.

Western blots were performed using sera of mice immunized with 50 μg of OMV-TC0210 (Group 2) and sera of mice immunized with 1 μg of TC0210His plus 50 μg of OMV without chlamydial antigens (Group 4), in order to compare the immunogenicity between TC0210 expressed on the OMV and the recombinant form. The quantity of chlamydial antigen present on the *E. coli* OMV surface is estimated to be 1% of the total content of *E. coli* proteins (about 0.5 ug of chlamydial protein in 50 ug of OMVs).

Figure 17B:
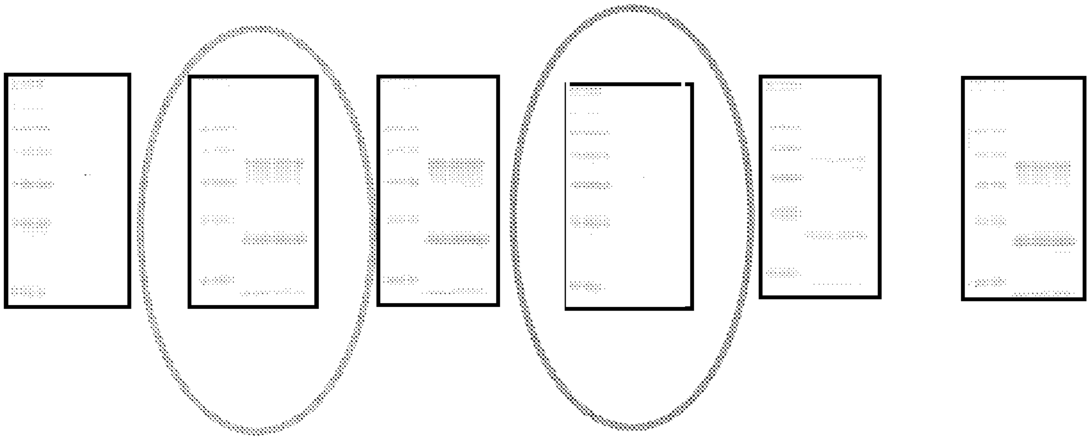
FIG. 17*b* is the results of 6 Western Blots in which 200 ng of purified TC0210His recombinant protein was loaded for each. From left to right, the membranes were incubated, respectively, with sera obtained from mice immunised with: Group 1 (50 μg OMV+alum); Group 2 (50 μg OMV-TC0210+alum); Group 3 (20 μg TC0210His+50 μg OMV+alum); Group 4 (1 μg TC0210His+50 μg OMV+alum); Group 5 (1 μg TC0210+alum) and Group 6 (20 μg TC0210His+alum)

The Western blot results of FIG. 17B show that sera of mice immunized with OMV-TC0210, or with TC0210-His, produce antibodies against the chlamydial antigen. However, as shown in FIG. 17B, following immunization of mice with a combination of 1 ug of TC0210-His plus 50 ug of OMV not expressing a chlamydial antigen, antibody production against TC0210 is not visible. In this case, 1 ug of TC0210His alone is immunogenic but 1 ug of recombinant protein TC0210-His in combination with OMV is not immunogenic. Thus, it seems that the presence of the separate OMVs inhibits the immunogenicity of the purified protein when 1 ug purified protein is used. However, the use of a lower concentration of protein (0.5 ug TC0210) expressed in the OMV system is immunogenic. The combination of 20 ug TC0210-His plus 50 ug OMV is suitable to elicit antibody production.

The Western Blot results of FIG. 17C further underline differences between sera produced by immunising with 50 ug OMV-TC210 and sera produced by immunising with 1 ug TC0210-His plus 50 ug OMV. The Western blot results of FIGS. 17B and 17C show that only sera of mice immunized with OMV-TC0210 produce antibodies against this antigen.

This suggests that the neutralizing effect elicited by sera obtained by immunising with OMV-TC0210 is not caused by an adjuvant effect of OMVs, but by the OMV's capability to present TC0210 in its natural conformation and composition.

ELISA Titers

Figure 18:
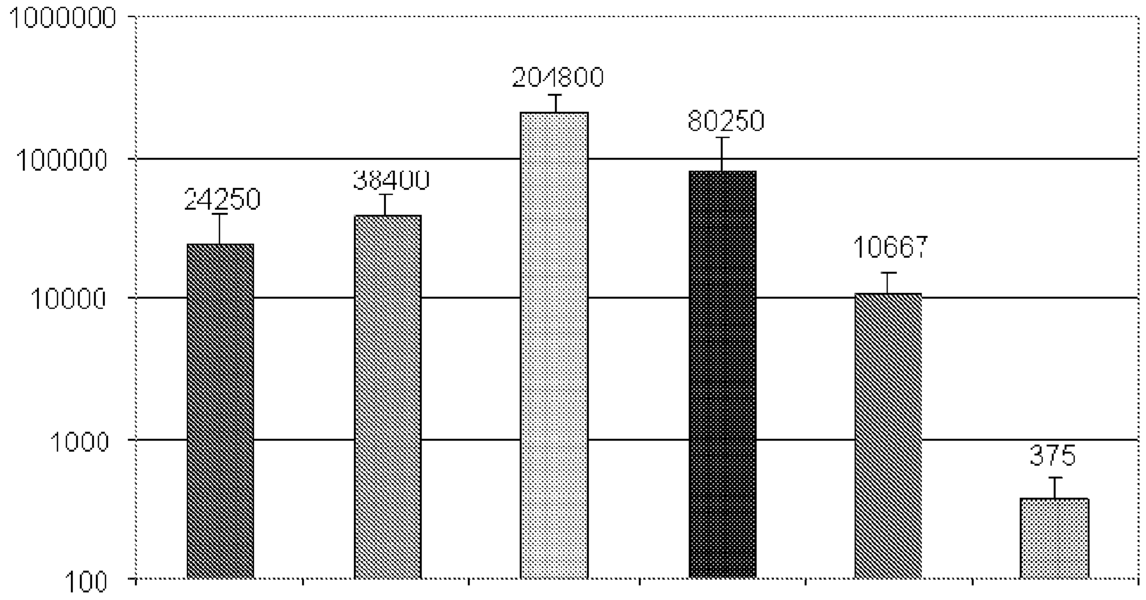
FIG. 18 is a bar chart showing the results of an ELISA assay. The ELISA titer is presented along the Y axis. The immunization groups are presented along the X axis. From left to right, the bars represent sera from mice immunised with: i) 50 μg OMV-TC0210+alum; ii) 20 μg TC0210His+50 μg OMV+alum; iii) 20 μg TC0210His+alum; 1 μg TC0210His+alum; 1 μg TC0210His+50 μg OMV+alum, vi) 50 μg OMV.

FIG. 18 shows the quantitative analysis of antibody production by ELISA. ELISA microplates were coated with 0.5 μg of TC0210His in PBS and stored at 4° C. overnight. Plates were saturated with PBS-1% BSA, and then antisera, at different serial dilutions in PBS-0.1% Tween, were added to the wells. Plates were then incubated with alkaline-phosphatase conjugated goat anti-mouse IgG (Sigma). After that 100 μl of PNPP (Sigma) were added to the samples. Optical densities were read at 405 nm and the serum-antibody titer was defined as the serum dilution yielding an OD value of 0.5. Total IgG titers of each mice group immunized with OMV expressing TC0210, or TC0210-His recombinant purified protein (1 μg or 50 μg) plus OMV, or with TC0210-His (1 μg or 50 μg) alone.

From left to right, the bars in FIG. 18 correspond to mice Groups 2, 3, 6, 5, 4 and 1, respectively.

Although antibody titres of sera from mice immunised with OMVs expressing TC0210 are lower than those obtained with TC0210His or with the same recombinant protein+OMVs, the antibodies that are present in sera from mice immunised with OMVs expressing TC0210 are better in terms of neutralizing activity (see below).

Although not yet investigated, it is reasonable that the ELISA results would have been different if *Chlamydia* EBs had been used for the coating, as these include TC0210 in its native conformation, instead of the recombinant protein as used in the present experiment. In fact, a coating with EBs would allow the detection of antibodies raised against conformational epitopes.

Neutralisation Assay

Figure 19:
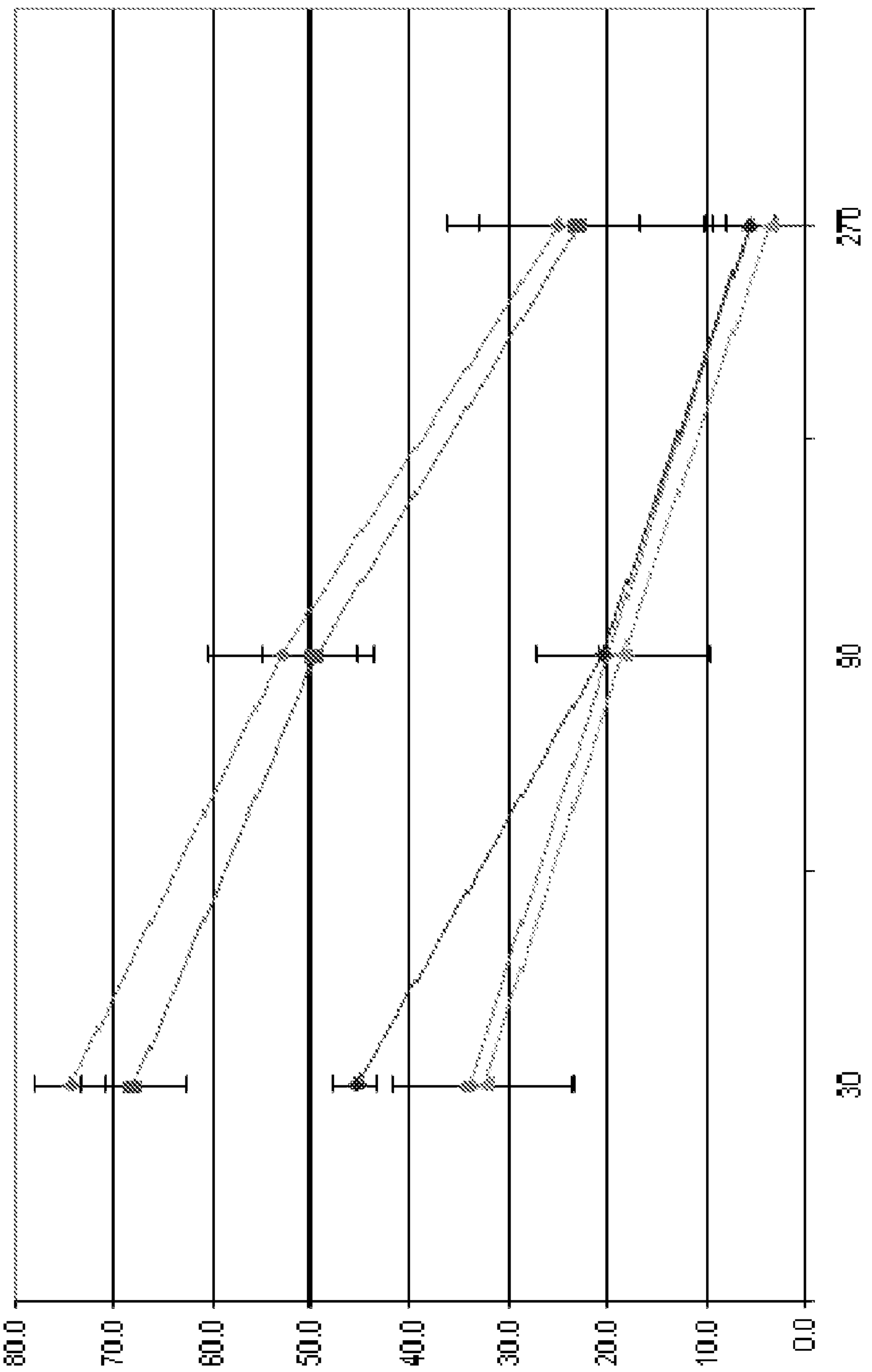
FIG. 19 is a graph showing the results of a *C. muridarum* neutralization assay using sera of CD1 mice that had been immunised with a) MOMP (20 μg); b) OMVs from *E. coli* BL21(DE3)ΔtolR presenting TC0210 (50 μg); c) OMVs from E. coli BL21(DE3)ΔtolR which do not express any heterologous antigens (50 μg); d) purified recombinant TC0210-His (20 μg); e) OMVs 50 μg plus TC0210HIS (1 μg). Serum dilution is presented along the X axis and % of neutralisation is presented along the Y axis. The results are the mean of 6 independent experiments.

FIG. 19 shows in vitro neutralization of *C. muridarum* infectivity on LL-CMK2 cells. Purified EBs were incubated with mouse sera at three different dilutions at 37° C. for 30 min. Residual infectivity was determined on LLC-MK2 cells by counting IFU/cs. Neutralization percentages were measured in six independently performed neutralization assays using sera from CD1 mice immunized with 50 ug of recombinant OMV expressing TC0210 (Group 2: -■-), with 20 μg of TC0210-His purified protein (Group 6: -○-). Sera of mice immunized with OMV alone (Group 1: -▲-) and with recombinant TC0210-His (1 μg) plus OMV alone (Group 4: -◆-), were included as negative controls, while sera of mice immunized with recombinant MOMP (-◆-) were used as the positive control. Data shown are the means and standard deviations of 12 samples.

Sera of mice immunized with OMV expressing TC0210 (-■-) were found to neutralize the Chlamydial muridarum infection as efficiently as MOMP (-◆-), while sera of mice immunized with OMV without chlamydial antigen or TC0210His do not.

Also the neutralization results indicate that OMVs do not have an adjuvant effect. Instead, the result is due to the capability of recombinant OMV-TC0210 to present the heterologous antigen in its natural conformation and composition.

Example 8

Epitope Mapping Analysis on TC0210

Epitope mapping experiments were performed in order to verify if there were some differences in terms of linear epitopes recognized between sera of mice immunized with OMV-TC0210 and sera of mice immunized with TC0210His. 95 overlapping synthetic peptides covering the full length of the TC0210 antigen were spotted on three membranes, respectively. Each peptide is constituted by 15 amino acids and overlaps 10 mers with the following peptide. On the three membranes, different sera pools were tested: sera of mice immunized a) with OMV expressing TC0210, b) with TC0210His, c) with OMV alone (sera of mice immunized with OMV without the chlamydial antigen were used as a negative control), respectively. An anti-mouse horseradish peroxidase conjugated IgG was used as the secondary antibody.

Figure 20:
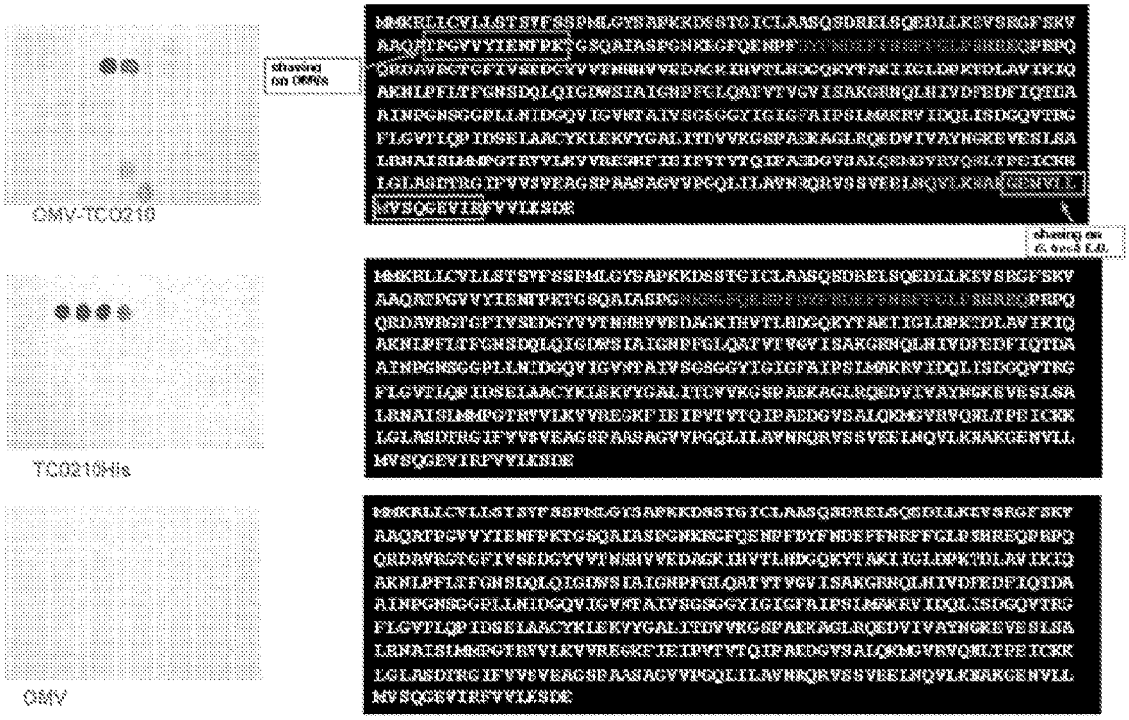
FIG. 20 shows the results of the epitope mapping experiment and shows the different epitopes of the TC0210 antigen (SEQ ID NO:19) that were recognised by sera of mice immunized with OMV-TC0210 (top), TC0210His (middle) or OMV (bottom)

FIG. 20 shows that sera of mice immunized with OMV expressing TC0210 (top membrane) recognize different epitopes compared to sera of mice immunized with TC0210 His recombinant purified protein (middle membrane). The sera of mice immunized with OMV-TC0210 recognised the following epitope with high specificity: DYFNDEFFNRFFGLP (SEQ ID NO: 36). The sera of mice immunised with OMV-TC0210 recognised the following epitopes with medium specificity: SHREQ (SEQ ID NO: 37), ALQKMGVRVQNLTPE (SEQ ID NO: 38) and NQVLKNAKGENVLLM (SEQ ID NO: 39). The sera of mice immunised with OMV-TC0210 recognised the following epitopes with low specificity: SPMLGYSAPKKDSSTGICLA (SEQ ID NO: 40); EDLLKEVSRGFSKVAAQATP (SEQ ID NO: 41); TGSQAIASPGNKRGFQENPF (SEQ ID NO: 42); PRPQQRDAVR (SEQ ID NO: 43), IAIGNPFGLQATVTVGVISAKGRNQLHIVD (SEQ ID NO: 44) and NTAIVSGSGGYIGIGFAIPSLMAKRVIDQL (SEQ ID NO:45).

Sera of mice immunised with TC0210His recognised the following epitope with high specificity: NKRGFQENPFDYFNDEFFNRFFGLP (SEQ ID NO: 84). Sera of mice immunised with TC0210His recognised the following epitope with medium specificity: SHREQ.

The epitope GENVLLMVSQGEVIR (SEQ ID NO: 55) indicated inside the box on the OMV-TC0210 membrane of FIG. 20 is the same epitope found in the shaving on the *C. trachomatis* E.B. (see GENVLLMVSQGDVVR (SEQ ID NO: 86 in present application), which corresponds to SEQ ID 43 from WO 2007/110700, Novartis Vaccines and Diagnostics, SRL), while the epitope TPGVVYIENFPK (SEQ ID NO: 85), indicated in the other box for the OMV-TC0210 membrane, is the same as the epitope found in the shaving on the OMV-TC0210 preparation that is described in Example 5.

It is hypothesized that sera produced by immunising with OMV-TC0210 and sera produced by immunising with TC0210 would be able to recognise the matching epitopes in CT823. Thus, it is hypothesised that the sera of mice immunized with OMV-TC0210 would presumably recognise the following CT823 epitope with high specificity: DYFNDEFFNRFFGLP (SEQ ID NO: 56). The sera of mice immunised with OMV-TC0210 would presumably recognise the following CT823 epitopes with medium specificity: SHREQ (SEQ ID NO: 57), ALQKMGVRVQNITPE (SEQ ID NO: 58) and NQVLKNSKGENVLLM (SEQ ID NO: 59). The sera of mice immunised with OMV-TC0210 would presumably recognise the following CT823 epitopes with low specificity: SPMLGYSASKKDSKADICLA (SEQ ID NO: 60), EDLLKEVSRGFSRVAAKATP (SEQ ID NO: 61), TGNQAIASPGNKRGFQENPF (SEQ ID NO: 62), IAIGNPFGLQATVTVGVISAKGRNQLHIVD (SEQ ID NO: 63) and NTAIVSGSGGYIGIGFAIPSLMAKRVIDQL (SEQ ID NO: 64). Sera of mice immunised with TC0210-His would presumably recognise the following CT823 epitope with high specificity: DYFNDEFFNRFFGLP. Sera of mice immunised with TC0210-His would presumably recognise the following CT823 epitope with medium specificity: SHREQ (SEQ ID NO: 57).

Example 9

Increasing the Quantity of Outer Membrane Proteins on the OMV

OmpA is involved in the structural maintenance of the membrane system. Probably for this reason, the absence of this protein destabilizes the bacterial outer membrane resulting in the release of an abundant quantity of OMV. Release of OMV in the culture supernatant of BL21(DE3)ΔompA mutant strain was observed here. The OMV preparation has been made as previously described and shown in the schematic diagram of FIG. 7. Shaving was performed on the OMVs in order to analyze their quality. The results are presented in FIG. 21. The 29 proteins (all outer membrane proteins) identified in the *E. coli* BL21(DE3)ΔompA OMV in the shaving and mass spectrometry analysis are: Hypothetical lipoprotein yiaD precursor [*Escherichia coli* CFT073], transport channel [*Escherichia coli* W3110], periplasmic chaperone [*Escherichia coli K*12], Putative toxin of osmotically regulated toxin-antitoxin system associated with programmed cell death [*Escherichia coli* cell death [*Escherichia coli* CFT073], murein lipoprotein [*Escherichia coli* K12], FKBP-type peptidyl-prolyl cis-trans isomerase (rotamase) [*Escherichia coli* K12], hypothetical protein b0177 [*Escherichia coli* K12], hypothetical protein ECP_0753 [*Escherichia coli* 536], maltoporin precursor [*Escherichia coli* K12], nucleoside channel, receptor of phage T6 and colicin K [*Escherichia coli* K12], peptidoglycan-associated outer membrane lipoprotein [*Escherichia coli* K12], Lipoprotein-34 precursor [*Escherichia coli* CFT073], scaffolding protein for murein synthesizing machinery [*Escherichia coli* K12], minor lipoprotein [*Escherichia coli* K12], predicted lipoprotein [*Escherichia coli* K12], Outer membrane lipoprotein slyB precursor [*Escherichia coli* CFT073], outer membrane protein X [*Escherichia coli* K12], maltose regulon periplasmic protein [*Escherichia coli* K12], maltose ABC transporter periplasmic protein [*Escherichia coli* K12], Hypothetical lipoprotein yajG precursor [*Escherichia coli* CFT073], long-chain fatty acid outer membrane transporter [*Escherichia coli* K12], Hypothetical protein ybaY precursor [*Escherichia coli* CFT073], predicted outer membrane lipoprotein [*Escherichia coli* K12], translocation protein TolB precursor [*Escherichia coli* K12], hypothetical protein b3147 [*Escherichia coli* K12], predicted iron outer membrane transporter [*Escherichia coli* K12], oligopeptide transporter subunit [*Escherichia coli* K12], hypothetical protein c4729 [*Escherichia coli* CFT073], hypothetical protein b1604 [*Escherichia coli* K12].

It was surprisingly found that all proteins present in this new OMV preparation are outer membrane proteins. This result underlines that the quality of the new OMV preparation is better than that obtained from the *E. coli* BL21(DE3)ΔtolR mutant strain, in which some cytoplasmic proteins were also found. Specifically, in the *E. coli* BL21(DE3)ΔtolR mutant strain, only about 75% of the 100 OMV proteins were outer membrane proteins.

Example 10

Expression of Chlamydial Antigens in the BL21(DE3)ΔompA Mutant Strain

Chlamydial antigens were expressed in the *E. coli* BL21 (DE3)ΔompA strain in order to verify if there is an increase in the quantity of chlamydial antigens in the derived recombinant OMV.

OMVs were prepared from culture supernatants of BL21 (DE3)ΔompA strain expressing TC0210 as previously described and shown in the schematic diagram of FIG. 4. Different amounts of each OMV preparation were loaded onto 4-12% polyacrylamide gel.

Figure 22:
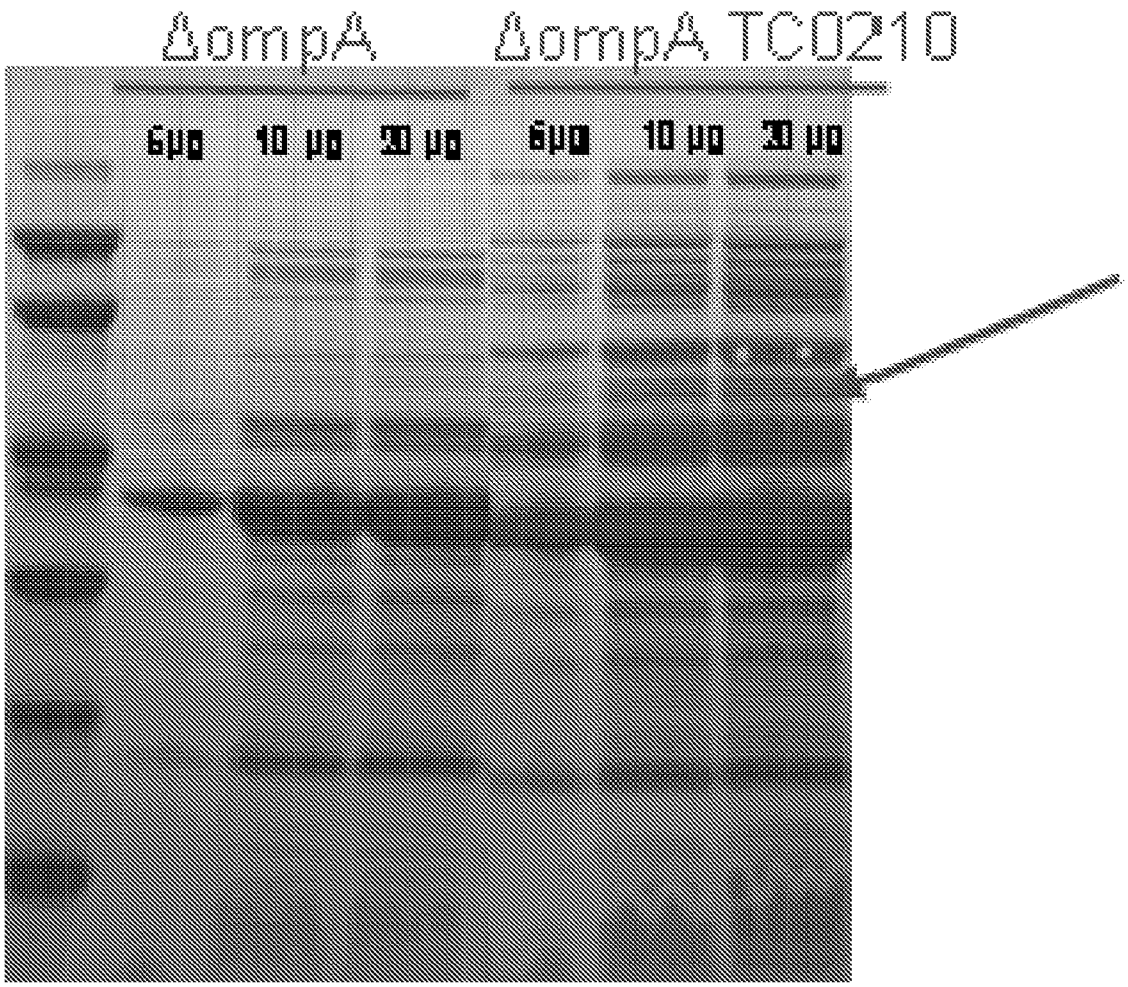
FIG. 22 is an SDS PAGE gel showing the protein content of E. coli BL21(DE3)ΔompA and the protein content of E. coli BL21(DE3)ΔompA expressing TC0210. The lanes were loaded with 5 μg, 10 μg and 20 μg, respectively. The TC0210 band is marked by the arrow.

As shown in FIG. 22, in these new OMV preparations from the BL21(DE3)ΔompA strain, it was possible to identify the presence of TC0210 directly on SDS PAGE (data confirmed by MASS spectrometry analysis—see the band indicated with the arrow on FIG. 22). The TC0210 band is clearly visible at all concentrations. In contrast, in OMV preparations obtained from the *E. coli* BL21(DE3)ΔtolR mutant strain, the presence of TC0210 was observed only by Western blot analysis. This confirms that the quantity of expressed TC0210 antigen is remarkably increased in the BL21(DE3)ΔompA strain relative to the BL21(DE3)ΔtolR mutant strain. Mass spectrometry confirmed the presence of the TC0210 peptide on the TC0210-OMV preparations (FIG. 23). The identified peptides are shown in bold. Specifically, the following peptides were identified:

```
                                   (SEQ ID NO: 46)
VAAQATPGVVYIENFPK,

                                   (SEQ ID NO: 47)
GFQENPFDYFNDEFFNRFFGLPSHREQPRPQQR,

                                   (SEQ ID NO: 48)
GTGFIVSEDGYVVTNHHVVEDAGK,

                                   (SEQ ID NO: 49)
TDLAVIKIQAK,

                                   (SEQ ID NO: 50)
VIDQLISDGQVTR,

                                   (SEQ ID NO: 51)
AGLRQEDVIVAYNGKEVESLSALR,

                                   (SEQ ID NO: 52)
FIEIPVTVTQIPAEDGVSALQK,

                                   (SEQ ID NO: 53)
VQNLTPEICK,
and

                                   (SEQ ID NO: 54)
NAKGENVLLMVSQGEVIR.
```

The inventors have surprisingly found that BL21(DE3) ΔompA mutant strains generate an increased quantity of heterologous antigen on their OMVs relative to OmpA wild type strains. OmpA is the most abundant protein on *E. coli* outer membrane. The inventors have found that, in the OMV, the deletion of this protein improves the relative abundance of chlamydial antigen with respect to the *E. coli* outer membrane proteins.

This increased amount of expressed chlamydial antigen suggests that OMVs from ΔompA strains, for example, BL21 (DE3)ΔompA-TC0210, are good candidates for raising neutralizing antibodies in mice.

It will be understood that the invention has been described by way of example only and modifications may be made whilst remaining within the scope and spirit of the invention.

SEQUENCE

SEQ ID NO: 1-CT823 protein sequence
MMKRLLCVLLSTSVFSSPMLGYSASKKDSKADICLAVSSGDQEVSQEDLLKEVSRGFSRVAAKATPGVVYI
ENFPKTGNQAIASPGNKRGFQENPFDYFNDEFFNRFFGLPSHREQQRPQQRDAVRGTGFIVSEDGYVVTNH
HVVEDAGKIHVTLHDGQKYTAKIVGLDPKTDLAVIKIQAEKLPFLTFGNSDQLQIGDWAIAIGNPFGLQAT
VTVGVISAKGRNQLHIVDFEDFIQTDAAINPGNSGGPLLNINGQVIGVNTAIVSGSGGYIGIGFAIPSLMA
KRVIDQLISDGQVTRGFLGVTLQPIDSELATCYKLEKVYGALVTDVVKGSPAEKAGLRQEDVIVAYNGKEV
ESLSALRNAISLMMPGTRVVLKIVREGKTIEIPVTVTQIPTEDGVSALQKMGVRVQNITPEICKKLGLAAD
TRGILVVAVEAGSPAASAGVAPGQLILAVNRQRVASVEELNQVLKNSKGENVLLMVSQGDVVRFIVLKSDE SEQ ID NO: 2-CT823 nucleotide sequence
ATGATGAAAAGATTATTATGTGTGTTGCTATCGACATCAGTTTTCTCTTCGCCAATGCTAGGCTATAGTGC
GTCAAAGAAAGATTCTAAGGCTGATATTTGTCTTGCAGTATCCTCAGGAGATCAAGAGGTTTCACAAGAAG
ATCTGCTCAAAGAAGTATCCCGAGGATTTTCTCGGGTCGCTGCTAAGGCAACGCCTGGAGTTGTATATATA
GAAAATTTTCCTAAAACAGGGAACCAGGCTATTGCTTCTCCAGGAAACAAAAGAGGCTTTCAAGAGAACCC
TTTTGATTATTTTAATGACGAATTTTTTAATCGATTTTTTGGATTGCCTTCGCATAGAGAGCAGCAGCGTC
CGCAGCAGCGTGATGCTGTAAGAGGAACTGGGTTCATTGTTTCTGAAGATGGTTATGTTGTTACTAACCAT
CATGTAGTCGAGGATGCAGGAAAAATTCATGTTACTCTCCACGACGGACAAAAATACACAGCTAAGATCGT
GGGGTTAGATCCAAAAACAGATCTTGCTGTGATCAAAATTCAAGCGGAGAAATTACCATTTTTGACTTTTG
GGAATTCTGATCAGCTGCAGATAGGTGACTGGGCTATTGCTATTGGAAATCCTTTTGGATTGCAAGCAACG
GTCACTGTCGGGGTCATTAGTGCTAAAGGAAGAAATCAGCTACATATTGTAGATTTCGAAGACTTTATTCA
AACAGATGCTGCCATTAATCCTGGGAATTCAGGCGGTCCATTGTTAAACATCAATGGTCAAGTTATCGGGG
TTAATACTGCCATTGTCAGTGGTAGCGGGGGATATATTGGAATAGGGTTTGCTATTCCTAGCTTGATGGCT
AAACGAGTCATTGATCAATTGATTAGTGATGGGCAGGTAACAAGAGGCTTTTTGGGAGTTACCTTGCAACC
GATAGATTCTGAATTGGCTACTTGTTACAAATTGGAAAAAGTGTACGGAGCTTTGGTGACGGATGTTGTTA
AAGGTTCTCCAGCAGAAAAAGCAGGGCTGCGCCAAGAAGATGTCATTGTGGCTTACAATGGAAAAGAAGTA
GAGTCTTTGAGTGCGTTGCGTAATGCCATTTCCCTAATGATGCCAGGGACTCGTGTTGTTTTAAAAATCGT
TCGTGAAGGGAAAACAATCGAGATACCTGTGACGGTTACACAGATCCCAACAGAGGATGGCGTTTCAGCGT
TGCAGAAGATGGGAGTCCGTGTTCAGAACATTACTCCAGAAATTTGTAAGAAACTCGGATTGGCAGCAGAT
ACCCGAGGGATTCTGGTAGTTGCTGTGGAGGCAGGCTCGCCTGCAGCTTCTGCAGGCGTCGCTCCTGGACA
GCTTATCTTAGCGGTGAATAGGCAGCGAGTCGCTTCCGTTGAAGAGTTAAATCAGGTTTTGAAAAACTCGA
AAGGAGAGAATGTTCTCCTTATGGTTTCTCAAGGAGATGTGGTGCGATTCATCGTCTTGAAATCAGACGAG
TAG SEQ ID NO: 3-CT733 nucleotide sequence
ATGTTAATAAACTTTACCTTTCGCAACTGTCTTTTGTTCCTTGTCACACTGTCTAGTGTCCCTGTTTTCTC
AGCACCTCAACCTCGCGGAACGCTTCCTAGCTCGACCACAAAAATTGGATCAGAAGTTTGGATTGAACAAA
AAGTCCGCCAATATCCAGAGCTTTTATGGTTAGTAGAGCCGTCCTCTACGGGAGCCTCTTTAAAATCTCCT
TCAGGAGCCATCTTTTCTCCAACATTATTCCAAAAAAAGGTCCCTGCTTTCGATATCGCAGTGCGCAGTTT
GATTCACTTACATTTATTAATCCAGGGTTCCCGCCAAGCCTATGCTCAACTGATCCAACTACAGACCAGCG
AATCCCCTCTAACATTTAAGCAATTCCTTGCATTGCATAAGCAATTAACTCTATTTTTAAATTCCCCTAAG
GAATTTTATGACTCTGTTAAAGTGTTAGAGACAGCTATCGTCTTACGTCACTTAGGCTGTTCAACTAAGGC
TGTTGCTGCGTTTAAACCTTATTTCTCAGAAATGCAAAGAGAGGCTTTTTACACTAAGGCTCTGCATGTAC
TACACACCTTCCCAGAGCTAAGCCCATCATTTGCTCGCCTCTCTCCGGAGCAGAAAACTCTCTTCTTCTCC
TTGAGAAAATTGGCGAATTACGATGAGTTACTCTCGCTGACGAACACCCCAAGTTTTCAGCTTCTGTCTGC
TGGGCGCTCGCAACGAGCTCTTTTAGCTCTGGACTTGTACCTCTATGCTTTGGATTCCTGTGGAGAACAGG
GGATGTCCTCTCAATTCCACACAAACTTCGCACCTCTACAGTCCATGTTGCAACAATACGCTACTGTAGAA
GAGGCCTTTTCTCGTTATTTTACTTACCGAGCTAATCGATTAGGATTTGATGGCTCTTCTCGATCCGAGAT
GGCTTTAGTAAGAATGGCCACCTTGATGAACTTGTCTCCTTCCGAAGCTGCGATTTTAACCACAAGCTTCA
AAACCCTTCCTACAGAAGAAGCGGATACTTTGATCAATAGTTTCTATACCAATAAGGGCGATTCGTTGGCT
CTTTCTCTGCGAGGGTTGCCTACACTTGTATCCGAACTGACGCGAACTGCCCATGGCAATACCAATGCAGA
AGCTCGATCTCAGCAAATTTATGCAACTACCCTATCGCTAGTAGTAAAGAGTCTGAAAGCGCACAAAGAAA
TGCTAAACAAGCAAATTCTTTCTAAGGAAATTGTTTTAGATTTCTCAGAAACTGCAGCTTCTTGCCAAGGA
TTGGATATCTTTTCCGAGAATGTCGCTGTTCAAATTCACTTAAATGGAACCGTTAGTATCCATTTATAA SEQ ID NO: 4-CT733 protein sequence
MLINFTFRNCLLFLVTLSSVPVFSAPQPRGTLPSSTTKIGSEVWIEQKVRQYPELLWLVEPSSTGASLKSP
SGAIFSPTLFQKKVPAFDIAVRSLIHLHLLIQGSRQAYAQLIQLQTSESPLTFKQFLALHKQLTLFLNSPK
EFYDSVKVLETAIVLRHLGCSTKAVAAFKPYFSEMQREAFYTKALHVLHTFPELSPSFARLSPEQKTLFFS
LRKLANYDELLSLTNTPSFQLLSAGRSQRALLALDLYLYALDSCGEQGMSSQFHTNFAPLQSMLQQYATVE
EAFSRYFTYRANRLGFDGSSRSEMALVRMATLMNLSPSEAAILTTSFKTLPTEEADTLINSFYTNKGDSLA
LSLRGLPTLVSELTRTAHGNTNAEARSQQIYATTLSLVVKSLKAHKEMLNKQILSKEIVLDFSETAASCQG
LDIFSENVAVQIHLNGTVSIHL SEQ ID NO: 5-CT153 nucleotide sequence
ATGACTAAGCCTTCTTTCTTATACGTTATTCAACCTTTTTCCGTATTTAATCCACGATTAGGACGTTTCTC
TACAGACTCAGATACTTATATCGAAGAAGAAAACCGCCTAGCATCGTTCATTGAGAGTTTGCCACTGGAGA
TCTTCGATATACCTTCTTTCATGGAAACCGCGATTTCCAATAGCCCCTATATTTTATCTTGGGAGACAACT
AAAGACGGCGCTCTGTTCACTATTCTTGAACCCAAACTCTCAGCTTGCGCAGCCACTTGCCTGGTAGCCCC
TTCTATACAAATGAAATCCGATGCGGAGCTCCTAGAAGAAATTAAGCAAGCGTTATTACGCAGCTCTCATG
ACGGTGTGAAATATCGCATCACCAGAGAATCCTTCTCTCCAGAAAAGAAAACTCCTAAGGTTGCTCTAGTC
GATGACGATATTGAATTGATTCGCAATGTCGACTTTTTGGGTAGAGCTGTTGACATTGTCAAATTAGACCC
TATTAATATTCTGAATACCGTAAGCGAAGAGAATATTCTAGATTACTCTTTTACAAGAGAAACGGCTCAGC
TGAGCGCGGATGGTCGTTTTGGTATTCCTCCAGGGACTAAGCTATTCCCTAAACCTTCTTTTGATGTAGAA
ATCAGTACCTCCATTTTCGAAGAAACAACTTCATTTACTCGAAGTTTTTCTGCATCGGTTACTTTTAGTGT
ACCAGACCTCGCGGCGACTATGCCTCTTCAAAGCCCTCCCATGGTAGAAAATGGTCAAAAAGAAATTTGTG
TCATTCAAAAACACTTATTCCCAAGCTACTCTCCTAAACTAGTCGATATTGTTAAACGATACAAAAGAGAG
GCTAAGATCTTGATTAACAAGCTTGCCTTTGGAATGTTATGGCGACATCGGGCTAAAAGCCAAATCCTCAC
CGAGGGAAGCGTACGTCTAGACTTACAAGGATTCACAGAATCGAAGTACAATTACCAGATTCAAGTAGGAT
CCCATACGATTGCAGCTGTATTAATCGATATGGATATTTCCAAGATTCAATCCAAATCAGAACAAGCTTAT -continued

| SEQUENCE |
|---|

GCAATTAGGAAAATCAAATCAGGCTTTCAACGTAGCTTGGATGACTATCATATTTATCAAATTGAAAGAAA
ACAAACCTTTTCTTTTTCTCCGAAGCATCGCAGCCTCTCATCCACATCCCATTCCGAAGATTCTGATTTGG
ATCTTTCTGAAGCAGCCGCCTTTTCAGGAAGTCTTACCTGCGAGTTTGTAAAAAAAAGCACTCAACATGCC
AAGAATACCGTCACATGTTCCACAGCCGCTCATTCCCTATACACACTCAAAGAAGATGACAGCTCGAACCC
CTCTGAAAAACGATTAGATAGTTGTTTCCGCAATTGGATTGAAAACAAACTAAGCGCCAATTCTCCAGATT
CCTGGTCAGCGTTTATTCAAAAATTCGGAACACACTATATTGCATCAGCAACTTTTGGAGGGATAGGTTTC
CAAGTGCTCAAACTATCTTTTGAACAGGTGGAGGATCTACATAGCAAAAAGATCTCCTTAGAAACCGCAGC
AGCCAACTCTCTATTAAAAGGTTCTGTATCCAGCAGCACAGAATCTGGATACTCCAGCTATAGCTCCACGT
CTTCTTCTCATACGGTATTTTTAGGAGGAACGGTCTTACCTTCGGTTCATGATGAACGTTTAGACTTTAAA
GATTGGTCGGAAAGTGTGCACCTGGAACCTGTTCCTATCCAGGTTTCTTTACAACCTATAACGAATTTACT
AGTTCCTCTCCATTTTCCTAATATCGGTGCTGCAGAGCTCTCTAATAAACGAGAATCTCTTCAACAAGCGA
TTCGAGTCTATCTCAAAGAACATAAAGTAGATGAGCAAGGAGAACGTACTACATTTACATCAGGAATCGAT
AATCCTTCTTCCTGGTTTACCTTAGAAGCTGCCCACTCTCCTCTTATAGTCAGTACTCCTTACATTGCTTC
GTGGTCTACGCTTCCTTATTTGTTCCCAACATTAAGAGAACGTTCTTCGGCAACCCCTATCGTTTTCTATT
TTGTGTAGATAATAATGAACATGCTTCGCAAAAAATATTAAACCAATCGTATTGCTTCCTCGGGTCCTTG
CCTATTCGACAAAAAATTTTTGGTAGCGAATTTGCTAGTTTCCCCTATCTATCTTTCTATGGAAATGCAAA
AGAGGCGTACTTTGATAACACGTACTACCCAACGCGTTGTGGGTGGATTGTTGAAAAGTTAAATACTACAC
AAGATCAATTCCTCCGGGATGGAGACGAGGTGCGACTAAAACATGTTTCCAGCGGAAAGTATCTAGCAACA
ACTCCTCTTAAGGATACCCATGGTACACTCACGCGTACAACGAACTGTGAAGATGCTATCTTTATTATTAA
AAAATCTTCAGGTTATTGA

SEQ ID NO: 6-CT153 protein sequence
MTKPSFLYVIQPFSVFNPRLGRFSTDSDTYIEEENRLASFIESLPLEIFDIPSFMETAISNSPYILSWETT
KDGALFTILEPKLSACAATCLVAPSIQMKSDAELLEEIKQALLRSSHDGVKYRITRESFSPEKKTPKVALV
DDDIELIRNVDFLGRAVDIVKLDPINILNTVSEENILDYSFTRETAQLSADGRFGIPPGTKLFPKPSFDVE
ISTSIFEETTSFTRSFSASVTFSVPDLAATMPLQSPPMVENGQKEICVIQKHLFPSYSPKLVDIVKRYKRE
AKILINKLAFGMLWRHRAKSQILTEGSVRLDLQGFTESKYNYQIQVGSHTIAAVLIDMDISKIQSKSEQAY
AIRKIKSGFQRSLDDYHIYQIERKQTFSFSPKHRSLSSTSHSEDSDLDLSEAAAFSGSLTCEFVKKSTQHA
KNTVTCSTAAHSLYTLKEDDSSNPSEKRLDSCFRNWIENKLSANSPDSWSAFIQKFGTHYIASATFGGIGF
QVLKLSFEQVEDLHSKKISLETAAANSLLKGSVSSSTESGYSSYSSTSSHTVFLGGTVLPSVHDERLDFK
DWSESVHLEPVPIQVSLQPITNLLVPLHFPNIGAAELSNKRESLQQAIRVYLKEHKVDEQGERTTFTSGID
NPSSWFTLEAAHSPLIVSTPYIASWSTLPYLFPTLRERSSATPIVFYFCVDNNEHASQKILNQSYCFLGSL
PIRQKIFGSEFASFPYLSFYGNAKEAYFDNTYYPTRCGWIVEKLNTTQDQFLRDGDEVRLKHVSSGKYLAT
TPLKDTHGTLTRTTNCEDAIFIIKKSSGY SEQ ID NO: 7-CT601 nucleotide sequence
ATGCTCGCTAATCGCTTATTCTTAATAACCCTTTTAGGGTTAAGTTCGTCTGTTTACGGCGCAGGTAAAGC
ACCGTCTTTGCAGGCTATTCTAGCCGAAGTCGAAGACACCTCCTCTCGTCTACACGCTCATCACAATGAGC
TTGCTATGATCTCTGAACGCCTCGATGAGCAAGACACGAAACTACAGCAACTTTCGTCAACACAAGATCAT
AACCTACCTCGACAAGTTCAGCGACTAGAAACGGACCAAAAAGCTTTGGCAAAAACACTGGCGATTCTTTC
GCAATCCGTCCAAGATATTCGGTCTTCTGTACAAAATAAATTACAAGAAATCCAACAAGAACAAAAAAAAT
TAGCACAAAATTTGCGAGCGCTTCGTAACTCTTTACAAGCTCTCGTTGATGGCTCTTCTCCAGAAAATTAT
ATTGATTTCCTAACTGGTGAAACCCCGGAACATATTCATATTGTTAAACAAGGAGAGACCCTGAGCAAGAT
CGCGAGTAAATATAACATCCCCGTCGTAGAATTAAAAAAACTTAATAAACTAAATTCGGATACTATTTTTA
CAGATCAAAGAATTCGCCTTCCGAAAAAGAAATAG SEQ ID NO: 8-CT601 protein sequence
MLANRLFLITLLGLSSSVYGAGKAPSLQAILAEVEDTSSRLHAHHNELAMISERLDEQDTKLQQLSSTQDH
NLPRQVQRLETDQKALAKTLAILSQSVQDIRSSVQNKLQEIQQEQKKLAQNLRALRNSLQALVDGSSPENY
IDFLTGETPEHIHIVKQGETLSKIASKYNIPVVELKKLNKLNSDTIFTDQRIRLPKKK SEQ ID NO: 9-CT279 nucleotide sequence
ATGGCATCCAAGTCTCGCCATTATCTTAATCAGCCTTGGTACATTATCTTATTCATCTTTGTTCTTAGTTT
AATTGCTGGTACCCTCCTGTCTTCTGTGTATTATGTCCTTGCACCTATCCAACAGCAAGCTGCGGAATTCG
ATCGCAATCAACAAATGCTAATGGCTGCACAAGTAATTTCTTCCGATAACACATTCCAAGTCTATGAAAAG
GGAGATTGGCACCCAGCCCTATATAATACTAAAAAGCAGTTGCTAGAGATCTCCTCTACTCCTCCTAAAGT
AACCGTGACAACTTTAAGCTCATATTTTCAAAACTTTGTTAGAGTCTTGCTTACAGATACACAAGGAAATC
TTTCTTCATTCGAAGACCATAATCTCAATCTAGAAGAATTTTTATCTCAACCAACTCCTGTAATACATGGT
CTTGCCCTTTATGTGGTCTACGCTATCCTACACAACGATGCAGCTTCCTCTAAATTATCTGCTTCCCAAGT
AGCGAAAAATCCAACAGCTATAGAATCTATAGTTCTTCCTATAGAAGGTTTTGGTTTGTGGGGACCTATCT
ATGGATTCCTTGCTCTAGAAAAAGACGGGAATACTGTTCTTGGTACTTCTTGGTATCAACATGGCGAGACT
CCTGGATTAGGAGCAAATATCGCTAACCCTCAATGGCAAAAAAATTTCAGAGGCAAAAAAGTATTTCTAGT
CTCAGCTTCTGGAGAAACAGATTTTGCTAAGACAACCCTAGGACTGGAAGTTATAAAAGGATCTGTATCTG
CAGCATTAGGAGACTCACCTAAAGCTGCTTCTTCCATCGACGGAATTTCAGGAGCTACTTTGACTTGTAAT
GGTGTTACCGAATCCTTCTCTCATTCTCTAGCTCCCTACCGCGCTTTGTTGACTTTCTTCGCCAACTCTAA
ACCTAGTGGAGAGTCTCATGACCACTAA SEQ ID NO: 10-CT279 protein sequence
MASKSRHYLNQPWYIILFIFVLSLIAGTLLSSVYYVLAPIQQQAAEFDRNQQMLMAAQVISSDNTFQVYEK
GDWHPALYNTKKQLLEISSTPPKVTVTTLSSYFQNFVRVLLTDTQGNLSSFEDHNLNLEEFLSQPTPVIHG
LALYVVYAILHNDAASSKLSASQVAKNPTAIESIVLPIEGFGLWGPIYGFLALEKDGNTVLGTSWYQHGET
PGLGANIANPQWQKNFRGKKVFLVSASGETDFAKTTLGLEVIKGSVSAALGDSPKAASSIDGISGATLTCN
GVTESFSHSLAPYRALLTFFANSKPSGESHDH SEQ ID NO:11-CT443 nucleotide sequence
ATGCGAATAGGAGATCCTATGAACAAACTCATCAGACGAGCAGTGACGATCTTCGCGGTGACTAGTGTGGC
GAGTTTATTTGCTAGCGGGGTGTTAGAGACCTCTATGGCAGAGTCTCTCTCTACAAACGTTATTAGCTTAG -continued

| SEQUENCE |
|---|
| CTGACACCAAAGCGAAAGACAACACTTCTCATAAAAGCAAAAAAGCAAGAAAAAAACCACAGCAAAGAGACT<br>CCCGTAGACCGTAAAGAGGTTGCTCCGGTTCATGAGTCTAAAGCTACAGGACCTAAACAGGATTCTTGCTT<br>TGGCAGAATGTATACAGTCAAAGTTAATGATGATCGCAATGTTGAAATCACACAAGCTGTTCCTGAATATG<br>CTACGGTAGGATCTCCCTATCCTATTGAAATTACTGCTACAGGTAAAAGGGATTGTGTTGATGTTATCATT<br>ACTCAGCAATTACCATGTGAAGCAGAGTTCGTACGCAGTGATCCAGCGACAACTCCTACTGCTGATGGTAA<br>GCTAGTTTGGAAAATTGACCGCTTAGGACAAGGCGAAAAGAGTAAAATTACTGTATGGGTAAAACCTCTTA<br>AAGAAGGTTGCTGCTTTACAGCTGCAACAGTATGCGCTTGTCCAGAGATCCGTTCGGTTACAAAATGTGGA<br>CAACCTGCTATCTGTGTTAAACAAGAAGGCCCAGAGAATGCTTGTTTGCGTTGCCCAGTAGTTTACAAAAT<br>TAATATAGTGAACCAAGGAACAGCAACAGCTCGTAACGTTGTTGTTGAAAATCCTGTTCCAGATGGTTACG<br>CTCATTCTTCTGGACAGCGTGTACTGACGTTTACTCTTGGAGATATGCAACCTGGAGAGCACAGAACAATT<br>ACTGTAGAGTTTTGTCCGCTTAAACGTGGTCGTGCTACCAATATAGCAACGGTTTCTTACTGTGGAGGACA<br>TAAAAATACAGCAAGCGTAACAACTGTGATCAACGAGCCTTGCGTACAAGTAAGTATTGCAGGAGCAGATT<br>GGTCTTATGTTTGTAAGCCTGTAGAATATGTGATCTCCGTTTCCAATCCTGGAGATCTTGTGTTGCGAGAT<br>GTCGTCGTTGAAGACACTCTTTCTCCCGGAGTCACAGTTCTTGAAGCTGCAGGAGCTCAAATTTCTTGTAA<br>TAAAGTAGTTTGGACTGTGAAAGAACTGAATCCTGGAGAGTCTCTACAGTATAAAGTTCTAGTAAGAGCAC<br>AAACTCCTGGACAATTCACAAATAATGTTGTTGTGAAGAGCTGCTCTGACTGTGGTACTTGTACTTCTTGC<br>GCAGAAGCGACAACTTACTGGAAAGGAGTTGCTGCTACTCATATGTGCGTAGTAGATACTTGTGACCCTGT<br>TTGTGTAGGAGAAAATACTGTTTACCGTATTTGTGTCACCAACAGAGGTTCTGCAGAAGATACAAATGTTT<br>CTTTAATGCTTAAATTCTCTAAAGAACTGCAACCTGTATCCTTCTCTGGACCAACTAAAGGAACGATTACA<br>GGCAATACAGTAGTATTCGATTCGTTACCTAGATTAGGTTCTAAAGAAACTGTAGAGTTTTCTGTAACATT<br>GAAAGCAGTATCAGCTGGAGATGCTCGTGGGGAAGCGATTCTTTCTTCCGATACATTGACTGTTCCAGTTT<br>CTGATACAGAGAATACACACATCTATTAA |
| SEQ ID NO: 12-CT443 protein sequence<br>MRIGDPMNKLIRRAVTIFAVTSVASLFASGVLETSMAESLSTNVISLADTKAKDNTSHKSKKARKNHSKET<br>PVDRKEVAPVHESKATGPKQDSCFGRMYTVKVNDDRNVEITQAVPEYATVGSPYPIEITATGKRDCVDVII<br>TQQLPCEAEFVRSDPATTPTADGKLVWKIDRLGQGEKSKITVWVKPLKEGCCFTAATVCACPEIRSVTKCG<br>QPAICVKQEGPENACLRCPVVYKINIVNQGTATARNVVVENPVPDGYAHSSGQRVLTFTLGDMQPGEHRTI<br>TVEFCPLKRGRATNIATVSYCGGHKNTASVTTVINEPCVQVSIAGADWSYVCKPVEYVISVSNPGDLVLRD<br>VVVEDTLSPGVTVLEAAGAQISCNKVVWTVKELNPGESLQYKVLVRAQTPGQFTNNVVVKSCSDCGTCTSC<br>AEATTYWKGVAATHMCVVDTCDPVCVGENTVYRICVTNRGSAEDTNVSLMLKFSKELQPVSFSGPTKGTIT<br>GNTVVFDSLPRLGSKETVEFSVTLKAVSAGDARGEAILSSDTLTVPVSDTENTHIY |
| SEQ ID NO: 13-CT372 nucleotide sequence<br>ATGCAGGCTGCACACCATCACTATCACCGCTACACAGATAAACTGCACAGACAAAACCATAAAAAAGATCT<br>CATCTCTCCCAAACCTACCGAACAAGAGGCGTGCAATACTTCTTCCCTTAGTAAGGAATTAATCCCTCTAT<br>CAGAACAAAGAGGCCTTTTATCCCCCATCTGTGACTTTATTTCGGAACGCCCTTGCTTACACGGAGTTTCT<br>GTTAGAAATCTCAAGCAAGCGCTAAAAAATTCTGCAGGAACCCAAATTGCACTGGATTGGTCTATTCTCCC<br>TCAATGGTTCAATCCTCGGGTCTCTCATGCCCCTAAGCTTTCTATCCGAGACTTTGGGTATAGCGCACACC<br>AAACTGTTACCGAAGCCACTCCTCCTTGCTGGCAAAACTGCTTTAATCCATCTGCGGCCGTTACTATCTAT<br>GATTCCTCATATGGGAAAGGGGTCTTTCAAATATCCTATACCCTTGTCCGCTATTGGAGAGAGAATGCTGC<br>GACTGCTGGCGATGCTATGATGCTCGCAGGGAGTATCAATGATTATCCCTCTCGTCAGAACATTTTCTCTC<br>AGTTTACTTTCTCCCAAAACTTCCCAAATGAACGGGTGAGTCTGACAATTGGTCAGTACTCACTCTATGCA<br>ATAGACGGAACATTATACAATAACGATCAACAACTTGGATTCATTAGTTACGCATTATCACAAAATCCAAC<br>AGCAACTTATTCCTCTGGAAGTCTTGGAGCTTACCTACAAGTCGCTCCTACCGCAAGCACAAGTCTTCAAA<br>TAGGATTTCAAGACGCTTATAATATCTCCGGATCCTCTATCAAATGGAGTAACCTTACAAAAAATAGATAC<br>AATTTTCACGGTTTTGCTTCCTGGGCTCCCCGCTGTTGCTTAGGATCTGGCCAGTACTCCGTGCTTCTTTA<br>TGTGACTAGACAAGTTCCAGAACAGATGGAACAAACAATGGGATGGTCAGTCAATGCGAGTCAACACATAT<br>CTTCTAAACTGTATGTGTTTGGAAGATACAGCGGTGTTACAGGACATGTGTTCCCGATTAACCGCACGTAT<br>TCATTCGGTATGGCCTCTGCAAATTTATTTAACCGTAACCCACAAGATTTATTTGGAATTGCTTGCGCATT<br>CAATAATGTACACCTCTCTGCTTCTCCAAATACTAAAAGAAAATACGAAACTGTAATCGAAGGGTTTGCAA<br>CTATCGGTTGCGGCCCCTATCTTTCTTTCGCTCCAGACTTCCAACTCTACCTCTACCCAGCTCTTCGTCCA<br>AACAAACAATCTGCCCGTGTTTATAGCGTGCGAGCTAATTTAGCTATCTAA |
| SEQ ID NO: 14-CT372 protein sequence<br>MQAAHHHYHRYTDKLHRQNHKKDLISPKPTEQEACNTSSLSKELIPLSEQRGLLSPICDFISERPCLHGVS<br>VRNLKQALKNSAGTQIALDWSILPQWFNPRVSHAPKLSIRDFGYSAHQTVTEATPPCWQNCFNPSAAVTIY<br>DSSYGKGVFQISYTLVRYWRENAATAGDAMMLAGSINDYPSRQNIFSQFTFSQNFPNERVSLTIGQYSLYA<br>IDGTLYNNDQQLGFISYALSQNPTATYSSGSLGAYLQVAPTASTSLQIGFQDAYNISGSSIKWSNLTKNRY<br>NFHGFASWAPRCCLGSGQYSVLLYVTRQVPEQMEQTMGWSVNASQHISSKLYVFGRYSGVTGHVFPINRTY<br>SFGMASANLFNRNPQDLFGIACAFNNVHLSASPNTKRKYETVIEGFATIGCGPYLSFAPDFQLYLYPALRP<br>NKQSARVYSVRANLAI |
| SEQ ID NO: 15: CT043 nucleotide sequence<br>ATGTCCAGGCAGAATGCTGAGGAAAATCTAAAAAATTTTGCTAAAGAGCTTAAACTCCCCGACGTGGCCTT<br>CGATCAGAATAATACGTGCATTTTGTTTGTTGATGGAGAGTTTTCTCTTCACCTGACCTACGAAGAACACT<br>CTGATCGCCTTTATGTTTACGCACCTCTTCTTGACGGACTGCCAGACAATCCGCAAAGAAGGTTAGCTCTA<br>TATGAGAAGTTGTTAGAAGGCTCTATGCTCGGAGGCCAAATGGCTGGTGGAGGGGTAGGAGTCGCTACTAA<br>GGAACAGTTGATCTTAATGCACTGCGTGTTAGACATGAAGTATGCAGAGACCAACCTACTCAAAGCTTTTG<br>CACAGCTTTTTATTGAAACCGTTGTGAAATGGCGAACTGTTTGTTCTGATATCAGCGCTGGACGAGAACCC<br>ACTGTTGATACCATGCCACAAATGCCTCAAGGGGGTGGCGGAGGAATTCAACCTCCTCCAGCAGGAATCCG<br>TGCATAA |
| SEQ ID NO: 16: CT043 protein sequence<br>MSRQNAEENLKNFAKELKLPDVAFDQNNTCILFVDGEFSLHLTYEEHSDRLYVYAPLLDGLPDNPQRRLAL<br>YEKLLEGSMLGGQMAGGGVGVATKEQLILMHCVLDMKYAETNLLKAFAQLFIETVVKWRTVCSDISAGREP<br>TVDTMPQMPQGGGGGIQPPPAGIRA |

-continued

| SEQUENCE |
|---|

SEQ ID NO: 17-CT681 protein sequence
MKKLLKSVLVFAALSSASSLQALPVGNPAEPSLMIDGILWEGFGGDPCDPCATWCDAISMRVGYYGDFVFD
RVLKTDVNKEFQMGAKPTTDTGNSAAPSTLTARENPAYGRHMQDAEMFTNAACMALNIWDRFDVFCTLGAT
SGYLKGNSASFNLVGLFGDNENQKTVKAESVPNMSFDQSVVELYTDTTFAWSVGARAALWECGCATLGASF
QYAQSKPKVEELNVLCNAAEFTINKPKGYVGKEFPLDLTAGTDAATGTKDASIDYHEWQASLALSYRLNMF
TPYIGVKWSRASFDADTIRIAQPKSATAIFDTTTLNPTIAGAGDVKTGAEGQLGDTMQIVSLQLNKMKSRK
SCGIAVGTTIVDADKYAVTVETRLIDERAAHVNAQFRF SEQ ID NO: 18-CT681 nucleotide sequence
ATGAAAAAACTCTTGAAATCGGTATTAGTATTTGCCGCTTTGAGTTCTGCTTCCTCCTTGCAAGCTCTGCC
TGTGGGGAATCCTGCTGAACCAAGCCTTATGATCGACGGAATTCTGTGGGAAGGTTTCGGCGGAGATCCTT
GCGATCCTTGCGCCACTTGGTGTGACGCTATCAGCATGCGTGTTGGTTACTACGGAGACTTTGTTTTCGAC
CGTGTTTTGAAAACAGATGTGAATAAAGAATTTCAGATGGGTGCCAAGCCTACAACTGATACAGGCAATAG
TGCAGCTCCATCCACTCTTACAGCAAGAGAGAATCCTGCTTACGGCCGACATATGCAGGATGCTGAGATGT
TTACAAATGCCGCTTGCATGGCATTGAATATTTGGGATCGTTTTGATGTATTCTGTACATTAGGAGCCACC
AGTGGATATCTTAAAGGAAACTCTGCTTCTTTCAATTTAGTTGGATTGTTTGGAGATAATGAAAATCAAAA
AACGGTCAAAGCGGAGTCTGTACCAAATATGAGCTTTGATCAATCTGTTGTTGAGTTGTATACAGATACTA
CTTTTGCGTGGAGCGTCGGCGCTCGCGCAGCTTTGTGGGAATGTGGATGTGCAACTTTAGGAGCTTCATTC
CAATATGCTCAATCTAAACCTAAAGTAGAAGAATTAAACGTTCTCTGCAATGCAGCAGAGTTTACTATTAA
TAAACCTAAAGGGTATGTAGGTAAGGAGTTTCCTCTTGATCTTACAGCAGGAACAGATGCTGCGACAGGAA
CTAAGGATGCCTCTATTGATTACCATGAATGGCAAGCAAGTTTAGCTCTCTCTTACAGACTGAATATGTTC
ACTCCCTACATTGGAGTTAAATGGTCTCGAGCAAGCTTTGATGCCGATACGATTCGTATAGCCCAGCCAAA
ATCAGCTACAGCTATTTTTGATACTACCACGCTTAACCCAACTATTGCTGGAGCTGGCGATGTGAAAACTG
GCGCAGAGGGTCAGCTCGGAGACACAATGCAAATCGTTTCCTTGCAATTGAACAAGATGAAATCTAGAAAA
TCTTGCGGTATTGCAGTAGGAACAACTATTGTGGATGCAGACAAATACGCAGTTACAGTTGAGACTCGCTT
GATCGATGAGAGAGCAGC SEQ ID NO: 19-TC0210 protein sequence
MMKRLLCVLLSTSVFSSPMLGYSAPKKDSSTGICLAASQSDRELSQEDLLKEVSRGFSKVAAQATPGVVYI
ENFPKTGSQAIASPGNKRGFQENPFDYFNDEFFNRFFGLPSHREQPRPQQRDAVRGTGFIVSEDGYVVTNH
HVVEDAGKIHVTLHDGQKYTAKIIGLDPKTDLAVIKIQAKNLPFLTFGNSDQLQIGDWSIAIGNPFGLQAT
VTVGVISAKGRNQLHIVDFEDFIQTDAAINPGNSGGPLLNIDGQVIGVNTAIVSGSGGYIGIGFAIPSLMA
KRVIDQLISDGQVTRGFLGVTLQPIDSELAACYKLEKVYGALITDVVKGSPAEKAGLRQEDVIVAYNGKEV
ESLSALRNAISLMMPGTRVVLKVVREGKFIEIPVTVTQIPAEDGVSALQKMGVRVQNLTPEICKKLGLASD
TRGIFVVSVEAGSPAASAGVVPGQLILAVNRQRVSSVEELNQVLKNAKGENVLLMVSQGEVIRFVVLKSDE SEQ ID NO: 20-TC0052 protein sequence
MKKLLKSVLAFAVLGSASSLHALPVGNPAEPSLMIDGILWEGFGGDPCDPCTTWCDAISLRLGYYGDFVFD
RVLKTDVNKQFEMGAAPTGDADLTTAPTPASRENPAYGKHMQDAEMFTNAAYMALNIWDRFDVFCTLGATS
GYLKGNSAAFNLVGLFGRDETAVAADDIPNVSLSQAVVELYTDTAFAWSVGARAALWECGCATLGASFQYA
QSKPKVEELNVLCNAAEFTINKPKGYVGQEFPLNIKAGTVSATDTKDASIDYHEWQASLALSYRLNMFTPY
IGVKWSRASFDADTIRIAQPKLETSILKMTTWNPTISGSGIDVDTKITDTLQIVSLQLNKMKSRKSCGLAI
GTTIVDADKYAVTVETRLIDERAAHVNAQFRF SEQ ID NO: 21-TC0052 nucleotide sequence
ATGAAAAAACTCTTGAAATCGGTATTAGCATTTGCCGTTTTGGGTTCTGCTTCCTCCTTGCATGCTCTGCC
TGTGGGGAATCCTGCTGAACCAAGCCTTATGATTGACGGGATTCTTTGGGAAGGTTTCGGTGGAGATCCTT
GCGATCCTTGCACAACTTGGTGTGATGCCATCAGCCTACGTCTCGGCTACTATGGGGACTTCGTTTTTGAT
CGTGTTTTGAAAACAGACGTGAACAAACAGTTCGAAATGGGAGCAGCTCCTACAGGAGATGCAGACCTTAC
TACAGCACCTACTCCTGCATCAAGAGAGAATCCCGCTTATGGCAAGCATATGCAAGATGCAGAAATGTTCA
CTAATGCTGCGTACATGGCTTTAAACATTTGGGACCGTTTCGATGTATTTTGTACATTGGGAGCAACTAGC
GGATATCTTAAAGGTAATTCTGCCGCCTTTAACTTAGTTGGTCTGTTTGGAAGAGATGAAACTGCAGTTGC
AGCTGACGACATACCTAACGTCAGCTTGTCTCAAGCTGTTGTCGAACTCTACACAGACACAGCTTTCGCTT
GGAGCGTCGGTGCTAGAGCAGCTTTATGGGAGTGCGGATGTGCAACTTTAGGAGCTTCCTTCCAATATGCT
CAATCTAAGCCAAAAGTAGAGGAATTAAACGTTCTCTGTAATGCGGCAGAATTCACTATTAACAAGCCTAA
AGGATACGTTGGACAAGAGTTTCCTCTTAACATTAAAGCTGGAACAGTTAGCGCTACAGATACTAAAGATG
CTTCCATCGATTACCATGAGTGGCAAGCAAGCTTGGCTTTGTCTTACAGACTGAATATGTTCACTCCTTAC
ATTGGAGTTAAGTGGTCTAGAGCAAGCTTTGATGCCGACACTATCCGCATTGCGCAGCCTAAGCTTGAGAC
CTCTATCTTAAAAATGACCACTTGGAACCCAACGATCTCTGGATCTGGTATAGACGTTGATACAAAAATCA
CGGATACATTACAAATTGTTTCCTTGCAGCTCAACAAGATGAAATCCAGAAAATCTTGCGGTCTTGCAATT
GGAACAACAATTGTAGATGCTGATAAATATGCAGTTACTGTTGAGACACGCTTGATCGATGAAAGAGCAGC
TCACGTAAATGCTCAGTTCCGTTTCTAA SEQ ID NO: 22-TC0106 protein sequence
MLTNFTFRNCLLFFVTLSSVPVFSAPQPRVTLPSGANKIGSEAWIEQKVRQYPELLWLVEPSPAGTSLNAP
SGMIFSPLLFQKKVPAFDIAVRSLIHLHLLIQGSRQAYAQLVQLQANESPMTFKQFLTLHKQLSLFLNSPK
EFYDSVKILETAIILRHLGCSTKAVATFKPYFSETQKEVFYTKALHVLHTFPELSPSFARLSPEQKTLFFS
LRKLANYDELLSLTNAPSLQLLSAVRSRRALLALDLYLYALDFCGEQGISSQFHMDFSPLQSMLQQYATVE
EAFSRYFTYRANRLGFAGSSRTEMALVRIATLMNLSPSEAAILTTSFKSLSLEDAESLVNSFYTNKGDSLA
LSLRGLPTLISELTRAAHGNTNAEARAQQIYATTLSLVAKSLKAHKEMQNKQILPEEVVLDFSETASSCQG
LDIFSENVAVQIHLNGSVSIHL SEQ ID NO: 23: CM homolog of CT601 = TC_0551
ATGGCATCCAAGTCTCGTCATTATCTTAACCAGCCTTGGTACATTATCTTATTCATCTTTGTTCTTAGTCT
GGTTGCTGGTACCCTTCTTTCTTCAGTTTCCTATGTTCTATCTCCAATCCAAAAACAAGCTGCAGAATTTG -continued

| SEQUENCE |
| --- |

ATCGTAATCAGCAAATGTTGATGGCCGCACAAATTATTTCCTATGACAATAAATTCCAAATATATGCTGAA
GGGGATTGGCAACCTGCTGTCTATAATACAAAAAAACAGATACTAGAAAAAAGCTCTTCCACTCCACCACA
AGTGACTGTGGCGACTCTATGCTCTTATTTTCAAAATTTTGTTAGAGTTTTGCTTACAGACTCCCAAGGGA
ATCTTTCTTCTTTTGAAGATCACAATCTTAACCTAGAAGAGTTCTTATCCCACCCCACATCTTCAGTACAA
GATCACTCTCTGCATGTAATTTATGCTATTCTAGCAAACGATGAATCCTCTAAAAAGTTATCATCCTCCCA
AGTAGCAAAAAATCCGGTATCCATAGAGTCTATTATTCTTCCTATAAAAGGATTTGGTTTATGGGGACCAA
TCTATGGATTTCTTGCTTTAGAAAAGGACGGTAATACGGTTCTAGGGACATGCTGGTATCAACATGGTGAG
ACTCCAGGATTAGGAGCAAATATAACTAATCCCCAATGGCAACAAAATTTCAGAGGAAAAAAAGTATTTCT
CGCTTCCTCTTCCGGAGAAACCGATTTTGCTAAAACAACTCTAGGACTAGAAGTTATAAAAGGATCTGTTT
CTGCATTATTAGGGGACTCTCCCAAAGCTAATTCCGCTGTTGATGGAATTTCAGGAGCTACACTGACCTGT
AATGGAGTTACTGAAGCTTTTGCTAATTCGCTAGCTCCTTACCGCCCCTTATTGACTTTCTTCGCCAATCT
TAACTCTAGTGGAGAATCTCATGACAACCAATAA

SEQ ID NO: 24: CM homologue of CT601 protein sequence = TC_0551
protein sequence
MASKSRHYLNQPWYIILFIFVLSLVAGTLLSSVSYVLSPIQKQAAEFDRNQQMLMAAQIISYDNKFQIYAE
GDWQPAVYNTKKQILEKSSSTPPQVTVATLCSYFQNFVRVLLTDSQGNLSSFEDHNLNLEEFLSHPTSSVQ
DHSLHVIYAILANDESSKKLSSSQVAKNPVSIESIILPIKGFGLWGPIYGFLALEKDGNTVLGTCWYQHGE
TPGLGANITNPQWQQNFRGKKVFLASSSGETDFAKTTLGLEVIKGSVSALLGDSPKANSAVDGISGATLTC
NGVTEAFANSLAPYRPLLTFFANLNSSGESHDNQ SEQ ID NO: 25: CM homologue of CT372 = TC_0651 nucleotide sequence
ATGAATGGAAAAGTTCTGTGTGAGGTTTCTGTGTCCTTCCGTTCGATTCTGCTGACGGCTCTGCTTTCACT
TTCTTTTACAAACACTATGCAGGCTGCACACCATCATTATCACCGTTATGATGATAAACTACGCAGACAAT
ACCATAAAAAGGACTTGCCCACTCAAGAGAATGTTCGGAAAGAGTTTTGTAATCCCTACTCTCATAGTAGT
GATCCTATCCCTTTGTCACAACAACGAGGAGTCCTATCTCCTATCTGTGATTTAGTCTCAGAGTGCTCGTT
TTTGAACGGGATTTCCGTTAGGAGTCTTAAACAAACACTGAAAAATTCTGCTGGGACTCAAGTTGCTTTAG
ACTGGTCTATCCTTCCTCAATGGTTCAATCCTAGATCCTCTTGGGCTCCTAAGCTCTCTATTCGAGATCTT
GGATATGGTAAACCCCAGTCCCTTATTGAAGCAGATTCCCCTTGTTGTCAAACCTGCTTCAACCCATCTGC
TGCTATTACGATTTACGATTCTTCATGTGGGAAGGGTGTTGTCCAAGTGTCATACACCCTTGTTCGTTATT
GGAGAGAAACGGCTGCACTTGCAGGGCAAACTATGATGCTTGCAGGAAGTATTAATGATTATCCTGCTCGC
CAAAACATATTCTCTCAACTTACATTTTCCCAAACTTTCCCTAATGAGAGAGTAAATCTAACTGTTGGTCA
ATACTCTCTTTACTCGATAGACGGAACGCTGTACAACAATGATCAGCAGCTAGGATTTATTAGTTATGCGT
TGTCGCAAAATCCAACAGCGACTTATTCCTCTGGAAGCCTTGGCGCCTATCTACAAGTCGCTCCAACAGAA
AGCACCTGTCTTCAAGTTGGGTTCCAAGATGCCTATAATATTTCAGGTTCCTCGATCAAATGGAATAATCT
TACAAAAAATAAGTATAACTTCCATGGCTATGCATCTTGGGCTCCACACTGTTGCTTAGGACCTGGACAAT
ACTCTGTTCTTCTTTATGTAACCAGAAAGGTTCCTGAGCAAATGATGCAGACAATGGGCTGGTCTGTGAAT
GCAAGTCAATACATCTCTTCTAAACTTTATGTATTTGGAAGATACAGCGGAGTCACAGGCCAATTGTCTCC
TATTAACCGAACCTATTCATTTGGCTTAGTCTCTCCTAATTTATTGAACCGTAACCCACAAGACTTATTTG
GAGTAGCTTGCGCATTCAATAATATACACGCCTCCGCCTTTCAAAATGCTCAAAGAAAATATGAAACTGTG
ATCGAGGGATTTGCAACTATTGGTTGCGGACCTTACATCTCCTTTGCTCCAGATTTCCAACTTTACCTCTA
TCCTGCTCTGCGTCCAAATAAACAAAGCGCCCGAGTCTATAGCGTTCGCGCAAACCTAGCTATTTAG SEQ ID NO: 26: CM homologue of CT372 = TC_0651 protein sequence
MNGKVLCEVSVSFRSILLTALLSLSFTNTMQAAHHHYHRYDDKLRRQYHKKDLPTQENVRKEFCNPYSHSS
DPIPLSQQRGVLSPICDLVSECSFLNGISVRSLKQTLKNSAGTQVALDWSILPQWFNPRSSWAPKLSIRDL
GYGKPQSLIEADSPCCQTCFNPSAAITIYDSSCGKGVVQVSYTLVRYWRETAALAGQTMMLAGSINDYPAR
QNIFSQLTFSQTFPNERVNLTVGQYSLYSIDGTLYNNDQQLGFISYALSQNPTATYSSGSLGAYLQVAPTE
STCLQVGFQDAYNISGSSIKWNNLTKNKYNFHGYASWAPHCCLGPGQYSVLLYVTRKVPEQMMQTMGWSVN
ASQYISSKLYVFGRYSGVTGQLSPINRTYSFGLVSPNLLNRNPQDLFGVACAFNNIHASAFQNAQRKYETV
IEGFATIGCGPYISFAPDFQLYLYPALRPNKQSARVYSVRANLAI SEQ ID NO: 27: CM homologue of CT443 = TC_0727
ATGCGAATAGGAGATCCTATGAACAAACTCATCAGACGAGCTGTGACGATCTTCGCGGTGACTAGTGTGGC
GAGTTTATTTGCTAGCGGGGTGTTAGAGACCTCTATGGCAGAGTCTCTCTCTACCAACGTTATTAGCTTAG
CTGACACCAAAGCGAAAGAGACCACTTCTCATCAAAAAGACAGAAAAGCAAGAAAAAAATCATCAAAATAGG
ACTTCCGTAGTCCGTAAAGAGGTTACTGCAGTTCGTGATACTAAAGCTGTAGAGCCTAGACAGGATTCTTG
CTTTGGCAAAATGTATACAGTCAAAGTTAATGATGATCGTAATGTAGAAATCGTGCAGTCCGTTCCTGAAT
ATGCTACGGTAGGATCTCCATATCCTATTGAGATTACTGCTATAGGGAAAAGAGACTGTGTTGATGTAATC
ATTACACAGCAATTACCATGCGAAGCAGAGTTTGTTAGCAGTGATCCAGCTACTACTCCTACTGCTGATGG
TAAGCTAGTTTGGAAAATTGATCGGTTAGGACAGGGCGAAAAGAGTAAAATTACTGTATGGGTAAAACCTC
TTAAAGAAGGTTGCTGCTTTACAGCTGCAACGGTTTGTGCTTGTCCAGAGATCCGTTCGGTTACGAAATGT
GGCCAGCCTGCTATCTGTGTTAAACAGGAAGGTCCAGAAAGCGCATGTTTGCGTTGCCCAGTAACTTATAG
AATTAATGTAGTCAACCAAGGAACAGCAACAGCACGTAATGTTGTTGTGGAAAATCCTGTTCCAGATGGCT
ATGCTCATGCATCCGGACAGCGTGTATTGACATATACTCTTGGGGATATGCAACCTGGAGAACAGAGAACA
ATCACCGTGGAGTTTTGTCCGCTTAAACGTGGTCGAGTCACAAATATTGCTACAGTTTCTTACTGTGGTGG
ACACAAAAATACTGCTAGCGTAACAACAGTGATCAATGAGCCTTGCGTGCAAGTTAACATCGAGGGAGCAG
ATTGGTCTTATGTTTGTAAGCCTGTAGAATATGTTATCTCTGTTTCTAACCCTGGTGACTTAGTTTTACGA
GACGTTGTAATTGAAGATACGCTTTCTCCTGGAATAACTGTTGTTGAAGCAGCTGGAGCTCAGATTTCTTG
TAATAAATTGGTTTGGACTTTGAAGGAACTCAATCCTGGAGAGTCTTTACAATATAAGGTTCTAGTAAGAG
CTCAAACTCCAGGGCAATTCACAAACAACGTTGTTGTGAAAAGTTGCTCTGATTGCGGTATTTGTACTTCT
TGCGCAGAAGCAACAACTTACTGGAAAGGAGTTGCTGCTACTCATATGTGCGTAGTAGATACTTGTGATCC
TATTTGCGTAGGAGAGAACACTGTTTATCGTATCTGTGTGACAAACAGAGGTTCTGCTGAAGATACAAATG
TGTCCTTAATTTTGAAATTCTCTAAAGAATTACAACCTATATCTTTCTCTGGACCAACTAAAGGAACCATT
ACAGGAAACACGGTAGTGTTTGATTCGTTACCTAGATTAGGTTCTAAAGAAACTGTAGAGTTTTCTGTAAC
GTTGAAAGCAGTATCCGCTGGAGATGCTCGTGGGGAAGCTATTCTTTCTTCCGATACATTGACAGTTCCTG
TATCTGATACGGAGAATACACATATCTATTAA -continued

| SEQUENCE |
|---|
| SEQ ID NO: 28: CM homologue of CT443 = TC_0727<br>MRIGDPMNKLIRRAVTIFAVTSVASLFASGVLETSMAESLSTNVISLADTKAKETTSHQKDRKARKNHQNR<br>TSVVRKEVTAVRDTKAVEPRQDSCFGKMYTVKVNDDRNVEIVQSVPEYATVGSPYPIEITAIGKRDCVDVI<br>ITQQLPCEAEFVSSDPATTPTADGKLVWKIDRLGQGEKSKITVWVKPLKEGCCFTAATVCACPEIRSVTKC<br>GQPAICVKQEGPESACLRCPVTYRINVVNQGTATARNVVVENPVPDGYAHASGQRVLTYTLGDMQPGEQRT<br>ITVEFCPLKRGRVTNIATVSYCGGHKNTASVTTVINEPCVQVNIEGADWSYVCKPVEYVISVSNPGDLVLR<br>DVVIEDTLSPGITVVEAAGAQISCNKLVWTLKELNPGESLQYKVLVRAQTPGQFTNNVVVKSCSDCGICTS<br>CAEATTYWKGVAATHMCVVDTCDPICVGENTVYRICVTNRGSAEDTNVSLILKFSKELQPISFSGPTKGTI<br>TGNTVVFDSLPRLGSKETVEFSVTLKAVSAGDARGEAILSSDTLTVPVSDTENTHIY |
| SEQ ID NO: 29: CM homologue of CT043 = TC_0313 nucleotide sequence<br>ATGTCCAGACAGAATGCTGAGGAAAATCTAAAAAATTTTGCTAAAGAGCTCAAGCTCCCCGACGTGGCCTT<br>CGATCAGAATAATACGTGCATTTTGTTTGTTGATGGAGAGTTTTCTCTTCACCTGACCTACGAAGAGCACT<br>CTGATCGCCTTTATGTTTACGCACCTCTCCTTGACGGACTCCCAGATAATCCGCAAAGAAAGTTGGCTCTG<br>TATGAGAAATTGTTGGAAGGCTCTATGCTCGGAGGCCAAATGGCTGGTGGAGGAGTAGGAGTTGCTACTAA<br>AGAACAGTTGATCCTAATGCATTGCGTGTTAGATATGAAATATGCAGAGACTAATCTATTGAAAGCTTTTG<br>CACAGCTTTTCATTGAAACTGTTGTGAAATGGCGAACGGTCTGTTCTGATATCAGCGCTGGACGAGAACCT<br>TCCGTTGACACTATGCCTCAAATGCCTCAAGGAGGCAGCGGAGGAATTCAACCTCCTCCAACAGGAATTCG<br>TGCGTAG |
| SEQ ID NO: 30: CM homologue of CT043 = TC_0313 protein sequence<br>MSRQNAEENLKNFAKELKLPDVAFDQNNTCILFVDGEFSLHLTYEEHSDRLYVYAPLLDGLPDNPQRKLAL<br>YEKLLEGSMLGGQMAGGGVGVATKEQLILMHCVLDMKYAETNLLKAFAQLFIETVVKWRTVCSDISAGREP<br>SVDTMPQMPQGGSGGIQPPPTGIRA |
| SEQ ID NO: 31-TC0431 protein sequence<br>MPHSPFLYVVQPHSVFNPRLGERHPITLDFIKEKNRLADFIENLPLEIFGAPSFLENASLEASYVLSREST<br>KDGTLFTVLEPKLSACVATCLVDSSIPMEPDNELLEEIKHTLLKSSCDGVQYRVTRETLQNKDEAPRVSLV<br>ADDIELIRNVDFLGRSVDIVKLDPLNIPNTVSEENALDYSFTRETAKLSPDGRVGIPQGTKILPAPSLEVE<br>ISTSIFEETSSFEQNFSSSITFCVPPLTSFSPLQEPPLVGAGQQEILVTKKHLFPSYTPKLIDIVKRHKRD<br>AKILVNKIQFEKLWRSHAKSQILKEGSVRLDLQGFTGELFNYQLQVGSHTIAAVLIDPEIANVKSLPEQTY<br>AVRKIKSGFQCSLDDQHIYQVAVKKHLSLSSQPPKISPLSQSESSDLSLFEAAAFSASLTYEFVKKNTYHA<br>KNTVTCSTVSHSLYILKEDDGANAAEKRLDNSFRNWVENKLNANSPDSCTAFIQKFGTHYITSATFGGSGF<br>QVLKLSFEQVEGLRSKKISLEAAAANSLLKSSVSNSTESGYSTYDSSSSSHTVFLGGTVLPSVHDGQLDFK<br>DWSESVCLEPVPIHISLLPLTDLLTPLYFPETDTTELSNKRNALQQAVRVYLKDHRSAKQSERSVFTAGIN<br>SPSSWFTLESANSPLVVSSPYMTYWSTLPYLFPTLKERSSAAPIVFYFCVDNNEHASQKILNQTYCFIGSL<br>PIRQKIFGREFAENPYLSFYGRFGEAYFDGGYPERCGWIVEKLNTTKDQILRDEDEVQLKHVYSGEYLSTI<br>PIKDSHCTLSRTCTESNAVFIIKKPSSY |
| SEQ ID NO: 32 CM homologue of CT279 = TC_0890 nucleotide sequence<br>ATGCTCGCTAATCGGTTATTTCTAATCACCCTTATAGGTTTTGGCTATTCTGCTTACGGTGCCAGCACAGG<br>GAAATCACCTTCTTTACAGGTTATTTTAGCTGAAGTCGAGGATACATCTTCGCGCTTACAAGCTCATCAGA<br>ATGAGCTTGTTATGCTCTCGGAACGTTTAGATGAGCAAGACACAAAACTTCAACAACTCTCGTCAACTCAG<br>GCCCGTAATCTTCCTCAACAAGTTCAACGGCTTGAGATTGATCTGAGAGCTCTGGCTAAAACAGCTGCTGT<br>GCTCTCGCAATCTGTTCAGGATATCCGATCATCCGTGCAAAATAAATTACAAGAAATCCAACAAGAACAAA<br>AAAATTTAGCTCAAAATTTACGAGCGCTTCGCAACTCCTTACAAGCACTAGTTGATGGCTCTTCCCCAGAA<br>AATTATATTGATTTTTTGGCCGGGGAGACACCTGAACATATTCACGTTGTTAAACAAGGAGAAACCCTGAG<br>TAAAATCGCTAGTAAGTACAATATCCCTGTCGCAGAATTGAAAAAACTTAATAAATTAAATTCCGATACTA<br>TTTTTACTGATCAAAGAATCCGACTTCCAAAAAAGAAATAA |
| SEQ ID NO: 33: CM homologue of CT279 = TC_0890 protein sequence<br>MLANRLFLITLIGFGYSAYGASTGKSPSLQVILAEVEDTSSRLQAHQNELVMLSERLDEQDTKLQQLSSTQ<br>ARNLPQQVQRLEIDLRALAKTAAVLSQSVQDIRSSVQNKLQEIQQEQKNLAQNLRALRNSLQALVDGSSPE<br>NYIDFLAGETPEHIHVVKQGETLSKIASKYNIPVAELKKLNKLNSDTIFTDQRIRLPKKK |
| SEQ ID NO: 34-TC0660 protein sequence<br>MSMYIKRKKAWMTFLAIVCSFCLAGCSKESKDSVSEKFIVGTNATYPPFEFVDERGETVGFDIDLAREISK<br>KLGKKLEVREFAFDALVLNLKQHRIDAIMAGVSITSSRLKEILMIPYYGEEIKSLVLVFKDGDSKSLPLDQ<br>YNSVAVQTGTYQEEYLQSLPGVRIRSFDSTLEVLMEVLHSKSPIAVLEPSIAQVVLKDFPTLTTETIDLPE<br>DKWVLGYGIGVASDRPSLASDIEAAVQEIKKEGVLAELEQKWGLNG |
| SEQ ID NO: 35-TC0741 protein sequence<br>MTTPISNSPSSIPTVTVSTTTASSGSLGTSTVSSTTTSTSVAQTATTTSSASTSIIQSSGENIQSTTGTPS<br>PITSSVSTSAPSPKASATANKTSSAVSGKITSQETSEESETQATTSDGEVSSNYDDVDTPTNSSDSTVDSD<br>YQDVETQYKTISNNGENTYETIGSHGEKNTHVQESHASGTGNPINNQQEAIRQLRSSTYTTSPRNENIFSP<br>GPEGLPNMSLPSYSPTDKSSLLAFLSNPNTKAKMLEHSGHLVFIDTTRSSFIFVPNGNWDQVCSMKVQNGK<br>TKEDLGLKDLEDMCAKFCTGYNKFSSDWGNRVDPLVSSKAGIESGGHLPSSVIINNKFRTCVAYGPWNPKE<br>NGPNYTPSAWRRGHRVDFGKIFDGTAPFNKINWGSSPTPGDDGISFSNETIGSEPFATPPSSPSQTPVINV<br>NVNVGGTNVNIGDTNVSKGSGTPTSSQSVDMSTDTSDLDTSDIDTNNQTNGDINTNDNSNNVDGSLSDVDS<br>RVEDDDGVSDTESTNGNDSGKTTSTEENGDPSGPDILAAVRKHLDTVYPGENGGSTEGPLPANQNLGNVIH<br>DVEQNGSAKETIITPGDTGPTDSSSSVDADADVEDTSDTDSGIGDDDGVSDTESTNGNNSGKTTSTEENGD<br>PSGPDILAAVRKHLDTVYPGENGGSTEGPLPANQNLGNVIHDVEQNGAAQETIITPGDTESTDTSSSVNAN |

-continued

| SEQUENCE |
| --- |
| ADLEDVSDADSGFGDDDGISDTESTNGNDSGKNTPVGDGGTPSGPDILAAVRKHLDTVYPGENGGSTERPL<br>PANQNLGDIIHDVEQNGSAKETVVSPYRGGGGNTSSPIGLASLLPATPSTPLMTTPRTNGKAAASSLMIKG<br>GETQAKLVKNGGNIPGETTLAELLPRLRGHLDKVFTSDGKFTNLNGPQLGAIIDQFRKETGSGGIIAHTDS<br>VPGENGTASPLTGSSGEKVSLYDAAKNVTQALTSVTNKVTLAMQGQKLEGIINNNNTPSSIGQNLFAAARA<br>TTQSLSSLIGTVQ |

REFERENCES

[1] Morrison S G & Morrison R P, (2005) J. Immunol., 175 (11):7536-42.
[2] Morrison R P and Caldwell, H D (2002) Infect. Immun., 70(6):2741-51, Review.
[3] Brunham R C and Rey-Ladino (2005) Nat. Rev. Immunol., 5(2):149-161, Review.
[4] Brunham R C and Rey-Ladino J (2005), Nat Rev Immuno. 5: 149-161.
[5] Su H and Caldwell H D (1995), Infect Immun 63: 3302-33085.
[6] Moore, T. et. al., J. Infect. Dis., 2003, 15, 188(4): 617-624
[7] Morrison S G and Morrison R P, (2001) Infect. Immun. 69(4): 2643-2649.
[8] Morrison S G & Morrison R P, (2005) J. Immunol., 175 (11):7536-42.
[9] WO03/049762.
[10] WO2006/138004.
[11] WO2007/110700.
[12] WO 2006/046143.
[13] Bernadec et al. (1998), J. Bacteriol 180(18):4872-4878.
[14] Berlanda Scorza, F. et al. Mol. Cell Proteomics (2008), 7(3): 473-485.
[15] Murakami et al. Oral Microbiol. Immunol. 2007, 22: 356-360.
[16] Thaler, D. S., Genome, 1989, 31(1): 53-67
[17] Infect Immun. 72: 1914-1919, 2004.
[18] WO 02/09643.
[19] Katial et al. 2002, Infect Immun, 70: 702-707.
[20] Beveridge, 1999, J. Bacteriol. 181: 4725-4733.
[21] Moe et al. 2002, Infect. Immun. 70:6021-6031.
[22] Argita et al. 2003, Vaccine, 21, 950-960.
[23. Lipinska, B. et al., J. Bacteriol., 172, 1791-1797.
[24] Gray, C. W. et al., Eur. J. Biochem., 2000, 267, 5699-5710.
[25] Savopoulos, J. W. et al., Protein Expres. Purif., 2000, 19, 227-234.
[26] Huston, W. M. et al., FEBS Letters, 2007, 3382-3386.
[27] Winter et al., (1991) *Nature* 349:293-99.
[28] U.S. Pat. No. 4,816,567.
[29] Inbar et al., (1972) *Proc. Natl. Acad. Sci. U.S.A.* 69:2659-62.
[30] Ehrlich et al., (1980) *Biochem* 19:4091-96.
[31] Huston et al., (1988) Proc. Natl. Acad. Sci. U.S.A. 85:5897-83.
[32] Pack et al., (1992) *Biochem* 31, 1579-84.
[33] Cumber et al., (1992) *J. Immunology* 149B, 120-26.
[34] Riechmann et al., (1988) *Nature* 332, 323-27.
[35] Verhoeyan et al., (1988) *Science* 239, 1534-36.
[36] GB 2,276,169.
[37*] Nature* (1975) 256:495-96.
[38] WO99/27961.
[39] WO02/074244.
[40] WO02/064162.
[41] WO03/028760.
[42] U.S. Pat. No. 6,355,271.
[43] WO00/23105.
[44] WO90/14837.
[45] WO90/14837.
[46] Podda & Del Giudice (2003) *Expert Rev Vaccines* 2:197-203.
[47] Podda (2001) *Vaccine* 19: 2673-2680.
[48*] Vaccine Design: The Subunit and Adjuvant Approach* (eds. Powell & Newman) Plenum Press 1995 (ISBN 0-306-44867-X).
[49*] Vaccine Adjuvants: Preparation Methods and Research Protocols* (Volume 42 of *Methods in Molecular Medicine* series). ISBN: 1-59259-083-7. Ed. O'Hagan.
[50] WO2008/043774.
[51] Allison & Byars (1992) *Res Immunol* 143:519-25.
[52] Hariharan et al. (1995) *Cancer Res* 55:3486-9.
[53] US-2007/014805.
[54] US-2007/0191314.
[55] Suli et al. (2004) *Vaccine* 22(25-26):3464-9.
[56] WO95/11700.
[57] U.S. Pat. No. 6,080,725.
[58] WO2005/097181.
[59] WO2006/113373.
[60] Han et al. (2005) *Impact of Vitamin E on Immune Function and Infectious Diseases in the Aged* at Nutrition, Immune functions and Health EuroConference, Paris, 9-10 Jun. 2005.
[61] U.S. Pat. No. 6,630,161.
[62] U.S. Pat. No. 5,057,540.
[63] WO96/33739.
[64] EP-A-0109942.
[65] WO96/11711.
[66] WO00/07621.
[67] Barr et al. (1998) *Advanced Drug Delivery Reviews* 32:247-271.
[68] Sjolanderet et al. (1998) *Advanced Drug Delivery Reviews* 32:321-338.
[69] Niikura et al. (2002) *Virology* 293:273-280.
[70] Lenz et al. (2001) *J Immunol* 166:5346-5355.
[71] Pinto et al. (2003) *J Infect Dis* 188:327-338.
[72] Gerber et al. (2001) *J Virol* 75:4752-4760.
[73] WO03/024480.
[74] WO03/024481.
[75] Gluck et al. (2002) *Vaccine* 20:B10-B16.
[76] EP-A-0689454.
[77] Johnson et al. (1999) *Bioorg Med Chem Lett* 9:2273-2278.
[78] Evans et al. (2003) *Expert Rev Vaccines* 2:219-229.
[79] Meraldi et al. (2003) *Vaccine* 21:2485-2491.
[80] Pajak et al. (2003) *Vaccine* 21:836-842.
[81] Kandimalla et al. (2003) *Nucleic Acids Research* 31:2393-2400.
[82] WO02/26757.
[83] WO99/62923.
[84] Krieg (2003) *Nature Medicine* 9:831-835.
[85] McCluskie et al. (2002) *FEMS Immunology and Medical Microbiology* 32:179-185.
[86] WO98/40100.

[87] U.S. Pat. No. 6,207,646.
[88] U.S. Pat. No. 6,239,116.
[89] U.S. Pat. No. 6,429,199.
[90] Kandimalla et al. (2003) *Biochemical Society Transactions* 31 (part 3):654-658.
[91] Blackwell et al. (2003) *J Immunol* 170:4061-4068.
[92] Krieg (2002) *Trends Immunol* 23:64-65.
[93] WO01/95935.
[94] Kandimalla et al. (2003) *BBRC* 306:948-953.
[95] Bhagat et al. (2003) *BBRC* 300:853-861.
[96] WO03/035836.
[97] WO01/22972.
[98] Schellack et al. (2006) *Vaccine* 24:5461-72.
[99] Kamath et al. (2008) *Eur J Immunol* 38:1247-56.
[100] Riedl et al. (2008) *Vaccine* 26:3461-8.
[101] WO95/17211.
[102] WO98/42375.
[103] Beignon et al. (2002) *Infect Immun* 70:3012-3019.
[104] Pizza et al. (2001) *Vaccine* 19:2534-2541.
[105] Pizza et al. (2000) *Int J Med Microbiol* 290:455-461.
[106] Scharton-Kersten et al. (2000) *Infect Immun* 68:5306-5313.
[107] Ryan et al. (1999) *Infect Immun* 67:6270-6280.
[108] Partidos et al. (1999) *Immunol Lett* 67:209-216.
[109] Peppoloni et al. (2003) *Expert Rev Vaccines* 2:285-293.
[110] Pine et al. (2002) *J Control Release* 85:263-270.
[111] Tebbey et al. (2000) *Vaccine* 18:2723-34.
[112] Domenighini et al. (1995) *Mol Microbiol* 15:1165-1167.
[113] WO99/40936.
[114] WO99/44636.
[115] Singh et al] (2001) *J Cont Release* 70:267-276.
[116] WO99/27960.
[117] U.S. Pat. No. 6,090,406.
[118] U.S. Pat. No. 5,916,588.
[119] EP-A-0626169.
[120] WO99/52549.
[121] WO01/21207.
[122] WO01/21152.
[123] Andrianov et al. (1998) *Biomaterials* 19:109-115.
[124] Payne et al. (1998) *Adv Drug Delivery Review* 31:185-196.
[125] U.S. Pat. No. 4,680,338.
[126] U.S. Pat. No. 4,988,815.
[127] WO92/15582.
[128] Stanley (2002) *Clin Exp Dermatol* 27:571-577.
[129] Wu et al. (2004) *Antiviral Res.* 64(2):79-83.
[130] Vasilakos et al. (2000) *Cell Immunol.* 204(1):64-74.
[131] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[132] Jones (2003) *Curr Opin Investig Drugs* 4:214-218.
[133] WO03/011223.
[134] Hu et al. (2009) *Vaccine* 27:4867-73.
[135] WO2004/060308.
[136] WO2004/064759.
[137] U.S. Pat. No. 6,924,271.
[138] US2005/0070556.
[139] U.S. Pat. No. 5,658,731.
[140] U.S. Pat. No. 5,011,828.
[141] WO2004/87153.
[142] U.S. Pat. No. 6,605,617.
[143] WO02/18383.
[144] WO2004/018455.
[145] WO03/082272.
[146] Wong et al. (2003) *J Clin Pharmacol* 43(7):735-42.
[147] US2005/0215517.
[148] Dyakonova et al. (2004) *Int Immunopharmacol* 4(13):1615-23.
[149] FR-2859633.
[150] Signorelli & Hadden (2003) *Int Immunopharmacol* 3(8):1177-86.
[151] WO2004/064715.
[152] De Libero et al, *Nature Reviews Immunology,* 2005, 5: 485-496.
[153] U.S. Pat. No. 5,936,076.
[154] Oki et al, *J. Clin. Investig.,* 113: 1631-1640.
[155] US2005/0192248.
[156] Yang et al, *Angew. Chem. Int. Ed.,* 2004, 43: 3818-3822.
[157] WO2005/102049.
[158] Goff et al, *J. Am. Chem., Soc.,* 2004, 126: 13602-13603.
[159] WO03/105769.
[160] Cooper (1995) *Pharm Biotechnol* 6:559-80.
[161] WO99/11241.
[162] WO94/00153.
[163] WO98/57659.
[164] European patent applications 0835318, 0735898 and 0761231.
[165] WO2006/110603.
[166] Gennaro (2000) *Remington: The Science and Practice of Pharmacy.* 20th edition, ISBN: 0683306472.
[167*] Methods In Enzymology* (S. Colowick and N. Kaplan, eds., Academic Press, Inc.).
[168*] Handbook of Experimental Immunology*, Vols. I-IV (D. M. Weir and C. C. Blackwell, eds, 1986, Blackwell Scientific Publications).
[169] Sambrook et al. (2001) *Molecular Cloning: A Laboratory Manual,* 3rd edition (Cold Spring Harbor Laboratory Press).
[170*] Handbook of Surface and Colloidal Chemistry* (Birdi, K. S. ed., CRC Press, 1997).
[171] Ausubel et al. (eds) (2002) *Short protocols in molecular biology,* 5th edition (Current Protocols).
[172*] Molecular Biology Techniques: An Intensive Laboratory Course*, (Ream et al., eds., 1998, Academic Press).
[173*] PCR* (*Introduction to Biotechniques Series*), 2nd ed. (Newton & Graham eds., 1997, Springer Verlag).
[174] Geysen et al. (1984) *PNAS USA* 81:3998-4002.
[175] Carter (1994) *Methods Mol Biol* 36:207-23.
[176] Jameson, B A et al. 1988, *CABIOS* 4(1):181-186.
[177] Raddrizzani & Hammer (2000) *Brief Bioinform* 1(2):179-89.
[178] Bublil et al. (2007) *Proteins* 68(1):294-304.
[179] De Lalla et al. (1999) *J. Immunol.* 163:1725-29.
[180] Kwok et al. (2001) *Trends Immunol* 22:583-88.
[181] Brusic et al. (1998) *Bioinformatics* 14(2):121-30.
[182] Meister et al. (1995) *Vaccine* 13(6):581-91.
[183] Roberts et al. (1996) *AIDS Res Hum Retroviruses* 12(7):593-610.
[184] Maksyutov & Zagrebelnaya (1993) *Comput Appl Biosci* 9(3):291-7.
[185] Feller & de la Cruz (1991) *Nature* 349(6311):720-1.
[186] Hopp (1993) *Peptide Research* 6:183-190.
[187] Welling et al. (1985) *FEBS Lett.* 188:215-218.
[188] Davenport et al. (1995) *Immunogenetics* 42:392-297.
[189] Tsurui & Takahashi (2007) *J Pharmacol Sci.* 105(4):299-316.
[190] Tong et al. (2007) *Brief Bioinform.* 8(2):96-108.
[191] Schirle et al. (2001) *J Immunol Methods.* 257(1-2):1-16.

[192] Chen et al. (2007) *Amino Acids* 33(3):423-8.

[193] Current Protocols in Molecular Biology (F. M. Ausubel et al., eds., 1987) Supplement 30.

[194] Smith & Waterman (1981) Adv. Appl. Math. 2: 482-489.

[195] Caldwell H. D. et al., (1981), Infect Immun. 31(3): 1161-1176.

[196] Montigiani S. et al., (2002), Infect. Immun. 7091): 368-379.

[197] Maxson and Darwin, (2004), J. Bacteriol., 186(13): 4199-4208.

[198] Klock H E, Lesley S A, (2009) Methods Mol Biol., 498:91-103.

[199] Berlanda Scorza F. et al., (2008) Mol. Cell Proteomics, 7(3): 473-485.

[200] Bombaci, M. et al., PLoS ONE, Jul. 4 (2009) (7), pp. 1-10.

[201] S.-P. Wang, J. Infect. Dis. 181 (Suppl 3) (2000), pp. S421-5.

The invention claimed is:

1. A bacterium which presents a heterologous antigen from *Chlamydia* on its surface, wherein the heterologous antigen is a *C. trachomatis* CT823 antigen, and wherein the bacterium is an ompA mutant and/or which is a mutant in one or more components of the Tol-Pal complex.

2. A bacterium according to claim 1, which does not express the OmpA protein.

3. A bacterium according to claim 2, which does not express one or more components of the Tol-Pal complex.

4. A bacterium according to claim 3, which does not express TolR.

5. A bacterium according to claim 1, which expresses the Braun lipoprotein lpp.

6. A bacterium according to claim 1, wherein the bacterium is *E. coli*.

7. A bacterium according to claim 6, wherein the *E. coli* is *E. coli* BL21(DE3).

8. A bacterium according to claim 1, wherein the heterologous antigen is selected from a CT823 peptide comprising or consisting of one or more of the following sequences: DYFNDEFFNRFFGLP (SEQ ID NO: 56), 10 or more consecutive amino acids of SEQ ID NO: 56, SHREQ (SEQ ID NO: 57), ALQKMGVRVQNITPE (SEQ ID NO: 58), NQVLKNSKGENVLLM (SEQ ID NO: 59), SPMLGYSASKKDSKADICLA (SEQ ID NO: 60), EDLLKEVSRGFSRVAAKATP (SEQ ID NO: 61) TGNQAIASPGNKRGFQENPF (SEQ ID NO: 62), IAIGNPFGLQATVTVGVISAKGRNQLHIVD (SEQ ID NO: 63) and NTAIVSGSGGYIGIGFAIPSLMAKRVIDQL (SEQ ID NO: 64).

9. An outer membrane vesicle obtained from a bacterium according to claim 1, wherein the outer membrane vesicle expresses the heterologous antigen on its surface.

10. An outer membrane vesicle according to claim 9, which does not express the OmpA protein.

11. An outer membrane vesicle according to claim 9, which does not express the TolR protein.

12. An outer membrane vesicle according to claim 9, which expresses the Braun lipoprotein lpp.

13. An immunogenic composition comprising an outer membrane vesicle according to claim 9.

14. An immunogenic composition according to claim 13 which further comprises one or more additional antigens in a combined preparation for simultaneous, separate or sequential administration.

15. An immunogenic composition according to claim 14, wherein the one or more additional antigens are also presented by the outer membrane vesicle.

16. An immunogenic composition according to claim 14, wherein at least one of the one or more additional antigens is presented by a different outer membrane vesicle.

17. An immunogenic composition according to claim 14, wherein the heterologous antigen and the one or more additional antigens are selected from the groups consisting of: CT823+CT089, CT823+CT089+CT381, CT823+CT372, CT823+CT279, CT823+CT443, CT823+CT456, CT823+CT601, CT823+CT153, CT823+CT733, CT823+CT043 or CT823+CT456+CT733+CT043.

18. An immunogenic composition according to claim 13, wherein at least one of the epitopes is a *C. trachomatis* epitope selected from an epitope comprising or consisting of the following sequence: DYFNDEFFNRFFGLP (SEQ ID NO: 56), 10 or more consecutive amino acids of SEQ ID NO: 56, SHREQ (SEQ ID NO: 57), ALQKMGVRVQNITPE (SEQ ID NO: 58), NQVLKNSKGENVLLM (SEQ ID NO: 59), SPMLGYSASKKDSKADICLA (SEQ ID NO: 60), EDLLKEVSRGFSRVAAKATP (SEQ ID NO: 61), TGNQAIASPGNKRGFQENPF (SEQ ID NO: 62), IAIGNPFGLQATVTVGVISAKGRNQLHIVD (SEQ ID NO: 63) and NTAIVSGSGGYIGIGFAIPSLMAKRVIDQL (SEQ ID NO: 64) or is a *C. muridarum* epitope selected from an epitope comprising or consisting of the following sequence:

DYFNDEFFNRFFGLP, (SEQ ID NO: 36)

SHREQ, (SEQ ID NO: 37)

ALQKMGVRVQNLTPE, (SEQ ID NO: 38)

NQVLKNAKGENVLLM, (SEQ ID NO: 39)

SPMLGYSAPKKDSSTGICLA, (SEQ ID NO: 40)

EDLLKEVSRGFSKVAAQATP, (SEQ ID NO: 41)

TGSQAIASPGNKRGFQENPF, (SEQ ID NO: 42)

PRPQQRDAVR, (SEQ ID NO: 43)

IAIGNPFGLQATVTVGVISAKGRNQLHIVD, (SEQ ID NO: 44)

NTAIVSGSGGYIGIGFAIPSLMAKRVIDQL, (SEQ ID NO: 45)

VAAQATPGVVYIENFPK, (SEQ ID NO: 46)

GFQENPFDYFNDEFFNRFFGLPSHREQPRPQQR, (SEQ ID NO: 47)

GTGFIVSEDGYVVTNHHVVEDAGK, (SEQ ID NO: 48)

TDLAVIKIQAK, (SEQ ID NO: 49)

VIDQLISDGQVTR, (SEQ ID NO: 50)

-continued (SEQ ID NO: 51)
AGLRQEDVIVAYNGKEVESLSALR, (SEQ ID NO: 52)
FIEIPVTVTQIPAEDGVSALQK, (SEQ ID NO: 53)
VQNLTPEICK, (SEQ ID NO: 54)
NAKGENVLLMVSQGEVIR
and (SEQ ID NO: 55)
GENVLLMVSQGEVIR.

19. A bacterium according to claim 8, wherein the heterologous antigen comprises amino acids 1-10 of SEQ ID NO: 56.

20. An immunogenic composition according to claim 18, wherein the *C. trachomatis* epitope comprises amino acids 1-10 of SEQ ID NO: 56.

* * * * *

SEQUENCE LISTING

```
<160> NUMBER OF SEQ ID NOS: 99

<210> SEQ ID NO 1
<211> LENGTH: 497
<212> TYPE: PRT
<213> ORGANISM: Chlamydia trachomatis

<400> SEQUENCE: 1

Met Met Lys Arg Leu Leu Cys Val Leu Leu Ser Thr Ser Val Phe Ser
1               5                   10                  15

Ser Pro Met Leu Gly Tyr Ser Ala Ser Lys Lys Asp Ser Lys Ala Asp
            20                  25                  30

Ile Cys Leu Ala Val Ser Ser Gly Asp Gln Glu Val Ser Gln Glu Asp
        35                  40                  45

Leu Leu Lys Glu Val Ser Arg Gly Phe Ser Arg Val Ala Ala Lys Ala
    50                  55                  60

Thr Pro Gly Val Val Tyr Ile Glu Asn Phe Pro Lys Thr Gly Asn Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
            100                 105                 110

His Arg Glu Gln Gln Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140

Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                165                 170                 175

Ile Lys Ile Gln Ala Glu Lys Leu Pro Phe Leu Thr Phe Gly Asn Ser
            180                 185                 190

Asp Gln Leu Gln Ile Gly Asp Trp Ala Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asn Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
        275                 280                 285

Asp Gln Leu Ile Ser Asp Gly Gln Val Thr Arg Gly Phe Leu Gly Val
    290                 295                 300
```

-continued

Thr Leu Gln Pro Ile Asp Ser Glu Leu Ala Thr Cys Tyr Lys Leu Glu
305 310 315 320

Lys Val Tyr Gly Ala Leu Val Thr Asp Val Val Lys Gly Ser Pro Ala
325 330 335

Glu Lys Ala Gly Leu Arg Gln Glu Asp Val Ile Val Ala Tyr Asn Gly
340 345 350

Lys Glu Val Glu Ser Leu Ser Ala Leu Arg Asn Ala Ile Ser Leu Met
355 360 365

Met Pro Gly Thr Arg Val Val Leu Lys Ile Val Arg Glu Gly Lys Thr
370 375 380

Ile Glu Ile Pro Val Thr Val Thr Gln Ile Pro Thr Glu Asp Gly Val
385 390 395 400

Ser Ala Leu Gln Lys Met Gly Val Arg Val Gln Asn Ile Thr Pro Glu
405 410 415

Ile Cys Lys Lys Leu Gly Leu Ala Ala Asp Thr Arg Gly Ile Leu Val
420 425 430

Val Ala Val Glu Ala Gly Ser Pro Ala Ala Ser Ala Gly Val Ala Pro
435 440 445

Gly Gln Leu Ile Leu Ala Val Asn Arg Gln Arg Val Ala Ser Val Glu
450 455 460

Glu Leu Asn Gln Val Leu Lys Asn Ser Lys Gly Glu Asn Val Leu Leu
465 470 475 480

Met Val Ser Gln Gly Asp Val Val Arg Phe Ile Val Leu Lys Ser Asp
485 490 495

Glu

<210> SEQ ID NO 2
<211> LENGTH: 1494
<212> TYPE: DNA
<213> ORGANISM: Chlamydia trachomatis

<400> SEQUENCE: 2
atgatgaaaa gattattatg tgtgttgcta tcgacatcag ttttctcttc gccaatgcta 60
ggctatagtg cgtcaaagaa agattctaag gctgatattt gtcttgcagt atcctcagga 120
gatcaagagg tttcacaaga agatctgctc aaagaagtat cccgaggatt ttctcgggtc 180
gctgctaagg caacgcctgg agttgtatat atagaaaatt ttcctaaaac agggaaccag 240
gctattgctt ctccaggaaa caaaagaggc tttcaagaga acccttttga ttattttaat 300
gacgaatttt ttaatcgatt ttttggattg ccttcgcata gagagcagca gcgtccgcag 360
cagcgtgatg ctgtaagagg aactgggttc attgtttctg aagatggtta tgttgttact 420
aaccatcatg tagtcgagga tgcaggaaaa attcatgtta ctctccacga cggacaaaaa 480
tacacagcta agatcgtggg gttagatcca aaaacagatc ttgctgtgat caaaattcaa 540
gcggagaaat taccattttt gacttttggg aattctgatc agctgcagat aggtgactgg 600
gctattgcta ttggaaatcc ttttggattg caagcaacgg tcactgtcgg ggtcattagt 660
gctaaaggaa gaaatcagct acatattgta gatttcgaag actttattca aacagatgct 720
gccattaatc ctgggaattc aggcggtcca ttgttaaaca tcaatggtca agttatcggg 780
gttaatactg ccattgtcag tggtagcggg ggatatattg gaatagggtt tgctattcct 840
agcttgatgg ctaaacgagt cattgatcaa ttgattagtg atgggcaggt aacaagaggc 900
tttttgggag ttaccttgca accgatagat tctgaattgg ctacttgtta caaattggaa 960

```
aaagtgtacg gagctttggt gacggatgtt gttaaaggtt ctccagcaga aaaagcaggg   1020

ctgcgccaag aagatgtcat tgtggcttac aatggaaaag aagtagagtc tttgagtgcg   1080

ttgcgtaatg ccatttccct aatgatgcca gggactcgtg ttgttttaaa aatcgttcgt   1140

gaagggaaaa caatcgagat acctgtgacg gttacacaga tcccaacaga ggatggcgtt   1200

tcagcgttgc agaagatggg agtccgtgtt cagaacatta ctccagaaat ttgtaagaaa   1260

ctcggattgg cagcagatac ccgagggatt ctggtagttg ctgtggaggc aggctcgcct   1320

gcagcttctg caggcgtcgc tcctggacag cttatcttag cggtgaatag gcagcgagtc   1380

gcttccgttg aagagttaaa tcaggttttg aaaaactcga aaggagagaa tgttctcctt   1440

atggtttctc aaggagatgt ggtgcgattc atcgtcttga aatcagacga gtag         1494
```

<210> SEQ ID NO 3
<211> LENGTH: 1347
<212> TYPE: DNA
<213> ORGANISM: Chlamydia trachomatis

<400> SEQUENCE: 3

```
atgttaataa actttacctt tcgcaactgt cttttgttcc ttgtcacact gtctagtgtc     60

cctgttttct cagcacctca acctcgcgga acgcttccta gctcgaccac aaaaattgga    120

tcagaagttt ggattgaaca aaaagtccgc caatatccag agcttttatg gttagtagag    180

ccgtcctcta cgggagcctc tttaaaatct ccttcaggag ccatcttttc tccaacatta    240

ttccaaaaaa aggtccctgc tttcgatatc gcagtgcgca gtttgattca cttacattta    300

ttaatccagg gttcccgcca agcctatgct caactgatcc aactacagac cagcgaatcc    360

cctctaacat ttaagcaatt ccttgcattg cataagcaat taactctatt tttaaattcc    420

cctaaggaat tttatgactc tgttaaagtg ttagagacag ctatcgtctt acgtcactta    480

ggctgttcaa ctaaggctgt tgctgcgttt aaaccttatt tctcagaaat gcaaagagag    540

gctttttaca ctaaggctct gcatgtacta cacaccttcc cagagctaag cccatcattt    600

gctcgcctct ctccggagca gaaaactctc ttcttctcct tgagaaaatt ggcgaattac    660

gatgagttac tctcgctgac gaacacccca agttttcagc ttctgtctgc tgggcgctcg    720

caacgagctc ttttagctct ggacttgtac ctctatgctt tggattcctg tggagaacag    780

gggatgtcct ctcaattcca cacaaacttc gcacctctac agtccatgtt gcaacaatac    840

gctactgtag aagaggcctt ttctcgttat tttacttacc gagctaatcg attaggattt    900

gatggctctt ctcgatccga gatggcttta gtaagaatgg ccaccttgat gaacttgtct    960

ccttccgaag ctgcgatttt aaccacaagc ttcaaaaccc ttcctacaga agaagcggat   1020

actttgatca atagtttcta taccaataag ggcgattcgt tggctctttc tctgcgaggg   1080

ttgcctacac ttgtatccga actgacgcga actgcccatg gcaataccaa tgcagaagct   1140

cgatctcagc aaatttatgc aactacccta tcgctagtag taaagagtct gaaagcgcac   1200

aaagaaatgc taaacaagca aattctttct aaggaaattg ttttagattt ctcagaaact   1260

gcagcttctt gccaaggatt ggatatcttt tccgagaatg tcgctgttca aattcactta   1320

aatggaaccg ttagtatcca tttataa                                       1347
```

<210> SEQ ID NO 4
<211> LENGTH: 448
<212> TYPE: PRT
<213> ORGANISM: Chlamydia trachomatis

<400> SEQUENCE: 4

-continued

```
Met Leu Ile Asn Phe Thr Phe Arg Asn Cys Leu Leu Phe Leu Val Thr
1               5                   10                  15

Leu Ser Ser Val Pro Val Phe Ser Ala Pro Gln Pro Arg Gly Thr Leu
            20                  25                  30

Pro Ser Ser Thr Thr Lys Ile Gly Ser Glu Val Trp Ile Glu Gln Lys
        35                  40                  45

Val Arg Gln Tyr Pro Glu Leu Leu Trp Leu Val Glu Pro Ser Ser Thr
    50                  55                  60

Gly Ala Ser Leu Lys Ser Pro Ser Gly Ala Ile Phe Ser Pro Thr Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Ile Gln Leu Gln Thr Ser Glu Ser Pro Leu Thr Phe Lys Gln Phe Leu
        115                 120                 125

Ala Leu His Lys Gln Leu Thr Leu Phe Leu Asn Ser Pro Lys Glu Phe
    130                 135                 140

Tyr Asp Ser Val Lys Val Leu Glu Thr Ala Ile Val Leu Arg His Leu
145                 150                 155                 160

Gly Cys Ser Thr Lys Ala Val Ala Ala Phe Lys Pro Tyr Phe Ser Glu
                165                 170                 175

Met Gln Arg Glu Ala Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Thr Pro Ser Phe Gln Leu Leu Ser Ala Gly Arg Ser
225                 230                 235                 240

Gln Arg Ala Leu Leu Ala Leu Asp Leu Tyr Leu Tyr Ala Leu Asp Ser
                245                 250                 255

Cys Gly Glu Gln Gly Met Ser Ser Gln Phe His Thr Asn Phe Ala Pro
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Asp Gly Ser Ser
    290                 295                 300

Arg Ser Glu Met Ala Leu Val Arg Met Ala Thr Leu Met Asn Leu Ser
305                 310                 315                 320

Pro Ser Glu Ala Ala Ile Leu Thr Thr Ser Phe Lys Thr Leu Pro Thr
                325                 330                 335

Glu Glu Ala Asp Thr Leu Ile Asn Ser Phe Tyr Thr Asn Lys Gly Asp
            340                 345                 350

Ser Leu Ala Leu Ser Leu Arg Gly Leu Pro Thr Leu Val Ser Glu Leu
        355                 360                 365

Thr Arg Thr Ala His Gly Asn Thr Asn Ala Glu Ala Arg Ser Gln Gln
    370                 375                 380

Ile Tyr Ala Thr Thr Leu Ser Leu Val Val Lys Ser Leu Lys Ala His
385                 390                 395                 400

Lys Glu Met Leu Asn Lys Gln Ile Leu Ser Lys Glu Ile Val Leu Asp
                405                 410                 415
```

-continued

```
Phe Ser Glu Thr Ala Ala Ser Cys Gln Gly Leu Asp Ile Phe Ser Glu
            420                 425                 430

Asn Val Ala Val Gln Ile His Leu Asn Gly Thr Val Ser Ile His Leu
        435                 440                 445


<210> SEQ ID NO 5
<211> LENGTH: 2433
<212> TYPE: DNA
<213> ORGANISM: Chlamydia trachomatis

<400> SEQUENCE: 5

atgactaagc cttctttctt atacgttatt caaccttttt ccgtatttaa tccacgatta     60

ggacgtttct ctacagactc agatacttat atcgaagaag aaaaccgcct agcatcgttc    120

attgagagtt tgccactgga gatcttcgat ataccttctt tcatggaaac cgcgatttcc    180

aatagcccct atattttatc ttgggagaca actaaagacg gcgctctgtt cactattctt    240

gaacccaaac tctcagcttg cgcagccact tgcctggtag ccccttctat acaaatgaaa    300

tccgatgcgg agctcctaga agaaattaag caagcgttat tacgcagctc tcatgacggt    360

gtgaaatatc gcatcaccag agaatccttc tctccagaaa agaaaactcc taaggttgct    420

ctagtcgatg acgatattga attgattcgc aatgtcgact tttgggtag agctgttgac     480

attgtcaaat tagaccctat taatattctg aataccgtaa gcgaagagaa tattctagat    540

tactctttta caagagaaac ggctcagctg agcgcggatg gtcgttttgg tattcctcca    600

gggactaagc tattccctaa accttctttt gatgtagaaa tcagtacctc cattttcgaa    660

gaaacaactt catttactcg aagtttttct gcatcggtta cttttagtgt accagacctc    720

gcggcgacta tgcctcttca aagccctccc atggtagaaa atggtcaaaa agaaatttgt    780

gtcattcaaa aacacttatt cccaagctac tctcctaaac tagtcgatat tgttaaacga    840

tacaaaagag aggctaagat cttgattaac aagcttgcct ttggaatgtt atggcgacat    900

cgggctaaaa gccaaatcct caccgaggga agcgtacgtc tagacttaca aggattcaca    960

gaatcgaagt acaattacca gattcaagta ggatcccata cgattgcagc tgtattaatc   1020

gatatggata tttccaagat tcaatccaaa tcagaacaag cttatgcaat taggaaaatc   1080

aaatcaggct ttcaacgtag cttggatgac tatcatattt atcaaattga aagaaaacaa   1140

accttttctt tttctccgaa gcatcgcagc ctctcatcca catcccattc cgaagattct   1200

gatttggatc tttctgaagc agccgccttt tcaggaagtc ttacctgcga gtttgtaaaa   1260

aaaagcactc aacatgccaa gaataccgtc acatgttcca cagccgctca ttccctatac   1320

acactcaaag aagatgacag ctcgaacccc tctgaaaaac gattagatag ttgtttccgc   1380

aattggattg aaaacaaact aagcgccaat tctccagatt cctggtcagc gtttattcaa   1440

aaattcggaa cacactatat tgcatcagca acttttggag ggataggttt ccaagtgctc   1500

aaactatctt ttgaacaggt ggaggatcta catagcaaaa agatctcctt agaaaccgca   1560

gcagccaact ctctattaaa aggttctgta tccagcagca cagaatctgg atactccagc   1620

tatagctcca cgtcttcttc tcatacggta tttttaggag gaacggtctt accttcggtt   1680

catgatgaac gtttagactt taaagattgg tcggaaagtg tgcacctgga acctgttcct   1740

atccaggttt ctttacaacc tataacgaat ttactagttc ctctccattt tcctaatatc   1800

ggtgctgcag agctctctaa taaacgagaa tctcttcaac aagcgattcg agtctatctc   1860

aaagaacata aagtagatga gcaaggagaa cgtactacat ttacatcagg aatcgataat   1920

ccttcttcct ggtttacctt agaagctgcc cactctcctc ttatagtcag tactccttac   1980
```

```
attgcttcgt ggtctacgct tccttatttg ttcccaacat taagagaacg ttcttcggca   2040

acccctatcg ttttctattt ttgtgtagat aataatgaac atgcttcgca aaaaatatta   2100

aaccaatcgt attgcttcct cgggtccttg cctattcgac aaaaaatttt tggtagcgaa   2160

tttgctagtt tcccctatct atctttctat ggaaatgcaa aagaggcgta ctttgataac   2220

acgtactacc caacgcgttg tgggtggatt gttgaaaagt taaatactac acaagatcaa   2280

ttcctccggg atggagacga ggtgcgacta aaacatgttt ccagcggaaa gtatctagca   2340

acaactcctc ttaaggatac ccatggtaca ctcacgcgta caacgaactg tgaagatgct   2400

atctttatta ttaaaaaatc ttcaggttat tga                                2433
```

```
<210> SEQ ID NO 6
<211> LENGTH: 350
<212> TYPE: PRT
<213> ORGANISM: Chlamydia trachomatis

<400> SEQUENCE: 6

Met Thr Lys Pro Ser Phe Leu Tyr Val Ile Gln Pro Phe Ser Val Phe
1               5                   10                  15

Asn Pro Arg Leu Gly Arg Phe Ser Thr Asp Ser Asp Thr Tyr Ile Glu
            20                  25                  30

Glu Glu Asn Arg Leu Ala Ser Phe Ile Glu Ser Leu Pro Leu Glu Ile
        35                  40                  45

Phe Asp Ile Pro Ser Phe Met Glu Thr Ala Ile Ser Asn Ser Pro Tyr
    50                  55                  60

Ile Leu Ser Trp Glu Thr Thr Lys Asp Gly Ala Leu Phe Thr Ile Leu
65                  70                  75                  80

Glu Pro Lys Leu Ser Ala Cys Ala Ala Thr Cys Leu Val Ala Pro Ser
                85                  90                  95

Ile Gln Met Lys Ser Asp Ala Glu Leu Leu Glu Glu Ile Lys Gln Ala
            100                 105                 110

Leu Leu Arg Ser Ser His Asp Gly Val Lys Tyr Arg Ile Thr Arg Glu
        115                 120                 125

Ser Phe Ser Pro Glu Lys Lys Thr Pro Lys Val Ala Leu Val Asp Asp
    130                 135                 140

Asp Ile Glu Leu Ile Arg Asn Val Asp Phe Leu Gly Arg Ala Val Asp
145                 150                 155                 160

Ile Val Lys Leu Asp Pro Ile Asn Ile Leu Asn Thr Val Ser Glu Glu
                165                 170                 175

Asn Ile Leu Asp Tyr Ser Phe Thr Arg Glu Thr Ala Gln Leu Ser Ala
            180                 185                 190

Asp Gly Arg Phe Gly Ile Pro Pro Gly Thr Lys Leu Phe Pro Lys Pro
        195                 200                 205

Ser Phe Asp Val Glu Ile Ser Thr Ser Ile Phe Glu Glu Thr Thr Ser
    210                 215                 220

Phe Thr Arg Ser Phe Ser Ala Ser Val Thr Phe Ser Val Pro Asp Leu
225                 230                 235                 240

Ala Ala Thr Met Pro Leu Gln Ser Pro Pro Met Val Glu Asn Gly Gln
                245                 250                 255

Lys Glu Ile Cys Val Ile Gln Lys His Leu Phe Pro Ser Tyr Ser Pro
            260                 265                 270

Lys Leu Val Asp Ile Val Lys Arg Tyr Lys Arg Glu Ala Lys Ile Leu
        275                 280                 285
```

Ile Asn Lys Leu Ala Phe Gly Met Leu Trp Arg His Arg Ala Lys Ser
290 295 300

Gln Ile Leu Thr Glu Gly Ser Val Arg Leu Asp Leu Gln Gly Phe Thr
305 310 315 320

Glu Ser Lys Tyr Asn Tyr Gln Ile Gln Val Gly Ser His Thr Ile Ala
325 330 335

Ala Val Leu Ile Asp Met Asp Ile Ser Lys Ile Gln Ser Lys
340 345 350

<210> SEQ ID NO 7
<211> LENGTH: 603
<212> TYPE: DNA
<213> ORGANISM: Chlamydia trachomatis

<400> SEQUENCE: 7
atgctcgcta atcgcttatt cttaataacc cttttagggt taagttcgtc tgtttacggc 60
gcaggtaaag caccgtcttt gcaggctatt ctagccgaag tcgaagacac ctcctctcgt 120
ctacacgctc atcacaatga gcttgctatg atctctgaac gcctcgatga gcaagacacg 180
aaactacagc aactttcgtc aacacaagat cataacctac ctcgacaagt tcagcgacta 240
gaaacggacc aaaaagcttt ggcaaaaaca ctggcgattc tttcgcaatc cgtccaagat 300
attcggtctt ctgtacaaaa taaattacaa gaaatccaac aagaacaaaa aaaattagca 360
caaaatttgc gagcgcttcg taactcttta caagctctcg ttgatggctc ttctccagaa 420
aattatattg atttcctaac tggtgaaacc ccggaacata ttcatattgt taaacaagga 480
gagaccctga gcaagatcgc gagtaaatat aacatccccg tcgtagaatt aaaaaaactt 540
aataaactaa attcggatac tatttttaca gatcaaagaa ttcgccttcc gaaaaagaaa 600
tag 603

<210> SEQ ID NO 8
<211> LENGTH: 200
<212> TYPE: PRT
<213> ORGANISM: Chlamydia trachomatis

<400> SEQUENCE: 8

Met Leu Ala Asn Arg Leu Phe Leu Ile Thr Leu Leu Gly Leu Ser Ser
1 5 10 15

Ser Val Tyr Gly Ala Gly Lys Ala Pro Ser Leu Gln Ala Ile Leu Ala
20 25 30

Glu Val Glu Asp Thr Ser Ser Arg Leu His Ala His His Asn Glu Leu
35 40 45

Ala Met Ile Ser Glu Arg Leu Asp Glu Gln Asp Thr Lys Leu Gln Gln
50 55 60

Leu Ser Ser Thr Gln Asp His Asn Leu Pro Arg Gln Val Gln Arg Leu
65 70 75 80

Glu Thr Asp Gln Lys Ala Leu Ala Lys Thr Leu Ala Ile Leu Ser Gln
85 90 95

Ser Val Gln Asp Ile Arg Ser Ser Val Gln Asn Lys Leu Gln Glu Ile
100 105 110

Gln Gln Glu Gln Lys Lys Leu Ala Gln Asn Leu Arg Ala Leu Arg Asn
115 120 125

Ser Leu Gln Ala Leu Val Asp Gly Ser Ser Pro Glu Asn Tyr Ile Asp
130 135 140

Phe Leu Thr Gly Glu Thr Pro Glu His Ile His Ile Val Lys Gln Gly
145 150 155 160

```
Glu Thr Leu Ser Lys Ile Ala Ser Lys Tyr Asn Ile Pro Val Val Glu
                165                 170                 175

Leu Lys Lys Leu Asn Lys Leu Asn Ser Asp Thr Ile Phe Thr Asp Gln
            180                 185                 190

Arg Ile Arg Leu Pro Lys Lys Lys
        195                 200


<210> SEQ ID NO 9
<211> LENGTH: 951
<212> TYPE: DNA
<213> ORGANISM: Chlamydia trachomatis

<400> SEQUENCE: 9

atggcatcca agtctcgcca ttatcttaat cagccttggt acattatctt attcatcttt      60

gttcttagtt taattgctgg taccctcctg tcttctgtgt attatgtcct tgcacctatc     120

caacagcaag ctgcggaatt cgatcgcaat caacaaatgc taatggctgc acaagtaatt     180

tcttccgata acacattcca agtctatgaa aagggagatt ggcacccagc cctatataat     240

actaaaaagc agttgctaga gatctcctct actcctccta aagtaaccgt gacaacttta     300

agctcatatt ttcaaaactt tgttagagtc ttgcttacag atacacaagg aaatctttct     360

tcattcgaag accataatct caatctagaa gaatttttat ctcaaccaac tcctgtaata     420

catggtcttg ccctttatgt ggtctacgct atcctacaca acgatgcagc ttcctctaaa     480

ttatctgctt cccaagtagc gaaaaatcca acagctatag aatctatagt tcttcctata     540

gaaggttttg gtttgtgggg acctatctat ggattccttg ctctagaaaa agacgggaat     600

actgttcttg gtacttcttg gtatcaacat ggcgagactc ctggattagg agcaaatatc     660

gctaaccctc aatggcaaaa aaatttcaga ggcaaaaaag tatttctagt ctcagcttct     720

ggagaaacag attttgctaa gacaacccta ggactggaag ttataaaagg atctgtatct     780

gcagcattag gagactcacc taaagctgct tcttccatcg acggaatttc aggagctact     840

ttgacttgta atggtgttac cgaatccttc tctcattctc tagctcccta ccgcgctttg     900

ttgactttct tcgccaactc taaacctagt ggagagtctc atgaccacta a              951


<210> SEQ ID NO 10
<211> LENGTH: 316
<212> TYPE: PRT
<213> ORGANISM: Chlamydia trachomatis

<400> SEQUENCE: 10

Met Ala Ser Lys Ser Arg His Tyr Leu Asn Gln Pro Trp Tyr Ile Ile
1               5                   10                  15

Leu Phe Ile Phe Val Leu Ser Leu Ile Ala Gly Thr Leu Leu Ser Ser
            20                  25                  30

Val Tyr Tyr Val Leu Ala Pro Ile Gln Gln Gln Ala Ala Glu Phe Asp
        35                  40                  45

Arg Asn Gln Gln Met Leu Met Ala Ala Gln Val Ile Ser Ser Asp Asn
    50                  55                  60

Thr Phe Gln Val Tyr Glu Lys Gly Asp Trp His Pro Ala Leu Tyr Asn
65                  70                  75                  80

Thr Lys Lys Gln Leu Leu Glu Ile Ser Ser Thr Pro Pro Lys Val Thr
                85                  90                  95

Val Thr Thr Leu Ser Ser Tyr Phe Gln Asn Phe Val Arg Val Leu Leu
            100                 105                 110
```

-continued

```
Thr Asp Thr Gln Gly Asn Leu Ser Ser Phe Glu Asp His Asn Leu Asn
        115                 120                 125

Leu Glu Glu Phe Leu Ser Gln Pro Thr Pro Val Ile His Gly Leu Ala
    130                 135                 140

Leu Tyr Val Val Tyr Ala Ile Leu His Asn Asp Ala Ala Ser Ser Lys
145                 150                 155                 160

Leu Ser Ala Ser Gln Val Ala Lys Asn Pro Thr Ala Ile Glu Ser Ile
                165                 170                 175

Val Leu Pro Ile Glu Gly Phe Gly Leu Trp Gly Pro Ile Tyr Gly Phe
            180                 185                 190

Leu Ala Leu Glu Lys Asp Gly Asn Thr Val Leu Gly Thr Ser Trp Tyr
        195                 200                 205

Gln His Gly Glu Thr Pro Gly Leu Gly Ala Asn Ile Ala Asn Pro Gln
    210                 215                 220

Trp Gln Lys Asn Phe Arg Gly Lys Lys Val Phe Leu Val Ser Ala Ser
225                 230                 235                 240

Gly Glu Thr Asp Phe Ala Lys Thr Thr Leu Gly Leu Glu Val Ile Lys
                245                 250                 255

Gly Ser Val Ser Ala Ala Leu Gly Asp Ser Pro Lys Ala Ala Ser Ser
            260                 265                 270

Ile Asp Gly Ile Ser Gly Ala Thr Leu Thr Cys Asn Gly Val Thr Glu
        275                 280                 285

Ser Phe Ser His Ser Leu Ala Pro Tyr Arg Ala Leu Leu Thr Phe Phe
    290                 295                 300

Ala Asn Ser Lys Pro Ser Gly Glu Ser His Asp His
305                 310                 315
```

<210> SEQ ID NO 11
<211> LENGTH: 1662
<212> TYPE: DNA
<213> ORGANISM: Chlamydia trachomatis

<400> SEQUENCE: 11

```
atgcgaatag gagatcctat gaacaaactc atcagacgag cagtgacgat cttcgcggtg     60

actagtgtgg cgagtttatt tgctagcggg gtgttagaga cctctatggc agagtctctc    120

tctacaaacg ttattagctt agctgacacc aaagcgaaag acaacacttc tcataaaagc    180

aaaaaagcaa gaaaaaacca cagcaaagag actcccgtag accgtaaaga ggttgctccg    240

gttcatgagt ctaaagctac aggacctaaa caggattctt gctttggcag aatgtataca    300

gtcaaagtta atgatgatcg caatgttgaa atcacacaag ctgttcctga atatgctacg    360

gtaggatctc cctatcctat tgaaattact gctacaggta aaagggattg tgttgatgtt    420

atcattactc agcaattacc atgtgaagca gagttcgtac gcagtgatcc agcgacaact    480

cctactgctg atggtaagct agtttggaaa attgaccgct taggacaagg cgaaaagagt    540

aaaattactg tatgggtaaa acctcttaaa gaaggttgct gctttacagc tgcaacagta    600

tgcgcttgtc cagagatccg ttcggttaca aaatgtggac aacctgctat ctgtgttaaa    660

caagaaggcc cagagaatgc ttgtttgcgt tgcccagtag tttacaaaat taatatagtg    720

aaccaaggaa cagcaacagc tcgtaacgtt gttgttgaaa atcctgttcc agatggttac    780

gctcattctt ctggacagcg tgtactgacg tttactcttg gagatatgca acctggagag    840

cacagaacaa ttactgtaga gttttgtccg cttaaacgtg gtcgtgctac caatatagca    900

acggtttctt actgtggagg acataaaaat acagcaagcg taacaactgt gatcaacgag    960
```

-continued

```
ccttgcgtac aagtaagtat tgcaggagca gattggtctt atgtttgtaa gcctgtagaa   1020

tatgtgatct ccgtttccaa tcctggagat cttgtgttgc gagatgtcgt cgttgaagac   1080

actctttctc ccggagtcac agttcttgaa gctgcaggag ctcaaatttc ttgtaataaa   1140

gtagtttgga ctgtgaaaga actgaatcct ggagagtctc tacagtataa agttctagta   1200

agagcacaaa ctcctggaca attcacaaat aatgttgttg tgaagagctg ctctgactgt   1260

ggtacttgta cttcttgcgc agaagcgaca acttactgga aaggagttgc tgctactcat   1320

atgtgcgtag tagatacttg tgaccctgtt tgtgtaggag aaaatactgt ttaccgtatt   1380

tgtgtcacca acagaggttc tgcagaagat acaaatgttt ctttaatgct taaattctct   1440

aaagaactgc aacctgtatc cttctctgga ccaactaaag gaacgattac aggcaataca   1500

gtagtattcg attcgttacc tagattaggt tctaaagaaa ctgtagagtt ttctgtaaca   1560

ttgaaagcag tatcagctgg agatgctcgt ggggaagcga ttctttcttc cgatacattg   1620

actgttccag tttctgatac agagaataca cacatctatt aa                      1662


<210> SEQ ID NO 12
<211> LENGTH: 553
<212> TYPE: PRT
<213> ORGANISM: Chlamydia trachomatis

<400> SEQUENCE: 12

Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Asp Asn Thr Ser His Lys Ser Lys Lys Ala Arg
    50                  55                  60

Lys Asn His Ser Lys Glu Thr Pro Val Asp Arg Lys Glu Val Ala Pro
65                  70                  75                  80

Val His Glu Ser Lys Ala Thr Gly Pro Lys Gln Asp Ser Cys Phe Gly
                85                  90                  95

Arg Met Tyr Thr Val Lys Val Asn Asp Asp Arg Asn Val Glu Ile Thr
            100                 105                 110

Gln Ala Val Pro Glu Tyr Ala Thr Val Gly Ser Pro Tyr Pro Ile Glu
        115                 120                 125

Ile Thr Ala Thr Gly Lys Arg Asp Cys Val Asp Val Ile Ile Thr Gln
    130                 135                 140

Gln Leu Pro Cys Glu Ala Glu Phe Val Arg Ser Asp Pro Ala Thr Thr
145                 150                 155                 160

Pro Thr Ala Asp Gly Lys Leu Val Trp Lys Ile Asp Arg Leu Gly Gln
                165                 170                 175

Gly Glu Lys Ser Lys Ile Thr Val Trp Val Lys Pro Leu Lys Glu Gly
            180                 185                 190

Cys Cys Phe Thr Ala Ala Thr Val Cys Ala Cys Pro Glu Ile Arg Ser
        195                 200                 205

Val Thr Lys Cys Gly Gln Pro Ala Ile Cys Val Lys Gln Glu Gly Pro
    210                 215                 220

Glu Asn Ala Cys Leu Arg Cys Pro Val Val Tyr Lys Ile Asn Ile Val
225                 230                 235                 240

Asn Gln Gly Thr Ala Thr Ala Arg Asn Val Val Val Glu Asn Pro Val
                245                 250                 255
```

```
Pro Asp Gly Tyr Ala His Ser Ser Gly Gln Arg Val Leu Thr Phe Thr
            260                 265                 270

Leu Gly Asp Met Gln Pro Gly Glu His Arg Thr Ile Thr Val Glu Phe
        275                 280                 285

Cys Pro Leu Lys Arg Gly Arg Ala Thr Asn Ile Ala Thr Val Ser Tyr
    290                 295                 300

Cys Gly Gly His Lys Asn Thr Ala Ser Val Thr Thr Val Ile Asn Glu
305                 310                 315                 320

Pro Cys Val Gln Val Ser Ile Ala Gly Ala Asp Trp Ser Tyr Val Cys
                325                 330                 335

Lys Pro Val Glu Tyr Val Ile Ser Val Ser Asn Pro Gly Asp Leu Val
            340                 345                 350

Leu Arg Asp Val Val Val Glu Asp Thr Leu Ser Pro Gly Val Thr Val
        355                 360                 365

Leu Glu Ala Ala Gly Ala Gln Ile Ser Cys Asn Lys Val Val Trp Thr
    370                 375                 380

Val Lys Glu Leu Asn Pro Gly Glu Ser Leu Gln Tyr Lys Val Leu Val
385                 390                 395                 400

Arg Ala Gln Thr Pro Gly Gln Phe Thr Asn Asn Val Val Val Lys Ser
                405                 410                 415

Cys Ser Asp Cys Gly Thr Cys Thr Ser Cys Ala Glu Ala Thr Thr Tyr
            420                 425                 430

Trp Lys Gly Val Ala Ala Thr His Met Cys Val Val Asp Thr Cys Asp
        435                 440                 445

Pro Val Cys Val Gly Glu Asn Thr Val Tyr Arg Ile Cys Val Thr Asn
    450                 455                 460

Arg Gly Ser Ala Glu Asp Thr Asn Val Ser Leu Met Leu Lys Phe Ser
465                 470                 475                 480

Lys Glu Leu Gln Pro Val Ser Phe Ser Gly Pro Thr Lys Gly Thr Ile
                485                 490                 495

Thr Gly Asn Thr Val Val Phe Asp Ser Leu Pro Arg Leu Gly Ser Lys
            500                 505                 510

Glu Thr Val Glu Phe Ser Val Thr Leu Lys Ala Val Ser Ala Gly Asp
        515                 520                 525

Ala Arg Gly Glu Ala Ile Leu Ser Ser Asp Thr Leu Thr Val Pro Val
    530                 535                 540

Ser Asp Thr Glu Asn Thr His Ile Tyr
545                 550
```

<210> SEQ ID NO 13
<211> LENGTH: 1329
<212> TYPE: DNA
<213> ORGANISM: Chlamydia trachomatis

<400> SEQUENCE: 13

```
atgcaggctg cacaccatca ctatcaccgc tacacagata aactgcacag acaaaaccat     60

aaaaaagatc tcatctctcc caaacctacc gaacaagagg cgtgcaatac ttcttccctt    120

agtaaggaat taatccctct atcagaacaa agaggccttt tatcccccat ctgtgacttt    180

atttcggaac gcccttgctt acacggagtt tctgttagaa atctcaagca agcgctaaaa    240

aattctgcag gaacccaaat tgcactggat tggtctattc tccctcaatg gttcaatcct    300

cgggtctctc atgcccctaa gctttctatc cgagactttg ggtatagcgc acaccaaact    360

gttaccgaag ccactcctcc ttgctggcaa aactgcttta atccatctgc ggccgttact    420
```

-continued atctatgatt cctcatatgg gaaaggggtc tttcaaatat cctataccct tgtccgctat 480
tggagagaga atgctgcgac tgctggcgat gctatgatgc tcgcagggag tatcaatgat 540
tatccctctc gtcagaacat tttctctcag tttactttct cccaaaactt cccaaatgaa 600
cgggtgagtc tgacaattgg tcagtactca ctctatgcaa tagacggaac attatacaat 660
aacgatcaac aacttggatt cattagttac gcattatcac aaaatccaac agcaacttat 720
tcctctggaa gtcttggagc ttacctacaa gtcgctccta ccgcaagcac aagtcttcaa 780
ataggatttc aagacgctta taatatctcc ggatcctcta tcaaatggag taaccttaca 840
aaaaatagat acaattttca cggttttgct tcctgggctc cccgctgttg cttaggatct 900
ggccagtact ccgtgcttct ttatgtgact agacaagttc cagaacagat ggaacaaaca 960
atgggatggt cagtcaatgc gagtcaacac atatcttcta aactgtatgt gtttggaaga 1020
tacagcggtg ttacaggaca tgtgttcccg attaaccgca cgtattcatt cggtatggcc 1080
tctgcaaatt tatttaaccg taacccacaa gatttatttg gaattgcttg cgcattcaat 1140
aatgtacacc tctctgcttc tccaaatact aaaagaaaat acgaaactgt aatcgaaggg 1200
tttgcaacta tcggttgcgg cccctatctt tctttcgctc cagacttcca actctacctc 1260
tacccagctc ttcgtccaaa caaacaatct gcccgtgttt atagcgtgcg agctaattta 1320
gctatctaa 1329

<210> SEQ ID NO 14
<211> LENGTH: 47
<212> TYPE: PRT
<213> ORGANISM: Chlamydia trachomatis

<400> SEQUENCE: 14

Met Gln Ala Ala His His His Tyr His Arg Tyr Thr Asp Lys Leu His
1               5                   10                  15

Arg Gln Asn His Lys Lys Asp Leu Ile Ser Pro Lys Pro Thr Glu Gln
            20                  25                  30

Glu Ala Cys Asn Thr Ser Ser Leu Ser Lys Glu Leu Ile Pro Leu
        35                  40                  45

<210> SEQ ID NO 15
<211> LENGTH: 504
<212> TYPE: DNA
<213> ORGANISM: Chlamydia trachomatis

<400> SEQUENCE: 15
atgtccaggc agaatgctga ggaaaatcta aaaaattttg ctaaagagct taaactcccc 60
gacgtggcct tcgatcagaa taatacgtgc attttgtttg ttgatggaga gttttctctt 120
cacctgacct acgaagaaca ctctgatcgc ctttatgttt acgcacctct tcttgacgga 180
ctgccagaca atccgcaaag aaggttagct ctatatgaga agttgttaga aggctctatg 240
ctcggaggcc aaatggctgg tggaggggta ggagtcgcta ctaaggaaca gttgatctta 300
atgcactgcg tgttagacat gaagtatgca gagaccaacc tactcaaagc ttttgcacag 360
ctttttattg aaaccgttgt gaaatggcga actgtttgtt ctgatatcag cgctggacga 420
gaacccactg ttgataccat gccacaaatg cctcaagggg gtggcggagg aattcaacct 480
cctccagcag gaatccgtgc ataa 504

<210> SEQ ID NO 16
<211> LENGTH: 167

<212> TYPE: PRT
<213> ORGANISM: Chlamydia trachomatis

<400> SEQUENCE: 16

```
Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Arg Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Thr Val
    130                 135                 140

Asp Thr Met Pro Gln Met Pro Gln Gly Gly Gly Gly Gly Ile Gln Pro
145                 150                 155                 160

Pro Pro Ala Gly Ile Arg Ala
                165
```

<210> SEQ ID NO 17
<211> LENGTH: 393
<212> TYPE: PRT
<213> ORGANISM: Chlamydia trachomatis

<400> SEQUENCE: 17

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175
```

```
Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390


<210> SEQ ID NO 18
<211> LENGTH: 1154
<212> TYPE: DNA
<213> ORGANISM: Chlamydia trachomatis

<400> SEQUENCE: 18

atgaaaaaac tcttgaaatc ggtattagta tttgccgctt tgagttctgc ttcctccttg      60

caagctctgc ctgtggggaa tcctgctgaa ccaagcctta tgatcgacgg aattctgtgg     120

gaaggtttcg gcggagatcc ttgcgatcct tgcgccactt ggtgtgacgc tatcagcatg     180

cgtgttggtt actacggaga ctttgttttc gaccgtgttt tgaaaacaga tgtgaataaa     240

gaatttcaga tgggtgccaa gcctacaact gatacaggca atagtgcagc tccatccact     300

cttacagcaa gagagaatcc tgcttacggc cgacatatgc aggatgctga gatgtttaca     360

aatgccgctt gcatggcatt gaatatttgg gatcgttttg atgtattctg tacattagga     420

gccaccagtg gatatcttaa aggaaactct gcttctttca atttagttgg attgtttgga     480

gataatgaaa atcaaaaaac ggtcaaagcg gagtctgtac caaatatgag ctttgatcaa     540

tctgttgttg agttgtatac agatactact tttgcgtgga gcgtcggcgc tcgcgcagct     600

ttgtgggaat gtggatgtgc aactttagga gcttcattcc aatatgctca atctaaacct     660

aaagtagaag aattaaacgt tctctgcaat gcagcagagt ttactattaa taaacctaaa     720

gggtatgtag gtaaggagtt tcctcttgat cttacagcag gaacagatgc tgcgacagga     780

actaaggatg cctctattga ttaccatgaa tggcaagcaa gtttagctct ctcttacaga     840

ctgaatatgt tcactcccta cattggagtt aaatggtctc gagcaagctt tgatgccgat     900
```

```
acgattcgta tagcccagcc aaaatcagct acagctattt ttgatactac cacgcttaac    960

ccaactattg ctggagctgg cgatgtgaaa actggcgcag agggtcagct cggagacaca   1020

atgcaaatcg tttccttgca attgaacaag atgaaatcta gaaaatcttg cggtattgca   1080

gtaggaacaa ctattgtgga tgcagacaaa tacgcagtta cagttgagac tcgcttgatc   1140

gatgagagag cagc                                                     1154


<210> SEQ ID NO 19
<211> LENGTH: 497
<212> TYPE: PRT
<213> ORGANISM: Chlamydia muridarum

<400> SEQUENCE: 19

Met Met Lys Arg Leu Leu Cys Val Leu Leu Ser Thr Ser Val Phe Ser
1               5                   10                  15

Ser Pro Met Leu Gly Tyr Ser Ala Pro Lys Lys Asp Ser Ser Thr Gly
            20                  25                  30

Ile Cys Leu Ala Ala Ser Gln Ser Asp Arg Glu Leu Ser Gln Glu Asp
        35                  40                  45

Leu Leu Lys Glu Val Ser Arg Gly Phe Ser Lys Val Ala Ala Gln Ala
    50                  55                  60

Thr Pro Gly Val Val Tyr Ile Glu Asn Phe Pro Lys Thr Gly Ser Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
            100                 105                 110

His Arg Glu Gln Pro Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140

Val Glu Asp Ala Gly Lys Ile His Val Thr Leu His Asp Gly Gln Lys
145                 150                 155                 160

Tyr Thr Ala Lys Ile Ile Gly Leu Asp Pro Lys Thr Asp Leu Ala Val
                165                 170                 175

Ile Lys Ile Gln Ala Lys Asn Leu Pro Phe Leu Thr Phe Gly Asn Ser
            180                 185                 190

Asp Gln Leu Gln Ile Gly Asp Trp Ser Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asp Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
        275                 280                 285

Asp Gln Leu Ile Ser Asp Gly Gln Val Thr Arg Gly Phe Leu Gly Val
    290                 295                 300

Thr Leu Gln Pro Ile Asp Ser Glu Leu Ala Ala Cys Tyr Lys Leu Glu
305                 310                 315                 320
```

-continued

Lys Val Tyr Gly Ala Leu Ile Thr Asp Val Val Lys Gly Ser Pro Ala
325 330 335

Glu Lys Ala Gly Leu Arg Gln Glu Asp Val Ile Val Ala Tyr Asn Gly
340 345 350

Lys Glu Val Glu Ser Leu Ser Ala Leu Arg Asn Ala Ile Ser Leu Met
355 360 365

Met Pro Gly Thr Arg Val Val Leu Lys Val Val Arg Glu Gly Lys Phe
370 375 380

Ile Glu Ile Pro Val Thr Val Thr Gln Ile Pro Ala Glu Asp Gly Val
385 390 395 400

Ser Ala Leu Gln Lys Met Gly Val Arg Val Gln Asn Leu Thr Pro Glu
405 410 415

Ile Cys Lys Lys Leu Gly Leu Ala Ser Asp Thr Arg Gly Ile Phe Val
420 425 430

Val Ser Val Glu Ala Gly Ser Pro Ala Ala Ser Ala Gly Val Val Pro
435 440 445

Gly Gln Leu Ile Leu Ala Val Asn Arg Gln Arg Val Ser Ser Val Glu
450 455 460

Glu Leu Asn Gln Val Leu Lys Asn Ala Lys Gly Glu Asn Val Leu Leu
465 470 475 480

Met Val Ser Gln Gly Glu Val Ile Arg Phe Val Val Leu Lys Ser Asp
485 490 495

Glu

<210> SEQ ID NO 20
<211> LENGTH: 387
<212> TYPE: PRT
<213> ORGANISM: Chlamydia muridarum

<400> SEQUENCE: 20

Met Lys Lys Leu Leu Lys Ser Val Leu Ala Phe Ala Val Leu Gly Ser
1 5 10 15

Ala Ser Ser Leu His Ala Leu Pro Val Gly Asn Pro Ala Glu Pro Ser
20 25 30

Leu Met Ile Asp Gly Ile Leu Trp Glu Gly Phe Gly Gly Asp Pro Cys
35 40 45

Asp Pro Cys Thr Thr Trp Cys Asp Ala Ile Ser Leu Arg Leu Gly Tyr
50 55 60

Tyr Gly Asp Phe Val Phe Asp Arg Val Leu Lys Thr Asp Val Asn Lys
65 70 75 80

Gln Phe Glu Met Gly Ala Ala Pro Thr Gly Asp Ala Asp Leu Thr Thr
85 90 95

Ala Pro Thr Pro Ala Ser Arg Glu Asn Pro Ala Tyr Gly Lys His Met
100 105 110

Gln Asp Ala Glu Met Phe Thr Asn Ala Ala Tyr Met Ala Leu Asn Ile
115 120 125

Trp Asp Arg Phe Asp Val Phe Cys Thr Leu Gly Ala Thr Ser Gly Tyr
130 135 140

Leu Lys Gly Asn Ser Ala Ala Phe Asn Leu Val Gly Leu Phe Gly Arg
145 150 155 160

Asp Glu Thr Ala Val Ala Ala Asp Asp Ile Pro Asn Val Ser Leu Ser
165 170 175

Gln Ala Val Val Glu Leu Tyr Thr Asp Thr Ala Phe Ala Trp Ser Val
180 185 190

-continued

```
Gly Ala Arg Ala Ala Leu Trp Glu Cys Gly Cys Ala Thr Leu Gly Ala
        195                 200                 205

Ser Phe Gln Tyr Ala Gln Ser Lys Pro Lys Val Glu Glu Leu Asn Val
    210                 215                 220

Leu Cys Asn Ala Ala Glu Phe Thr Ile Asn Lys Pro Lys Gly Tyr Val
225                 230                 235                 240

Gly Gln Glu Phe Pro Leu Asn Ile Lys Ala Gly Thr Val Ser Ala Thr
                245                 250                 255

Asp Thr Lys Asp Ala Ser Ile Asp Tyr His Glu Trp Gln Ala Ser Leu
            260                 265                 270

Ala Leu Ser Tyr Arg Leu Asn Met Phe Thr Pro Tyr Ile Gly Val Lys
        275                 280                 285

Trp Ser Arg Ala Ser Phe Asp Ala Asp Thr Ile Arg Ile Ala Gln Pro
    290                 295                 300

Lys Leu Glu Thr Ser Ile Leu Lys Met Thr Thr Trp Asn Pro Thr Ile
305                 310                 315                 320

Ser Gly Ser Gly Ile Asp Val Asp Thr Lys Ile Thr Asp Thr Leu Gln
                325                 330                 335

Ile Val Ser Leu Gln Leu Asn Lys Met Lys Ser Arg Lys Ser Cys Gly
            340                 345                 350

Leu Ala Ile Gly Thr Thr Ile Val Asp Ala Asp Lys Tyr Ala Val Thr
        355                 360                 365

Val Glu Thr Arg Leu Ile Asp Glu Arg Ala Ala His Val Asn Ala Gln
    370                 375                 380

Phe Arg Phe
385


<210> SEQ ID NO 21
<211> LENGTH: 1164
<212> TYPE: DNA
<213> ORGANISM: Chlamydia muridarum

<400> SEQUENCE: 21

atgaaaaaac tcttgaaatc ggtattagca tttgccgttt tgggttctgc ttcctccttg      60

catgctctgc ctgtggggaa tcctgctgaa ccaagcctta tgattgacgg gattctttgg     120

gaaggtttcg gtggagatcc ttgcgatcct tgcacaactt ggtgtgatgc catcagccta     180

cgtctcggct actatgggga cttcgttttt gatcgtgttt tgaaaacaga cgtgaacaaa     240

cagttcgaaa tgggagcagc tcctacagga gatgcagacc ttactacagc acctactcct     300

gcatcaagag agaatcccgc ttatggcaag catatgcaag atgcagaaat gttcactaat     360

gctgcgtaca tggctttaaa catttgggac cgtttcgatg tattttgtac attgggagca     420

actagcggat atcttaaagg taattctgcc gcctttaact tagttggtct gtttggaaga     480

gatgaaactg cagttgcagc tgacgacata cctaacgtca gcttgtctca agctgttgtc     540

gaactctaca cagacacagc tttcgcttgg agcgtcggtg ctagagcagc tttatgggag     600

tgcggatgtg caactttagg agcttccttc caatatgctc aatctaagcc aaaagtagag     660

gaattaaacg ttctctgtaa tgcggcagaa ttcactatta acaagcctaa aggatacgtt     720

ggacaagagt ttcctcttaa cattaaagct ggaacagtta gcgctacaga tactaaagat     780

gcttccatcg attaccatga gtggcaagca agcttggctt tgtcttacag actgaatatg     840

ttcactcctt acattggagt taagtggtct agagcaagct ttgatgccga cactatccgc     900

attgcgcagc ctaagcttga gacctctatc ttaaaaatga ccacttggaa cccaacgatc     960
```

-continued

```
tctggatctg gtatagacgt tgatacaaaa atcacggata cattacaaat tgtttccttg   1020

cagctcaaca agatgaaatc cagaaaatct tgcggtcttg caattggaac aacaattgta   1080

gatgctgata aatatgcagt tactgttgag acacgcttga tcgatgaaag agcagctcac   1140

gtaaatgctc agttccgttt ctaa                                          1164


<210> SEQ ID NO 22
<211> LENGTH: 448
<212> TYPE: PRT
<213> ORGANISM: Chlamydia muridarum

<400> SEQUENCE: 22

Met Leu Thr Asn Phe Thr Phe Arg Asn Cys Leu Leu Phe Phe Val Thr
1               5                   10                  15

Leu Ser Ser Val Pro Val Phe Ser Ala Pro Gln Pro Arg Val Thr Leu
            20                  25                  30

Pro Ser Gly Ala Asn Lys Ile Gly Ser Glu Ala Trp Ile Glu Gln Lys
        35                  40                  45

Val Arg Gln Tyr Pro Glu Leu Leu Trp Leu Val Glu Pro Ser Pro Ala
    50                  55                  60

Gly Thr Ser Leu Asn Ala Pro Ser Gly Met Ile Phe Ser Pro Leu Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Val Gln Leu Gln Ala Asn Glu Ser Pro Met Thr Phe Lys Gln Phe Leu
        115                 120                 125

Thr Leu His Lys Gln Leu Ser Leu Phe Leu Asn Ser Pro Lys Glu Phe
    130                 135                 140

Tyr Asp Ser Val Lys Ile Leu Glu Thr Ala Ile Ile Leu Arg His Leu
145                 150                 155                 160

Gly Cys Ser Thr Lys Ala Val Ala Thr Phe Lys Pro Tyr Phe Ser Glu
                165                 170                 175

Thr Gln Lys Glu Val Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Ala Pro Ser Leu Gln Leu Leu Ser Ala Val Arg Ser
225                 230                 235                 240

Arg Arg Ala Leu Leu Ala Leu Asp Leu Tyr Leu Tyr Ala Leu Asp Phe
                245                 250                 255

Cys Gly Glu Gln Gly Ile Ser Ser Gln Phe His Met Asp Phe Ser Pro
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Ala Gly Ser Ser
    290                 295                 300

Arg Thr Glu Met Ala Leu Val Arg Ile Ala Thr Leu Met Asn Leu Ser
305                 310                 315                 320

Pro Ser Glu Ala Ala Ile Leu Thr Thr Ser Phe Lys Ser Leu Ser Leu
                325                 330                 335
```

-continued

```
Glu Asp Ala Glu Ser Leu Val Asn Ser Phe Tyr Thr Asn Lys Gly Asp
            340                 345                 350

Ser Leu Ala Leu Ser Leu Arg Gly Leu Pro Thr Leu Ile Ser Glu Leu
        355                 360                 365

Thr Arg Ala Ala His Gly Asn Thr Asn Ala Glu Ala Arg Ala Gln Gln
    370                 375                 380

Ile Tyr Ala Thr Thr Leu Ser Leu Val Ala Lys Ser Leu Lys Ala His
385                 390                 395                 400

Lys Glu Met Gln Asn Lys Gln Ile Leu Pro Glu Glu Val Val Leu Asp
                405                 410                 415

Phe Ser Glu Thr Ala Ser Ser Cys Gln Gly Leu Asp Ile Phe Ser Glu
            420                 425                 430

Asn Val Ala Val Gln Ile His Leu Asn Gly Ser Val Ser Ile His Leu
        435                 440                 445


<210> SEQ ID NO 23
<211> LENGTH: 957
<212> TYPE: DNA
<213> ORGANISM: Chlamydia muridarum

<400> SEQUENCE: 23

atggcatcca agtctcgtca ttatcttaac cagccttggt acattatctt attcatcttt      60

gttcttagtc tggttgctgg tacccttctt tcttcagttt cctatgttct atctccaatc     120

caaaaacaag ctgcagaatt tgatcgtaat cagcaaatgt tgatggccgc acaaattatt     180

tcctatgaca ataaattcca aatatatgct gaaggggatt ggcaacctgc tgtctataat     240

acaaaaaaac agatactaga aaaaagctct tccactccac cacaagtgac tgtggcgact     300

ctatgctctt attttcaaaa ttttgttaga gttttgctta cagactccca agggaatctt     360

tcttcttttg aagatcacaa tcttaaccta gaagagttct tatcccaccc cacatcttca     420

gtacaagatc actctctgca tgtaatttat gctattctag caaacgatga atcctctaaa     480

aagttatcat cctcccaagt agcaaaaaat ccggtatcca tagagtctat tattcttcct     540

ataaaaggat ttggtttatg ggaccaatc tatggatttc ttgctttaga aaaggacggt      600

aatacggttc tagggacatg ctggtatcaa catggtgaga ctccaggatt aggagcaaat     660

ataactaatc cccaatggca acaaaatttc agaggaaaaa aagtatttct cgcttcctct     720

tccggagaaa ccgattttgc taaaacaact ctaggactag aagttataaa aggatctgtt     780

tctgcattat taggggactc tcccaaagct aattccgctg ttgatggaat ttcaggagct     840

acactgacct gtaatggagt tactgaagct tttgctaatt cgctagctcc ttaccgcccc     900

ttattgactt tcttcgccaa tcttaactct agtggagaat ctcatgacaa ccaataa        957


<210> SEQ ID NO 24
<211> LENGTH: 318
<212> TYPE: PRT
<213> ORGANISM: Chlamydia muridarum

<400> SEQUENCE: 24

Met Ala Ser Lys Ser Arg His Tyr Leu Asn Gln Pro Trp Tyr Ile Ile
1               5                   10                  15

Leu Phe Ile Phe Val Leu Ser Leu Val Ala Gly Thr Leu Leu Ser Ser
            20                  25                  30

Val Ser Tyr Val Leu Ser Pro Ile Gln Lys Gln Ala Ala Glu Phe Asp
        35                  40                  45

Arg Asn Gln Gln Met Leu Met Ala Ala Gln Ile Ile Ser Tyr Asp Asn
```

```
    50                  55                  60

Lys Phe Gln Ile Tyr Ala Glu Gly Asp Trp Gln Pro Ala Val Tyr Asn
65                  70                  75                  80

Thr Lys Lys Gln Ile Leu Glu Lys Ser Ser Ser Thr Pro Pro Gln Val
                85                  90                  95

Thr Val Ala Thr Leu Cys Ser Tyr Phe Gln Asn Phe Val Arg Val Leu
            100                 105                 110

Leu Thr Asp Ser Gln Gly Asn Leu Ser Ser Phe Glu Asp His Asn Leu
        115                 120                 125

Asn Leu Glu Glu Phe Leu Ser His Pro Thr Ser Ser Val Gln Asp His
    130                 135                 140

Ser Leu His Val Ile Tyr Ala Ile Leu Ala Asn Asp Glu Ser Ser Lys
145                 150                 155                 160

Lys Leu Ser Ser Ser Gln Val Ala Lys Asn Pro Val Ser Ile Glu Ser
                165                 170                 175

Ile Ile Leu Pro Ile Lys Gly Phe Gly Leu Trp Gly Pro Ile Tyr Gly
            180                 185                 190

Phe Leu Ala Leu Glu Lys Asp Gly Asn Thr Val Leu Gly Thr Cys Trp
        195                 200                 205

Tyr Gln His Gly Glu Thr Pro Gly Leu Gly Ala Asn Ile Thr Asn Pro
    210                 215                 220

Gln Trp Gln Gln Asn Phe Arg Gly Lys Lys Val Phe Leu Ala Ser Ser
225                 230                 235                 240

Ser Gly Glu Thr Asp Phe Ala Lys Thr Thr Leu Gly Leu Glu Val Ile
                245                 250                 255

Lys Gly Ser Val Ser Ala Leu Leu Gly Asp Ser Pro Lys Ala Asn Ser
            260                 265                 270

Ala Val Asp Gly Ile Ser Gly Ala Thr Leu Thr Cys Asn Gly Val Thr
        275                 280                 285

Glu Ala Phe Ala Asn Ser Leu Ala Pro Tyr Arg Pro Leu Leu Thr Phe
    290                 295                 300

Phe Ala Asn Leu Asn Ser Ser Gly Glu Ser His Asp Asn Gln
305                 310                 315


<210> SEQ ID NO 25
<211> LENGTH: 1416
<212> TYPE: DNA
<213> ORGANISM: Chlamydia muridarum

<400> SEQUENCE: 25

atgaatggaa aagttctgtg tgaggtttct gtgtccttcc gttcgattct gctgacggct     60

ctgctttcac tttcttttac aaacactatg caggctgcac accatcatta tcaccgttat    120

gatgataaac tacgcagaca ataccataaa aaggacttgc ccactcaaga gaatgttcgg    180

aaagagtttt gtaatcccta ctctcatagt agtgatccta tccctttgtc acaacaacga    240

ggagtcctat ctcctatctg tgatttagtc tcagagtgct cgtttttgaa cgggatttcc    300

gttaggagtc ttaaacaaac actgaaaaat tctgctggga ctcaagttgc tttagactgg    360

tctatccttc ctcaatggtt caatcctaga tcctcttggg ctcctaagct ctctattcga    420

gatcttggat atggtaaacc ccagtccctt attgaagcag attccccttg ttgtcaaacc    480

tgcttcaacc catctgctgc tattacgatt tacgattctt catgtgggaa gggtgttgtc    540

caagtgtcat acacccttgt tcgttattgg agagaaacgg ctgcacttgc agggcaaact    600

atgatgcttg caggaagtat taatgattat cctgctcgcc aaaacatatt ctctcaactt    660
```

```
acattttccc aaactttccc taatgagaga gtaaatctaa ctgttggtca atactctctt    720

tactcgatag acggaacgct gtacaacaat gatcagcagc taggatttat tagttatgcg    780

ttgtcgcaaa atccaacagc gacttattcc tctggaagcc ttggcgccta tctacaagtc    840

gctccaacag aaagcacctg tcttcaagtt gggttccaag atgcctataa tatttcaggt    900

tcctcgatca aatggaataa tcttacaaaa aataagtata acttccatgg ctatgcatct    960

tgggctccac actgttgctt aggacctgga caatactctg ttcttcttta tgtaaccaga   1020

aaggttcctg agcaaatgat gcagacaatg ggctggtctg tgaatgcaag tcaatacatc   1080

tcttctaaac tttatgtatt tggaagatac agcggagtca caggccaatt gtctcctatt   1140

aaccgaacct attcatttgg cttagtctct cctaatttat tgaaccgtaa cccacaagac   1200

ttatttggag tagcttgcgc attcaataat atacacgcct ccgcctttca aaatgctcaa   1260

agaaaatatg aaactgtgat cgagggattt gcaactattg gttgcggacc ttacatctcc   1320

tttgctccag atttccaact ttacctctat cctgctctgc gtccaaataa acaaagcgcc   1380

cgagtctata gcgttcgcgc aaacctagct atttag                             1416


<210> SEQ ID NO 26
<211> LENGTH: 471
<212> TYPE: PRT
<213> ORGANISM: Chlamydia muridarum

<400> SEQUENCE: 26

Met Asn Gly Lys Val Leu Cys Glu Val Ser Val Ser Phe Arg Ser Ile
1               5                   10                  15

Leu Leu Thr Ala Leu Leu Ser Leu Ser Phe Thr Asn Thr Met Gln Ala
            20                  25                  30

Ala His His His Tyr His Arg Tyr Asp Asp Lys Leu Arg Arg Gln Tyr
        35                  40                  45

His Lys Lys Asp Leu Pro Thr Gln Glu Asn Val Arg Lys Glu Phe Cys
    50                  55                  60

Asn Pro Tyr Ser His Ser Ser Asp Pro Ile Pro Leu Ser Gln Gln Arg
65                  70                  75                  80

Gly Val Leu Ser Pro Ile Cys Asp Leu Val Ser Glu Cys Ser Phe Leu
                85                  90                  95

Asn Gly Ile Ser Val Arg Ser Leu Lys Gln Thr Leu Lys Asn Ser Ala
            100                 105                 110

Gly Thr Gln Val Ala Leu Asp Trp Ser Ile Leu Pro Gln Trp Phe Asn
        115                 120                 125

Pro Arg Ser Ser Trp Ala Pro Lys Leu Ser Ile Arg Asp Leu Gly Tyr
    130                 135                 140

Gly Lys Pro Gln Ser Leu Ile Glu Ala Asp Ser Pro Cys Cys Gln Thr
145                 150                 155                 160

Cys Phe Asn Pro Ser Ala Ala Ile Thr Ile Tyr Asp Ser Ser Cys Gly
                165                 170                 175

Lys Gly Val Val Gln Val Ser Tyr Thr Leu Val Arg Tyr Trp Arg Glu
            180                 185                 190

Thr Ala Ala Leu Ala Gly Gln Thr Met Met Leu Ala Gly Ser Ile Asn
        195                 200                 205

Asp Tyr Pro Ala Arg Gln Asn Ile Phe Ser Gln Leu Thr Phe Ser Gln
    210                 215                 220

Thr Phe Pro Asn Glu Arg Val Asn Leu Thr Val Gly Gln Tyr Ser Leu
225                 230                 235                 240
```

-continued

Tyr Ser Ile Asp Gly Thr Leu Tyr Asn Asn Asp Gln Gln Leu Gly Phe
245 250 255

Ile Ser Tyr Ala Leu Ser Gln Asn Pro Thr Ala Thr Tyr Ser Ser Gly
260 265 270

Ser Leu Gly Ala Tyr Leu Gln Val Ala Pro Thr Glu Ser Thr Cys Leu
275 280 285

Gln Val Gly Phe Gln Asp Ala Tyr Asn Ile Ser Gly Ser Ser Ile Lys
290 295 300

Trp Asn Asn Leu Thr Lys Asn Lys Tyr Asn Phe His Gly Tyr Ala Ser
305 310 315 320

Trp Ala Pro His Cys Cys Leu Gly Pro Gly Gln Tyr Ser Val Leu Leu
325 330 335

Tyr Val Thr Arg Lys Val Pro Glu Gln Met Met Gln Thr Met Gly Trp
340 345 350

Ser Val Asn Ala Ser Gln Tyr Ile Ser Ser Lys Leu Tyr Val Phe Gly
355 360 365

Arg Tyr Ser Gly Val Thr Gly Gln Leu Ser Pro Ile Asn Arg Thr Tyr
370 375 380

Ser Phe Gly Leu Val Ser Pro Asn Leu Leu Asn Arg Asn Pro Gln Asp
385 390 395 400

Leu Phe Gly Val Ala Cys Ala Phe Asn Asn Ile His Ala Ser Ala Phe
405 410 415

Gln Asn Ala Gln Arg Lys Tyr Glu Thr Val Ile Glu Gly Phe Ala Thr
420 425 430

Ile Gly Cys Gly Pro Tyr Ile Ser Phe Ala Pro Asp Phe Gln Leu Tyr
435 440 445

Leu Tyr Pro Ala Leu Arg Pro Asn Lys Gln Ser Ala Arg Val Tyr Ser
450 455 460

Val Arg Ala Asn Leu Ala Ile
465 470

<210> SEQ ID NO 27
<211> LENGTH: 1665
<212> TYPE: DNA
<213> ORGANISM: Chlamydia muridarum

<400> SEQUENCE: 27
atgcgaatag gagatcctat gaacaaactc atcagacgag ctgtgacgat cttcgcggtg 60
actagtgtgg cgagtttatt tgctagcggg gtgttagaga cctctatggc agagtctctc 120
tctaccaacg ttattagctt agctgacacc aaagcgaaag agaccacttc tcatcaaaaa 180
gacagaaaag caagaaaaaa tcatcaaaat aggacttccg tagtccgtaa agaggttact 240
gcagttcgtg atactaaagc tgtagagcct agacaggatt cttgctttgg caaaatgtat 300
acagtcaaag ttaatgatga tcgtaatgta gaaatcgtgc agtccgttcc tgaatatgct 360
acggtaggat ctccatatcc tattgagatt actgctatag ggaaaagaga ctgtgttgat 420
gtaatcatta cacagcaatt accatgcgaa gcagagtttg ttagcagtga tccagctact 480
actcctactg ctgatggtaa gctagtttgg aaaattgatc ggttaggaca gggcgaaaag 540
agtaaaatta ctgtatgggt aaaacctctt aaagaaggtt gctgctttac agctgcaacg 600
gtttgtgctt gtccagagat ccgttcggtt acgaaatgtg gccagcctgc tatctgtgtt 660
aaacaggaag gtccagaaag cgcatgtttg cgttgcccag taacttatag aattaatgta 720
gtcaaccaag gaacagcaac agcacgtaat gttgttgtgg aaaatcctgt tccagatggc 780

```
tatgctcatg catccggaca gcgtgtattg acatatactc ttggggatat gcaacctgga    840

gaacagagaa caatcaccgt ggagttttgt ccgcttaaac gtggtcgagt cacaaatatt    900

gctacagttt cttactgtgg tggacacaaa aatactgcta gcgtaacaac agtgatcaat    960

gagccttgcg tgcaagttaa catcgaggga gcagattggt cttatgtttg taagcctgta   1020

gaatatgtta tctctgtttc taaccctggt gacttagttt tacgagacgt tgtaattgaa   1080

gatacgcttt ctcctggaat aactgttgtt gaagcagctg gagctcagat ttcttgtaat   1140

aaattggttt ggactttgaa ggaactcaat cctggagagt ctttacaata taaggttcta   1200

gtaagagctc aaactccagg gcaattcaca aacaacgttg ttgtgaaaag ttgctctgat   1260

tgcggtattt gtacttcttg cgcagaagca acaacttact ggaaaggagt tgctgctact   1320

catatgtgcg tagtagatac ttgtgatcct atttgcgtag gagagaacac tgtttatcgt   1380

atctgtgtga caaacagagg ttctgctgaa gatacaaatg tgtccttaat tttgaaattc   1440

tctaaagaat tacaacctat atctttctct ggaccaacta aaggaaccat tacaggaaac   1500

acggtagtgt ttgattcgtt acctagatta ggttctaaag aaactgtaga gttttctgta   1560

acgttgaaag cagtatccgc tggagatgct cgtggggaag ctattctttc ttccgataca   1620

ttgacagttc ctgtatctga tacggagaat acacatatct attaa                   1665
```

<210> SEQ ID NO 28
<211> LENGTH: 554
<212> TYPE: PRT
<213> ORGANISM: Chlamydia muridarum

<400> SEQUENCE: 28

```
Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Glu Thr Thr Ser His Gln Lys Asp Arg Lys Ala
    50                  55                  60

Arg Lys Asn His Gln Asn Arg Thr Ser Val Val Arg Lys Glu Val Thr
65                  70                  75                  80

Ala Val Arg Asp Thr Lys Ala Val Glu Pro Arg Gln Asp Ser Cys Phe
                85                  90                  95

Gly Lys Met Tyr Thr Val Lys Val Asn Asp Asp Arg Asn Val Glu Ile
            100                 105                 110

Val Gln Ser Val Pro Glu Tyr Ala Thr Val Gly Ser Pro Tyr Pro Ile
        115                 120                 125

Glu Ile Thr Ala Ile Gly Lys Arg Asp Cys Val Asp Val Ile Ile Thr
    130                 135                 140

Gln Gln Leu Pro Cys Glu Ala Glu Phe Val Ser Ser Asp Pro Ala Thr
145                 150                 155                 160

Thr Pro Thr Ala Asp Gly Lys Leu Val Trp Lys Ile Asp Arg Leu Gly
                165                 170                 175

Gln Gly Glu Lys Ser Lys Ile Thr Val Trp Val Lys Pro Leu Lys Glu
            180                 185                 190

Gly Cys Cys Phe Thr Ala Ala Thr Val Cys Ala Cys Pro Glu Ile Arg
        195                 200                 205

Ser Val Thr Lys Cys Gly Gln Pro Ala Ile Cys Val Lys Gln Glu Gly
```

210 215 220

Pro Glu Ser Ala Cys Leu Arg Cys Pro Val Thr Tyr Arg Ile Asn Val
225 230 235 240

Val Asn Gln Gly Thr Ala Thr Ala Arg Asn Val Val Val Glu Asn Pro
245 250 255

Val Pro Asp Gly Tyr Ala His Ala Ser Gly Gln Arg Val Leu Thr Tyr
260 265 270

Thr Leu Gly Asp Met Gln Pro Gly Glu Gln Arg Thr Ile Thr Val Glu
275 280 285

Phe Cys Pro Leu Lys Arg Gly Arg Val Thr Asn Ile Ala Thr Val Ser
290 295 300

Tyr Cys Gly Gly His Lys Asn Thr Ala Ser Val Thr Thr Val Ile Asn
305 310 315 320

Glu Pro Cys Val Gln Val Asn Ile Glu Gly Ala Asp Trp Ser Tyr Val
325 330 335

Cys Lys Pro Val Glu Tyr Val Ile Ser Val Ser Asn Pro Gly Asp Leu
340 345 350

Val Leu Arg Asp Val Val Ile Glu Asp Thr Leu Ser Pro Gly Ile Thr
355 360 365

Val Val Glu Ala Ala Gly Ala Gln Ile Ser Cys Asn Lys Leu Val Trp
370 375 380

Thr Leu Lys Glu Leu Asn Pro Gly Glu Ser Leu Gln Tyr Lys Val Leu
385 390 395 400

Val Arg Ala Gln Thr Pro Gly Gln Phe Thr Asn Asn Val Val Val Lys
405 410 415

Ser Cys Ser Asp Cys Gly Ile Cys Thr Ser Cys Ala Glu Ala Thr Thr
420 425 430

Tyr Trp Lys Gly Val Ala Ala Thr His Met Cys Val Val Asp Thr Cys
435 440 445

Asp Pro Ile Cys Val Gly Glu Asn Thr Val Tyr Arg Ile Cys Val Thr
450 455 460

Asn Arg Gly Ser Ala Glu Asp Thr Asn Val Ser Leu Ile Leu Lys Phe
465 470 475 480

Ser Lys Glu Leu Gln Pro Ile Ser Phe Ser Gly Pro Thr Lys Gly Thr
485 490 495

Ile Thr Gly Asn Thr Val Val Phe Asp Ser Leu Pro Arg Leu Gly Ser
500 505 510

Lys Glu Thr Val Glu Phe Ser Val Thr Leu Lys Ala Val Ser Ala Gly
515 520 525

Asp Ala Arg Gly Glu Ala Ile Leu Ser Ser Asp Thr Leu Thr Val Pro
530 535 540

Val Ser Asp Thr Glu Asn Thr His Ile Tyr
545 550

<210> SEQ ID NO 29
<211> LENGTH: 504
<212> TYPE: DNA
<213> ORGANISM: Chlamydia muridarum

<400> SEQUENCE: 29
atgtccagac agaatgctga ggaaaatcta aaaaattttg ctaaagagct caagctcccc 60
gacgtggcct tcgatcagaa taatacgtgc attttgtttg ttgatggaga gttttctctt 120
cacctgacct acgaagagca ctctgatcgc ctttatgttt acgcacctct ccttgacgga 180

-continued

```
ctcccagata atccgcaaag aaagttggct ctgtatgaga aattgttgga aggctctatg    240

ctcggaggcc aaatggctgg tggaggagta ggagttgcta ctaaagaaca gttgatccta    300

atgcattgcg tgttagatat gaaatatgca gagactaatc tattgaaagc ttttgcacag    360

cttttcattg aaactgttgt gaaatggcga acggtctgtt ctgatatcag cgctggacga    420

gaaccttccg ttgacactat gcctcaaatg cctcaaggag gcagcggagg aattcaacct    480

cctccaacag gaattcgtgc gtag                                          504
```

```
<210> SEQ ID NO 30
<211> LENGTH: 167
<212> TYPE: PRT
<213> ORGANISM: Chlamydia muridarum

<400> SEQUENCE: 30

Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Lys Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Ser Val
    130                 135                 140

Asp Thr Met Pro Gln Met Pro Gln Gly Gly Ser Gly Gly Ile Gln Pro
145                 150                 155                 160

Pro Pro Thr Gly Ile Arg Ala
                165


<210> SEQ ID NO 31
<211> LENGTH: 809
<212> TYPE: PRT
<213> ORGANISM: Chlamydia muridarum

<400> SEQUENCE: 31

Met Pro His Ser Pro Phe Leu Tyr Val Val Gln Pro His Ser Val Phe
1               5                   10                  15

Asn Pro Arg Leu Gly Glu Arg His Pro Ile Thr Leu Asp Phe Ile Lys
            20                  25                  30

Glu Lys Asn Arg Leu Ala Asp Phe Ile Glu Asn Leu Pro Leu Glu Ile
        35                  40                  45

Phe Gly Ala Pro Ser Phe Leu Glu Asn Ala Ser Leu Glu Ala Ser Tyr
    50                  55                  60

Val Leu Ser Arg Glu Ser Thr Lys Asp Gly Thr Leu Phe Thr Val Leu
65                  70                  75                  80

Glu Pro Lys Leu Ser Ala Cys Val Ala Thr Cys Leu Val Asp Ser Ser
                85                  90                  95
```

-continued

```
Ile Pro Met Glu Pro Asp Asn Glu Leu Leu Glu Glu Ile Lys His Thr
            100                 105                 110

Leu Leu Lys Ser Ser Cys Asp Gly Val Gln Tyr Arg Val Thr Arg Glu
        115                 120                 125

Thr Leu Gln Asn Lys Asp Glu Ala Pro Arg Val Ser Leu Val Ala Asp
    130                 135                 140

Asp Ile Glu Leu Ile Arg Asn Val Asp Phe Leu Gly Arg Ser Val Asp
145                 150                 155                 160

Ile Val Lys Leu Asp Pro Leu Asn Ile Pro Asn Thr Val Ser Glu Glu
                165                 170                 175

Asn Ala Leu Asp Tyr Ser Phe Thr Arg Glu Thr Ala Lys Leu Ser Pro
            180                 185                 190

Asp Gly Arg Val Gly Ile Pro Gln Gly Thr Lys Ile Leu Pro Ala Pro
        195                 200                 205

Ser Leu Glu Val Glu Ile Ser Thr Ser Ile Phe Glu Glu Thr Ser Ser
    210                 215                 220

Phe Glu Gln Asn Phe Ser Ser Ser Ile Thr Phe Cys Val Pro Pro Leu
225                 230                 235                 240

Thr Ser Phe Ser Pro Leu Gln Glu Pro Pro Leu Val Gly Ala Gly Gln
                245                 250                 255

Gln Glu Ile Leu Val Thr Lys Lys His Leu Phe Pro Ser Tyr Thr Pro
            260                 265                 270

Lys Leu Ile Asp Ile Val Lys Arg His Lys Arg Asp Ala Lys Ile Leu
        275                 280                 285

Val Asn Lys Ile Gln Phe Glu Lys Leu Trp Arg Ser His Ala Lys Ser
    290                 295                 300

Gln Ile Leu Lys Glu Gly Ser Val Arg Leu Asp Leu Gln Gly Phe Thr
305                 310                 315                 320

Gly Glu Leu Phe Asn Tyr Gln Leu Gln Val Gly Ser His Thr Ile Ala
                325                 330                 335

Ala Val Leu Ile Asp Pro Glu Ile Ala Asn Val Lys Ser Leu Pro Glu
            340                 345                 350

Gln Thr Tyr Ala Val Arg Lys Ile Lys Ser Gly Phe Gln Cys Ser Leu
        355                 360                 365

Asp Asp Gln His Ile Tyr Gln Val Ala Val Lys Lys His Leu Ser Leu
    370                 375                 380

Ser Ser Gln Pro Pro Lys Ile Ser Pro Leu Ser Gln Ser Glu Ser Ser
385                 390                 395                 400

Asp Leu Ser Leu Phe Glu Ala Ala Ala Phe Ser Ala Ser Leu Thr Tyr
                405                 410                 415

Glu Phe Val Lys Lys Asn Thr Tyr His Ala Lys Asn Thr Val Thr Cys
            420                 425                 430

Ser Thr Val Ser His Ser Leu Tyr Ile Leu Lys Glu Asp Asp Gly Ala
        435                 440                 445

Asn Ala Ala Glu Lys Arg Leu Asp Asn Ser Phe Arg Asn Trp Val Glu
    450                 455                 460

Asn Lys Leu Asn Ala Asn Ser Pro Asp Ser Cys Thr Ala Phe Ile Gln
465                 470                 475                 480

Lys Phe Gly Thr His Tyr Ile Thr Ser Ala Thr Phe Gly Gly Ser Gly
                485                 490                 495

Phe Gln Val Leu Lys Leu Ser Phe Glu Gln Val Glu Gly Leu Arg Ser
            500                 505                 510

Lys Lys Ile Ser Leu Glu Ala Ala Ala Ala Asn Ser Leu Leu Lys Ser
```

-continued

```
        515                 520                 525

Ser Val Ser Asn Ser Thr Glu Ser Gly Tyr Ser Thr Tyr Asp Ser Ser
    530                 535                 540

Ser Ser Ser His Thr Val Phe Leu Gly Gly Thr Val Leu Pro Ser Val
545                 550                 555                 560

His Asp Gly Gln Leu Asp Phe Lys Asp Trp Ser Glu Ser Val Cys Leu
                565                 570                 575

Glu Pro Val Pro Ile His Ile Ser Leu Leu Pro Leu Thr Asp Leu Leu
            580                 585                 590

Thr Pro Leu Tyr Phe Pro Glu Thr Asp Thr Thr Glu Leu Ser Asn Lys
        595                 600                 605

Arg Asn Ala Leu Gln Gln Ala Val Arg Val Tyr Leu Lys Asp His Arg
    610                 615                 620

Ser Ala Lys Gln Ser Glu Arg Ser Val Phe Thr Ala Gly Ile Asn Ser
625                 630                 635                 640

Pro Ser Ser Trp Phe Thr Leu Glu Ser Ala Asn Ser Pro Leu Val Val
                645                 650                 655

Ser Ser Pro Tyr Met Thr Tyr Trp Ser Thr Leu Pro Tyr Leu Phe Pro
            660                 665                 670

Thr Leu Lys Glu Arg Ser Ser Ala Ala Pro Ile Val Phe Tyr Phe Cys
        675                 680                 685

Val Asp Asn Asn Glu His Ala Ser Gln Lys Ile Leu Asn Gln Thr Tyr
    690                 695                 700

Cys Phe Ile Gly Ser Leu Pro Ile Arg Gln Lys Ile Phe Gly Arg Glu
705                 710                 715                 720

Phe Ala Glu Asn Pro Tyr Leu Ser Phe Tyr Gly Arg Phe Gly Glu Ala
                725                 730                 735

Tyr Phe Asp Gly Gly Tyr Pro Glu Arg Cys Gly Trp Ile Val Glu Lys
            740                 745                 750

Leu Asn Thr Thr Lys Asp Gln Ile Leu Arg Asp Glu Asp Glu Val Gln
        755                 760                 765

Leu Lys His Val Tyr Ser Gly Glu Tyr Leu Ser Thr Ile Pro Ile Lys
    770                 775                 780

Asp Ser His Cys Thr Leu Ser Arg Thr Cys Thr Glu Ser Asn Ala Val
785                 790                 795                 800

Phe Ile Ile Lys Lys Pro Ser Ser Tyr
                805


<210> SEQ ID NO 32
<211> LENGTH: 609
<212> TYPE: DNA
<213> ORGANISM: Chlamydia muridarum

<400> SEQUENCE: 32

atgctcgcta atcggttatt tctaatcacc cttataggtt ttggctattc tgcttacggt      60

gccagcacag ggaaatcacc ttctttacag gttattttag ctgaagtcga ggatacatct     120

tcgcgcttac aagctcatca gaatgagctt gttatgctct cggaacgttt agatgagcaa     180

gacacaaaac ttcaacaact ctcgtcaact caggcccgta atcttcctca acaagttcaa     240

cggcttgaga ttgatctgag agctctggct aaaacagctg ctgtgctctc gcaatctgtt     300

caggatatcc gatcatccgt gcaaaataaa ttacaagaaa tccaacaaga acaaaaaaat     360

ttagctcaaa atttacgagc gcttcgcaac tccttacaag cactagttga tggctcttcc     420

ccagaaaatt atattgattt tttggccggg gagacacctg aacatattca cgttgttaaa     480
```

-continued caaggagaaa ccctgagtaa aatcgctagt aagtacaata tccctgtcgc agaattgaaa 540
aaacttaata aattaaattc cgatactatt tttactgatc aaagaatccg acttccaaaa 600
aagaaataa 609

<210> SEQ ID NO 33
<211> LENGTH: 202
<212> TYPE: PRT
<213> ORGANISM: Chlamydia muridarum

<400> SEQUENCE: 33

Met Leu Ala Asn Arg Leu Phe Leu Ile Thr Leu Ile Gly Phe Gly Tyr
1 5 10 15

Ser Ala Tyr Gly Ala Ser Thr Gly Lys Ser Pro Ser Leu Gln Val Ile
20 25 30

Leu Ala Glu Val Glu Asp Thr Ser Ser Arg Leu Gln Ala His Gln Asn
35 40 45

Glu Leu Val Met Leu Ser Glu Arg Leu Asp Glu Gln Asp Thr Lys Leu
50 55 60

Gln Gln Leu Ser Ser Thr Gln Ala Arg Asn Leu Pro Gln Gln Val Gln
65 70 75 80

Arg Leu Glu Ile Asp Leu Arg Ala Leu Ala Lys Thr Ala Ala Val Leu
85 90 95

Ser Gln Ser Val Gln Asp Ile Arg Ser Ser Val Gln Asn Lys Leu Gln
100 105 110

Glu Ile Gln Gln Glu Gln Lys Asn Leu Ala Gln Asn Leu Arg Ala Leu
115 120 125

Arg Asn Ser Leu Gln Ala Leu Val Asp Gly Ser Ser Pro Glu Asn Tyr
130 135 140

Ile Asp Phe Leu Ala Gly Glu Thr Pro Glu His Ile His Val Val Lys
145 150 155 160

Gln Gly Glu Thr Leu Ser Lys Ile Ala Ser Lys Tyr Asn Ile Pro Val
165 170 175

Ala Glu Leu Lys Lys Leu Asn Lys Leu Asn Ser Asp Thr Ile Phe Thr
180 185 190

Asp Gln Arg Ile Arg Leu Pro Lys Lys Lys
195 200

<210> SEQ ID NO 34
<211> LENGTH: 259
<212> TYPE: PRT
<213> ORGANISM: Chlamydia muridarum

<400> SEQUENCE: 34

Met Ser Met Tyr Ile Lys Arg Lys Lys Ala Trp Met Thr Phe Leu Ala
1 5 10 15

Ile Val Cys Ser Phe Cys Leu Ala Gly Cys Ser Lys Glu Ser Lys Asp
20 25 30

Ser Val Ser Glu Lys Phe Ile Val Gly Thr Asn Ala Thr Tyr Pro Pro
35 40 45

Phe Glu Phe Val Asp Glu Arg Gly Glu Thr Val Gly Phe Asp Ile Asp
50 55 60

Leu Ala Arg Glu Ile Ser Lys Lys Leu Gly Lys Lys Leu Glu Val Arg
65 70 75 80

Glu Phe Ala Phe Asp Ala Leu Val Leu Asn Leu Lys Gln His Arg Ile
85 90 95

```
Asp Ala Ile Met Ala Gly Val Ser Ile Thr Ser Ser Arg Leu Lys Glu
            100                 105                 110

Ile Leu Met Ile Pro Tyr Tyr Gly Glu Glu Ile Lys Ser Leu Val Leu
        115                 120                 125

Val Phe Lys Asp Gly Asp Ser Lys Ser Leu Pro Leu Asp Gln Tyr Asn
    130                 135                 140

Ser Val Ala Val Gln Thr Gly Thr Tyr Gln Glu Glu Tyr Leu Gln Ser
145                 150                 155                 160

Leu Pro Gly Val Arg Ile Arg Ser Phe Asp Ser Thr Leu Glu Val Leu
                165                 170                 175

Met Glu Val Leu His Ser Lys Ser Pro Ile Ala Val Leu Glu Pro Ser
            180                 185                 190

Ile Ala Gln Val Val Leu Lys Asp Phe Pro Thr Leu Thr Thr Glu Thr
        195                 200                 205

Ile Asp Leu Pro Glu Asp Lys Trp Val Leu Gly Tyr Gly Ile Gly Val
    210                 215                 220

Ala Ser Asp Arg Pro Ser Leu Ala Ser Asp Ile Glu Ala Ala Val Gln
225                 230                 235                 240

Glu Ile Lys Lys Glu Gly Val Leu Ala Glu Leu Glu Gln Lys Trp Gly
                245                 250                 255

Leu Asn Gly


<210> SEQ ID NO 35
<211> LENGTH: 1007
<212> TYPE: PRT
<213> ORGANISM: Chlamydia muridarum

<400> SEQUENCE: 35

Met Thr Thr Pro Ile Ser Asn Ser Pro Ser Ser Ile Pro Thr Val Thr
1               5                   10                  15

Val Ser Thr Thr Thr Ala Ser Ser Gly Ser Leu Gly Thr Ser Thr Val
            20                  25                  30

Ser Ser Thr Thr Thr Ser Thr Ser Val Ala Gln Thr Ala Thr Thr Thr
        35                  40                  45

Ser Ser Ala Ser Thr Ser Ile Ile Gln Ser Ser Gly Glu Asn Ile Gln
    50                  55                  60

Ser Thr Thr Gly Thr Pro Ser Pro Ile Thr Ser Ser Val Ser Thr Ser
65                  70                  75                  80

Ala Pro Ser Pro Lys Ala Ser Ala Thr Ala Asn Lys Thr Ser Ser Ala
                85                  90                  95

Val Ser Gly Lys Ile Thr Ser Gln Glu Thr Ser Glu Glu Ser Glu Thr
            100                 105                 110

Gln Ala Thr Thr Ser Asp Gly Glu Val Ser Ser Asn Tyr Asp Asp Val
        115                 120                 125

Asp Thr Pro Thr Asn Ser Ser Asp Ser Thr Val Asp Ser Asp Tyr Gln
    130                 135                 140

Asp Val Glu Thr Gln Tyr Lys Thr Ile Ser Asn Asn Gly Glu Asn Thr
145                 150                 155                 160

Tyr Glu Thr Ile Gly Ser His Gly Glu Lys Asn Thr His Val Gln Glu
                165                 170                 175

Ser His Ala Ser Gly Thr Gly Asn Pro Ile Asn Asn Gln Gln Glu Ala
            180                 185                 190

Ile Arg Gln Leu Arg Ser Ser Thr Tyr Thr Thr Ser Pro Arg Asn Glu
        195                 200                 205
```

-continued

```
Asn Ile Phe Ser Pro Gly Pro Glu Gly Leu Pro Asn Met Ser Leu Pro
    210                 215                 220

Ser Tyr Ser Pro Thr Asp Lys Ser Ser Leu Leu Ala Phe Leu Ser Asn
225                 230                 235                 240

Pro Asn Thr Lys Ala Lys Met Leu Glu His Ser Gly His Leu Val Phe
                245                 250                 255

Ile Asp Thr Thr Arg Ser Ser Phe Ile Phe Val Pro Asn Gly Asn Trp
            260                 265                 270

Asp Gln Val Cys Ser Met Lys Val Gln Asn Gly Lys Thr Lys Glu Asp
        275                 280                 285

Leu Gly Leu Lys Asp Leu Glu Asp Met Cys Ala Lys Phe Cys Thr Gly
    290                 295                 300

Tyr Asn Lys Phe Ser Ser Asp Trp Gly Asn Arg Val Asp Pro Leu Val
305                 310                 315                 320

Ser Ser Lys Ala Gly Ile Glu Ser Gly Gly His Leu Pro Ser Ser Val
                325                 330                 335

Ile Ile Asn Asn Lys Phe Arg Thr Cys Val Ala Tyr Gly Pro Trp Asn
            340                 345                 350

Pro Lys Glu Asn Gly Pro Asn Tyr Thr Pro Ser Ala Trp Arg Arg Gly
        355                 360                 365

His Arg Val Asp Phe Gly Lys Ile Phe Asp Gly Thr Ala Pro Phe Asn
    370                 375                 380

Lys Ile Asn Trp Gly Ser Ser Pro Thr Pro Gly Asp Asp Gly Ile Ser
385                 390                 395                 400

Phe Ser Asn Glu Thr Ile Gly Ser Glu Pro Phe Ala Thr Pro Pro Ser
                405                 410                 415

Ser Pro Ser Gln Thr Pro Val Ile Asn Val Asn Val Asn Val Gly Gly
            420                 425                 430

Thr Asn Val Asn Ile Gly Asp Thr Asn Val Ser Lys Gly Ser Gly Thr
        435                 440                 445

Pro Thr Ser Ser Gln Ser Val Asp Met Ser Thr Asp Thr Ser Asp Leu
    450                 455                 460

Asp Thr Ser Asp Ile Asp Thr Asn Asn Gln Thr Asn Gly Asp Ile Asn
465                 470                 475                 480

Thr Asn Asp Asn Ser Asn Asn Val Asp Gly Ser Leu Ser Asp Val Asp
                485                 490                 495

Ser Arg Val Glu Asp Asp Asp Gly Val Ser Asp Thr Glu Ser Thr Asn
            500                 505                 510

Gly Asn Asp Ser Gly Lys Thr Thr Ser Thr Glu Glu Asn Gly Asp Pro
        515                 520                 525

Ser Gly Pro Asp Ile Leu Ala Ala Val Arg Lys His Leu Asp Thr Val
    530                 535                 540

Tyr Pro Gly Glu Asn Gly Gly Ser Thr Glu Gly Pro Leu Pro Ala Asn
545                 550                 555                 560

Gln Asn Leu Gly Asn Val Ile His Asp Val Glu Gln Asn Gly Ser Ala
                565                 570                 575

Lys Glu Thr Ile Ile Thr Pro Gly Asp Thr Gly Pro Thr Asp Ser Ser
            580                 585                 590

Ser Ser Val Asp Ala Asp Ala Asp Val Glu Asp Thr Ser Asp Thr Asp
        595                 600                 605

Ser Gly Ile Gly Asp Asp Asp Gly Val Ser Asp Thr Glu Ser Thr Asn
    610                 615                 620
```

-continued

```
Gly Asn Asn Ser Gly Lys Thr Thr Ser Thr Glu Glu Asn Gly Asp Pro
625                 630                 635                 640

Ser Gly Pro Asp Ile Leu Ala Ala Val Arg Lys His Leu Asp Thr Val
                645                 650                 655

Tyr Pro Gly Glu Asn Gly Gly Ser Thr Glu Gly Pro Leu Pro Ala Asn
            660                 665                 670

Gln Asn Leu Gly Asn Val Ile His Asp Val Glu Gln Asn Gly Ala Ala
        675                 680                 685

Gln Glu Thr Ile Ile Thr Pro Gly Asp Thr Glu Ser Thr Asp Thr Ser
    690                 695                 700

Ser Ser Val Asn Ala Asn Ala Asp Leu Glu Asp Val Ser Asp Ala Asp
705                 710                 715                 720

Ser Gly Phe Gly Asp Asp Asp Gly Ile Ser Asp Thr Glu Ser Thr Asn
                725                 730                 735

Gly Asn Asp Ser Gly Lys Asn Thr Pro Val Gly Asp Gly Gly Thr Pro
            740                 745                 750

Ser Gly Pro Asp Ile Leu Ala Ala Val Arg Lys His Leu Asp Thr Val
        755                 760                 765

Tyr Pro Gly Glu Asn Gly Gly Ser Thr Glu Arg Pro Leu Pro Ala Asn
    770                 775                 780

Gln Asn Leu Gly Asp Ile Ile His Asp Val Glu Gln Asn Gly Ser Ala
785                 790                 795                 800

Lys Glu Thr Val Val Ser Pro Tyr Arg Gly Gly Gly Gly Asn Thr Ser
                805                 810                 815

Ser Pro Ile Gly Leu Ala Ser Leu Leu Pro Ala Thr Pro Ser Thr Pro
            820                 825                 830

Leu Met Thr Thr Pro Arg Thr Asn Gly Lys Ala Ala Ala Ser Ser Leu
        835                 840                 845

Met Ile Lys Gly Gly Glu Thr Gln Ala Lys Leu Val Lys Asn Gly Gly
    850                 855                 860

Asn Ile Pro Gly Glu Thr Thr Leu Ala Glu Leu Leu Pro Arg Leu Arg
865                 870                 875                 880

Gly His Leu Asp Lys Val Phe Thr Ser Asp Gly Lys Phe Thr Asn Leu
                885                 890                 895

Asn Gly Pro Gln Leu Gly Ala Ile Ile Asp Gln Phe Arg Lys Glu Thr
            900                 905                 910

Gly Ser Gly Gly Ile Ile Ala His Thr Asp Ser Val Pro Gly Glu Asn
        915                 920                 925

Gly Thr Ala Ser Pro Leu Thr Gly Ser Ser Gly Glu Lys Val Ser Leu
    930                 935                 940

Tyr Asp Ala Ala Lys Asn Val Thr Gln Ala Leu Thr Ser Val Thr Asn
945                 950                 955                 960

Lys Val Thr Leu Ala Met Gln Gly Gln Lys Leu Glu Gly Ile Ile Asn
                965                 970                 975

Asn Asn Asn Thr Pro Ser Ser Ile Gly Gln Asn Leu Phe Ala Ala Ala
            980                 985                 990

Arg Ala Thr Thr Gln Ser Leu Ser  Ser Leu Ile Gly Thr  Val Gln
        995                 1000                 1005
```

<210> SEQ ID NO 36
<211> LENGTH: 15
<212> TYPE: PRT
<213> ORGANISM: Chlamydia muridarum

<400> SEQUENCE: 36

Asp Tyr Phe Asn Asp Glu Phe Phe Asn Arg Phe Phe Gly Leu Pro
1               5                   10                  15

<210> SEQ ID NO 37
<211> LENGTH: 5
<212> TYPE: PRT
<213> ORGANISM: Chlamydia muridarum

<400> SEQUENCE: 37

Ser His Arg Glu Gln
1               5

<210> SEQ ID NO 38
<211> LENGTH: 15
<212> TYPE: PRT
<213> ORGANISM: Chlamydia muridarum

<400> SEQUENCE: 38

Ala Leu Gln Lys Met Gly Val Arg Val Gln Asn Leu Thr Pro Glu
1               5                   10                  15

<210> SEQ ID NO 39
<211> LENGTH: 15
<212> TYPE: PRT
<213> ORGANISM: Chlamydia muridarum

<400> SEQUENCE: 39

Asn Gln Val Leu Lys Asn Ala Lys Gly Glu Asn Val Leu Leu Met
1               5                   10                  15

<210> SEQ ID NO 40
<211> LENGTH: 20
<212> TYPE: PRT
<213> ORGANISM: Chlamydia muridarum

<400> SEQUENCE: 40

Ser Pro Met Leu Gly Tyr Ser Ala Pro Lys Lys Asp Ser Ser Thr Gly
1               5                   10                  15

Ile Cys Leu Ala
            20

<210> SEQ ID NO 41
<211> LENGTH: 20
<212> TYPE: PRT
<213> ORGANISM: Chlamydia muridarum

<400> SEQUENCE: 41

Glu Asp Leu Leu Lys Glu Val Ser Arg Gly Phe Ser Lys Val Ala Ala
1               5                   10                  15

Gln Ala Thr Pro
            20

<210> SEQ ID NO 42
<211> LENGTH: 20
<212> TYPE: PRT
<213> ORGANISM: Chlamydia muridarum

<400> SEQUENCE: 42

Thr Gly Ser Gln Ala Ile Ala Ser Pro Gly Asn Lys Arg Gly Phe Gln
1               5                   10                  15

Glu Asn Pro Phe
            20

-continued

<210> SEQ ID NO 43
<211> LENGTH: 10
<212> TYPE: PRT
<213> ORGANISM: Chlamydia muridarum

<400> SEQUENCE: 43

Pro Arg Pro Gln Gln Arg Asp Ala Val Arg
1 5 10

<210> SEQ ID NO 44
<211> LENGTH: 30
<212> TYPE: PRT
<213> ORGANISM: Chlamydia muridarum

<400> SEQUENCE: 44

Ile Ala Ile Gly Asn Pro Phe Gly Leu Gln Ala Thr Val Thr Val Gly
1 5 10 15

Val Ile Ser Ala Lys Gly Arg Asn Gln Leu His Ile Val Asp
20 25 30

<210> SEQ ID NO 45
<211> LENGTH: 30
<212> TYPE: PRT
<213> ORGANISM: Chlamydia muridarum

<400> SEQUENCE: 45

Asn Thr Ala Ile Val Ser Gly Ser Gly Gly Tyr Ile Gly Ile Gly Phe
1 5 10 15

Ala Ile Pro Ser Leu Met Ala Lys Arg Val Ile Asp Gln Leu
20 25 30

<210> SEQ ID NO 46
<211> LENGTH: 17
<212> TYPE: PRT
<213> ORGANISM: Chlamydia muridarum

<400> SEQUENCE: 46

Val Ala Ala Gln Ala Thr Pro Gly Val Val Tyr Ile Glu Asn Phe Pro
1 5 10 15

Lys

<210> SEQ ID NO 47
<211> LENGTH: 33
<212> TYPE: PRT
<213> ORGANISM: Chlamydia muridarum

<400> SEQUENCE: 47

Gly Phe Gln Glu Asn Pro Phe Asp Tyr Phe Asn Asp Glu Phe Phe Asn
1 5 10 15

Arg Phe Phe Gly Leu Pro Ser His Arg Glu Gln Pro Arg Pro Gln Gln
20 25 30

Arg

<210> SEQ ID NO 48
<211> LENGTH: 24
<212> TYPE: PRT
<213> ORGANISM: Chlamydia muridarum

<400> SEQUENCE: 48

Gly Thr Gly Phe Ile Val Ser Glu Asp Gly Tyr Val Val Thr Asn His
1 5 10 15

-continued

His Val Val Glu Asp Ala Gly Lys
20

<210> SEQ ID NO 49
<211> LENGTH: 11
<212> TYPE: PRT
<213> ORGANISM: Chlamydia muridarum

<400> SEQUENCE: 49

Thr Asp Leu Ala Val Ile Lys Ile Gln Ala Lys
1 5 10

<210> SEQ ID NO 50
<211> LENGTH: 13
<212> TYPE: PRT
<213> ORGANISM: Chlamydia muridarum

<400> SEQUENCE: 50

Val Ile Asp Gln Leu Ile Ser Asp Gly Gln Val Thr Arg
1 5 10

<210> SEQ ID NO 51
<211> LENGTH: 24
<212> TYPE: PRT
<213> ORGANISM: Chlamydia muridarum

<400> SEQUENCE: 51

Ala Gly Leu Arg Gln Glu Asp Val Ile Val Ala Tyr Asn Gly Lys Glu
1 5 10 15

Val Glu Ser Leu Ser Ala Leu Arg
20

<210> SEQ ID NO 52
<211> LENGTH: 22
<212> TYPE: PRT
<213> ORGANISM: Chlamydia muridarum

<400> SEQUENCE: 52

Phe Ile Glu Ile Pro Val Thr Val Thr Gln Ile Pro Ala Glu Asp Gly
1 5 10 15

Val Ser Ala Leu Gln Lys
20

<210> SEQ ID NO 53
<211> LENGTH: 10
<212> TYPE: PRT
<213> ORGANISM: Chlamydia muridarum

<400> SEQUENCE: 53

Val Gln Asn Leu Thr Pro Glu Ile Cys Lys
1 5 10

<210> SEQ ID NO 54
<211> LENGTH: 18
<212> TYPE: PRT
<213> ORGANISM: Chlamydia muridarum

<400> SEQUENCE: 54

Asn Ala Lys Gly Glu Asn Val Leu Leu Met Val Ser Gln Gly Glu Val
1 5 10 15

Ile Arg

<210> SEQ ID NO 55

<211> LENGTH: 15
<212> TYPE: PRT
<213> ORGANISM: Chlamydia muridarum

<400> SEQUENCE: 55

Gly Glu Asn Val Leu Leu Met Val Ser Gln Gly Glu Val Ile Arg
1 5 10 15

<210> SEQ ID NO 56
<211> LENGTH: 15
<212> TYPE: PRT
<213> ORGANISM: Chlamydia trachomatis

<400> SEQUENCE: 56

Asp Tyr Phe Asn Asp Glu Phe Phe Asn Arg Phe Phe Gly Leu Pro
1 5 10 15

<210> SEQ ID NO 57
<211> LENGTH: 5
<212> TYPE: PRT
<213> ORGANISM: Chlamydia trachomatis

<400> SEQUENCE: 57

Ser His Arg Glu Gln
1 5

<210> SEQ ID NO 58
<211> LENGTH: 15
<212> TYPE: PRT
<213> ORGANISM: Chlamydia trachomatis

<400> SEQUENCE: 58

Ala Leu Gln Lys Met Gly Val Arg Val Gln Asn Ile Thr Pro Glu
1 5 10 15

<210> SEQ ID NO 59
<211> LENGTH: 15
<212> TYPE: PRT
<213> ORGANISM: Chlamydia trachomatis

<400> SEQUENCE: 59

Asn Gln Val Leu Lys Asn Ser Lys Gly Glu Asn Val Leu Leu Met
1 5 10 15

<210> SEQ ID NO 60
<211> LENGTH: 20
<212> TYPE: PRT
<213> ORGANISM: Chlamydia trachomatis

<400> SEQUENCE: 60

Ser Pro Met Leu Gly Tyr Ser Ala Ser Lys Lys Asp Ser Lys Ala Asp
1 5 10 15

Ile Cys Leu Ala
20

<210> SEQ ID NO 61
<211> LENGTH: 20
<212> TYPE: PRT
<213> ORGANISM: Chlamydia trachomatis

<400> SEQUENCE: 61

Glu Asp Leu Leu Lys Glu Val Ser Arg Gly Phe Ser Arg Val Ala Ala
1 5 10 15

Lys Ala Thr Pro

20

<210> SEQ ID NO 62
<211> LENGTH: 20
<212> TYPE: PRT
<213> ORGANISM: Chlamydia trachomatis

<400> SEQUENCE: 62

Thr Gly Asn Gln Ala Ile Ala Ser Pro Gly Asn Lys Arg Gly Phe Gln
1 5 10 15

Glu Asn Pro Phe
20

<210> SEQ ID NO 63
<211> LENGTH: 30
<212> TYPE: PRT
<213> ORGANISM: Chlamydia trachomatis

<400> SEQUENCE: 63

Ile Ala Ile Gly Asn Pro Phe Gly Leu Gln Ala Thr Val Thr Val Gly
1 5 10 15

Val Ile Ser Ala Lys Gly Arg Asn Gln Leu His Ile Val Asp
20 25 30

<210> SEQ ID NO 64
<211> LENGTH: 30
<212> TYPE: PRT
<213> ORGANISM: Chlamydia muridarum

<400> SEQUENCE: 64

Asn Thr Ala Ile Val Ser Gly Ser Gly Gly Tyr Ile Gly Ile Gly Phe
1 5 10 15

Ala Ile Pro Ser Leu Met Ala Lys Arg Val Ile Asp Gln Leu
20 25 30

<210> SEQ ID NO 65
<211> LENGTH: 6
<212> TYPE: PRT
<213> ORGANISM: Artificial Sequence
<220> FEATURE:
<223> OTHER INFORMATION: protein linker sequence

<400> SEQUENCE: 65

Gly Ser Gly Gly Gly Gly
1 5

<210> SEQ ID NO 66
<211> LENGTH: 26
<212> TYPE: DNA
<213> ORGANISM: Artificial Sequence
<220> FEATURE:
<223> OTHER INFORMATION: immunostimulatory oligonucleotide
<220> FEATURE:
<221> NAME/KEY: misc_feature
<222> LOCATION: (1)..(26)
<223> OTHER INFORMATION: any “n” is inosine

<400> SEQUENCE: 66
ncncncncnc ncncncncnc ncncnc 26

<210> SEQ ID NO 67
<211> LENGTH: 11
<212> TYPE: PRT
<213> ORGANISM: Artificial Sequence
<220> FEATURE:

<223> OTHER INFORMATION: polycationic olipopeptide

<400> SEQUENCE: 67

Lys Leu Lys Leu Leu Leu Leu Leu Lys Leu Lys
1 5 10

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
tctggaatcg aactctctcg 20

<210> SEQ ID NO 69
<211> LENGTH: 42
<212> TYPE: DNA
<213> ORGANISM: Artificial Sequence
<220> FEATURE:
<223> OTHER INFORMATION: primer

<400> SEQUENCE: 69
attttgagac acaacgtggc tttcatggct taccccttgt tg 42

<210> SEQ ID NO 70
<211> LENGTH: 39
<212> TYPE: DNA
<213> ORGANISM: Artificial Sequence
<220> FEATURE:
<223> OTHER INFORMATION: primer

<400> SEQUENCE: 70
ttcacgaggc agacctcata aacatctgcg tttcccttg 39

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
ttgcttctgc tttaactcgg 20

<210> SEQ ID NO 72
<211> LENGTH: 23
<212> TYPE: DNA
<213> ORGANISM: Artificial Sequence
<220> FEATURE:
<223> OTHER INFORMATION: primer

<400> SEQUENCE: 72
atgagccata ttcaacggga aac 23

<210> SEQ ID NO 73
<211> LENGTH: 25
<212> TYPE: DNA
<213> ORGANISM: Artificial Sequence
<220> FEATURE:
<223> OTHER INFORMATION: primer

<400> SEQUENCE: 73
ttagaaaaac tcatcgagca tcaaa 25

<210> SEQ ID NO 74
<211> LENGTH: 18
<212> TYPE: DNA
<213> ORGANISM: Artificial Sequence
<220> FEATURE:
<223> OTHER INFORMATION: primer

<400> SEQUENCE: 74
cggacccgta ttcttaac 18

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
gccttcgctt tagcatct 18

<210> SEQ ID NO 76
<211> LENGTH: 19
<212> TYPE: DNA
<213> ORGANISM: Artificial Sequence
<220> FEATURE:
<223> OTHER INFORMATION: primer

<400> SEQUENCE: 76
gatcggttgg ttggcagat 19

<210> SEQ ID NO 77
<211> LENGTH: 43
<212> TYPE: DNA
<213> ORGANISM: Artificial Sequence
<220> FEATURE:
<223> OTHER INFORMATION: primer

<400> SEQUENCE: 77
caccaggatt tatttattct gcgtttttgc gcctcgttat cat 43

<210> SEQ ID NO 78
<211> LENGTH: 39
<212> TYPE: DNA
<213> ORGANISM: Artificial Sequence
<220> FEATURE:
<223> OTHER INFORMATION: primer

<400> SEQUENCE: 78
tactgcgatg agtggcaggc gcaggcttaa gttctcgtc 39

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
aaaatcttga aagcggttgg 20

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
cgcagaataa ataaatcctg gtg 23

<210> SEQ ID NO 81
<211> LENGTH: 19
<212> TYPE: DNA
<213> ORGANISM: Artificial Sequence
<220> FEATURE:
<223> OTHER INFORMATION: primer

<400> SEQUENCE: 81
cctgccactc atcgcagta 19

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
atgaaaaaga cagctatcgc 20

<210> SEQ ID NO 83
<211> LENGTH: 19
<212> TYPE: DNA
<213> ORGANISM: Artificial Sequence
<220> FEATURE:
<223> OTHER INFORMATION: primer

<400> SEQUENCE: 83
ttaagcctgc ggctgagtt 19

<210> SEQ ID NO 84
<211> LENGTH: 25
<212> TYPE: PRT
<213> ORGANISM: Chlamydia muridarum

<400> SEQUENCE: 84

Asn Lys Arg Gly Phe Gln Glu Asn Pro Phe Asp Tyr Phe Asn Asp Glu
1 5 10 15

Phe Phe Asn Arg Phe Phe Gly Leu Pro
20 25

<210> SEQ ID NO 85
<211> LENGTH: 12
<212> TYPE: PRT
<213> ORGANISM: Chlamydia muridarum

<400> SEQUENCE: 85

Thr Pro Gly Val Val Tyr Ile Glu Asn Phe Pro Lys
1 5 10

<210> SEQ ID NO 86
<211> LENGTH: 15
<212> TYPE: PRT
<213> ORGANISM: Chlamydia trachomatis

<400> SEQUENCE: 86

Gly Glu Asn Val Leu Leu Met Val Ser Gln Gly Asp Val Val Arg
1 5 10 15

<210> SEQ ID NO 87

-continued

<211> LENGTH: 19
<212> TYPE: PRT
<213> ORGANISM: Chlamydia muridarum

<400> SEQUENCE: 87

```
Lys Val Ala Ala Gln Ala Thr Pro Gly Val Val Tyr Ile Glu Asn Phe
1               5                   10                  15

Pro Lys Thr
```

<210> SEQ ID NO 88
<211> LENGTH: 19
<212> TYPE: PRT
<213> ORGANISM: Chlamydia muridarum

<400> SEQUENCE: 88

```
Arg Gly Phe Gln Glu Asn Pro Phe Asp Tyr Phe Asn Asp Glu Phe Phe
1               5                   10                  15

Asn Arg Phe
```

<210> SEQ ID NO 89
<211> LENGTH: 10
<212> TYPE: PRT
<213> ORGANISM: Chlamydia muridarum

<400> SEQUENCE: 89

```
Arg Phe Phe Gly Leu Pro Ser His Arg Glu
1               5                   10
```

<210> SEQ ID NO 90
<211> LENGTH: 10
<212> TYPE: PRT
<213> ORGANISM: Chlamydia muridarum

<400> SEQUENCE: 90

```
Arg Glu Gln Pro Arg Pro Gln Gln Arg Asp
1               5                   10
```

<210> SEQ ID NO 91
<211> LENGTH: 26
<212> TYPE: PRT
<213> ORGANISM: Chlamydia muridarum

<400> SEQUENCE: 91

```
Arg Gly Thr Gly Phe Ile Val Ser Glu Asp Gly Tyr Val Val Thr Asn
1               5                   10                  15

His His Val Val Glu Asp Ala Gly Lys Ile
            20                  25
```

<210> SEQ ID NO 92
<211> LENGTH: 13
<212> TYPE: PRT
<213> ORGANISM: Chlamydia muridarum

<400> SEQUENCE: 92

```
Lys Thr Asp Leu Ala Val Ile Lys Ile Gln Ala Lys Asn
1               5                   10
```

<210> SEQ ID NO 93
<211> LENGTH: 15
<212> TYPE: PRT
<213> ORGANISM: Chlamydia muridarum

<400> SEQUENCE: 93

Arg Val Ile Asp Gln Leu Ile Ser Asp Gly Gln Val Thr Arg Gly
1 5 10 15

<210> SEQ ID NO 94
<211> LENGTH: 17
<212> TYPE: PRT
<213> ORGANISM: Chlamydia muridarum

<400> SEQUENCE: 94

Lys Ala Gly Leu Arg Gln Glu Asp Val Ile Val Ala Tyr Asn Gly Lys
1 5 10 15

Glu

<210> SEQ ID NO 95
<211> LENGTH: 26
<212> TYPE: PRT
<213> ORGANISM: Chlamydia muridarum

<400> SEQUENCE: 95

Lys Ala Gly Leu Arg Gln Glu Asp Val Ile Val Ala Tyr Asn Gly Lys
1 5 10 15

Glu Val Glu Ser Leu Ser Ala Leu Arg Asn
20 25

<210> SEQ ID NO 96
<211> LENGTH: 24
<212> TYPE: PRT
<213> ORGANISM: Chlamydia muridarum

<400> SEQUENCE: 96

Lys Phe Ile Glu Ile Pro Val Thr Val Thr Gln Ile Pro Ala Glu Asp
1 5 10 15

Gly Val Ser Ala Leu Gln Lys Met
20

<210> SEQ ID NO 97
<211> LENGTH: 12
<212> TYPE: PRT
<213> ORGANISM: Chlamydia muridarum

<400> SEQUENCE: 97

Arg Val Gln Asn Leu Thr Pro Glu Ile Cys Lys Lys
1 5 10

<210> SEQ ID NO 98
<211> LENGTH: 20
<212> TYPE: PRT
<213> ORGANISM: Chlamydia muridarum

<400> SEQUENCE: 98

Lys Asn Ala Lys Gly Glu Asn Val Leu Leu Met Val Ser Gln Gly Glu
1 5 10 15

Val Ile Arg Phe
20

<210> SEQ ID NO 99
<211> LENGTH: 17
<212> TYPE: PRT

-continued

```
<213> ORGANISM: Chlamydia muridarum

<400> SEQUENCE: 99

Lys Gly Glu Asn Val Leu Leu Met Val Ser Gln Gly Glu Val Ile Arg
1               5                   10                  15

Phe
```